(12) United States Patent
Aehle et al.

(10) Patent No.: US 8,679,816 B2
(45) Date of Patent: Mar. 25, 2014

(54) CELLULASE VARIANTS WITH IMPROVED EXPRESSION, ACTIVITY AND STABILITY, AND USE THEREOF

(75) Inventors: Wolfgang Aehle, Zwingenberg (DE); Richard R. Bott, Burlingame, CA (US); Benjamin Bower, Newark, CA (US); Jonathan Caspi, Sunnyvale, CA (US); David A. Estell, San Francisco, CA (US); Frits Goedegebuur, Vlaardingen (NL); Ronaldus W. J. Hommes, Haarlem (NL); Thijs Kaper, Half Moon Bay, CA (US); Bradley Kelemen, Menlo Park, CA (US); Slavko Kralj, Oegstgeest (NL); Johan Van Lieshout, Utrecht (NL); Igor Nikolaev, Noordwijk (NL); Sander Van Stigt Thans, Zevenbergen (NL); Louise Wallace, Palo Alto, CA (US); Gudrun Vogtentanz, Sunnyvale, CA (US); Mats Sandgren, Uppsala (SE)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/321,928

(22) PCT Filed: Jun. 3, 2010

(86) PCT No.: PCT/US2010/037328
§ 371 (c)(1),
(2), (4) Date: Feb. 15, 2012

(87) PCT Pub. No.: WO2010/141779
PCT Pub. Date: Dec. 9, 2010

(65) Prior Publication Data
US 2012/0135500 A1    May 31, 2012

Related U.S. Application Data

(60) Provisional application No. 61/183,959, filed on Jun. 3, 2009.

(51) Int. Cl.
| | | |
|---|---|---|
| *C12N 9/42* | (2006.01) | |
| *C12P 19/00* | (2006.01) | |
| *C12P 19/02* | (2006.01) | |
| *C07H 21/04* | (2006.01) | |

(52) U.S. Cl.
USPC ............ 435/209; 435/69.1; 435/72; 435/105; 536/23.2

(58) Field of Classification Search
None
See application file for complete search history.

(56) References Cited

FOREIGN PATENT DOCUMENTS

| WO | 2006/074005 A2 | 7/2006 |
| WO | WO 2006-074005 | * 7/2006 |
| WO | 2008/039370 A1 | 3/2008 |
| WO | 2009/149202 A2 | 12/2009 |

OTHER PUBLICATIONS

UniProt Accession No. Q0D1J1 (Exoglucanase 2, created Oct. 17, 2006).*

* cited by examiner

*Primary Examiner* — Iqbal H Chowdhury
(74) *Attorney, Agent, or Firm* — Danisco US Inc.

(57) ABSTRACT

The present disclosure relates to cellulase variants. In particular the present disclosure relates to cellulase variants having improved expression, activity and/or stability. Also described are nucleic acids encoding the cellulase variants, compositions comprising the cellulase variants, and methods of use thereof.

7 Claims, 13 Drawing Sheets

FIG. 1

Figure 2A:
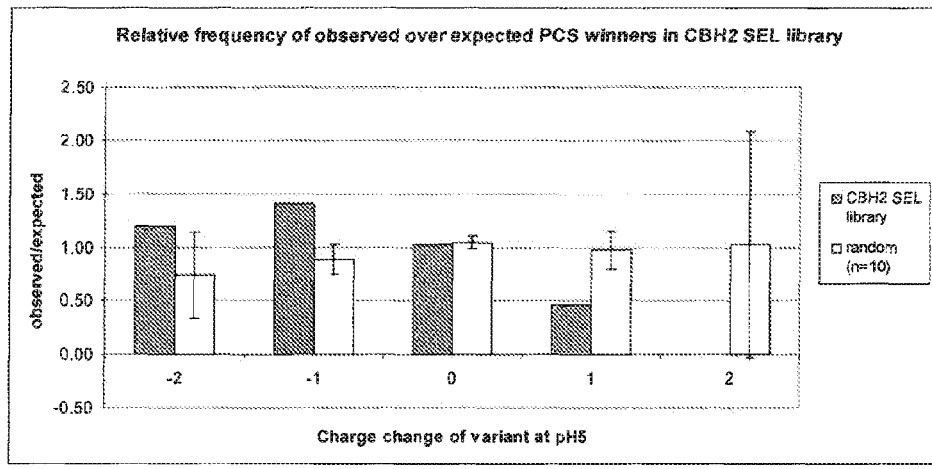

```
T. reesei CBH #3              ------------------------------QACSSVWGQCGGQN----W
H. koningii CBH #4            ------------------------------QACSSVWGQCGGQN----W
H. insolens CBH #5            -----------------------APVVEERQNCAPTWGQCGGIG----F
A. cellulolyticus CBH #6      --------------MLRYLSIVAATAILTGVEAQQSVWGQCGGQG----W
A. bisporus CBH #7            -------------------------QSPV----------WGQCGGNG----W
F. oxysporum EG #8            -----------------------APVEERQSCSNGVWAQCGGQN----W
P. chrysosporium CBH #9       ----------MKSTAFFAALVTLLPAYVAGQASE--WGQCGGIG----W
T. emersonii CBH #10          -------------MRNLLALAPAALLVGAAEAQQSLWGQCGGSS----W
T. fusc CBH #11               -AGCSVDYTVN-SWGTGFTANVTITNLGSAINGWTLEWDFPGNQQVTNLW
T. fusc EG #12                --------------------NDSPFYVNPNMSSAEWVRNNPND-----
C. fimi EG #13                APGCRVDYAVTNQWPGGFGANVTITNLGDPVSSWKLDWTYTAGQRIQQLW
                                                              *

T. reesei CBH #3              SGPTCCASGSTCVYSNDYYSQCLP--GA---ASSSSSTRAAST----TSR
H. koningii CBH #4            SGPTCCASGSTCVYSNDYYSQCLP--GA--------ASSSSTRASSTTA
H. insolens CBH #5            NGPTCCQSGSTCVKQNDWYSQCLP--GSQVTTTSTTSTSSSST----TSR
A. cellulolyticus CBH #6      SGATSCAAGSTCSTLNPYYAQCIP--GT--------ATSTTLV----KTT
A. bisporus CBH #7            TGPTTCASGSTCVKQNDFYSQCLP--NN--------------------Q
F. oxysporum EG #8            SGTPCCTSGNKCVKLNDFYSQCQP--GS-----------AEPS----STA
P. chrysosporium CBH #9       TGPTTCVSGTTCTVLNPYYSQCLP--GS-AVTTTSVITSHSSS----VSS
T. emersonii CBH #10          TGATSCAAGATCSTINPYYAQCVP--AT--------ATPTTLT----TTT
T. fusc CBH #11               NGTYTQSGQHVSVSNAPYNASI-PANGTVEFGFNGSYSGSNDIPSSFKLN
T. fusc EG #12                PRTPVIRDRIASVPQGTWFAHHNP--GQ--------ITGQVDA----LMS
C. fimi EG #13                NGTASTNGGQVSVTSLPWNGSI-PTGGTASFGFNGSWAGSNPTPASFSLN
                                  .    .    :  .    *

T. reesei CBH #3              VSPTTSR---SSSATPPPGSTTTRVPP-VGSGTATYSGNPFVGVTPWANA
H. koningii CBH #4            RASSTTS---RSSATPPPGSSTTRVPP-VGSGTATYSGNPFVGVTPWANA
H. insolens CBH #5            ATSTTRT---GGVTSITTAPTRTVTIPGGATTTASYNGNPFEGVQLWANN
A. cellulolyticus CBH #6      SSTSVGT-------TSPPTTTTTKAST-TATTTAAASGNPFSGYQLYANP
A. bisporus CBH #7            APPSTTT---QPGTTPPATTTSGGTGP-TSGA-----GNPYTGKTVWLSP
F. oxysporum EG #8            AGPSSTT---ATKTTATGGSSTTAGGS-VTSAPPAASDNPYAGVDLWANN
P. chrysosporium CBH #9       VSSHSGS---STSTSSPTGPTGTNPPP-PPSA-----NNPWTGFQIFLSP
T. emersonii CBH #10          KPTSTGG---AAPTTPPPTTTGTTTSP-VVTRPASASGNPFEGYQLYANP
T. fusc CBH #11               GVTCDGSDDPDPEPSPSPSPSPSPTDPDEPGCPTNPPTNPGEKVD---NP
T. fusc EG #12                AAQAAGK---IPILVVYNAPGRDCGNH-SSGGAPSHS-----AYRSWIDE
C. fimi EG #13                GTTCTGT---VPTTSPTPTPTPTTPTP-TPTPTPTPT--PTVTPQPTSGF
                                  .

T. reesei CBH #3              YYASEVSSLAIPSLTG-AMATAAAAVAKVPSFMWLDTL-----DKTP-LM
H. koningii CBH #4            YYASEVSSLAIPSLTG-AMATAAAAVAKVPSSMWLDTF-----DKTP-LM
H. insolens CBH #5            YYRSEVHTLAIPQITDPALRAAASAVAEVPSFQWLDRN-----VTVDTLL
A. cellulolyticus CBH #6      YYSSEVHTLAIPSLTG-SLAAAATKAAEIPSFVWLDTA-----AKVP-TM
A. bisporus CBH #7            FYADEVAQ-AAADISNPSLATKAASVAKIPTFVWFDTV-----AKVP-DL
F. oxysporum EG #8            YYRSEVMNLAVPKLSG-AKATAAAKVADVPSFQWMDTY-----DHIS-LM
P. chrysosporium CBH #9       YYANEVAA-AAKQITDPTLSSKAASVANIPTFTWLDSV-----AKIP-DL
T. emersonii CBH #10          YYASEVISLAIPSLSS-ELVPKASEVAKVPSFVWLDQA-----AKVP-SM
T. fusc CBH #11               FEGAKLYVNPVWSAKA-AAEPGGSAVANESTAVWLDRIGAIEGNDSPTTG
T. fusc EG #12                F-AAGLKNRPAYIIVEPDLISLMSSCMQHVQQEVLETM-----AYAGKAL
C. fimi EG #13                YVDPTTQGYRAWQAASGTDKALLEKIALTPQAYWVGNW-----ADAS---
                                  :              .        .
```

Figure 1 continued

```
T. reesei CBH        #3       EQTLAD-IRTANKNGGN--YAGQFVVYDLPDRDCAALASNGEYSIADGGV
H. koningii CBH      #4       EQTLAD-IRTANKNGGN--YAGQFVVYDLPDRDCAALASNGEYSIADGGV
H. insolens CBH      #5       VETLSE-IRAANQAGANPPYAAQIVVYDLPDRDCAAAASNGEWAIANNGA
A. cellulolyticus CBH #6      GTYLAN-IEAANKAGASPPIAGIFVVYDLPDRDCAAAASNGEYTVANNGV
A. bisporus CBH      #7       GGYLAD-ARSKNQ------LVQIVVYDLPDRDCAALASNGEFSLANDGL
F. oxysporum EG      #8       EDTLAD-IRKANKAGGK--YAGQFVVYDLPNRDCAAAASNGEYSLDKDGA
P. chrysosporium CBH #9       GTYLAS--ASALGKSTGTKQLVQIVIYDLPDRDCAAKASNGEFSIANNGQ
T. emersonii CBH     #10      GDYLKD-IQSQNAAGADPPIAGIFVVYDLPDRDCAAAASNGEFSIANNGV
T. fusc CBH          #11      SMGLRDHLEEAVRQSGGDPLTIQVVIYNLPGRDCAALASNGELGP--DEL
T. fusc EG           #12      KAGSSQ-ARIYFDAGHSAWHSPAQMASWL----QQADISNSAHGIA-TNT
C. fimi EG           #13      -HAQAE-VADYTGRAVAAGKTPMLVVYAIPGRDCGSHSGGG------VSE
                                      .            :   :      :   ...

T. reesei CBH        #3       AKYKN-YIDTIRQIVVEYSD---IRTLLVIEPDSLANLVTNLGTPK----
H. koningii CBH      #4       DKYKN-YIDTIRQIVVEYSD---IRTLLVIEPDSLANLVTNLGTPK----
H. insolens CBH      #5       NNYKG-YINRIREILISFSD---VRTILVIEPDSLANMVTNMNVAK----
A. cellulolyticus CBH #6      ANYKA-YIDSIVAQLKAYPD---VHTILIIEPDSLANMVTNLSTAK----
A. bisporus CBH      #7       NKYKN-YVDQIAAQIKQFPD---VSVVAVIEPDSLANLVTNLNVQK----
F. oxysporum EG      #8       NKYKA-YIAKIKGILQNYSD---TKVILVIEPDSLANLVTNLNVDK----
P. chrysosporium CBH #9       ANYEN-YIDQIVAQIQQFPD---VRVVAVIEPDSLANLVTNLNVQK----
T. emersonii CBH     #10      ALYKQ-YIDSIREQLTTYSD---VHTILVIEPDSLANVVTNLNVPK----
T. fusc CBH          #11      DRYKSEYIDPIADIMWDFADYENLRIVAIIEIDSLPNLVTNVGGNGGTEL
T. fusc EG           #12      SNYRW-TADEVA-----YAK---AVLSAIGNPSLRAVIDTSRNGNG----
C. fimi EG           #13      SEYAR-WVDTVAQGIK-------GNPIVILEPDALAQLGD----------
                                   *    :                 : :  .  . :

T. reesei CBH        #3       CA--NAQSAYLECINYAVTQL-NLPNVAMYLDAGHAGWLGWPANQDPAAQ
H. koningii CBH      #4       CA--NAQSAYLECINYAVTQL-NLPNVAMYLDAGHAGWLGWPANQDPAAQ
H. insolens CBH      #5       CS--GAASTYRELTIYALKQL-DLPHVAMYMDAGHAGWLGWPANIQPAAE
A. cellulolyticus CBH #6      CA--EAQSAYYECVNYALINL-NLANVAMYIDAGHAGWLGWSANLSPAAQ
A. bisporus CBH      #7       CA--NAQSAYKEGVIYAVQKL-NAVGVTMYIDAGHAGWLGWPANLSPAAQ
F. oxysporum EG      #8       CA--KAESAYKELTVYAIKEL-NLPNVSMYLDAGHGGWLGWPANIGPAAK
P. chrysosporium CBH #9       CA--NAKTTYLACVNYALTNL-AKVGVYMYMDAGHAGWLGWPANLSPAAQ
T. emersonii CBH     #10      CA--NAQDAYLECINYAITQL-DLPNVAMYLDAGHAGWLGWQANLAPAAQ
T. fusc CBH          #11      CAYMKQNGGYVNGVGYALRKLGEIPNVYNYIDAAHHGWIGWDSNFGPSVD
T. fusc EG           #12      ----PAGNEWCDPSGRAIGTPSTTNTGDPMIDAFL--WIKLPGEADGCIA
C. fimi EG           #13      CS---GQGDRVGFLKYAAKSL-TLKGARVYIDAGHAKWLSVDTPVNRLNQ
                                        *          :**    *:

T. reesei CBH        #3       LFANVYKNAS-SPRALRGLATNVANYNGWNIT-------------SPPSY
H. koningii CBH      #4       LFANVYKNAS-SPRALRGLATNVANYNGWNIT-------------SPPSY
H. insolens CBH      #5       LFAKIYEDAG-KPRAVRGLATNVANYNAWSIS-------------SPPPY
A. cellulolyticus CBH #6      LFATVYKNAS-APASLRGLATNVANYNAWSIS-------------SPPSY
A. bisporus CBH      #7       LFAQIYRDAG-SPRNLRGIATNVANFNALRAS-------------SPDPI
F. oxysporum EG      #8       LYAQIYKDAG-KPSRVRGLVTNVSNYNGWKLS-------------TKPDY
P. chrysosporium CBH #9       LFTQVWQNAG-KSPFIKGLATNVANYNALQAA-------------SPDPI
T. emersonii CBH     #10      LFASVYKNAS-SPASVRGLATNVANYNAWSIS-------------RCPSY
T. fusc CBH          #11      IFYEAANASGSTVDYVHGFISNTANYSATVEPYLDVNGTVNGQLIRQSKW
T. fusc EG           #12      GAGQFVPQAAYEMAIAAGGTNPNPNPNP--TP-------------TPTPT
C. fimi EG           #13      V---------GFEYAVGFALNTSNYQT-----------------------
                                      *    . * .
```

Figure 1 continued

```
T. reesei CBH #3            TQGNAVYNEKLYIHAIGPLLANHGWSN-AFFITDQGRSGK----QPTGQQ
H. koningii CBH #4          TQGNAVYNEQLYIHAIGPLLANHGWSN-AFFITDQGRSGK----QPTGQQ
H. insolens CBH #5          TSPNPNYDEKHYIEAFRPLLEARGFP--AQFIVDQGRSGK----QPTGQK
A. cellulolyticus CBH #6    TSGDSNYDEKLYINALSPLLTSNGWPN-AHFIMDTSRNGV----QPTKQQ
A. bisporus CBH #7          TQGNSNYDEIHYIEALAPMLSNAGFP--AHFIVDQGRSGV-----QNIRD
F. oxysporum EG #8          TESNPNYDEQRYINAFAPLLAQEGWSN-VKFIVDQGRSGK----QPTGQK
P. chrysosporium CBH #9     TQGNPNYDEIHYINALAPLLQQAGWD--ATFIVDQGRSGV-----QNIRQ
T. emersonii CBH #10        TQGDANCDEEDYVNALGPLFQEQGFP--AYFIIDTSRNGV----RPTKQS
T. fusc CBH #11             VDWNQYVDELSFVQDLRQALIAKGFRSDIGMLIDTSRNGWGGPNRPTGPS
T. fusc EG #12              PTPPPGSSGACTATYTIANEWNDGFQATVTVTANQNITGW--------TV
C. fimi EG #13              -----TADSKAYGQQISQRLGG------KKFVIDTSRNGN---------G
                                 .                        .  : . .*

T. reesei CBH #3            QWGD----------------WCNVIGTGFGIRPSANTGDSLLDSFVWV
H. koningii CBH #4          QWGD----------------WCNVIGTGFGIRPSANTGDSLLDSFVWI
H. insolens CBH #5          EWGH----------------WCNAIGTGFGMRPTANTGHQYVDAFVWV
A. cellulolyticus CBH #6    AWGD----------------WCNVIGTGFGVQPTTNTGDPLEDAFVWV
A. bisporus CBH #7          QWGD----------------WCNVKGAGFGQRPTTNTGSSLIDAIVWV
F. oxysporum EG #8          AQGD----------------WCNAKGTGFGLRPSTNTGDALADAFVWV
P. chrysosporium CBH #9     QWGD----------------WCNIKGAGFGTRPTTNTGSQFIDSIVWV
T. emersonii CBH #10        QWGD----------------WCNVIGTGFGVRPTTDTGNPLEDAFVWV
T. fusc CBH #11             SSTDLNTYVDESRIDRRIHPGNWCNQAGAGLGERPTVNPA-PGVDAYVWV
T. fusc EG #12              TWT----------------FTDGQTITNAWNADVSTSGSSVTARNVG
C. fimi EG #13              SNGE----------------WCNPRGRALGERPVAVNDGSGLDALLWV
                                : :          . ... :            :

T. reesei CBH #3            KPGGECDGTSDSS----APRFDSHCA-----------LPDALQPAPQAG
H. koningii CBH #4          KPGGECDGTSDSS----APRFDSHCA-----------LPDALQPAPQAG
H. insolens CBH #5          KPGGECDGTSDTT----AARYDYHCG-----------LEDALKPAPEAG
A. cellulolyticus CBH #6    KPGGESDGTSNSS----ATRYDFHCG-----------YSDALQPAPEAG
A. bisporus CBH #7          KPGGECDGTSDNS----SPRFDSHCS-----------LSDAHQPAPEAG
F. oxysporum EG #8          KPGGESDGTSDTS----AARYDYHCG-----------LDDALKPAPEAG
P. chrysosporium CBH #9     KPGGECDGTSNSS----SPRYDSTCS-----------LPDAAQPAPEAG
T. emersonii CBH #10        KPGGESDGTSNTT----SPRYDYHCG-----------LSDALQPAPEAG
T. fusc CBH #11             KPPGESDGASEEIPNDEGKGFDRMCDPTYQGNARNGNNPSGALPNAPISG
T. fusc EG #12              HNGTLSQGASTEF--------------------------------GFVG
C. fimi EG #13              KLPGESDGACNGG--------------------------------PAAG
                            :   .:*:.                                        *

T. reesei CBH #3            AWFQAYFVQLLTNANPSFL
H. koningii CBH #4          AWFQAYFVQLLTNANPSFL
H. insolens CBH #5          QWFQAYFEQLLRNANPPF-
A. cellulolyticus CBH #6    TWFQAYFVQLLTNANPALV
A. bisporus CBH #7          TWFQAYFETLVANANPAL-
F. oxysporum EG #8          TWFQAYFEQLLDNANPSFL
P. chrysosporium CBH #9     TWFQAYFQTLVSAANPPL-
T. emersonii CBH #10        TWFQAYFEQLLTNANPLF-
T. fusc CBH #11             HWFSAQFRELLANAYPPL-
T. fusc EG #12              SKGNSNSVPTLTCAAS---
C. fimi EG #13              QWWQEIALEMARNARW---
                              .                *
```

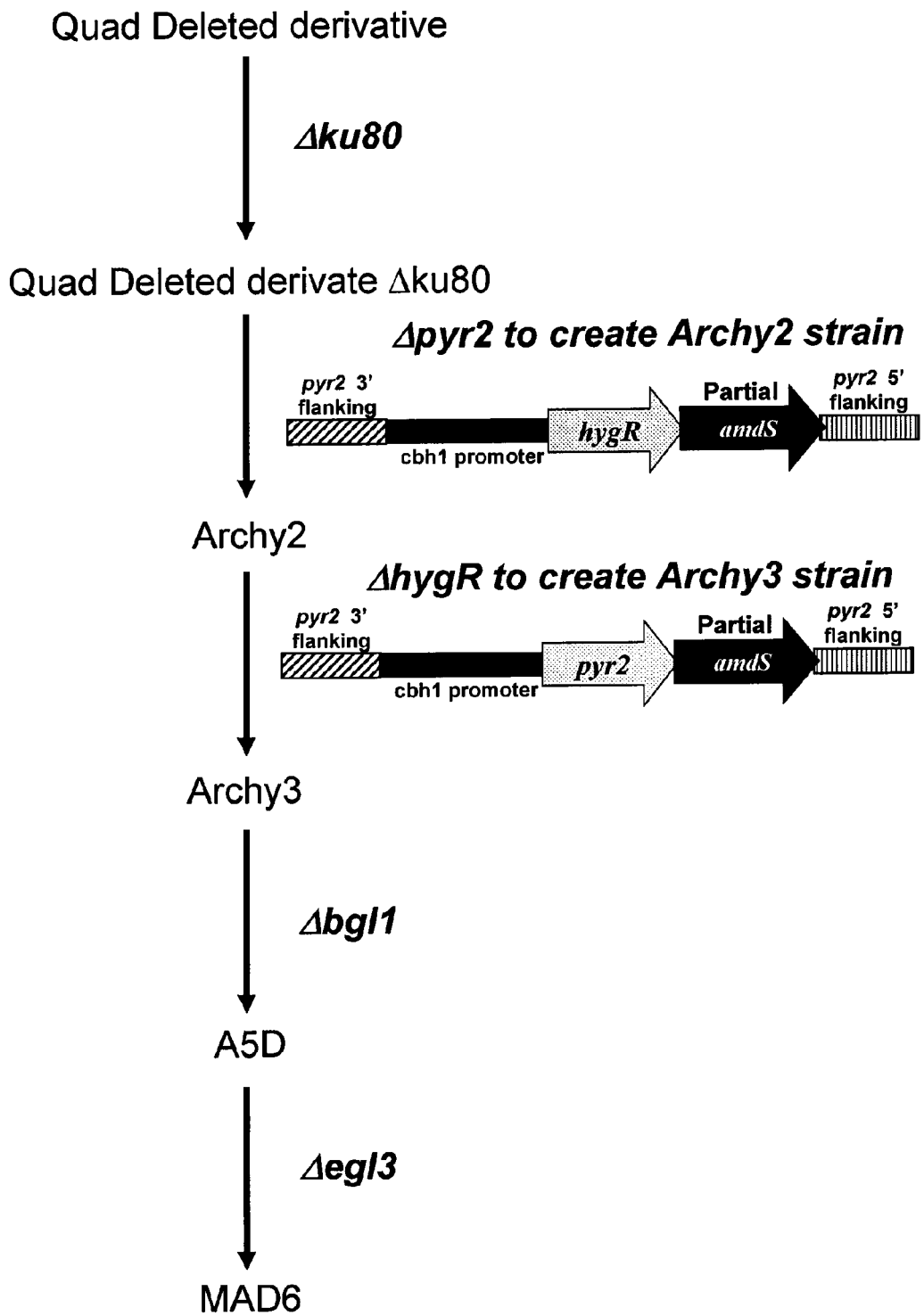
Figure 4. Deletion vectors used to create screening strains

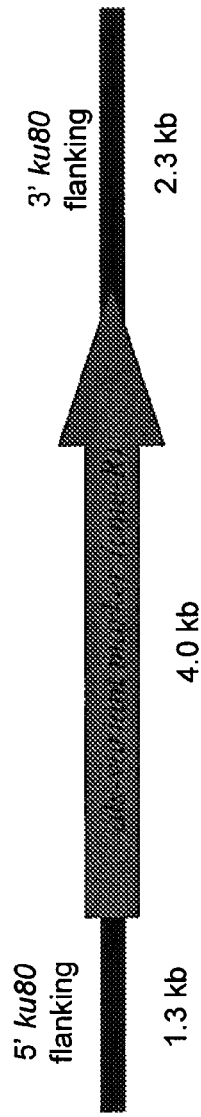
Figure 5. Δku80 deletion cassette
this vector deleted the native T.reesei ku80

Figure 6. ΔpyR2 deletion cassette to create Archy2 strain
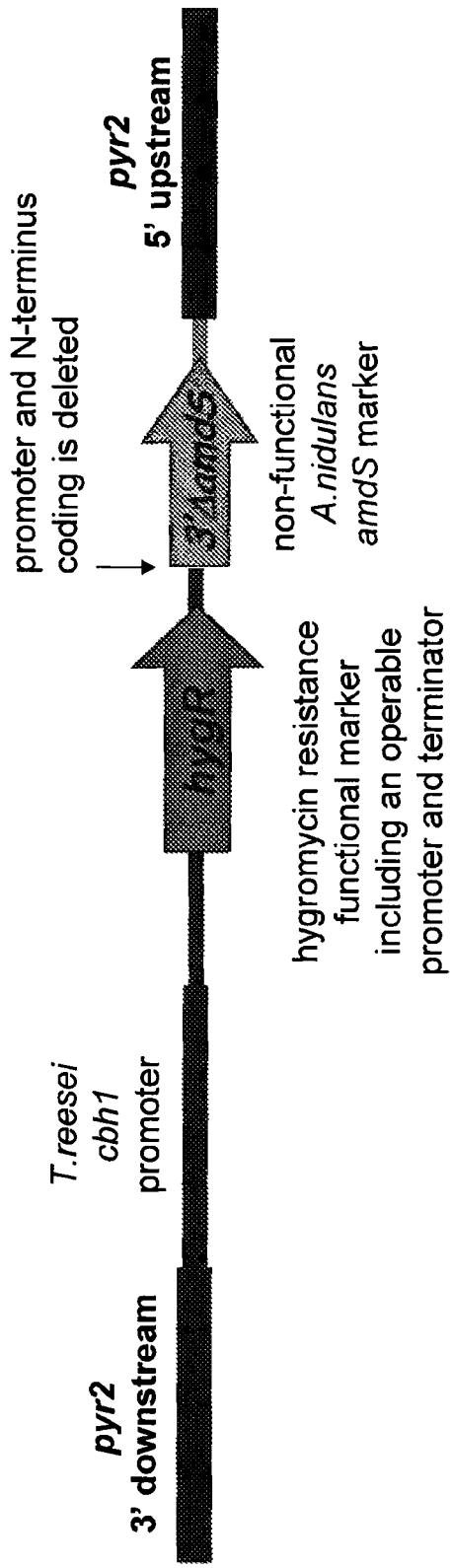
this vector deleted the native T.reesei pyr2

Figure 7. *ΔhygR* deletion cassette to create Archy3 strain
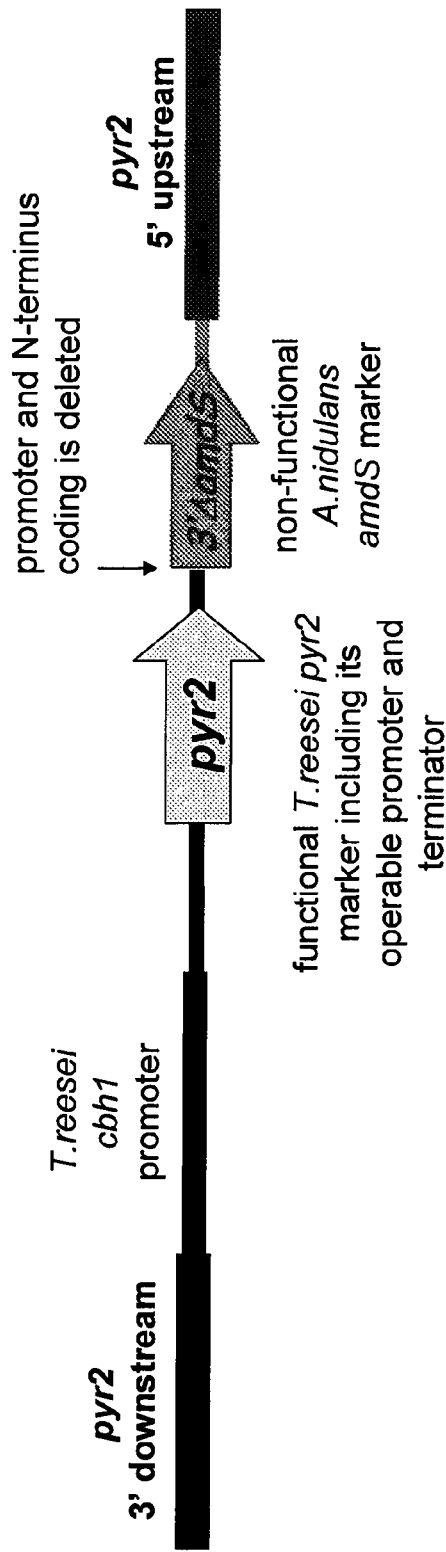
this vector deleted the hygromycin resistance marker that was formerly inserted into the pyr2 locus

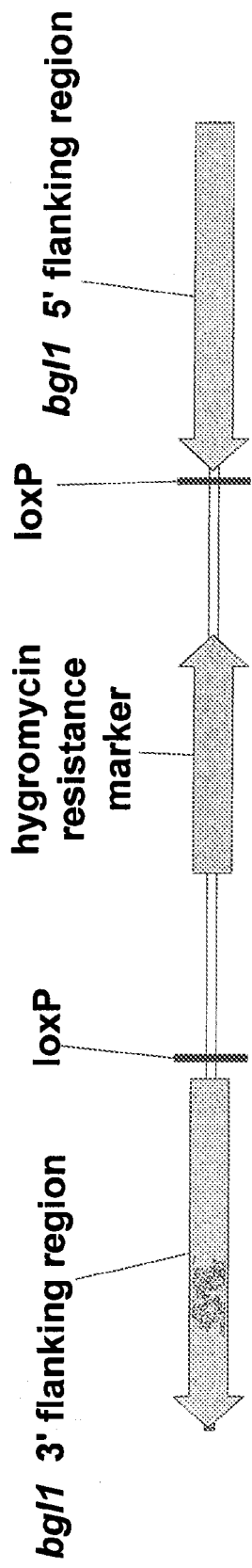
Figure 8. Δbgl1 deletion cassette (5610 bp)

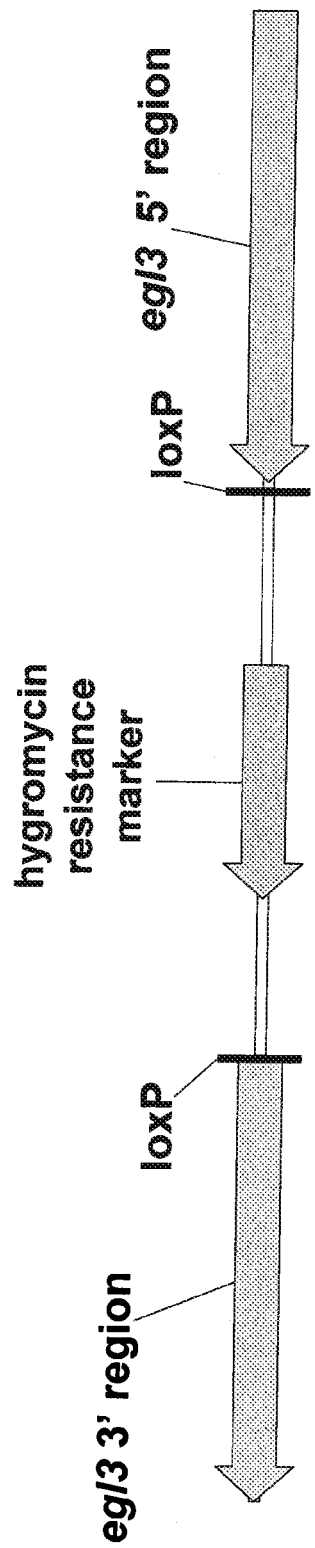
Figure 9. Δegl3 deletion cassette (6511 bp)

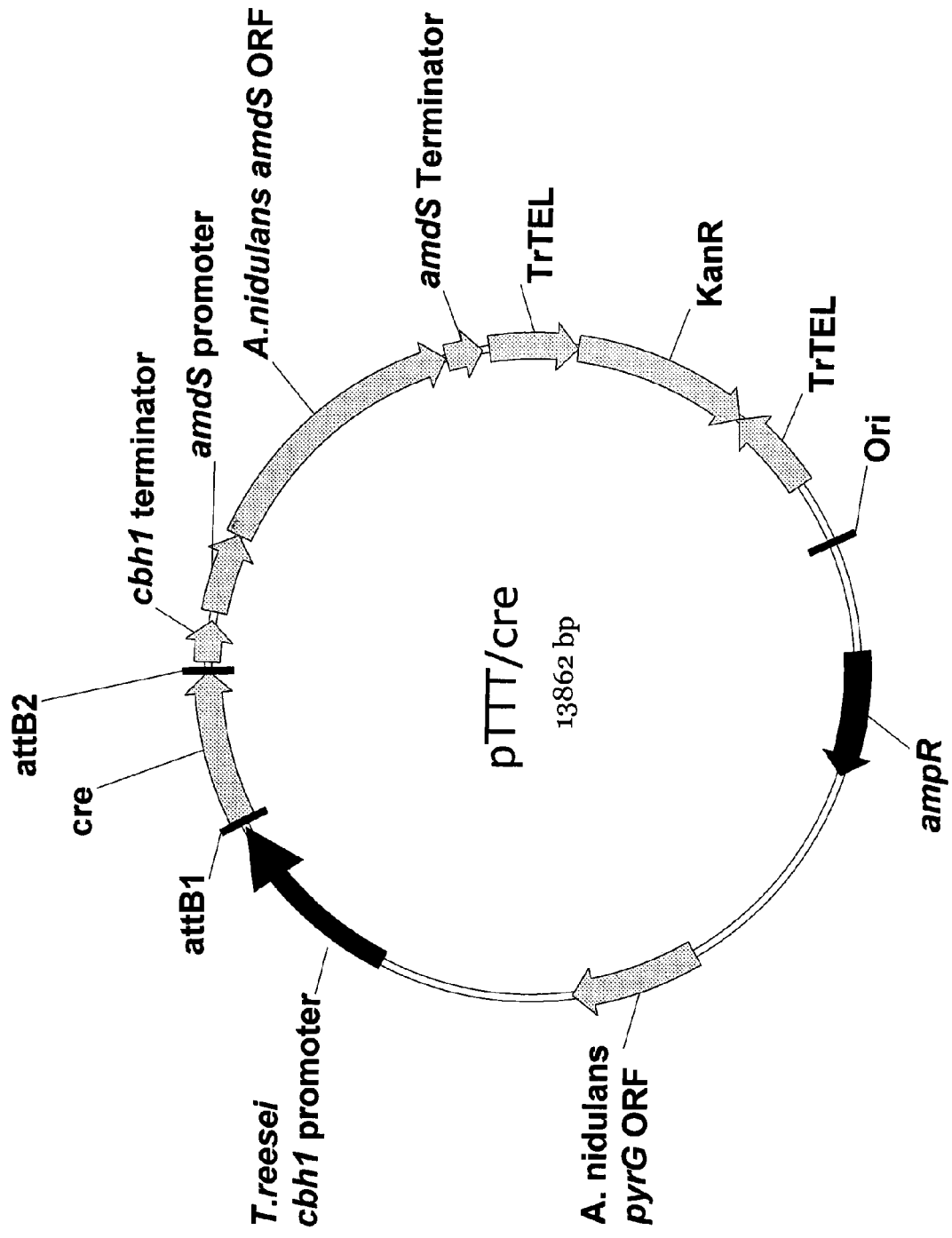
Figure 10. telomeric plasmid for expression of cre recombinase

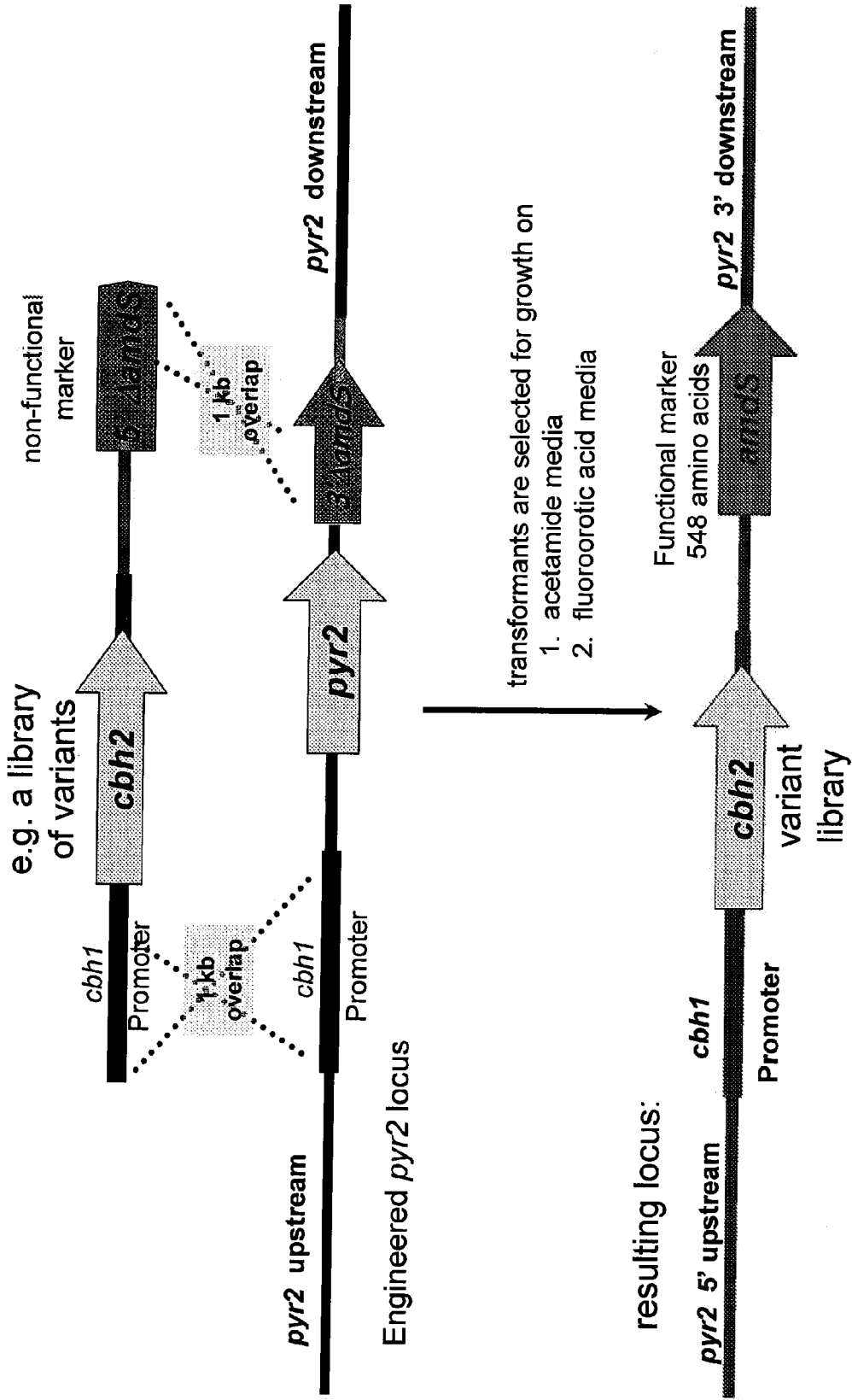
Figure 11. Homologous recombination of expression cassette into targeted locus:

CELLULASE VARIANTS WITH IMPROVED EXPRESSION, ACTIVITY AND STABILITY, AND USE THEREOF

CROSS-REFERENCE TO RELATED APPLICATION

This application claims the benefit of U.S. Provisional Application No. 61/183,959, filed on Jun. 3, 2009, which is hereby incorporated by reference in its entirety.

This application claims priority under 35 USC §371 to International Application No. PCT/US2010/037328, filed Jun. 3, 2010, which claims the benefit of U.S. Provisional Application No. 61/183,959, filed on Jun. 3, 2009, each of which is hereby incorporated by reference in its entirety.

STATEMENT AS TO RIGHTS TO INVENTIONS MADE UNDER FEDERALLY SPONSORED RESEARCH AND DEVELOPMENT

This invention was made with Government support under conditional award no: DE-FC36-08GO18078 awarded by the Department of Energy. The Government has certain rights in this invention.

SEQUENCE LISTING

The sequence listing submitted via EFS, in compliance with 37 C.F.R. §1.52(e), is incorporated herein by reference. The sequence listing text file submitted via EFS contains the file "31414US2_SequenceListing", created on Nov. 9, 2011, which is 129,438 bytes in size.

I. FIELD

The present disclosure relates to enzymes and in particular cellulase variants. Also described are nucleic acids encoding the cellulase variants, compositions comprising the cellulase variants, methods of identifying additional useful cellulase variants and methods of use thereof.

II. BACKGROUND

Cellulose and hemicellulose are the most abundant plant materials produced by photosynthesis. They can be degraded and used as an energy source by numerous microorganisms (e.g., bacteria, yeast and fungi) that produce extracellular enzymes capable of hydrolysis of the polymeric substrates to monomeric sugars (Aro et al., J Biol Chem, 276: 24309-24314, 2001). As the limits of non-renewable resources approach, the potential of cellulose to become a major renewable energy resource is enormous (Krishna et al., Bioresource Tech, 77: 193-196, 2001). The effective utilization of cellulose through biological processes is one approach to overcoming the shortage of foods, feeds, and fuels (Ohmiya et al., Biotechnol Gen Engineer Rev, 14: 365-414, 1997).

Cellulases are enzymes that hydrolyze cellulose (beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG") (Knowles et al., TIBTECH 5: 255-261, 1987; and Schulein, Methods Enzymol, 160: 234-243, 1988). Endoglucanases act mainly on the amorphous parts of the cellulose fibre, whereas cellobiohydrolases are also able to degrade crystalline cellulose (Nevalainen and Penttila, Mycota, 303-319, 1995). Thus, the presence of a cellobiohydrolase in a cellulase system is required for efficient solubilization of crystalline cellulose (Suurnakki et al., Cellulose 7: 189-209, 2000). Beta-glucosidase acts to liberate D-glucose units from cellobiose, cello-oligosaccharides, and other glucosides (Freer, J Biol Chem, 268: 9337-9342, 1993).

Cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeast, such as *Saccharomyces cerevisiae*, lack the ability to hydrolyze cellulose (See, e.g., Wood et al., Methods in Enzymology, 160: 87-116, 1988).

The fungal cellulase classifications of CBH, EG and BG can be further expanded to include multiple components within each classification. For example, multiple CBHs, EGs and BGs have been isolated from a variety of fungal sources including *Trichoderma reesei* (also referred to as *Hypocrea jecorina*), which contains known genes for two CBHs, i.e., CBH I ("CBH1") and CBH II ("CBH2"), at least 8 EGs, i.e., EG I, EG II, EG III, EGIV, EGV, EGVI, EGVII and EGVIII, and at least 5 BGs, i.e., BG1, BG2, BG3, BG4 and BG5. EGIV, EGVI and EGVIII also have xyloglucanase activity.

In order to efficiently convert crystalline cellulose to glucose the complete cellulase system comprising components from each of the CBH, EG and BG classifications is required, with isolated components less effective in hydrolyzing crystalline cellulose (Filho et al., Can J Microbiol, 42:1-5, 1996). A synergistic relationship has been observed between cellulase components from different classifications. In particular, the EG-type cellulases and CBH-type cellulases synergistically interact to more efficiently degrade cellulose.

Cellulases are known in the art to be useful in the treatment of textiles for the purposes of enhancing the cleaning ability of detergent compositions, for use as a softening agent, for improving the feel and appearance of cotton fabrics, and the like (Kumar et al., Textile Chemist and Colorist, 29:37-42, 1997). Cellulase-containing detergent compositions with improved cleaning performance (U.S. Pat. No. 4,435,307; GB App. Nos. 2,095,275 and 2,094,826) and for use in the treatment of fabric to improve the feel and appearance of the textile (U.S. Pat. Nos. 5,648,263, 5,691,178, and 5,776,757; and GB App. No. 1,358,599), have been described. Hence, cellulases produced in fungi and bacteria have received significant attention. In particular, fermentation of *Trichoderma* spp. (e.g., *Trichoderma longibrachiatum* or *Trichoderma reesei*) has been shown to produce a complete cellulase system capable of degrading crystalline forms of cellulose.

Although cellulase compositions have been previously described, there remains a need for new and improved cellulase compositions. Improved cellulose compositions find used in household detergents, textile treatments, biomass conversion and paper manufacturing. Cellulases that exhibit improved expression, activity and stability are of particular interest.

III. SUMMARY

The present disclosure relates to enzymes and in particular cellulase variants. Also described are nucleic acids encoding the cellulase variants, compositions comprising the cellulase variants, methods of identifying additional useful cellulase variants and methods of use thereof.

The present disclosure provides cellulase variants, wherein the variants are mature forms having cellulase activity and comprising a substitution at one or more positions selected from the group consisting of: 5, 18, 19, 28, 30, 32, 35, 38, 79, 80, 89, 100, 102, 103, 104, 105, 111, 117, 119, 121, 125, 126, 133, 137, 138, 139, 140, 141, 143, 150, 158, 162, 177, 180, 181, 182, 185, 186, 188, 190, 191, 192, 193, 196, 201, 207, 225, 226, 228, 229, 230, 233, 234, 236, 240, 243, 245, 251, 252, 258, 267, 268, 274, 292, 293, 303, 304, 306, 307, 313, 319, 322, 328, 331, 338, 340, 346, 361, 362, 363, 364, 365, 371, 384, 394, 396, 400, 406, 407, 414, 417, 422, 427, 431, 433, 436, 440, 441, 443, 444, 445 and 447, wherein the positions are numbered by correspondence with the amino acid sequence of a reference cellobiohydrolase II (CBH2) set forth as SEQ ID NO:3. In some embodiments, the substitution at one or more positions results in a cellulase variant with improved expression, activity and/or stability in comparison to the reference CBH2. In some embodiments, the variant comprises a further substitution at one or more further positions selected from: (i) a first group consisting of 63, 77, 129, 146, 147, 151, 153, 157, 161, 189, 194, 197, 203, 204, 208, 211, 237, 239, 244, 247, 254, 277, 281, 285, 288, 289, 294, 327, 339, 344, 356, 378, 382 and 405; or (ii) a second group consisting of 94, 98, 107, 120, 134, 144, 147, 154, 178, 179, 206, 210, 214, 231, 232, 266, 272, 275, 316, 323, 343, 360, 380, 381, 386, 399, 410, 413, 416, 426, and 429, wherein the further positions are numbered by correspondence with the amino acid sequence of the reference cellobiohydrolase II (CBH2) set forth as SEQ ID NO:3. In some embodiments, the substitution at one or more positions is selected from the group consisting of 1, 2, 3, 4, 5, 6, 7, 8, 9 and 10 positions. In some embodiments, the substitution at one or more positions refers to substitutions at 2, 3, 4, 5, 6, 7, 8, 9, 10, 11, 12, 13, 14, 15, 16, 17, 18, 19, 20, 21, 22, 23, 24, or 25 positions.

In another aspect the disclosure provides cellulase variants, wherein the variants are mature forms having cellulase activity and comprising a substitution at one or more positions selected from the group consisting of: 63, 77, 129, 146, 147, 151, 153, 157, 161, 189, 194, 197, 203, 204, 208, 211, 237, 239, 244, 247, 254, 277, 281, 285, 288, 289, 294, 327, 339, 344, 356, 378, 382 and 405, wherein the positions are numbered by correspondence with the amino acid sequence of a reference cellobiohydrolase II (CBH2) set forth as SEQ ID NO:3 and wherein when the cellulase variant consists of a single substitution, the single substitution is not a K/E, R/Q, N/D, Q/E, D/N or E/Q substitution. In some embodiments, the substitution at one or more positions results in a cellulase variant with improved expression, activity and/or stability in comparison to the reference CBH2. In some embodiments, the isolated cellulase variant comprises a further substitution at one or more further positions selected from: (i) a first group consisting of 5, 18, 19, 28, 30, 32, 35, 38, 79, 80, 89, 100, 102, 103, 104, 105, 111, 117, 119, 121, 125, 126, 133, 137, 138, 139, 140, 141, 143, 150, 158, 162, 177, 180, 181, 182, 185, 186, 188, 190, 191, 192, 193, 196, 201, 207, 225, 226, 228, 229, 230, 233, 234, 236, 240, 243, 245, 251, 252, 258, 267, 268, 274, 292, 293, 303, 304, 306, 307, 313, 319, 322, 328, 331, 338, 340, 346, 361, 362, 363, 364, 365, 371, 384, 394, 396, 400, 406, 407, 414, 417, 422, 427, 431, 433, 436, 440, 441, 443, 444, 445 and 447; or (ii) a second group consisting of 94, 98, 107, 120, 134, 144, 147, 154, 178, 179, 206, 210, 214, 231, 232, 266, 272, 275, 316, 323, 343, 360, 380, 381, 386, 399, 410, 413, 416, 426, and 429, wherein the further positions are numbered by correspondence with the amino acid sequence of the reference cellobiohydrolase II (CBH2) set forth as SEQ ID NO:3. In some embodiments, the substitution at one or more positions is selected from the group consisting of 1, 2, 3, 4, 5, 6, 7, 8, 9 and 10 positions. In some embodiments, the substitution at one or more positions refers to substitutions at 2, 3, 4, 5, 6, 7, 8, 9, 10, 11, 12, 13, 14, 15, 16, 17, 18, 19, 20, 21, 22, 23, 24, or 25 positions.

In another aspect the disclosure provides cellulase variants, wherein the variants are mature forms having cellulase activity and comprising a substitution at one or more positions selected from the group consisting of: 94, 98, 107, 120, 134, 144, 147, 154, 178, 179, 206, 210, 214, 231, 232, 266, 272, 275, 316, 323, 343, 360, 380, 381, 386, 399, 410, 413, 416, 426, and 429, wherein the positions are numbered by correspondence with the amino acid sequence of a reference cellobiohydrolase II (CBH2) set forth as SEQ ID NO:3, and wherein when the cellulase variant consists of a single substitution, the single substitution is not one of the group consisting of V94E, P98L, E107Q, M120L, M134G, M134L, M134V, L144G, L144R, L144S, T154A, A178V, L179C, V206L, S210L, S210R, T214M, T214Y, G231P, G231I, G231A, G231N, G231S, G231T, T232V, H266S, H266A, W272A, W272D, W272Y, N275L, S316P, V323L, V323N, V323Y, G360R, S380T, A381T, E399N, E399D, R413Y, R413P, and A416G. In some embodiments, the substitution at one or more positions results in a cellulase variant with improved expression, activity and/or stability in comparison to the reference CBH2. In some embodiments, the variant comprises a further substitution at one or more further positions selected from: (i) a first group consisting of 5, 18, 19, 28, 30, 32, 35, 38, 79, 80, 89, 100, 102, 103, 104, 105, 111, 117, 119, 121, 125, 126, 133, 137, 138, 139, 140, 141, 143, 150, 158, 162, 177, 180, 181, 182, 185, 186, 188, 190, 191, 192, 193, 196, 201, 207, 225, 226, 228, 229, 230, 233, 234, 236, 240, 243, 245, 251, 252, 258, 267, 268, 274, 292, 293, 303, 304, 306, 307, 313, 319, 322, 328, 331, 338, 340, 346, 361, 362, 363, 364, 365, 371, 384, 394, 396, 400, 406, 407, 414, 417, 422, 427, 431, 433, 436, 440, 441, 443, 444, 445 and 447; or (ii) a second group consisting of 63, 77, 129, 146, 147, 151, 153, 157, 161, 189, 194, 197, 203, 204, 208, 211, 237, 239, 244, 247, 254, 277, 281, 285, 288, 289, 294, 327, 339, 344, 356, 378, 382 and 405, wherein the further positions are numbered by correspondence with the amino acid sequence of the reference cellobiohydrolase II (CBH2) set forth as SEQ ID NO:3. In some embodiments, the substitution at one or more positions is selected from the group consisting of 1, 2, 3, 4, 5, 6, 7, 8, 9 and 10 positions. In some embodiments, the substitution at one or more positions refers to substitutions at 2, 3, 4, 5, 6, 7, 8, 9, 10, 11, 12, 13, 14, 15, 16, 17, 18, 19, 20, 21, 22, 23, 24, or 25 positions.

The present disclosure further provides cellulase variants, wherein the variants are mature forms having cellulase activity and comprising a substitution at from one to six positions selected from the group consisting of 111, 144, 154, 162, 410 and 413, wherein the cellulase variant comprises: a leucine or a serine at position 111; a leucine, a glutamine or a tryptophan at position 144; a threonine, a cysteine or a valine at position 154; a tyrosine or an asparagine at position 162; an arginine or a serine at position 410; and a serine, a tryptophan or a tyrosine at position 413; wherein the positions are numbered by correspondence with the amino acid sequence of the reference cellobiohydrolase II (CBH2) set forth as SEQ ID NO:3, and wherein when the cellulase variant consists of a single substitution, the single substitution is not a S413Y substitution.

Also provided by the present disclosure are cellulase variants, wherein the variants are mature forms having cellulase activity and comprising a substitution at from one to six positions selected from the group consisting of 98, 194, 313, 316, 384 and 443, wherein the cellulase variant comprises: a proline or a leucine at position 98; a lysine, a cysteine or a glutamic acid at position 194; a serine or a threonine at position 313; a serine or a proline at position 316; a glycine, a cysteine or a glutamine at position 384; and an asparagine or an isoleucine at position 443; wherein the positions are numbered by correspondence with the amino acid sequence of the reference cellobiohydrolase II (CBH2) set forth as SEQ ID NO:3, and wherein when the cellulase variant consists of a single substitution, the single substitution is not one of the group selected from a P98L substitution, a K194E substitution, and a S316P substitution.

In addition the present disclosure provides cellulase variants, wherein the variants are mature forms having cellulase activity and comprising a substitution at from one to six positions selected from the group consisting of 153, 161, 203, 233, 422 and 444, wherein the cellulase variant comprises: an arginine or a glutamine at position 153; an asparagine, an alanine or a tryptophan at position 161; an arginine or a histidine at position 203; a proline or an aspartic acid at position 233; a glutamine or a valine at position 422; and a proline or a glutamine at position 443; wherein the positions are numbered by correspondence with the amino acid sequence of the reference cellobiohydrolase II (CBH2) set forth as SEQ ID NO:3, and wherein when the cellulase variant consists of a single substitution, the single substitution is not a R153Q substitution.

Moreover the present disclosure provides cellulase variants, wherein the variants are mature forms having cellulase activity and comprising a substitution at from one to seven positions selected from the group consisting of 98, 111, 144, 313, 316, 413 and 422, wherein the cellulase variant comprises: a proline or a leucine at position 98; a leucine or a serine at position 111; a leucine or a tryptophan at position 144; a serine or a threonine at position 313; a serine or a proline at position 316; a serine or a tryptophan at position 413; and a glutamine or a valine at position 422; wherein the positions are numbered by correspondence with the amino acid sequence of the reference cellobiohydrolase II (CBH2) set forth as SEQ ID NO:3, and wherein when the cellulase variant consists of a single substitution, the single substitution is not one of the group selected from a P98L substitution, and a S316P substitution.

In further aspects of the disclosure cellulase variants are provided, wherein the variants comprise a glutamine at position 98, and a substitution selected from the group consisting of a T138C, a S316P, a S343Q, a Q362I, a S386C, a C400S and a S406P, wherein the positions are numbered by correspondence with the amino acid sequence of the reference cellobiohydrolase II (CBH2) set forth as SEQ ID NO:3.

Additionally, cellulase variants are provided which comprise a cysteine at position 138, and a substitution selected from the group consisting of a S316P, a S343Q, a Q362I, a S386C, a C400S and a S406P, wherein the positions are numbered by correspondence with the amino acid sequence of the reference cellobiohydrolase II (CBH2) set forth as SEQ ID NO:3.

In another aspect, cellulase variants are provided which comprise a proline at position 316, and a substitution selected from the group consisting of a S343Q, a Q362I, a S386C, a C400S and a S406P, wherein the positions are numbered by correspondence with the amino acid sequence of the reference cellobiohydrolase II (CBH2) set forth as SEQ ID NO:3.

Moreover, the present disclosure provides cellulase variants comprising a glutamine at position 343, and a substitution selected from the group consisting of a Q362I, a S386C, a C400S and a S406P, wherein the positions are numbered by correspondence with the amino acid sequence of the reference cellobiohydrolase II (CBH2) set forth as SEQ ID NO:3.

The present disclosure also provides cellulase variants comprising an isoleucine at position 362, and a substitution selected from the group consisting of a S386C, a C400S and a S406P, wherein the positions are numbered by correspondence with the amino acid sequence of the reference cellobiohydrolase II (CBH2) set forth as SEQ ID NO:3.

In one aspect, cellulase variants are provided comprising a cysteine at position 386, and a substitution selected from the group consisting of a C400S and a S406P, wherein the positions are numbered by correspondence with the amino acid sequence of the reference cellobiohydrolase II (CBH2) set forth as SEQ ID NO:3. In some embodiments, the variants comprise a serine at position 400 and a proline at position 406.

In addition, the present disclosure provides cellulase variants, wherein the variant is a mature form having cellulase activity and comprising a substitution at from one to seven positions selected from the group consisting of 98, 111, 182, 291, 316, 362 and 400, wherein the cellulase variant comprises: proline, leucine or glutamine at position 98; leucine or serine at position 111; aspargine or tryptophan at position 182; serine or a glutamic acid at position 291; serine or proline at position 316; glutamine, isoleucine or leucine at position 362; and cysteine or serine at position 400; wherein the positions are numbered by correspondence with the amino acid sequence of the reference cellobiohydrolase II (CBH2) set forth as SEQ ID NO:3, and wherein when the cellulase variant consists of a single substitution, the single substitution is not a P98L substitution or a S316P substitution. In some embodiments, the variant further comprises a L439P substitution or a T74S substitution.

In some preferred embodiments of the disclosure, the cellulase variants of any of the preceding paragraphs of the summary are derived from a parent cellulase selected from the group consisting of *Hypocrea jecorina* CBH2, *Hypocrea koningii* CBH2, *Humicola insolens* CBH2, *Acremonium cellulolyticus* CBH2, *Agaricus bisporus* CBH2, *Fusarium osysporum* EG, *Phanerochaete chrysosporium* CBH2, *Talaromyces emersonii* CBH2, *Thermobifida. fusca* 6B/E3 CBH2, *Thermobifida fusca* 6A/E2 EG, and *Cellulomonas fimi* CenA EG. In some embodiments, the cellulase variant is derived from a parent cellulase whose amino acid sequence is at least 75% 80%, 85%, 90%, 95%, 96%, 97%, 98% or 99% identical to a member of the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13. In some embodiments, the variants are isolated. Also provided are compositions comprising a cellulase variant. In some preferred embodiments, the composition is enriched in the cellulase variant.

In other aspects, the present disclosure provides an isolated nucleic acid encoding the cellulase variant of any of the preceding paragraphs of the summary. An expression vector comprising the isolated nucleic acid operably linked to a regulatory sequence is also provided, as is a host cell comprising the expression vector. In some embodiments, methods are provided for producing a cellulase variant, comprising culturing the host cells in a culture medium under suitable conditions to produce the cellulase variant.

Also provided are compositions comprising the cellulase variant of any of the preceding paragraphs of the summary. In some preferred embodiments, the compositions further comprising at least one additional enzyme selected from the group consisting of a subtilisin, a neutral metalloprotease, a lipase, a cutinase, an amylase, a carbohydrase, a pectinase, a mannanase, an arabinase, a galactanase, a xylanase, an oxidase, and a peroxidase. The disclosure further provides methods of cleaning or fabric care comprising contacting a surface or an article comprising a fabric with the composition. Additionally, methods are provided for depilling and surface finishing a fabric comprising contacting a surface or an article comprising a fabric with the composition.

In some preferred embodiments, methods are provided for converting biomass to sugars comprising contacting the biomass with the cellulase variant of any of the preceding paragraphs of the summary. In some preferred embodiments methods are provided for producing a fuel comprising: contacting a biomass composition with an enzymatic composition comprising the cellulase variant of any of the preceding paragraphs to yield a sugar solution; and culturing the sugar solution with a fermentative microorganism under conditions sufficient to produce a fuel.

Other objects, features and advantages of the present disclosure will become apparent from the following detailed description. It should be understood, however, that the detailed description and specific examples, while indicating preferred embodiments of the disclosure, are given by way of illustration only, since various changes and modifications within the scope and spirit of the disclosure will become apparent to one skilled in the art from reading this detailed description.

IV. BRIEF DESCRIPTION OF THE DRAWINGS

FIG. 1 provides an alignment of the amino acid sequences of the mature form of various cellulases: *Hypocrea jecorina* (also known as *T. reesei*) CBH2 (SEQ ID NO:3), *Hypocrea koningii* CBH2 (SEQ ID NO:4), *Humicola insolens* CBH2 (SEQ ID NO:5), *Acremonium cellulolyticus* CBH2 (SEQ ID NO:6), *Agaricus bisporus* CBH2 (SEQ ID NO:7), *Fusarium osysporum* EG (SEQ ID NO:8), *Phanerochaete chrysosporium* CBH2 (SEQ ID NO:9), *Talaromyces emersonii* CBH2 (SEQ ID NO:10), *Thermobifida. fusca* 6B/E3 CBH2 (SEQ ID NO:11), *Thermobifida fusca* 6A/E2 EG (SEQ ID NO:12), and *Cellulomonas fimi* CenA EG (SEQ ID NO:13).

Figure 2B:
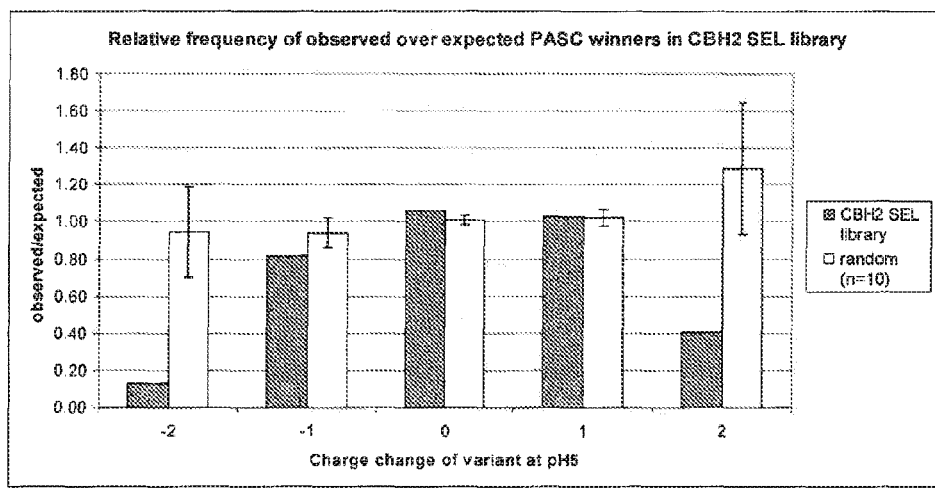

FIG. 2A provides a graph of the relative frequency of observed over expected pretreated corn stover (PCS) assay winners as a product of charge change of the CBH2 SELs. Decreasing CBH2 charge results in a significantly higher frequency of PCS assay winners. FIG. 2B provides a graph of the relative frequency of observed over expected phosphoric acid swollen cellulose (PASC) assay winners as a product of charge change of the CBH2 SELs. A significantly higher frequency of PASC winners is observed for variants without a charge change.

Figure 3:
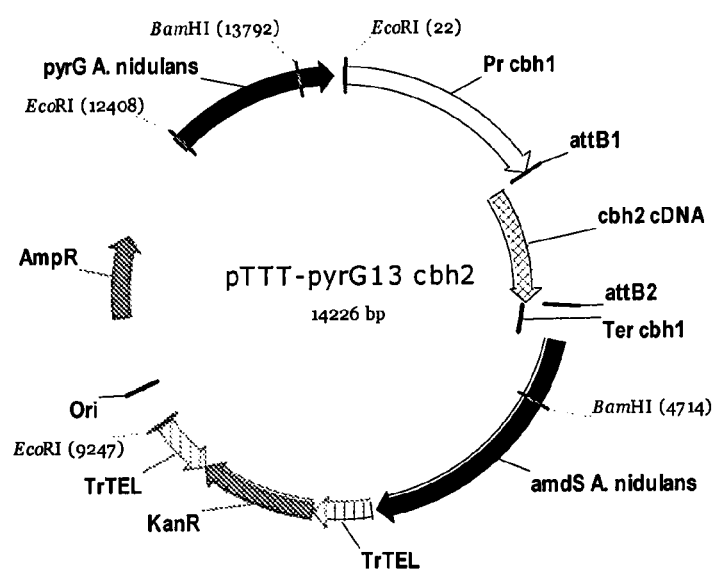

FIG. 3 provides a plasmid map for pTTTpyrG-cbh2.

FIG. 4 provides a schematic of the *T. reesei* ku80 deletion cassette.

FIG. 5 illustrates the inactivation of the native ku80 gene as a consequence of its replacement with an als selectable marker.

FIG. 6 provides a schematic of the *T. reesei* pyr2 deletion cassette, wherein the inactivation of the native pyr2 gene was a consequence of its replacement with a hygR selectable marker and an amdS fragment.

FIG. 7 provides a schematic of the *T. reesei* hygR deletion cassette, wherein the inactivation of the heterologous hygR gene was a consequence of its replacement with a pyr2 selectable marker.

FIG. 8 provides a schematic of the *T. reesei* bgl1 deletion cassette.

FIG. 9 provides a schematic of the *T. reesei* egl3 deletion cassette.

FIG. 10 provides a schematic of the *T. reesei* telomeric plasmid vector used for expression of cre recombinase.

FIG. 11 illustrates the inactivation of the pyr2 selectable marker and activation of the amdS selectable marker as a consequence of introduction of a polynucleotide of a gene of interest (GOI). In exemplary embodiments, the GOI encodes a CBH2 variant.

V. DETAILED DESCRIPTION OF VARIOUS EMBODIMENTS

The present disclosure relates to enzymes and in particular cellulase variants. Also described are nucleic acids encoding the cellulase variants, compositions comprising the cellulase variants, methods of identifying additional useful cellulase variants and methods of using the compositions.

It is to be understood that both the foregoing general description and the following detailed description are exemplary and explanatory only and are not restrictive of the compositions and methods described herein. Unless defined otherwise herein, all technical and scientific terms used herein have the same meaning as commonly understood by one of ordinary skill in the art to which this disclosure belongs. In this application, the use of the singular includes the plural unless specifically stated otherwise. The use of "or" means "and/or" unless state otherwise. Likewise, the terms "comprise," "comprising," "comprises," "include," "including" and "includes" are not intended to be limiting. All patents and publications, including all amino acid and nucleotide sequences disclosed within such patents and publications, referred to herein are expressly incorporated by reference. The headings provided herein are not limitations of the various aspects or embodiments of the disclosure, which can be had by reference to the specification as a whole. Accordingly, the terms herein are more fully defined by reference to the specification as a whole.

Unless defined otherwise herein, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this disclosure. Although any methods and materials similar or equivalent to those described herein can be used in the practice or testing of the present disclosure, the preferred methods and materials are described. Numeric ranges are inclusive of the numbers defining the range. Unless otherwise indicated, nucleic acids are written left to right in 5' to 3' orientation; amino acid sequences are written left to right in amino to carboxyl orientation, respectively. Practitioners are particularly directed to Sambrook et al., MOLECULAR CLONING: A LABORATORY MANUAL (Second Edition), Cold Spring Harbor Press, Plainview, N.Y., 1989, and Ausubel F M et al., Current Protocols in Molecular Biology, John Wiley & Sons, New York, N.Y., 1993, for definitions and terms of the art. It is to be understood that this disclosure is not limited to the particular methodology, protocols, and reagents described, as these may vary.

I. Definitions

The terms below are more fully defined by reference to the specification as a whole.

The term "polypeptide" as used herein refers to a compound made up of a single chain of amino acid residues linked by peptide bonds. The term "protein" as used herein may be synonymous with the term "polypeptide".

"Variant" means a protein which is derived from a precursor protein (e.g., the native protein) by addition of one or more amino acids to either or both the C- and N-terminal end, substitution of one or more amino acids at one or a number of different sites in the amino acid sequence, or deletion of one or more amino acids at either or both ends of the protein or at one or more sites in the amino acid sequence. The preparation of a cellulase variant may be performed by any means know in the art. In preferred embodiments, a cellulase variant is prepared by modifying a DNA sequence which encodes for the native protein, transformation of the modified DNA sequence into a suitable host, and expression of the modified DNA sequence to form the variant enzyme. The variant cellulase of the disclosure includes peptides comprising altered amino acid sequences in comparison with a precursor enzyme amino acid sequence wherein the variant cellulase retains the characteristic cellulolytic nature of the precursor enzyme but which may have altered properties in some specific aspect. For example, a variant cellulase may have an increased pH optimum or increased temperature or oxidative stability or decreased affinity or binding to non-cellulosic materials but will retain its characteristic cellulolytic activity. It is contemplated that the variants according to the present disclosure may be derived from a DNA fragment encoding a cellulase variant wherein the functional activity of the expressed cellulase variant is retained. For example, a DNA fragment encoding a cellulase may further include a DNA sequence or portion thereof encoding a hinge or linker attached to the cellulase DNA sequence at either the 5' or 3' end wherein the functional activity of the encoded cellulase domain is retained. The terms variant and derivative may be used interchangeably herein.

"Equivalent residues" may also be defined by determining homology at the level of tertiary structure for a precursor cellulase whose tertiary structure has been determined by x-ray crystallography. Equivalent residues are defined as those for which the atomic coordinates of two or more of the main chain atoms of a particular amino acid residue of a cellulase and *Hypocrea jecorina* CBH2 (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the cellulase in question to the *H. jecorina* CBH2. The best model is the crystallographic model giving the lowest R factor for experimental diffraction data at the highest resolution available see for examples US 2006/0205042.

Equivalent residues which are functionally analogous to a specific residue of *H. jecorina* CBH2 are defined as those amino acids of a cellulase which may adopt a conformation such that they either alter, modify or contribute to protein structure, substrate binding or catalysis in a manner defined and attributed to a specific residue of the *H. jecorina* CBH2. Further, they are those residues of the cellulase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *H. jecorina* CBH2. The crystal structure of *H. jecorina* CBH2 is shown in Zou et al. (1999) (Ref. 5, supra).

The term "nucleic acid molecule" includes RNA, DNA and cDNA molecules. It will be understood that, as a result of the degeneracy of the genetic code, a multitude of nucleotide sequences encoding a given protein such as CBH2 and/or variants thereof may be produced. The present disclosure contemplates every possible variant nucleotide sequence, encoding variant cellulase such as CBH2, all of which are possible given the degeneracy of the genetic code.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring, for example, antibiotic resistance to transformed cells. A typical chimeric gene of the present disclosure, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In general, nucleic acid molecules which encode the variant cellulase such as CBH2 will hybridize, under moderate to high stringency conditions to the wild type sequence such as provided herein as SEQ ID NO:1. However, in some cases a CBH2-encoding nucleotide sequence is employed that possesses a substantially different codon usage, while the protein encoded by the CBH2-encoding nucleotide sequence has the same or substantially the same amino acid sequence as the native protein. For example, the coding sequence may be modified to facilitate faster expression of CBH2 in a particular prokaryotic or eukaryotic expression system, in accordance with the frequency with which a particular codon is utilized by the host (Te'o et al., FEMS Microbiology Letters, 190: 13-19, 2000, for example, describes the optimization of genes for expression in filamentous fungi).

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° C. below the Tm of the probe); "high stringency" at about 5-10° C. below the Tm; "moderate" or "intermediate stringency" at about 10-20°. C. below the Tm of the probe; and "low stringency" at about 20-25° C. below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5.times.Denhardt's solution, 0.5% SDS and 100 ug/ml denatured carrier DNA followed by washing two times in 2.times.SSC and 0.5% SDS at room temperature and two additional times in 0.1×SSC and 0.5% SDS at 42° degree. C.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "CBH2 expression" refers to transcription and translation of the cbh2 gene or variants thereof, the products of which include precursor RNA, mRNA, polypeptide, post-translationally processed polypeptides, and derivatives thereof, including CBH2 from related species such as *Trichoderma koningii*, *Hypocrea jecorina* (also known as *Trichoderma longibrachiatum*, *Trichoderma reesei* or *Trichoderma viride*) and *Hypocrea schweinitzii*. By way of example, assays for CBH2 expression include Western blot for CBH2 protein, Northern blot analysis and reverse transcriptase polymerase chain reaction (RT-PCR) assays for cbh2 mRNA, and Phosphoric Acid Swollen Cellulose (PASC) and p-hydroxybenzoic acid hydrazide (PAHBAH) assays as described in the following: (a) PASC: (Karlsson, J. et al. (2001), Eur. J. Biochem, 268, 6498-6507, Wood, T. (1988) in Methods in Enzymology, Vol. 160. Biomass Part a Cellulose and Hemicellulose (Wood, W. & Kellog, S. Eds.), pp. 19-25, Academic Press, San Diego, Calif., USA) and (b) PAHBAH: (Lever, M. (1972) Analytical Biochemistry, 47, 273, Blakeney, A. B. & Mutton, L. L. (1980) Journal of Science of Food and Agriculture, 31, 889, Henry, R. J. (1984) Journal of the Institute of Brewing, 90, 37).

The term "alternative splicing" refers to the process whereby multiple polypeptide isoforms are generated from a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

The term "signal sequence" refers to a sequence of amino acids at the N-terminal portion of a protein that facilitates the secretion of the mature form of the protein outside the cell. The mature form of the extracellular protein lacks the signal sequence that is cleaved off during the secretion process.

By the term "host cell" is meant a cell that contains a vector and supports the replication, and/or transcription or transcription and translation (expression) of the expression construct. Host cells for use in the present disclosure can be prokaryotic cells, such as *E. coli*, or eukaryotic cells such as yeast, plant, insect, amphibian, or mammalian cells. In general, host cells are filamentous fungi.

The term "filamentous fungi" means any and all filamentous fungi recognized by those of skill in the art. A preferred fungus is selected from the group consisting of *Aspergillus, Trichoderma, Fusarium, Chrysosporium, Penicillium, Humicola, Neurospora*, or alternative sexual forms thereof such as *Emericella, Hypocrea*. It has now been demonstrated that the asexual industrial fungus *Trichoderma reesei* is a clonal derivative of the ascomycete *Hypocrea jecorina* (See, Kuhls et al., PNAS, 93:7755-7760, 1996).

The term "cellooligosaccharide" refers to oligosaccharide groups containing from 2-8 glucose units and having .beta.-1,4 linkages, e.g., cellobiose.

The terms "cellulase" "cellulolytic enzymes" or "cellulase enzymes" refer to a category of enzymes capable of hydrolyzing cellulose polymers to shorter cello-oligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, plants and bacteria. The enzymes made by these microbes are mixtures of proteins with three types of actions useful in the conversion of cellulose to glucose: endoglucanases (EG), cellobiohydrolases (CBH), and beta-glucosidase. These three different types of cellulase enzymes act synergistically to convert cellulose and its derivatives to glucose.

Many microbes make enzymes that hydrolyze cellulose, including the wood rotting fungus *Trichoderma*, the compost bacteria *Thermomonospora, Bacillus*, and *Cellulomonas; Streptomyces*; and the fungi *Humicola, Aspergillus* and *Fusarium*.

CBH2 from *Hypocrea jecorina* is a member of the Glycosyl Hydrolase Family 6 (hence Cel6) and, specifically, was the first member of that family identified in *Hypocrea jecorina* (hence Cel6A). The Glycosyl Hydrolase Family 6 contains both Endoglucanases and Cellobiohydrolases/exoglucanases, and that CBH2 is the latter. Thus, the phrases CBH2, CBH2-type protein and Cel6 cellobiohydrolases may be used interchangeably herein.

The term "cellulose binding domain" as used herein refers to portion of the amino acid sequence of a cellulase or a region of the enzyme that is involved in the cellulose binding activity of a cellulase or derivative thereof. Cellulose binding domains generally function by non-covalently binding the cellulase to cellulose, a cellulose derivative or other polysaccharide equivalent thereof. Cellulose binding domains permit or facilitate hydrolysis of cellulose fibers by the structurally distinct catalytic core region, and typically function independent of the catalytic core. Thus, a cellulose binding domain will not possess the significant hydrolytic activity attributable to a catalytic core. In other words, a cellulose binding domain is a structural element of the cellulase enzyme protein tertiary structure that is distinct from the structural element which possesses catalytic activity. Cellulose binding domain and cellulose binding module may be used interchangeably herein.

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

As used herein, the term "detergent composition" refers to a mixture which is intended for use in a wash medium for the laundering of soiled cellulose containing fabrics. In the context of the present disclosure, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the term "decrease or elimination in expression of the cbh2 gene" means that either that the cbh2 gene has been deleted from the genome and therefore cannot be expressed by the recombinant host microorganism; or that the cbh2 gene or transcript has been modified such that a functional CBH2 enzyme is not produced by the host microorganism or at levels that are significantly less than the unmodified cbh2 gene or transcript.

The term "variant cbh2 gene" means that the nucleic acid sequence of the cbh2 gene from *H. jecorina* has been altered by removing, adding, and/or manipulating the coding sequence.

As used herein, the term "purifying" generally refers to subjecting transgenic nucleic acid or protein containing cells to biochemical purification and/or column chromatography.

As used herein, the terms "active" and "biologically active" refer to a biological activity associated with a particular protein and are used interchangeably herein. For example, the enzymatic activity associated with a protease is proteolysis and, thus, an active protease has proteolytic activity. It follows that the biological activity of a given protein refers to any biological activity typically attributed to that protein by those of skill in the art.

As used herein, the term "enriched" means that the cellulase such as CBH2 is found in a concentration that is greater relative to the CBH2 concentration found in a wild-type, or naturally occurring, fungal cellulase composition. The terms enriched, elevated and enhanced may be used interchangeably herein.

A wild type fungal cellulase composition is one produced by a naturally occurring fungal source and which comprises one or more BGL, CBH and EG components wherein each of these components is found at the ratio produced by the fungal source. Thus, an enriched CBH composition would have CBH at an altered ratio wherein the ratio of CBH to other cellulase components (i.e., EGs, beta-glucosidases and other endoglucanases) is elevated. This ratio may be increased by either increasing CBH or decreasing (or eliminating) at least one other component by any means known in the art.

The term "isolated" or "purified" as used herein refers to a nucleic acid or amino acid that is removed from at least one component with which it is naturally associated.

Thus, to illustrate, a naturally occurring cellulase system may be purified into substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. The purified CBH may then be added to the enzymatic solution resulting in an enriched CBH solution. It is also possible to elevate the amount of CBH produced by a microbe using molecular genetics methods to overexpress the gene encoding CBH, possibly in conjunction with deletion of one or more genes encoding other cellulases.

Fungal cellulases may contain more than one CBH component. The different components generally have different isoelectric points which allow for their separation via ion exchange chromatography and the like. Either a single CBH component or a combination of CBH components may be employed in an enzymatic solution.

When employed in enzymatic solutions, the homolog or variant CBH2 component is generally added in an amount sufficient to allow the highest rate of release of soluble sugars from the biomass. The amount of homolog or variant CBH2 component added depends, upon the type of biomass to be saccharified, which can be readily determined by the skilled artisan when employed, the weight percent of the homolog or variant CBH2 component present in the cellulase composition is from preferably between 1 and 100 with illustrative examples being about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 50 weight percent, from about 15 to about 60 weight percent, from about 15 to about 65 weight percent, from about 15 to about 70 weight percent, from about 15 to about 75 weight percent, from about 15 to about 80 weight percent, from about 15 to about 85 weight percent, from about 15 to about 95 weight percent. However, when employed, the weight percent of the homolog or variant CBH2 component relative to any EG type components present in the cellulase composition is from preferably about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 30 weight percent, from about 15 to about 45 weight percent, from about 15 to about 50 weight percent.

II. Cellulases

Cellulases are known in the art as enzymes that hydrolyze cellulose (beta-1,4-glucan or beta D-glucosidic linkages) resulting in the formation of glucose, cellobiose, cellooligosaccharides, and the like. As set forth above, cellulases have been traditionally divided into three major classes: endoglucanases (EC 3.2.1.4) ("EG"), exoglucanases or cellobiohydrolases (EC 3.2.1.91) ("CBH") and beta-glucosidases (EC 3.2.1.21) ("BG").

Certain fungi produce complete cellulase systems which include exo-cellobiohydrolases or CBH-type cellulases, endoglucanases or EG-type cellulases and beta-glucosidases or BG-type cellulases. However, sometimes these systems lack CBH-type cellulases and bacterial cellulases also typically include little or no CBH-type cellulases. In addition, it has been shown that the EG components and CBH components synergistically interact to more efficiently degrade cellulose. The different components, i.e., the various endoglucanases and exocellobiohydrolases in a multi-component or complete cellulase system, generally have different properties, such as isoelectric point, molecular weight, degree of glycosylation, substrate specificity and enzymatic action patterns.

It is believed that endoglucanase-type cellulases hydrolyze internal beta-1,4-glucosidic bonds in regions of low crystallinity of the cellulose and exo-cellobiohydrolase-type cellulases hydrolyze cellobiose from the reducing or non-reducing end of cellulose. It follows that the action of endoglucanase components can greatly facilitate the action of exo-cellobiohydrolases by creating new chain ends which are recognized by exo-cellobiohydrolase components. Further, beta-glucosidase-type cellulases have been shown to catalyze the hydrolysis of alkyl and/or aryl .beta.-D-glucosides such as methyl .beta.-D-glucoside and p-nitrophenyl glucoside as well as glycosides containing only carbohydrate residues, such as cellobiose. This yields glucose as the sole product for the microorganism and reduces or eliminates cellobiose which inhibits cellobiohydrolases and endoglucanases.

Cellulases also find a number of uses in detergent compositions including to enhance cleaning ability, as a softening agent and to improve the feel of cotton fabrics (Hemmpel, ITB Dyeing/Printing/Finishing 3:5-14, 1991; Tyndall, Textile Chemist and Colorist 24:23-26, 1992; and Kumar et al., Textile Chemist and Colorist, 29:37-42, 1997). While the mechanism is not part of the disclosure, softening and color restoration properties of cellulase have been attributed to the alkaline endoglucanase components in cellulase compositions, as exemplified by U.S. Pat. Nos. 5,648,263, 5,691,178, and 5,776,757, which disclose that detergent compositions containing a cellulase composition enriched in a specified alkaline endoglucanase component impart color restoration and improved softening to treated garments as compared to cellulase compositions not enriched in such a component. In addition, the use of such alkaline endoglucanase components in detergent compositions has been shown to complement the pH requirements of the detergent composition (e.g., by exhibiting maximal activity at an alkaline pH of 7.5 to 10, as described in U.S. Pat. Nos. 5,648,263, 5,691,178, and 5,776, 757).

Cellulase compositions have also been shown to degrade cotton-containing fabrics, resulting in reduced strength loss in the fabric (U.S. Pat. No. 4,822,516), contributing to reluctance to use cellulase compositions in commercial detergent applications. Cellulase compositions comprising endoglucanase components have been suggested to exhibit reduced strength loss for cotton-containing fabrics as compared to compositions comprising a complete cellulase system.

Cellulases have also been shown to be useful in degradation of cellulase biomass to ethanol (wherein the cellulase degrades cellulose to glucose and yeast or other microbes further ferment the glucose into ethanol), in the treatment of mechanical pulp (Pere et al., In Proc. Tappi Pulping Conf., Nashville, Term., 27-31, pp. 693-696, 1996), for use as a feed additive (WO 91/04673) and in grain wet milling.

Most CBHs and EGs have a multidomain structure consisting of a core domain separated from a cellulose binding domain (CBD) by a linker peptide (Suurnakki et al., 2000). The core domain contains the active site whereas the CBD interacts with cellulose by binding the enzyme to it (van Tilbeurgh et al., FEBS Lett. 204:223-227, 1986; Tomme et al., Eur. J. Biochem. 170:575-581, 1988). The CBDs are particularly important in the hydrolysis of crystalline cellulose. It has been shown that the ability of cellobiohydrolases to degrade crystalline cellulose clearly decreases when the CBD is absent (Linder and Teeri, J. Biotechnol. 57:15-28, 1997). However, the exact role and action mechanism of CBDs is still a matter of speculation. It has been suggested that the CBD enhances the enzymatic activity merely by increasing the effective enzyme concentration at the surface of cellulose (Stahlberg et al., Bio/Technol. 9:286-290, 1991), and/or by loosening single cellulose chains from the cellulose surface (Tormo et al., EMBO J. vol. 15, no. 21, pp. 5739-5751, 1996). Most studies concerning the effects of cellulase domains on different substrates have been carried out with core proteins of cellobiohydrolases, as their core proteins can easily be produced by limited proteolysis with papain (Tomme et al., 1988). Numerous cellulases have been described in the scientific literature, examples of which include: from *Trichoderma reesei*: Shoemaker, S. et al., Bio/ Technology, 1:691-696, 1983, which discloses CBH1; Teeri, T. et al., Gene, 51:43-52, 1987, which discloses CBH2. Cellulases from species other than *Trichoderma* have also been described e.g., Ooi et al., Nucleic Acids Research, vol. 18, no. 19, 1990, which discloses the cDNA sequence coding for endoglucanase F1-CMC produced by *Aspergillus aculeatus*; Kawaguchi T et al., Gene 173 (2):287-8, 1996, which discloses the cloning and sequencing of the cDNA encoding beta-glucosidase 1 from *Aspergillus aculeatus*; Sakamoto et al., Curr. Genet. 27:435-439, 1995, which discloses the cDNA sequence encoding the endoglucanase CMCase-1 from *Aspergillus kawachii* IFO 4308; Saarilahti et al., Gene 90:9-14, 1990, which discloses an endoglucanase from *Erwinia carotovara*; Spilliaert R, et al., Eur J. Biochem. 224 (3):923-30, 1994, which discloses the cloning and sequencing of bglA, coding for a thermostable beta-glucanase from *Rhodothermus marinus*; and Halldorsdottir S et al., Appl Microbiol Biotechnol. 49 (3):277-84, 1998, which discloses the cloning, sequencing and overexpression of a *Rhodothermus marinus* gene encoding a thermostable cellulase of glycosyl hydrolase family 12. However, there remains a need for identification and characterization of novel cellulases, with improved properties, such as improved performance under conditions of thermal stress or in the presence of surfactants, increased specific activity, altered substrate cleavage pattern, and/or high level expression in vitro.

The development of new and improved cellulase compositions that comprise varying amounts CBH-type, EG-type and BG-type cellulases is of interest for use: (1) in detergent compositions that exhibit enhanced cleaning ability, function as a softening agent and/or improve the feel of cotton fabrics (e.g., "stone washing" or "biopolishing"); (2) in compositions for degrading wood pulp or other biomass into sugars (e.g., for bio-fuel production); and/or (3) in feed compositions.

Also provided herein are whole cellulase preparation comprising cellulase variants. As used herein, the phrase "whole cellulase preparation" refers to both naturally occurring and non-naturally occurring cellulase containing compositions. A "naturally occurring" composition is one produced by a naturally occurring source and which comprises one or more cellobiohydrolase-type, one or more endoglucanase-type, and one or more beta-glucosidase components wherein each of these components is found at the ratio produced by the source. A naturally occurring composition is one that is produced by an organism unmodified with respect to the cellulolytic enzymes such that the ratio of the component enzymes is unaltered from that produced by the native organism. A "non-naturally occurring" composition encompasses those compositions produced by: (1) combining component cellulolytic enzymes either in a naturally occurring ratio or non-naturally occurring, i.e., altered, ratio; or (2) modifying an organism to overexpress or underexpress one or more cellulolytic enzyme; or (3) modifying an organism such that at least one cellulolytic enzyme is deleted. Accordingly, in some embodiments, the whole cellulase preparation can have one or more of the various EGs and/or CBHs, and/or beta-glucosidase deleted. For example, EG1 may be deleted alone or in combination with other EGs and/or CBHs.

In general, the whole cellulase preparation includes enzymes including, but are not limited to: (i) endoglucanases (EG) or 1,4-β-d-glucan-4-glucanohydrolases (EC 3.2.1.4), (ii) exoglucanases, including 1,4-β-d-glucan glucanohydrolases (also known as cellodextrinases) (EC 3.2.1.74) and 1,4-β-d-glucan cellobiohydrolases (exo-cellobiohydrolases, CBH) (EC 3.2.1.91), and (iii) β-glucosidase (BG) or β-glucoside glucohydrolases (EC 3.2.1.21).

In the present disclosure, the whole cellulase preparation can be from any microorganism that is useful for the hydrolysis of a cellulosic material. In some embodiments, the whole cellulase preparation is a filamentous fungi whole cellulase. "Filamentous fungi" include all filamentous forms of the subdivision Eumycota and Oomycota. In some embodiments, the whole cellulase preparation is a *Acremonium, Aspergillus, Emericella, Fusarium, Humicola, Mucor, Myceliophthora, Neurospora, Scytalidium, Thielavia, Tolypocladium*, or *Trichoderma* species, whole cellulase. In some embodiments, the whole cellulase preparation is an *Aspergillus aculeatus, Aspergillus awamori, Aspergillus foetidus, Aspergillus japonicus, Aspergillus nidulans, Aspergillus niger*, or *Aspergillus oryzae* whole cellulase. In another aspect, whole cellulase preparation is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* whole cellulase. In another aspect, the whole cellulase preparation is a *Humicola insolens, Humicola lanuginosa, Mucor miehei, Myceliophthora thermophila, Neurospora crassa, Scytalidium thermophilum*, or *Thielavia terrestris* whole cellulase. In another aspect, the whole cellulase preparation a *Trichoderma harzianum, Trichoderma koningii, Trichoderma longibrachiatum, Trichoderma reesei* e.g., RL-P37 (Sheir-Neiss et al., Appl. Microbiol. Biotechnology, 20 (1984) pp. 46-53; Montenecourt B. S., Can., 1-20, 1987), QM9414 (ATCC No. 26921), NRRL 15709, ATCC 13631, 56764, 56466, 56767, or *Trichoderma viride* e.g., ATCC 32098 and 32086, whole cellulase. In some embodiments, the whole cellulase preparation is a *Trichoderma reesei* RutC30 whole cellulase, which is available from the American Type Culture Collection as *Trichoderma reesei* ATCC 56765.

Examples of commercial cellulase preparations suitable for use in the present disclosure include, for example, CELLUCLAST™ (available from Novozymes A/S) and LAMINEX™, IndiAge™ and Primafast™ LAMINEX BG enzyme (available Genencor Division, Danisco US. Inc.)

In the present disclosure, the whole cellulase preparation can be from any microorganism cultivation method known in the art resulting in the expression of enzymes capable of hydrolyzing a cellulosic material. Fermentation can include shake flask cultivation, small- or large-scale fermentation, such as continuous, batch, fed-batch, or solid state fermentations in laboratory or industrial fermenters performed in a suitable medium and under conditions allowing the cellulase to be expressed or isolated.

Generally, the microorganism is cultivated in a cell culture medium suitable for production of enzymes capable of hydrolyzing a cellulosic material. The cultivation takes place in a suitable nutrient medium comprising carbon and nitrogen sources and inorganic salts, using procedures known in the art. Suitable culture media, temperature ranges and other conditions suitable for growth and cellulase production are known in the art. As a non-limiting example, the normal temperature range for the production of cellulases by *Trichoderma reesei* is 24° C. to 28° C.

Generally, the whole cellulase preparation is used as is produced by fermentation with no or minimal recovery and/or purification. For example, once cellulases are secreted by a cell into the cell culture medium, the cell culture medium containing the cellulases can be used. In some embodiments the whole cellulase preparation comprises the unfractionated contents of fermentation material, including cell culture medium, extracellular enzymes and cells. Alternatively, the whole cellulase preparation can be processed by any convenient method, e.g., by precipitation, centrifugation, affinity, filtration or any other method known in the art. In some embodiments, the whole cellulase preparation can be concentrated, for example, and then used without further purification. In some embodiments the whole cellulase preparation comprises chemical agents that decrease cell viability or kills the cells. In some embodiments, the cells are lysed or permeabilized using methods known in the art.

III. Molecular Biology

In one embodiment this disclosure provides for the expression of variant cbh2 genes under control of a promoter functional in a filamentous fungus. Therefore, this disclosure relies on routine techniques in the field of recombinant genetics (See, e.g., Sambrook et al., Molecular Cloning, A Laboratory Manual, 2nd ed., 1989; Kriegler, Gene Transfer and Expression: A Laboratory Manual, 1990; and Ausubel et al., eds., CURRENT PROTOCOLS IN MOLECULAR BIOLOGY, Greene Publishing and Wiley-Interscience, New York, 1994).

Methods of Mutating cbh2 Nucleic Acid Sequences

Any method known in the art that can introduce mutations is contemplated by the present disclosure.

The present disclosure relates to the expression, purification and/or isolation and use of variant CBH2. These enzymes are preferably prepared by recombinant methods utilizing the cbh2 gene from *H. jecorina*. The fermentation broth may be used with or without purification.

After the isolation and cloning of the cbh2 gene from *H. jecorina*, other methods known in the art, such as site directed mutagenesis, are used to make the substitutions, additions or deletions that correspond to substituted amino acids in the expressed CBH2 variant. Again, site directed mutagenesis and other methods of incorporating amino acid changes in expressed proteins at the DNA level are known in the art (Sambrook et al., supra; and Ausubel et al., supra).

DNA encoding an amino acid sequence variant of the *H. jecorina* CBH2 is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the *H. jecorina* CBH2.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the starting polypeptide, i.e., *H. jecorina* CBH2. See Higuchi, in PCR Protocols, pp. 177-183 (Academic Press, 1990); and Vallette et al., Nuc. Acids Res. 17:723-733 (1989). See, also, for example Cadwell et al., PCR Methods and Applications, Vol 2, 28-33 (1992). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a variant CBH2 can be determined, and a nucleic acid sequence encoding such amino acid sequence variant can be generated synthetically.

The variant CBH2(s) so prepared may be subjected to further modifications, oftentimes depending on the intended use of the cellulase. Such modifications may involve further alteration of the amino acid sequence, fusion to heterologous polypeptide(s) and/or covalent modifications.

IV. cbh2 Nucleic Acids and CBH2 Polypeptides

A. Variant cbh2-Type Nucleic Acids

The nucleic acid sequence for the wild type cbh2 is shown in SEQ ID NO:1. The disclosure encompasses a nucleic acid molecule encoding the variant cellulases described herein. The nucleic acid may be a DNA molecule.

After DNA sequences that encode the CBH2 variants have been cloned into DNA constructs, the DNA is used to transform microorganisms. The microorganism to be transformed for the purpose of expressing a variant CBH2 according to the present disclosure may advantageously comprise a strain derived from *Trichoderma* sp. Thus, a preferred mode for preparing variant CBH2 cellulases according to the present disclosure comprises transforming a *Trichoderma* sp. host cell with a DNA construct comprising at least a fragment of DNA encoding a portion or all of the variant CBH2. The DNA construct will generally be functionally attached to a promoter. The transformed host cell is then grown under conditions so as to express the desired protein. Subsequently, the desired protein product may be purified to substantial homogeneity.

However, it may in fact be that the best expression vehicle for a given DNA encoding a variant CBH2 may differ from *H. jecorina*. Thus, it may be that it will be most advantageous to express a protein in a transformation host that bears phylogenetic similarity to the source organism for the variant CBH2. In an alternative embodiment, *Aspergillus niger* can be used as an expression vehicle. For a description of transformation techniques with *A. niger*, see WO 98/31821, the disclosure of which is incorporated by reference in its entirety.

Accordingly, the present description of an *Aspergillus* spp. expression system is provided for illustrative purposes only and as one option for expressing the variant CBH2 of the disclosure. One of skill in the art, however, may be inclined to express the DNA encoding variant CBH2 in a different host cell if appropriate and it should be understood that the source of the variant CBH2 should be considered in determining the optimal expression host. Additionally, the skilled worker in the field will be capable of selecting the best expression system for a particular gene through routine techniques utilizing the tools available in the art.

B. Variant CBH2 Polypeptides

The variant CBH2's of this disclosure have amino acid sequences that are derived from the amino acid sequence of a precursor CBH2. The amino acid sequence of the CBH2 variant differs from the precursor CBH2 amino acid sequence by the substitution, deletion or insertion of one or more amino acids of the precursor amino acid sequence. In a preferred embodiment, the precursor CBH2 is *Hypocrea jecorina* CBH2. The mature amino acid sequence of *H. jecorina* CBH2 is shown in Example 2 (SEQ ID NO:3). Thus, this disclosure is directed to CBH2 variants which contain amino acid residues at positions which are equivalent to the particular identified residue in *H. jecorina* CBH2. A residue (amino acid) of an CBH2 homolog is equivalent to a residue of *Hypocrea jecorina* CBH2 if it is either homologous (i.e., corresponding in position in either primary or tertiary structure) or is functionally analogous to a specific residue or portion of that residue in *Hypocrea jecorina* CBH2 (i.e., having the same or similar functional capacity to combine, react, or interact chemically or structurally). As used herein, numbering is intended to correspond to that of the mature CBH2 amino acid sequence (SEQ ID NO:3).

Alignment of amino acid sequences to determine homology is preferably determined by using a "sequence comparison algorithm." Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection, Visual inspection may utilize graphics packages such as, for example, MOE by Chemical Computing Group, Montreal Canada.

An example of an algorithm that is suitable for determining sequence similarity is the BLAST algorithm, which is described in Altschul, et al., J. Mol. Biol. 215:403-410 (1990). Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

For purposes of the present disclosure, the degree of identity may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polynucleotide sequence comparison: GAP creation penalty of 5.0 and GAP extension penalty of 0.3.

A structural alignment between a *T. reesei* CBH2 and other cellulases may be used to identify equivalent/corresponding positions in other cellulases having a moderate to high degree of homology, e.g., about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or even 99%, with *T. reesei* CBH2 (SEQ ID NO: 3). One method of obtaining the structural alignment is to use the Pile Up programme from the GCG package using default values of gap penalties, i.e., a gap creation penalty of 3.0 and gap extension penalty of 0.1. Other structural alignment methods include the hydrophobic cluster analysis (Gaboriaud et al., FEBS Letters, 224:149-155, 1987) and reverse threading (Huber and Torda, Protein Science, 7:142-149, 1998).

An exemplary alignment of the mature form of various reference cellulases is provided as FIG. 1. The reference cellulases include: *Hypocrea jecorina* (also known as *T. reesei*) CBH2 (SEQ ID NO:3), *Hypocrea koningii* CBH2 (SEQ ID NO:4), *Humicola insolens* CBH2 (SEQ ID NO:5), *Acremonium cellulolyticus* CBH2 (SEQ ID NO:6), *Agaricus bisporus* CBH2 (SEQ ID NO:7), *Fusarium osysporum* EG (SEQ ID NO:8), *Phanerochaete chrysosporium* CBH2 (SEQ ID NO:9), *Talaromyces emersonii* CBH2 (SEQ ID NO:10), *Thermobifida. fusca* 6B/E3 CBH2 (SEQ ID NO:11), *Thermobifida fusca* 6A/E2 EG (SEQ ID NO:12), and *Cellulomonas fimi* CenA EG (SEQ ID NO:13). Sequences were aligned using the ClustalW and MUSCLE multiple sequence alignment algorithms. A matrix showing the percent identity of cellulases of the sequence alignment of FIG. 1 is provided in Table 1.

TABLE 1

Cellulase Percent Identity Matrix*

| Percent_ID | 3 | 4 | 5 | 6 | 7 | 8 | 9 | 10 | 11 | 12 | 13 |
|---|---|---|---|---|---|---|---|---|---|---|---|
| 3 | 100 | 95.5 | 62.3 | 64.7 | 59.6 | 63.1 | 55.4 | 63.4 | 31.9 | 13.5 | 27 |
| 4 | 95.5 | 100 | 61.6 | 64 | 59.1 | 63.6 | 54.7 | 63 | 32.9 | 13.5 | 26.8 |
| 5 | 62.3 | 61.6 | 100 | 59.1 | 57.6 | 61.3 | 54 | 58.8 | 31.9 | 15.9 | 26.6 |
| 6 | 64.7 | 64 | 59.1 | 100 | 58.6 | 56.4 | 54 | 72.6 | 32.8 | 13.5 | 29.2 |
| 7 | 59.6 | 59.1 | 57.6 | 58.6 | 100 | 55.8 | 69.1 | 58.1 | 34.9 | 17.5 | 27.6 |
| 8 | 63.1 | 63.6 | 61.3 | 56.4 | 55.8 | 100 | 48.7 | 54.8 | 31.1 | 13.9 | 25.2 |
| 9 | 55.4 | 54.7 | 54 | 54 | 69.1 | 48.7 | 100 | 52.6 | 32.4 | 15.4 | 25.6 |
| 10 | 63.4 | 63 | 58.8 | 72.6 | 58.1 | 54.8 | 52.6 | 100 | 33.9 | 13.2 | 27.3 |
| 11 | 31.9 | 32.9 | 31.9 | 32.8 | 34.9 | 31.1 | 32.4 | 33.9 | 100 | 15.9 | 36.3 |
| 12 | 13.5 | 13.5 | 15.9 | 13.5 | 17.5 | 13.9 | 15.4 | 13.2 | 15.9 | 100 | 12.8 |
| 13 | 27 | 26.8 | 26.6 | 29.2 | 27.6 | 25.2 | 25.6 | 27.3 | 36.3 | 12.8 | 100 |

*Numbers in the top row and left column correspond to the SEQ ID NOS of the aligned sequences of FIG. 1.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

V. Expression of Recombinant CBH2 Variants

The methods of the disclosure rely on the use cells to express variant CBH2, with no particular method of CBH2 expression required. The variant CBH2 is preferably secreted from the cells. The disclosure provides host cells which have been transduced, transformed or transfected with an expression vector comprising a variant CBH2-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression vector having a promoter or biologically active promoter fragment or one or more (e.g., a series) of enhancers which functions in the host cell line, operably linked to a DNA segment encoding variant CBH2, such that variant CBH2 is expressed in the cell line.

A. Nucleic Acid Constructs/Expression Vectors.

Natural or synthetic polynucleotide fragments encoding variant CBH2 ("CBH2-encoding nucleic acid sequences") may be incorporated into heterologous nucleic acid constructs or vectors, capable of introduction into, and replication in, a filamentous fungal or yeast cell. The vectors and methods disclosed herein are suitable for use in host cells for the expression of variant CBH2. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., The Molecular Biology of the Yeast *Saccharomyces,* 1981, each of which is expressly incorporated by reference herein. Appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Recombinant filamentous fungi comprising the coding sequence for variant CBH2 may be produced by introducing a heterologous nucleic acid construct comprising the variant CBH2 coding sequence into the cells of a selected strain of the filamentous fungi.

Once the desired form of a variant cbh2 nucleic acid sequence is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A selected variant cbh2 coding sequence may be inserted into a suitable vector according to well-known recombinant techniques and used to transform filamentous fungi capable of CBH2 expression. Due to the inherent degeneracy of the genetic code, other nucleic acid sequences which encode substantially the same or a functionally equivalent amino acid sequence may be used to clone and express variant CBH2. Therefore it is appreciated that such substitutions in the coding region fall within the sequence variants covered by the present disclosure. Any and all of these sequence variants can be utilized in the same way as described herein for a parent CBH2-encoding nucleic acid sequence.

The present disclosure also includes recombinant nucleic acid constructs comprising one or more of the variant CBH2-encoding nucleic acid sequences as described above. The constructs comprise a vector, such as a plasmid or viral vector, into which a sequence of the disclosure has been inserted, in a forward or reverse orientation.

Heterologous nucleic acid constructs may include the coding sequence for variant cbh2. (i) in isolation; (ii) in combination with additional coding sequences; such as fusion protein or signal peptide coding sequences, where the cbh2 coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the cbh2 coding sequence is a heterologous gene.

In one aspect of the present disclosure, a heterologous nucleic acid construct is employed to transfer a variant CBH2-encoding nucleic acid sequence into a cell in vitro, with established filamentous fungal and yeast lines preferred. For long-term, production of variant CBH2, stable expression is preferred. It follows that any method effective to generate stable transformants may be used in practicing the disclosure.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1.alpha. promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular filamentous fungus for expression purposes. It is operably linked to DNA sequence encoding a variant CBH2 polypeptide. Such linkage comprises positioning of the promoter with respect to the initiation codon of the DNA sequence encoding the variant CBH2 polypeptide in the disclosed expression vectors. The promoter sequence contains transcription and translation control sequence which mediate the expression of the variant CBH2 polypeptide. Examples include the promoters from the *Aspergillus niger, A. awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *H. jecorina* (*T. reesei*) cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *T. reesei*, amdS from *A. nidulans*, pyr4 from *Neurospora crassa* or *T. reesei*, pyrG from *Aspergillus niger* or *A. nidulans*. Additional exemplary selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *H. jecorina* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Exemplary plasmids include pUC18, pBR322, pRAX and pUC100. The pRAX plasmid contains AMAL sequences from *A. nidulans*, which make it possible to replicate in *A. niger.*

The practice of the present disclosure will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, Animal Cell Culture, 1987; Ausubel, et al., 1993; and Coligan et al., Current Protocols in Immunology, 1991.

B. Host Cells and Culture Conditions for CBH2 Production (i) Filamentous Fungi

Thus, the present disclosure provides filamentous fungi comprising cells which have been modified, selected and cultured in a manner effective to result in variant CBH2 production or expression relative to the corresponding non-transformed parental fungi.

Examples of species of parental filamentous fungi that may be treated and/or modified for variant CBH2 expression include, but are not limited to *Trichoderma*, e.g., *Trichoderma reesei*, *Trichoderma longibrachiatum*, *Trichoderma viride*, *Trichoderma koningii*; *Penicillium* sp., *Humicola* sp., including *Humicola insolens*; *Aspergillus* sp., *Chrysosporium* sp., *Fusarium* sp., *Hypocrea* sp., and *Emericella* sp.

CBH2 expressing cells are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Culture conditions are also standard, e.g., cultures are incubated at 28.degree. C. in shaker cultures or fermenters until desired levels of CBH2 expression are achieved.

Preferred culture conditions for a given filamentous fungus may be found in the scientific literature and/or from the source of the fungi such as the American Type Culture Collection (ATCC; www.atcc.org/). After fungal growth has been established, the cells are exposed to conditions effective to cause or permit the expression of variant CBH2.

In cases where a CBH2 coding sequence is under the control of an inducible promoter, the inducing agent, e.g., a sugar, metal salt or antibiotics, is added to the medium at a concentration effective to induce CBH2 expression.

In one embodiment, the strain comprises *Aspergillus niger*, which is a useful strain for obtaining overexpressed protein. For example *A. niger* var *awamori* dgr246 is known to secrete elevated amounts of secreted cellulases (Goedegebuur et al., Curr. Genet (2002) 41: 89-98). Other strains of *Aspergillus niger* var *awamori* such as GCDAP3, GCDAP4 and GAP3-4 are known Ward et al (Ward, M, Wilson, L. J. and Kodama, K. H., 1993, Appl. Microbiol. Biotechnol. 39:738-743).

In another embodiment, the strain comprises *Trichoderma reesei*, which is a useful strain for obtaining overexpressed protein. For example, RL-P37, described by Sheir-Neiss, et al., Appl. Microbiol. Biotechnol. 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing variant CBH2.

Where it is desired to obtain the variant CBH2 in the absence of potentially detrimental native cellulolytic activity, it is useful to obtain a *Trichoderma* host cell strain which has had one or more cellulase genes deleted prior to introduction of a DNA construct or plasmid containing the DNA fragment encoding the variant CBH2. Such strains may be prepared by the method disclosed in U.S. Pat. No. 5,246,853 and WO 92/06209, which disclosures are hereby incorporated by reference. By expressing a variant CBH2 cellulase in a host microorganism that is missing one or more cellulase genes, the identification and subsequent purification procedures are simplified. Any gene from *Trichoderma* sp. which has been cloned can be deleted, for example, the cbh1, cbh2, eg11, and eg12 genes as well as those encoding EG III and/or EGV protein (see e.g., U.S. Pat. No. 5,475,101 and WO 94/28117, respectively).

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, preferably between about 0.5 to 2.0 kb, remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

A selectable marker must be chosen so as to enable detection of the transformed microorganism. Any selectable marker gene that is expressed in the selected microorganism will be suitable. For example, with *Aspergillus* sp., the selectable marker is chosen so that the presence of the selectable marker in the transformants will not significantly affect the properties thereof. Such a selectable marker may be a gene that encodes an assayable product. For example, a functional copy of an *Aspergillus* sp. gene may be used which if lacking in the host strain results in the host strain displaying an auxotrophic phenotype. Similarly, selectable markers exist for *Trichoderma* sp.

In one embodiment, a pyrG-derivative strain of *Aspergillus* sp. is transformed with a functional pyrG gene, which thus provides a selectable marker for transformation. A pyrG-derivative strain may be obtained by selection of *Aspergillus* sp. strains that are resistant to fluoroorotic acid (FOA). The pyrG gene encodes orotidine-5'-monophosphate decarboxylase, an enzyme required for the biosynthesis of uridine. Strains with an intact pyrG gene grow in a medium lacking uridine but are sensitive to fluoroorotic acid. It is possible to select pyrG-derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophosphoribosyl transferase. It is possible to transform these cells with a functional copy of the gene encoding this enzyme (Berges & Barreau, Curr. Genet. 19:359-365 (1991), and van Hartingsveldt et al., (1986) Development of a homologous transformation system for *Aspergillus niger* based on the pyrG gene. Mol. Gen. Genet. 206:71-75). Selection of derivative strains is easily performed using the FOA resistance technique referred to above, and thus, the pyrG gene is preferably employed as a selectable marker.

In a second embodiment, a pyr4.-derivative strain of *Hyprocrea* sp. (*Hyprocrea* sp. (*Trichoderma* sp.)) is transformed with a functional pyr4 gene, which thus provides a selectable marker for transformation. A pyr4.sup.-derivative strain may be obtained by selection of *Hyprocrea* sp. (*Trichoderma* sp.) strains that are resistant to fluoroorotic acid (FOA). The pyr4 gene encodes orotidine-5'-monophosphate decarboxylase, an enzyme required for the biosynthesis of uridine. Strains with an intact pyr4 gene grow in a medium lacking uridine but are sensitive to fluoroorotic acid. It is possible to select pyr4.sup.-derivative strains that lack a functional orotidine monophosphate decarboxylase enzyme and require uridine for growth by selecting for FOA resistance. Using the FOA selection technique it is also possible to obtain uridine-requiring strains which lack a functional orotate pyrophoribosyl transferase. It is possible to transform these cells with a functional copy of the gene encoding this enzyme (Berges & Barreau, 1991). Selection of derivative strains is easily performed using the FOA resistance technique referred to above, and thus, the pyr4 gene is preferably employed as a selectable marker.

To transform pyrG.-*Aspergillus* sp. or pyr4-*Hyprocrea* sp. (*Trichoderma* sp.) so as to be lacking in the ability to express one or more cellulase genes, a single DNA fragment comprising a disrupted or deleted cellulase gene is then isolated from the deletion plasmid and used to transform an appropriate pyr-*Aspergillus* or pyr-*Trichoderma* host. Transformants are then identified and selected based on their ability to express the pyrG or pyr4, respectively, gene product and thus compliment the uridine auxotrophy of the host strain. Southern blot analysis is then carried out on the resultant transformants to identify and confirm a double crossover integration event that replaces part or all of the coding region of the genomic copy of the gene to be deleted with the appropriate pyr selectable markers.

Although the specific plasmid vectors described above relate to preparation of pyr-transformants, the present disclosure is not limited to these vectors. Various genes can be deleted and replaced in the *Aspergillus* sp. or *Hyprocrea* sp. (*Trichoderma* sp.) strain using the above techniques. In addition, any available selectable markers can be used, as discussed above. In fact, any host, e.g., *Aspergillus* sp. or *Hyprocrea* sp., gene that has been cloned, and thus identified, can be deleted from the genome using the above-described strategy.

As stated above, the host strains used may be derivatives of *Hyprocrea* sp. (*Trichoderma* sp.) that lack or have a nonfunctional gene or genes corresponding to the selectable marker chosen. For example, if the selectable marker of pyrG is chosen for *Aspergillus* sp., then a specific pyrG-derivative strain is used as a recipient in the transformation procedure. Also, for example, if the selectable marker of pyr4 is chosen for a *Hyprocrea* sp., then a specific pyr4-derivative strain is used as a recipient in the transformation procedure. Similarly, selectable markers comprising *Hyprocrea* sp. (*Trichoderma* sp.) genes equivalent to the *Aspergillus nidulans* genes amdS, argB, trpC, niaD may be used. The corresponding recipient strain must therefore be a derivative strain such as argB-, trpC-, niaD-, respectively.

DNA encoding the CBH2 variant is then prepared for insertion into an appropriate microorganism. According to the present disclosure, DNA encoding a CBH2 variant comprises the DNA necessary to encode for a protein that has functional cellulolytic activity. The DNA fragment encoding the CBH2 variant may be functionally attached to a fungal promoter sequence, for example, the promoter of the glaA gene in *Aspergillus* or the promoter of the cbh1 or egl1 genes in *Trichoderma*.

It is also contemplated that more than one copy of DNA encoding a CBH2 variant may be recombined into the strain to facilitate overexpression. The DNA encoding the CBH2 variant may be prepared by the construction of an expression vector carrying the DNA encoding the variant. The expression vector carrying the inserted DNA fragment encoding the CBH2 variant may be any vector which is capable of replicating autonomously in a given host organism or of integrating into the DNA of the host, typically a plasmid. In preferred embodiments two types of expression vectors for obtaining expression of genes are contemplated. The first contains DNA sequences in which the promoter, gene-coding region, and terminator sequence all originate from the gene to be expressed. Gene truncation may be obtained where desired by deleting undesired DNA sequences (e.g., coding for unwanted domains) to leave the domain to be expressed under control of its own transcriptional and translational regulatory sequences. A selectable marker may also be contained on the vector allowing the selection for integration into the host of multiple copies of the novel gene sequences.

The second type of expression vector is preassembled and contains sequences required for high-level transcription and a selectable marker. It is contemplated that the coding region for a gene or part thereof can be inserted into this general-purpose expression vector such that it is under the transcriptional control of the expression cassettes promoter and terminator sequences.

For example, in *Aspergillus*, pRAX is such a general-purpose expression vector. Genes or part thereof can be inserted downstream of the strong glaa promoter.

For example, in *Hypocrea*, pTEX is such a general-purpose expression vector. Genes or part thereof can be inserted downstream of the strong cbh1 promoter.

In the vector, the DNA sequence encoding the CBH2 variant of the present disclosure should be operably linked to transcriptional and translational sequences, i.e., a suitable promoter sequence and signal sequence in reading frame to the structural gene. The promoter may be any DNA sequence that shows transcriptional activity in the host cell and may be derived from genes encoding proteins either homologous or heterologous to the host cell. An optional signal peptide provides for extracellular production of the CBH2 variant. The DNA encoding the signal sequence is preferably that which is naturally associated with the gene to be expressed, however the signal sequence from any suitable source, for example an exo-cellobiohydrolase or endoglucanase from *Trichoderma*, is contemplated in the present disclosure.

The procedures used to ligate the DNA sequences coding for the variant CBH2 of the present disclosure with the promoter, and insertion into suitable vectors are well known in the art.

The DNA vector or construct described above may be introduced in the host cell in accordance with known techniques such as transformation, transfection, microinjection, microporation, biolistic bombardment and the like.

In the preferred transformation technique, it must be taken into account that the permeability of the cell wall to DNA in *Hyprocrea* sp. (*Trichoderma* sp.) is very low. Accordingly, uptake of the desired DNA sequence, gene or gene fragment is at best minimal There are a number of methods to increase the permeability of the *Hyprocrea* sp. (*Trichoderma* sp.) cell wall in the derivative strain (i.e., lacking a functional gene corresponding to the used selectable marker) prior to the transformation process.

The preferred method in the present disclosure to prepare *Aspergillus* sp. or *Hyprocrea* sp. (*Trichoderma* sp.) for transformation involves the preparation of protoplasts from fungal mycelium. See Campbell et al. Improved transformation efficiency of *A. niger* using homologous niaD gene for nitrate reductase. Curr. Genet. 16:53-56; 1989. The mycelium can be obtained from germinated vegetative spores. The mycelium is treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate and the like. Usually the concentration of these stabilizers varies between 0.8 M and 1.2 M. It is preferable to use about a 1.2 M solution of sorbitol in the suspension medium.

Uptake of the DNA into the host strain, (*Aspergillus* sp. or *Hyprocrea* sp. (*Trichoderma* sp.), is dependent upon the calcium ion concentration. Generally between about 10 mM CaCl.sub.2 and 50 mM CaCl.sub.2 is used in an uptake solution. Besides the need for the calcium ion in the uptake solution, other items generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes thus permitting the contents of the medium to be delivered into the cytoplasm of the host cell, by way of example either *Aspergillus* sp. or *Hyprocrea* sp. strain, and the plasmid DNA is transferred to the nucleus. This fusion frequently leaves multiple copies of the plasmid DNA integrated into the host chromosome.

Usually a suspension containing the *Aspergillus* sp. protoplasts or cells that have been subjected to a permeability treatment at a density of 10.sup.5 to 10.sup.6/mL, preferably 2.times.10.sup.5/mL are used in transformation. Similarly, a suspension containing the *Hyprocrea* sp. (*Trichoderma* sp.) protoplasts or cells that have been subjected to a permeability treatment at a density of 10.sup.8 to 10.sup.9/mL, preferably 2.times.10.sup.8/mL are used in transformation. A volume of 100 .mu.L of these protoplasts or cells in an appropriate solution (e.g., 1.2 M sorbitol; 50 mM CaCl.sub.2) are mixed with the desired DNA. Generally a high concentration of PEG is added to the uptake solution. From 0.1 to 1 volume of 25% PEG 4000 can be added to the protoplast suspension. However, it is preferable to add about 0.25 volumes to the protoplast suspension. Additives such as dimethyl sulfoxide, heparin, spermidine, potassium chloride and the like may also be added to the uptake solution and aid in transformation.

Generally, the mixture is then incubated at approximately 0.degree. C. for a period of between 10 to 30 minutes. Additional PEG is then added to the mixture to further enhance the uptake of the desired gene or DNA sequence. The 25% PEG 4000 is generally added in volumes of 5 to 15 times the volume of the transformation mixture; however, greater and lesser volumes may be suitable. The 25% PEG 4000 is preferably about 10 times the volume of the transformation mixture. After the PEG is added, the transformation mixture is then incubated either at room temperature or on ice before the addition of a sorbitol and CaCl.sub.2 solution. The protoplast suspension is then further added to molten aliquots of a growth medium. This growth medium permits the growth of transformants only. Any growth medium can be used in the present disclosure that is suitable to grow the desired transformants. However, if Pyr.sup.+ transformants are being selected it is preferable to use a growth medium that contains no uridine. The subsequent colonies are transferred and purified on a growth medium depleted of uridine.

At this stage, stable transformants may be distinguished from unstable transformants by their faster growth rate and, in *Trichoderma*, for example, the formation of circular colonies with a smooth, rather than ragged outline on solid culture medium lacking uridine. Additionally, in some cases a further test of stability may made by growing the transformants on solid non-selective medium (i.e. containing uridine), harvesting spores from this culture medium and determining the percentage of these spores which will subsequently germinate and grow on selective medium lacking uridine.

In a particular embodiment of the above method, the CBH2 variant(s) are recovered in active form from the host cell after growth in liquid media as a result of the appropriate post translational processing of the CBH2 variant.

(ii) Yeast

The present disclosure also contemplates the use of yeast as a host cell for CBH2 production. Several other genes encoding hydrolytic enzymes have been expressed in various strains of the yeast *S. cerevisiae*. These include sequences encoding for two endoglucanases (Penttila et al., Yeast vol. 3, pp 175-185, 1987), two cellobiohydrolases (Penttila et al., Gene, 63: 103-112, 1988) and one beta-glucosidase from *Trichoderma reesei* (Cummings and Fowler, Curr. Genet. 29:227-233, 1996), a xylanase from *Aureobasidlium pullulans* (Li and Ljungdahl, Appl. Environ. Microbiol. 62, no. 1, pp. 209-213, 1996), an alpha-amylase from wheat (Rothstein et al., Gene 55:353-356, 1987), etc. In addition, a cellulase gene cassette encoding the Butyrivibrio fibrisolvens endo-[beta]-1,4-glucanase (END1), *Phanerochaete chrysosporium* cellobiohydrolase (CBH1), the *Ruminococcus flavefaciens* cellodextrinase (CEL1) and the Endomyces fibrilizer cellobiase (Bgl1) was successfully expressed in a laboratory strain of *S. cerevisiae* (Van Rensburg et al., Yeast, vol. 14, pp. 67-76, 1998).

C. Introduction of a CBH2-Encoding Nucleic Acid Sequence into Host Cells.

The disclosure further provides cells and cell compositions which have been genetically modified to comprise an exogenously provided variant CBH2-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc, as further described above.

The methods of transformation of the present disclosure may result in the stable integration of all or part of the transformation vector into the genome of the filamentous fungus. However, transformation resulting in the maintenance of a self-replicating extra-chromosomal transformation vector is also contemplated.

Many standard transfection methods can be used to produce *Trichoderma reesei* cell lines that express large quantities of the heterologus protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138).

Other methods for introducing a heterologous nucleic acid construct (expression vector) into filamentous fungi (e.g., *H. jecorina*) include, but are not limited to the use of a particle or gene gun, permeabilization of filamentous fungi cells walls prior to the transformation process (e.g., by use of high concentrations of alkali, e.g., 0.05 M to 0.4 M CaCl.sub.2 or lithium acetate), protoplast fusion or *Agrobacterium* mediated transformation. An exemplary method for transformation of filamentous fungi by treatment of protoplasts or spheroplasts with polyethylene glycol and CaCl.sub.2 is described in Campbell, E. I. et al., Curr. Genet. 16:53-56, 1989 and Penttila, M. et al., Gene, 63:11-22, 1988.

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the heterologous gene.

In addition, heterologous nucleic acid constructs comprising a variant CBH2-encoding nucleic acid sequence can be transcribed in vitro, and the resulting RNA introduced into the host cell by well-known methods, e.g., by injection.

The disclosure further includes novel and useful transformants of filamentous fungi such as *H. jecorina* and *A. niger* for use in producing fungal cellulase compositions. The disclosure includes transformants of filamentous fungi especially fungi comprising the variant CBH2 coding sequence, or deletion of the endogenous cbh coding sequence.

Following introduction of a heterologous nucleic acid construct comprising the coding sequence for a variant cbh2, the genetically modified cells can be cultured in conventional nutrient media modified as appropriate for activating promoters, selecting transformants or amplifying expression of a variant CBH2-encoding nucleic acid sequence. The culture conditions, such as temperature, pH and the like, are those previously used for the host cell selected for expression, and will be apparent to those skilled in the art.

The progeny of cells into which such heterologous nucleic acid constructs have been introduced are generally considered to comprise the variant CBH2-encoding nucleic acid sequence found in the heterologous nucleic acid construct.

The disclosure further includes novel and useful transformants of filamentous fungi such as *H. jecorina* for use in producing fungal cellulase compositions. *Aspergillus niger* may also be used in producing the variant CBH2. The disclosure includes transformants of filamentous fungi especially fungi comprising the variant cbh 2 coding sequence, or deletion of the endogenous cbh2 coding sequence.

Stable transformants of filamentous fungi can generally be distinguished from unstable transformants by their faster growth rate and, in *Trichoderma*, for example, the formation of circular colonies with a smooth rather than ragged outline on solid culture medium. Additionally, in some cases, a further test of stability can be made by growing the transformants on solid non-selective medium, harvesting the spores from this culture medium and determining the percentage of these spores which will subsequently germinate and grow on selective medium.

VI. Isolation and Purification of Recombinant CBH2 Protein

In general, a variant CBH2 protein produced in cell culture is secreted into the medium and may be purified or isolated, e.g., by removing unwanted components from the cell culture medium. However, in some cases, a variant CBH2 protein may be produced in a cellular form necessitating recovery from a cell lysate. In such cases the variant CBH2 protein is purified from the cells in which it was produced using techniques routinely employed by those of skill in the art. Examples include, but are not limited to, affinity chromatography (Tilbeurgh et al., FEBS Lett. 16:215, 1984), ion-exchange chromatographic methods (Goyal et al., Bioresource Technol. 36:37-50, 1991; Fliess et al., Eur. J. Appl. Microbiol. Biotechnol. 17:314-318, 1983; Bhikhabhai et al., J. Appl. Biochem. 6:336-345, 1984; Ellouz et al., J. Chromatography 396:307-317, 1987), including ion-exchange using materials with high resolution power (Medve et al., J. Chromatography A 808:153-165, 1998), hydrophobic interaction chromatography (Tomaz and Queiroz, J. Chromatography A 865:123-128, 1999), and two-phase partitioning (Brumbauer, et al., Bioseparation 7:287-295, 1999).

Typically, the variant CBH2 protein is fractionated to segregate proteins having selected properties, such as binding affinity to particular binding agents, e.g., antibodies or receptors; or which have a selected molecular weight range, or range of isoelectric points.

Once expression of a given variant CBH2 protein is achieved, the CBH2 protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, Methods in Enzymology, vol. 182, no. 57, pp. 779, 1990; Scopes, Methods Enzymol. 90: 479-91, 1982. The purification step(s) selected will depend, e.g., on the nature of the production process used and the particular protein produced.

VII. Utility of cbh2 and CBH2

It can be appreciated that the variant cbh nucleic acids, the variant CBH2 protein and compositions comprising variant CBH2 protein activity find utility in a wide variety applications, some of which are described below.

New and improved cellulase compositions that comprise varying amounts BG-type, EG-type and variant CBH-type cellulases find utility in detergent compositions that exhibit enhanced cleaning ability, function as a softening agent and/or improve the feel of cotton fabrics (e.g., "stone washing" or "biopolishing"), in compositions for degrading wood pulp into sugars (e.g., for bio-ethanol production), and/or in feed compositions. The isolation and characterization of cellulase of each type provides the ability to control the aspects of such compositions.

In one approach, the cellulase of the disclosure finds utility in detergent compositions or in the treatment of fabrics to improve the feel and appearance.

Since the rate of hydrolysis of cellulosic products may be increased by using a transformant having at least one additional copy of the cbh gene inserted into the genome, products that contain cellulose or heteroglycans can be degraded at a faster rate and to a greater extent. Products made from cellulose such as paper, cotton, cellulosic diapers and the like can be degraded more efficiently in a landfill. Thus, the fermentation product obtainable from the transformants or the transformants alone may be used in compositions to help degrade by liquefaction a variety of cellulose products that add to the overcrowded landfills.

Separate saccharification and fermentation is a process whereby cellulose present in biomass, e.g., corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Thus, in another approach, the variant CBH type cellulase of the disclosure finds utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol.

A large variety of feedstocks may be used with the inventive variant CBH and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

The methods of the present disclosure can be used in the production of monosaccharides, disaccharides, and polysaccharides as chemical or fermentation feedstocks for microorganism for the production of organic products, chemicals and fuels, plastics, and other products or intermediates. In particular, the value of processing residues (dried distillers grain, spent grains from brewing, sugarcane bagasse, etc.) can be increased by partial or complete solubilization of cellulose or hemicellulose. In addition to ethanol, some chemicals that can be produced from cellulose and hemicellulose include, acetone, acetate, glycine, lysine, organic acids (e.g., lactic acid), 1,3-propanediol, butanediol, glycerol, ethylene glycol, furfural, polyhydroxyalkanoates, cis, cis-muconic acid, animal feed and xylose.

A cellulase composition containing an enhanced amount of cellobiohydrolase finds utility in ethanol production. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petrochemical supplies.

Ethanol can be produced via saccharification and fermentation processes from cellulosic biomass such as trees, herbaceous plants, municipal solid waste and agricultural and forestry residues. However, the ratio of individual cellulase enzymes within a naturally occurring cellulase mixture produced by a microbe may not be the most efficient for rapid conversion of cellulose in biomass to glucose. It is known that endoglucanases act to produce new cellulose chain ends which themselves are substrates for the action of cellobiohydrolases and thereby improve the efficiency of hydrolysis of the entire cellulase system. Therefore, the use of increased or optimized cellobiohydrolase activity may greatly enhance the production of ethanol.

Thus, the inventive cellobiohydrolase finds use in the hydrolysis of cellulose to its sugar components. In one embodiment, a variant cellobiohydrolase is added to the biomass prior to the addition of a fermentative organism. In a second embodiment, a variant cellobiohydrolase is added to the biomass at the same time as a fermentative organism. Optionally, there may be other cellulase components present in either embodiment.

In another embodiment the cellulosic feedstock may be pretreated. Pretreatment may be by elevated temperature and the addition of either of dilute acid, concentrated acid or dilute alkali solution. The pretreatment solution is added for a time sufficient to at least partially hydrolyze the hemicellulose components and then neutralized.

The major product of CBH2 action on cellulose is cellobiose which is available for conversion to glucose by BG activity (for instance in a fungal cellulase product). Either by the pretreatment of the cellulosic biomass or by the enzymatic action on the biomass, other sugars, in addition to glucose and cellobiose, can be made available from the biomass. The hemi-cellulose content of the biomass can be converted (by hemi-cellulases) to sugars such as xylose, galactose, mannose and arabinose. Thus, in a biomass conversion process, enzymatic saccharification can produce sugars that are made available for biological or chemical conversions to other intermediates or end-products. Therefore, the sugars generated from biomass find use in a variety of processes in addition to the generation of ethanol. Examples of such conversions are fermentation of glucose to ethanol (as reviewed by M. E. Himmel et al. pp 2-45, in "Fuels and Chemicals from Biomass", ACS Symposium Series 666, ed B. C. Saha and J. Woodward, 1997) and other biological conversions of glucose to 2,5-diketo-D-gluconate (U.S. Pat. No. 6,599,722), lactic acid (R. Datta and S-P. Tsai pp 224-236, ibid), succinate (R. R. Gokarn, M. A. Eiteman and J. Sridhar pp 237-263, ibid), 1,3-propanediol (A-P. Zheng, H. Biebl and W-D. Deckwer pp 264-279, ibid), 2,3-butanediol (C. S. Gong, N. Cao and G. T. Tsao pp 280-293, ibid), and the chemical and biological conversions of xylose to xylitol (B. C. Saha and R. J. Bothast pp 307-319, ibid). See also, for example, WO 98/21339.

The detergent compositions of this disclosure may employ besides the cellulase composition (irrespective of the cellobiohydrolase content, i.e., cellobiohydrolase-free, substantially cellobiohydrolase-free, or cellobiohydrolase enhanced), a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. The cellulase composition as described above can be added to the detergent composition either in a liquid diluent, in granules, in emulsions, in gels, in pastes, and the like. Such forms are well known to the skilled artisan. When a solid detergent composition is employed, the cellulase composition is preferably formulated as granules. Preferably, the granules can be formulated so as to contain a cellulase protecting agent. For a more thorough discussion, see U.S. Pat. No. 6,162,782 entitled "Detergent compositions containing cellulase compositions deficient in CBH2 type components," which is incorporated herein by reference.

Preferably the cellulase compositions are employed from about 0.00005 weight percent to about 5 weight percent relative to the total detergent composition. More preferably, the cellulase compositions are employed from about 0.0002 weight percent to about 2 weight percent relative to the total detergent composition.

In addition the variant CBH2 nucleic acid sequence finds utility in the identification and characterization of related nucleic acid sequences. A number of techniques useful for determining (predicting or confirming) the function of related genes or gene products include, but are not limited to, (A) DNA/RNA analysis, such as (1) overexpression, ectopic expression, and expression in other species; (2) gene knock-out (reverse genetics, targeted knock-out, viral induced gene silencing (VIGS, see Baulcombe, 100 Years of Virology, Calisher and Horzinek eds., Springer-Verlag, New York, N.Y. 15:189-201, 1999); (3) analysis of the methylation status of the gene, especially flanking regulatory regions; and (4) in situ hybridization; (B) gene product analysis such as (1) recombinant protein expression; (2) antisera production, (3) immunolocalization; (4) biochemical assays for catalytic or other activity; (5) phosphorylation status; and (6) interaction with other proteins via yeast two-hybrid analysis; (C) pathway analysis, such as placing a gene or gene product within a particular biochemical or signaling pathway based on its overexpression phenotype or by sequence homology with related genes; and (D) other analyses which may also be performed to determine or confirm the participation of the isolated gene and its product in a particular metabolic or signaling pathway, and help determine gene function.

EXPERIMENTAL

The present disclosure is described in further detail in the following examples, which are not in any way intended to limit the scope of the disclosure as claimed. The attached figures are meant to be considered as integral parts of the specification and description of the disclosure. The following examples are offered to illustrate, but not to limit the claimed disclosure In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); um (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); HCl (hydrochloric acid); aa (amino acid); by (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); CNPG (chloro-nitro-phenyl-beta-D-glucoside); CNP (2-chloro-4-nitrophenol); APB (acid-pretreated bagasse); PASC (phosphoric acid swollen cellulose) PCS (acid-pretreated corn stover); Pi or PI (performance index); HPLC (high pressure liquid chromatography); PAGE (polyacrylamide gel electrophoresis); PCR (polymerase chain reaction); RT-PCR (reverse transcription PCR); and SEL (site evaluation library).

Example 1

Assays

The following assays were used in the examples described below. Any deviations from the protocols provided below are indicated in the examples. In these experiments, a spectrophotometer was used to measure the absorbance of the products formed after the completion of the reactions.

A. Hexokinase Assay for Measurement of Residual Glucose

Residual glucose from *H. jecorina* culture supernatants expressing CBH2 variants was measured using a hexokinase assay. A volume of 5 μl of supernatant was added to 195 μl glucose hexokinase assay (Instrumentation Laboratory, Breda, Netherlands) in a 96-well microtiterplate (Costar Flat Bottom PS). The plates were incubated at room temperature for 15 min. Following incubation, the absorbance was measured at 340 nm OD. Supernatants of cultures expressing residual glucose were excluded from pooling for further studies.

B. HPLC Assay for Protein Content Determination

The concentration of CBH2 variant proteins from pooled culture supernatants was determined using an Agilent 1100 (Hewlett Packard) HPLC equipped with a Proswift RP 2H column (Dionex). Ten microliters of sample, mixed with 50 μl of 10% acetonitrile in filtered demineralized water was injected following equilibration of the HPLC column with 10% acetonitrile containing 0.01% trifluoroacetic acid. Compounds were eluted using a gradient of 10% to 30% acetonitrile from 0.3 min to 1 min, followed by a gradient of 30% to 65% from 1 min to 4 mins. Protein concentrations of CBH2 variants were determined from a calibration curve generated using purified wild-type CBH2 (6.25, 12.5, 25, 50 μg/ml). To calculate performance index ($P_i$ or PI), the ratio of the (average) total protein produced by a variant and (average) total protein produced by the wild-type at the same dose were averaged.

C. Specific Activity Determination by Phosphoric Acid Swollen Cellulose (PASC) Hydrolysis Assay Cellulose hydrolysis: Phosphoric acid swollen cellulose (PASC) was prepared from Avicel according to a published method (Walseth, Tappi 35:228, 1971; and Wood, Biochem J, 121:353-362, 1971). This material was diluted with buffer and water to achieve a 1% w/v mixture such that the final concentration of sodium acetate was 50 mM, pH 5.0. One hundred microliters of a 1% suspension of PASC in 50 mM sodium acetate buffer (pH5.0) was dispensed in a 96-well microtiterplate (Costar Flat Bottom PS). Ten microliters of a 5 mg/ml culture supernatant from a CBH2 deleted strain was added to the PASC, and 5, 10, 15, or 20 μl of pooled culture supernatants from *H. jecorina* cells expressing either wild-type CBH2 or CBH2 variants were added to it. Deletion of the CBH2 gene from *Hypocrea jecorina* (also referred to as *Trichoderma reesei*) is described in U.S. Pat. Nos. 5,861,271 and 5,650,322. Compensating volumes of acetate buffer were added to make up for differences in total volume. The microtiterplate was sealed and incubated in a thermostatted incubator at 50° C. under continuous shaking at 900 rpm. After two hours, the hydrolysis reaction was stopped by the addition of 100 μl glycine buffer, pH 10 to each well. To calculate performance index ($P_i$ or PI), the ratio of the (average) total sugar produced by a variant and (average) total sugar produced by the wild-type at the same dose were averaged. The hydrolysis reaction products were analyzed with the PAHBAH assay. PAHBAH assay: Aliquots of 150 μl of PAHBAH reducing sugar reagent (5% w/v p-hydroxybenzoic acid hydrazide (PAHBAH, Sigma # H9882, dissolved in 0.5 N HCl), (Lever, Anal Biochem, 47:273-279, 1972) were added to all wells of an empty microtiter plate. Ten microliters of the hydrolysis reaction supernatants were added to the PABAH reaction plate. All plates were sealed and incubated at 69° C. under continuous shaking of 900 rpm. After one hour the plates were placed on ice for five minutes and centrifuged at 720×g at room temperature for five minutes. Samples of 80 μL of the developed PAHBAH reaction mixtures were transferred to a fresh (read) plate and absorbance was measured at 410 nm in a spectrophotometer. A cellobiose standard was included as control. A dose response curve was generated for wild-type CBH2 protein.

D. Specific Activity Determination by Hydrolysis of Dilute Acid Pretreated Corn Stover (PCS)

Pretreated Corn Stover (PCS):

Corn stover was pretreated with 2% w/w $H_2SO_4$ as described (Schell et al., J Appl Biochem Biotechnol, 105:69-86, 2003) and followed by multiple washes with deionized water to obtain a paste having a pH of 4.5. Sodium acetate buffer (pH 5.0) was then added to a final concentration of 50 mM sodium acetate and, if necessary, this mixture was then titrated to pH 5.0 using 1N NaOH. The cellulase concentration in the reaction mixture was approximately 7%. Sixty-five microliters of this cellulose suspension was added per well to a 96-well microtiterplate (Nunc Flat Bottom PS). Ten microliters of a 5 mg/ml culture supernatant from a CBH2 deleted strain was added to the PCS, and 5, 10, 15, or 20 µl of pooled culture supernatants from *H. jecorina* cells expressing either wild-type CBH2 or CBH2 variants were added to it. Compensating volumes of acetate buffer were added to make up for differences in total volume. After sealing of the plate, the plates were placed in a thermostatted incubator at 50° C. under continuous shaking of 1300 rpm for 5 minutes. The plates were then incubated at 50° C. while shaking at 220 rpm under 80% humidity to prevent drying. After 7 days the plates were put on ice for 5 min and the hydrolysis reaction was stopped by the addition of 100 µl glycine buffer, pH 10 to each well. The hydrolysis reaction products were analyzed with the PAHBAH assay. To calculate performance index ($P_i$ or PI), the ratio of the (average) total sugar produced by a variant and (average) total sugar produced by the wild-type at the same dose were averaged. PAHBAH assay: Aliquots of 150 µl of PAHBAH reducing sugar reagent (5% w/v p-hydroxybenzoic acid hydrazide (PAHBAH, Sigma # H9882, dissolved in 0.5 N HCl), (Lever, Anal Biochem, 47:273-279, 1972) were added to all wells of an empty microtiter plate. Ten microliters of the hydrolysis reaction supernatants were added to the PABAH reaction plate. All plates were sealed and incubated at 69° C. under continuous shaking of 900 rpm. After one hour the plates were placed on ice for five minutes and centrifuged at 720×g at room temperature for five minutes. Samples of 80 µL of the developed PAHBAH reaction mixtures were transferred to a fresh (read) plate and absorbance was measured at 410 nm in a spectrophotometer. A cellobiose standard was included as control. A dose response curve was generated for wild-type CBH2 protein.

E. Specific Activity Determination by Hydrolysis of Ammonia Pretreated Corncob (CC)

Corn cob was ground to pass through a 0.9 mm screen then pretreated as described in Example 4 of patent application WO2006110901 (herein incorporated by reference for this method). Pretreated corn cob was used as a 7% cellulose suspension in 50 mM sodium acetate pH 5.0. Sixty-five microliters of the suspension was added per well to a 96-well microtiterplate (Nunc Flat Bottom PS). To each well, 20 µl of 3.4 mg/ml supernatant from a strain (Δegl1, Δegl2, Δcbh1, Δcbh2) supplemented with 0.23 mg/ml purified *T. reesei* beta-glucosidase 1 (Cel3A) was added. Twenty or forty microliters of pooled culture supernatants from *H. jecorina* cells expressing either wild-type CBH2 or CBH2 variants were added. Compensating volumes of acetate buffer were added to make up for differences in total volume. The plate was incubated at 50° C. while shaking at 220 rpm under 80% humidity to prevent drying. After 3 days the plate was put on ice for 5 min and 100 µl of 100 mM glycine pH 10.0 was added. After mixing, the plate was centrifuged at 3000 rpm for 5 min. A volume of 10 µl supernatant was diluted in 190 µl water. Twenty µl of the diluted solution was transferred to a new 96-well microtiterplate (Costar Flat Bottom PS) containing 100 µl ABTS glucose assay mixture (2.74 mg/ml 2,2' azino-bis(3-ethylbenzo-thiazoline-6-sulfonic acid, 0.333 U/ml horseradish peroxidase type VI, 1 U/ml glucose oxidase) and increase in $A_{420}$ was recorded in a microtiterplate spectrophotometer (Spectramax Plus 384, Molecular Devices). A range of glucose concentrations was included as a standard on each plate (6.25, 12.5, 25, 50, 100, 200, 400 mM). Assays were done in duplicate. A dose response curve was generated for the wild-type CBH2 by fitting the data with the Langmuir equation ($y=(x*a)/(x+b)$) and the activities of the CBH2 variants were divided by a calculated activity of wild-type CBH2 of the same plate to yield a performance index.

F. Stability of CBH2 Variants in Presence of Ethanol

The stability of wild-type CBH2 and CBH2 variants was tested in the presence of 4.5% ethanol (EtOH) at 49° C. Pooled culture supernatants (80 µL) of *H. jecorina* cells expressing CBH2 variants were added to a 96-well plate (Greiner V-bottom PS) containing 10 µl of 40.5% EtOH per well. The plates were sealed and incubated in a thermostatted incubator at 49° C. for 16 hours with shaking at 900 rpm. Following incubation, the plates were placed on ice for 5 minutes. Residual CBH2 activity was determined using the phosphoric acid swollen cellulose (PASC) hydrolysis assay as described above.

To calculate residual activity, the value of the product formed by the addition of 5, 10, and 20 µl of EtOH-incubated CBH2 to the residual activity PASC assay was divided by the value of the product formed by the addition of 5, 10, 15 and 20 µl of EtOH-free CBH2 to the PASC assay. The individual values of these four ratios were then averaged to give the average residual activity. To determine PI value for the variant, the value of average residual activity for the variants was then divided by the average of the residual activity values of the wild-type CBH2 controls.

G. Thermostability of CBH2 Variants

The thermostability of wild-type CBH2 and CBH2 variants was tested at 53° C. Pooled culture supernatant (80 uL) of *H. jecorina* cells expressing CBH2 variants were added to a 96-well plate (Greiner V-bottom PS). The plates were sealed and incubated in a thermostatted incubator at 53° C. for 16 hours with shaking at 900 rpm. Following incubation, the plates were placed on ice for 5 minutes. Residual CBH2 activity was determined using the phosphoric acid swollen cellulose (PASC) hydrolysis assay as described above.

To calculate residual activity, the value of the product formed by the addition of 5, 10, 15 and 20 µl of heat-treated CBH2 to the residual activity PASC assay was divided by the value of the product formed by the addition of 5, 10, 15 and 20 µl of unheated CBH2 to the PASC assay. The individual values of these four ratios were then averaged to give the average residual activity. To determine PI value for the variant, the value of average residual activity for the variants was then divided by the average of the residual activity values of the wild-type CBH2 controls.

Example 2

Generation of *Hypocrea jecorina* CBH2 Site Evaluation and Combinatorial Libraries The pTTTpyr-cbh2 plasmid containing the *Hypocrea jecorina* CBH2 protein encoding sequence (SEQ ID NO:1) was sent to BASEClear (Leiden, The Netherlands), GeneArt AG (Regensburg, Germany), and Sloning BioTechnology GmbH (Puchheim, Germany) for the generation of Site Evaluation Libraries (SELs). A map of pTTTpyr-cbh2 is provided in FIG. 3. A request was made to the vendors for the generation of positional libraries at each of the sites in *Hypocrea jecorina* CBH2 mature protein (SEQ ID NO:3) shown in Table 2-1. The amino acid sequence of CBH2 full length protein is shown in SEQ ID NO:2.

SEQ ID NO:1 sets forth the reference *Hypocrea jecorina* CBH2 coding DNA sequence:

```
atgattgtcggcattctcaccacgctggctacgctggccacactcgcagctagtgtgcctctagaggagcggcaagcttgctcaagcgt
ctggggccaatgtggtggccagaattggtcgggtccgacttgctgtgatccggaagcacatgcgtctactccaacgactattactccc
agtgtcttccccggcgctgcaagctcaagctcgtccacgcgcgccgcgtcgacgacttctcgagtatcccccacaacatcccggtcga
gctccgcgacgcctccacctggactactactaccagagtacctccagtcggatcgggaaccgctacgtattcaggcaacccttgttg
gggtcactccttgggccaatgcatattacgcctctgaagttagcagcctcgctattcctagcttgactggagccatggccactgctgcag
cagctgtcgcaaaggttccctcttttatgtggctagatactcttgacaagacccctctcatggagcaaaccttggccgacatccgcaccg
ccaacaagaatggcggtaactatgccggacagttgtggtgtatgacttgccggatcgcgattgcgctgcccttgcctcgaatggcgaa
tactctattgccgatggtggcgtcgccaaatataagaactatatcgacaccattcgtcaaattgtcgtggaatattccgatatccggaccct
cctggttattgagcctgactctcttgccaacctggtgaccaacctcggtactccaaagtgtgccaatgctcagtcagcctaccttgagtgc
atcaactacgccgtcacacagctgaaccttccaaatgttgcgatgtatttggacgctggccatgcaggatggcttggctggccggcaaa
ccaagacccggccgctcagctatttgcaaatgtttacaagaatgcatcgtctccgagagctcttcgcggattggcaaccaatgtcgcca
actacaacgggtggaacattaccagcccccatcgtacacgcaaggcaacgctgtctacaacgagaagctgtacatccacgctattg
gacctcttcttgccaatcacggctggtccaacgccttcttcatcactgatcaaggtcgatcgggaaagcagcctaccggacagcaaca
gtggggagactggtgcaatgtgatcggcaccggatttggtattcgcccatccgcaaacactggggactcgttgctggattcgtttgtctg
ggtcaagccaggcggcgagtgtgacggcaccagcgacagcagtgcgccacgatttgactcccactgtgcgctcccagatgccttgc
aaccggcgcctcaagctggtgcttggttccaagcctactttgtgcagcttctcacaaacgcaaacccatcgttcctgtaa.
```

SEQ ID NO:2 sets forth the *Hypocrea jecorina* CBH2 full length protein sequence:

MIVGILTTLATLATLAASVPLEERQACSSVWGQCGGQNWSGPTCCASGSTCVYSNDYYSQCL
PGAASSSSTRAASTTSRVSPTTSRSSSATPPPGSTTTRVPPVGSGTATYSGNPFVGVTPWA
NAYYASEVSSLAIPSLTGAMATAAAAVAKVPSFMWLDTLDKTPLMEQTLADIRTANKNGGNY
AGQGVVYDLPDRDCAALASNGEYSIADGGVAKYKNYIDTIRQIVVEYSDIRTLLVIEPDSLA
NLVTNLGTPKCANAQSAYLECINYAVTQLNLPNVAMYLDAGHAGWLGWPANQDPAAQLFANV
YKNASSPRALRGLATNVANYNGWNITSPPSYTQGNAVYNEKLYIHAIGPLLANHGWSNAFFI
TDQGRSGKQPTGQQQWGDWCNVIGTGFGIRPSANTGDSLLDSFVWVKPGGECDGTSDSSAPR
FSSHCALPDALQPAPQAGAWFQAYFVQLLTNANPSFL.

SEQ ID NO:3 sets forth the *Hypocrea jecorina* CBH2 mature protein sequence:

QACSSVWGQCGGQNWSGPTCCASGSTCVYSNDYYSQCLPGAASSSSSTRAASTTSRVSPTTS
RSSSATPPPGSTTTRVPPVGSGTATYSGNPFVGVTPWANAYYASEVSSLAIPSLTGAMATAA
AAVAKVPSFMWLDTLDKTPLMEQTLADIRTANKNGGNYAGQFVVYDLPDRDCAALASNGEYS
IADGGVAKYKNYIDTIRQIVVEYSDIRTLLVIEPDSLANLVTNLGTPKCANAQSAYLECINY
AVTQLNLPNVAMYLDAGHAGWLGWPANQDPAAQLFANVYKNASSPRALRGLATNVANYNGWN
ITSPPSYTQGNAVYNEKLYIHAIGPLLANHGWSNAFFITDQGRSGKQPTGQQQWGDWCNVIG
TGFGIRPSANTGDSLLDSFVWVKPGGECDGTSDSSAPRFDSHCALPDALQPAPQAGAWFQAY
FVQLLTNANPSFL.

For each of the 162 sites listed in Table 2-1, an average of 18 substitution variants were generated. The libraries were received as purified plasmids encoding CBH2 variant proteins.

TABLE 2-1

Selected Positions of the Mature CBH2 Protein

| Region | CBH2 Position |
|---|---|
| CBM | 5 |
| CBM | 18 |
| CBM | 19 |
| CBM | 28 |
| CBM | 30 |
| CBM | 32 |
| CBM | 35 |
| CBM | 38 |
| Linker | 63 |
| Linker | 77 |
| Linker | 79 |
| Linker | 80 |
| Catalytic | 89 |
| Catalytic | 94 |
| catalytic | 98 |
| catalytic | 100 |
| catalytic | 102 |
| catalytic | 103 |
| catalytic | 104 |
| catalytic | 105 |
| catalytic | 107 |
| catalytic | 111 |
| catalytic | 117 |
| catalytic | 119 |
| catalytic | 120 |
| catalytic | 121 |
| catalytic | 125 |
| catalytic | 126 |
| Catalytic | 129 |
| Catalytic | 133 |
| Catalytic | 134 |
| Catalytic | 137 |
| catalytic | 138 |
| catalytic | 139 |
| catalytic | 140 |
| catalytic | 141 |
| catalytic | 143 |
| catalytic | 144 |
| catalytic | 147 |
| catalytic | 150 |
| catalytic | 153 |
| catalytic | 154 |
| catalytic | 157 |
| catalytic | 158 |
| catalytic | 161 |
| catalytic | 162 |
| catalytic | 177 |
| catalytic | 178 |
| catalytic | 179 |
| catalytic | 180 |
| catalytic | 181 |
| catalytic | 182 |
| catalytic | 185 |
| catalytic | 186 |
| catalytic | 188 |
| catalytic | 189 |
| Catalytic | 190 |
| Catalytic | 191 |
| Catalytic | 192 |
| Catalytic | 193 |
| Catalytic | 194 |
| Catalytic | 196 |
| Catalytic | 197 |
| Catalytic | 201 |
| Catalytic | 203 |
| Catalytic | 204 |
| Catalytic | 206 |
| Catalytic | 207 |
| Catalytic | 210 |
| Catalytic | 214 |
| Catalytic | 225 |
| Catalytic | 226 |
| Catalytic | 228 |
| Catalytic | 229 |
| Catalytic | 230 |
| Catalytic | 231 |
| Catalytic | 232 |
| Catalytic | 233 |
| Catalytic | 234 |
| Catalytic | 236 |
| Catalytic | 237 |
| Catalytic | 239 |
| Catalytic | 240 |
| Catalytic | 243 |
| catalytic | 245 |
| catalytic | 247 |
| catalytic | 251 |
| catalytic | 252 |
| catalytic | 254 |
| catalytic | 258 |
| catalytic | 266 |
| catalytic | 267 |
| catalytic | 268 |
| catalytic | 272 |
| catalytic | 274 |
| catalytic | 275 |
| catalytic | 281 |
| catalytic | 285 |
| catalytic | 288 |
| catalytic | 289 |
| catalytic | 291 |
| catalytic | 292 |
| catalytic | 293 |
| catalytic | 294 |
| catalytic | 303 |
| catalytic | 304 |
| catalytic | 306 |
| catalytic | 307 |
| catalytic | 312 |
| catalytic | 313 |
| catalytic | 316 |
| catalytic | 319 |
| catalytic | 322 |
| catalytic | 323 |
| catalytic | 327 |
| catalytic | 328 |
| catalytic | 331 |
| catalytic | 338 |
| catalytic | 339 |
| catalytic | 340 |
| catalytic | 343 |
| catalytic | 344 |
| catalytic | 346 |
| catalytic | 356 |
| catalytic | 360 |
| catalytic | 361 |
| catalytic | 362 |
| catalytic | 363 |
| catalytic | 364 |
| catalytic | 365 |
| catalytic | 371 |
| catalytic | 378 |
| catalytic | 380 |
| catalytic | 381 |
| catalytic | 382 |
| catalytic | 384 |
| catalytic | 386 |
| catalytic | 394 |
| catalytic | 396 |
| catalytic | 399 |
| Catalytic | 400 |
| Catalytic | 405 |
| Catalytic | 406 |
| Catalytic | 407 |
| Catalytic | 410 |
| Catalytic | 413 |
| Catalytic | 414 |
| Catalytic | 416 |
| Catalytic | 417 |
| Catalytic | 422 |

TABLE 2-1-continued

Selected Positions of the Mature CBH2 Protein

| Region | CBH2 Position |
|---|---|
| Catalytic | 426 |
| Catalytic | 427 |
| Catalytic | 429 |
| Catalytic | 431 |
| Catalytic | 433 |
| Catalytic | 436 |
| Catalytic | 440 |
| Catalytic | 441 |
| Catalytic | 443 |
| Catalytic | 444 |
| Catalytic | 445 |
| Catalytic | 447 |

Four synthetic CBH2 combinatorial libraries were also produced by Sloning Biotechnology GmbH (Puchheim, Germany) and BaseClear (Leiden, The Netherlands). Tables 2-2 to 2-5 list the substitutions that could be present in members of the synthetic CBH2 combinatorial libraries (numbered according to the CBH2 mature amino acid sequence).

TABLE 2-2

CBH2 Combinatorial Library 1 Design (RCL 1)

| Targeted Position | Wild-Type Residue | Substitution |
|---|---|---|
| 111 | L | L, S |
| 144 | L | L, Q, W |
| 154 | T | T, C, V |
| 162 | Y | Y, N |
| 410 | R | R, S |
| 413 | S | S, W, Y |

TABLE 2-3

CBH2 Combinatorial Library 2 Design (RCL 2)

| Targeted Position | Wild-Type Residue | Substitution |
|---|---|---|
| 98 | P | P, L |
| 194 | K | K, C, E |
| 313 | S | S, T |
| 316 | S | S, P |
| 384 | G | G, C, Q |
| 443 | N | N, I |

TABLE 2-4

CBH2 Combinatorial Library 3 Design (RCL 3)

| Targeted Position | Wild-Type Residue | Substitution |
|---|---|---|
| 153 | R | R, Q |
| 161 | N | N, A, W |
| 203 | R | R, H |
| 233 | P | P, D |
| 422 | Q | Q, V |
| 444 | P | P, Q |

TABLE 2-5

CBH2 Combinatorial Library 4 Design (RCL 4)

| Targeted Position | Wild-Type Residue | Substitution |
|---|---|---|
| 98 | P | P, L |
| 111 | L | L, S |
| 144 | L | L, W |
| 313 | S | S, T |
| 316 | S | S, P |
| 413 | S | S, W |
| 422 | Q | Q, V |

Production of CBH2 Variant Proteins

Purified pTTTpyr-cbh2 plasmids ($p_{cbh1}$, $Amp^R$, Acetamide$^R$) containing open reading frames encoding CBH2 variant sequences were obtained from the vendors specified above. Protoplasts of a quad-deleted *H. jecorina* strain (Δegl1, Δegl2, Δcbh1 Δcbh2) were transformed with the pTTTpyrG constructs and grown on selective agar containing acetamide at 28° C. for 7 days as described (WO 2009/048488). Genes encoding cellobiohydrolase I (CBHI, Cel7a), cellobiohydrolase II (CBHII, Cel6a), endoglucanase I (EGI, Cel7b), and endoglucanase II (EGII, Cel5a) have been inactivated in the quad-deleted strain. Spores were harvested, replated on acetamide agar, and incubated at 28° C. for 7 days. In addition, spores were harvested in 15% glycerol and stored at −20° C. for further use. For CBH2 variant protein production, a volume of 10 µl spore suspension was added to 200 µl glycine minimal medium supplemented with 2% glucose/sophorose mixture in a PVDF filter plate: 6.0 g/L glycine, 4.7 g/L $(NH_4)_2SO_4$; 5.0 g/L $KH_2PO_4$; 1.0 g/L $MgSO_4.7H_2O$; 33.0 g/L PIPPS; pH 5.5; with post sterile addition of ~2% glucose/sophorose mixture as the carbon source, 10 ml/L of 100 g/L of $CaCl_{2, 2.5}$ ml/L of *T. reesei* trace elements (400×): 175 g/L Citric acid anhydrous; 200 g/L $FeSO_4.7H_2O$; 16 g/L $ZnSO_4.7H_2O$; 3.2 g/L $CuSO_4.5H_2O$; 1.4 g/L $MnSO_4.H_2O$; 0.8 g/L $H_3BO_3$. Each CBH2 variant was grown in quadruplicate. After sealing the plate with an oxygen permeable membrane, the plates were incubated at 28° C. for 6 days, while shaking at 220 rpm. Supernatant was harvested by transferring the culture medium to a microtiter plate under low pressure and tested for residual glucose using the hexokinase assay as described in Example 1.

Example 3

Expression, Activity and Stability of CBH2 Variants

*H. jecorina* CBH2 SEL and combinatorial variant proteins were tested various properties of interest. In particular, the cellulase variants were tested for protein expression using the HPLC assay (HPLC), specific activity using the PASC hydrolysis assay (Act. PASC) and the PCS hydrolysis assay (Act. PCS), stability in the presence of ethanol (EtOH ratio) and thermostability (heat ratio) as described in Example 1. Combinatorial variants were also tested for specific activity by hydrolysis of ammonia pretreated corncob (Sp. Act. CC) as described in Example 1. Performance data for CBH2 SEL variants are shown in Table 3-1, and performance data for the CBH2 combinatorial variants are shown in Table 3-2. Rows of Table 3-2 lacking performance data correspond to CBH2 combinatorial variants that were not expressed in initial tests.

Performance index (Pi or PI) is the ratio of performance of the variant to the parent or reference cellulase. Various terms set forth below are used to describe the mutation: up mutations have a Pi>1; neutral mutations have a Pi>0.5, non-deleterious mutations have a Pi>0.05; deleterious mutations have a Pi=0.05; combinable mutations are those mutations for which the variant has PI values=0.5 for at least one property, and >0.05 for all properties. Combinable mutations are mutations that can be combined to deliver proteins with appropriate PIs for one or more desired properties. Positions at which mutations occur are classed as follows: Non-restrictive positions have ≥20% neutral mutations for at least one property; and Restrictive positions have <20% neutral mutations for activity and stability.

This data may be used to engineer any CBH. Even if the CBH to be engineered has an amino acid different from that of CBH2 at a particular position, this data may be used to find a substitution that will alter the desired properties by identifying the best choice substitution, including substitution to the CBH2 wild type amino acid Table 3-1 shows performance index values (Pi or PI) for 2,828 variants of *Hypocrea jecorina* CBH2 at 162 positions. Performance indices less than or equal to 0.05 were fixed to 0.05 and indicated in bold italics in the table.

TABLE 3-1

Performance Index Values for CBH2 Variants

| Position | Variant | HPLC | PASC Sp. Ac. | PCS Sp. Ac. | Res. EtOH | Res. Heat |
|---|---|---|---|---|---|---|
| 5 | S005A | 1.73 | 1.06 | 1.01 | 0.99 | 0.95 |
| 5 | S005C | 0.34 | 1.03 | 0.92 | 0.95 | 0.76 |
| 5 | S005D | 0.08 | 0.69 | 0.44 | 1.87 | 2.70 |
| 5 | S005E | 0.82 | 1.10 | 1.00 | 0.85 | 0.63 |
| 5 | S005F | 0.35 | 2.69 | 0.87 | 0.99 | 0.98 |
| 5 | S005G | 0.73 | 1.06 | 0.84 | 0.97 | 0.89 |
| 5 | S005H | 0.14 | 0.77 | 0.50 | 1.06 | 0.68 |
| 5 | S005I | 1.35 | 0.57 | 0.54 | 1.77 | 1.07 |
| 5 | S005K | 0.52 | 0.98 | 0.68 | 0.97 | 0.94 |
| 5 | S005L | 1.25 | 1.10 | 0.99 | 0.99 | 0.96 |
| 5 | S005M | 0.44 | 1.11 | 0.82 | 0.96 | 0.89 |
| 5 | S005N | 0.28 | 0.74 | 0.41 | 1.78 | 3.67 |
| 5 | S005P | 0.46 | 0.66 | 0.63 | 1.46 | 1.25 |
| 5 | S005Q | 0.72 | 1.17 | 0.98 | 0.94 | 0.92 |
| 5 | S005R | 0.36 | 1.01 | 0.73 | 0.89 | 0.82 |
| 5 | S005T | 0.28 | 1.05 | 0.73 | 0.98 | 0.84 |
| 5 | S005V | 0.40 | 1.15 | 0.79 | 0.91 | 0.85 |
| 5 | S005W | 0.61 | 1.11 | 1.00 | 0.95 | 0.87 |
| 5 | S005Y | 0.98 | 1.08 | 0.84 | 0.95 | 0.96 |
| 18 | P18A | 0.57 | 1.11 | 1.05 | 0.94 | 0.90 |
| 18 | P18C | 0.16 | 0.63 | 0.48 | 1.14 | 1.09 |
| 18 | P18D | 0.20 | 0.66 | 0.93 | 0.52 | 1.20 |
| 18 | P18E | 0.51 | 0.87 | 0.42 | 1.01 | 1.09 |
| 18 | P18F | 0.22 | 0.69 | 0.37 | 1.02 | 0.92 |
| 18 | P18G | 0.88 | 1.03 | 0.57 | 0.31 | 0.18 |
| 18 | P18H | 0.88 | 1.08 | 0.89 | 0.92 | 0.98 |
| 18 | P18I | 0.77 | 1.00 | 0.89 | 0.88 | 0.90 |
| 18 | P18K | 0.24 | 0.50 | 0.39 | 2.14 | 2.11 |
| 18 | P18L | 0.56 | 1.14 | 0.77 | 0.91 | 0.91 |
| 18 | P18M | 1.38 | 0.98 | 0.84 | 0.97 | 1.01 |
| 18 | P18N | 0.24 | 0.46 | 0.35 | 4.62 | 7.95 |
| 18 | P18Q | 0.12 | 0.28 | *0.05* | 10.15 | 19.36 |
| 18 | P18R | 0.39 | 0.98 | 0.75 | 0.93 | 0.81 |
| 18 | P18S | 0.88 | 1.12 | 0.86 | 0.94 | 1.02 |
| 18 | P18T | 0.46 | 0.69 | 0.45 | 0.85 | 1.14 |
| 18 | P18V | 0.62 | 0.95 | 0.93 | 0.93 | 0.89 |
| 18 | P18W | 0.70 | 1.09 | 0.98 | 0.92 | 0.93 |
| 18 | P18Y | 0.91 | 1.08 | 0.91 | 0.91 | 0.95 |
| 19 | T19A | 0.96 | 1.06 | 0.96 | 0.89 | 0.87 |
| 19 | T19C | 0.08 | 0.12 | *0.05* | 3.22 | 3.56 |
| 19 | T19E | 0.68 | 1.17 | 0.87 | 0.88 | 0.89 |
| 19 | T19F | 0.75 | 1.15 | 0.91 | 0.92 | 0.95 |
| 19 | T19G | 1.92 | 1.03 | 0.99 | 0.94 | 1.00 |
| 19 | T19I | 1.08 | 1.19 | 1.01 | 0.85 | 0.95 |
| 19 | T19K | 1.01 | 1.25 | 1.00 | 0.91 | 0.94 |
| 19 | T19L | 0.45 | 1.18 | 0.92 | 0.83 | 0.85 |
| 19 | T19M | 1.71 | 1.04 | 0.80 | 0.89 | 1.04 |
| 19 | T19N | 0.11 | 0.20 | 0.07 | 4.18 | 10.48 |
| 19 | T19P | 0.77 | 1.08 | 1.08 | 0.87 | 0.98 |
| 19 | T19Q | 0.67 | 1.07 | 0.84 | 0.92 | 0.95 |
| 19 | T19R | 1.11 | 1.08 | 0.89 | 0.91 | 1.04 |
| 19 | T19S | 0.81 | 1.13 | 0.84 | 0.87 | 0.95 |
| 19 | T19V | 0.09 | 0.18 | 0.09 | 13.65 | 56.16 |
| 19 | T19W | 0.25 | 0.51 | 0.47 | 0.77 | 0.59 |
| 19 | T19Y | 0.69 | 1.08 | 0.97 | 0.85 | 0.92 |
| 28 | V28A | 0.55 | 0.97 | 1.10 | 0.99 | 0.94 |
| 28 | V28C | 0.82 | 1.00 | 0.96 | 0.92 | 0.71 |
| 28 | V28D | 0.11 | *0.05* | 0.29 | 1.43 | 6.68 |
| 28 | V28E | 0.43 | 0.90 | 0.75 | 0.96 | 0.94 |
| 28 | V28F | 0.47 | 0.93 | 0.71 | 0.95 | 0.95 |
| 28 | V28G | 0.88 | 0.92 | 0.84 | 0.95 | 0.99 |
| 28 | V28H | 0.08 | *0.05* | 0.15 | 5.35 | 18.58 |
| 28 | V28I | 1.01 | 1.02 | 0.75 | 1.00 | 1.00 |
| 28 | V28K | 0.67 | 1.03 | 0.88 | 0.96 | 0.96 |
| 28 | V28L | 0.86 | 1.02 | 0.83 | 0.92 | 1.05 |
| 28 | V28M | 0.71 | 1.02 | 0.71 | 0.95 | 0.98 |
| 28 | V28N | 0.72 | 0.53 | 0.65 | 0.81 | 0.97 |
| 28 | V28P | 0.80 | 0.52 | 0.72 | 0.83 | 0.93 |
| 28 | V28Q | 0.56 | 0.97 | 0.73 | 0.95 | 0.98 |
| 28 | V28R | 0.76 | 1.01 | 0.74 | 0.95 | 0.98 |
| 28 | V28S | 0.52 | 0.96 | 0.88 | 0.97 | 0.98 |
| 28 | V28T | 0.52 | 1.03 | 0.84 | 1.02 | 1.00 |
| 28 | V28W | 0.42 | 0.84 | 0.75 | 0.95 | 0.90 |
| 28 | V28Y | 0.51 | 0.95 | 0.83 | 0.95 | 0.90 |
| 30 | S30A | 1.09 | 1.06 | 1.01 | 1.08 | 1.06 |
| 30 | S30C | 1.26 | 0.99 | 0.96 | 1.08 | 1.09 |
| 30 | S30D | 0.30 | 0.57 | 0.50 | 0.57 | 0.94 |
| 30 | S30E | 0.14 | 0.44 | 0.25 | 0.69 | 1.00 |
| 30 | S30F | 0.58 | 0.91 | 0.67 | 0.96 | 0.97 |
| 30 | S30G | 0.70 | 0.98 | 0.72 | 1.10 | 1.02 |
| 30 | S30H | 0.30 | 0.61 | 0.56 | 0.84 | 2.68 |
| 30 | S30I | 0.66 | 1.02 | 0.72 | 1.03 | 1.02 |
| 30 | S30K | 1.31 | 0.94 | 0.70 | 1.12 | 1.16 |
| 30 | S30L | 0.46 | 0.93 | 0.44 | 0.93 | 0.85 |
| 30 | S30M | 0.81 | 1.03 | 0.89 | 1.14 | 1.00 |
| 30 | S30N | 0.19 | 0.57 | 0.42 | 0.95 | 1.12 |
| 30 | S30P | 0.31 | 0.42 | 0.50 | 0.88 | 1.02 |
| 30 | S30Q | 0.63 | 0.65 | 0.43 | 0.85 | 1.65 |
| 30 | S30R | 0.50 | 0.67 | 0.45 | 1.11 | 1.37 |
| 30 | S30T | 0.81 | 0.99 | 0.76 | 1.09 | 1.05 |
| 30 | S30V | 0.76 | 1.04 | 0.73 | 1.02 | 1.02 |
| 30 | S30W | 0.41 | 0.92 | 0.59 | 0.93 | 0.78 |
| 30 | S30Y | 0.21 | 0.52 | 0.40 | 1.11 | 1.14 |
| 32 | D32A | 0.51 | 1.10 | 1.32 | 1.00 | 1.10 |
| 32 | D32C | 0.24 | 0.93 | 1.02 | 0.92 | 0.89 |
| 32 | D32E | 0.44 | 1.31 | 0.42 | 0.44 | 0.47 |
| 32 | D32F | 0.18 | 0.65 | 0.45 | 0.77 | 0.93 |
| 32 | D32G | 0.32 | 1.17 | 1.08 | 0.97 | 0.92 |
| 32 | D32H | 0.41 | 0.65 | 0.63 | 0.78 | 1.12 |
| 32 | D32I | 0.64 | 1.10 | 1.06 | 0.99 | 1.00 |
| 32 | D32K | 0.39 | 1.00 | 0.77 | 0.95 | 0.93 |
| 32 | D32L | 0.43 | 1.10 | 1.17 | 0.94 | 1.02 |
| 32 | D32M | 0.37 | 1.14 | 0.96 | 0.90 | 0.91 |
| 32 | D32N | 0.61 | 0.73 | 0.55 | 0.94 | 1.12 |
| 32 | D32P | 0.49 | 0.99 | 0.80 | 0.59 | 0.56 |
| 32 | D32Q | 0.65 | 1.11 | 1.00 | 0.94 | 0.97 |
| 32 | D32R | 0.28 | 1.05 | 0.78 | 0.87 | 0.87 |
| 32 | D32S | 0.31 | 0.91 | 0.78 | 0.91 | 0.87 |
| 32 | D32T | 0.38 | 0.74 | 0.67 | 1.00 | 1.10 |
| 32 | D32V | 0.49 | 1.01 | 0.96 | 1.02 | 1.04 |
| 32 | D32W | 0.69 | 0.91 | 0.93 | 0.97 | 0.99 |
| 32 | D32Y | 0.82 | 1.02 | 1.04 | 1.00 | 1.03 |
| 35 | S35A | 0.86 | 0.92 | 0.87 | 1.05 | 0.92 |
| 35 | S35C | 0.59 | 0.84 | 0.99 | 0.92 | 0.68 |
| 35 | S35E | 0.29 | 0.91 | 0.98 | 1.06 | 0.94 |
| 35 | S35F | 0.08 | 1.17 | 0.90 | 1.02 | 0.89 |
| 35 | S35G | 0.67 | 0.88 | 0.76 | 1.03 | 0.93 |
| 35 | S35I | 0.58 | 0.61 | 0.65 | 0.78 | 0.70 |
| 35 | S35L | 0.37 | 0.93 | 1.02 | 0.92 | 0.85 |
| 35 | S35M | 0.57 | 0.95 | 1.01 | 0.96 | 0.87 |
| 35 | S35N | 0.42 | 0.88 | 1.04 | 1.00 | 1.01 |
| 35 | S35P | 0.55 | 0.48 | 0.74 | 0.82 | 0.86 |
| 35 | S35Q | 0.53 | 0.90 | 0.88 | 0.98 | 0.94 |
| 35 | S35R | 0.38 | 0.91 | 0.99 | 0.87 | 0.83 |
| 35 | S35V | 0.89 | 0.65 | 0.57 | 0.86 | 0.93 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 35 | S35W | 1.60 | 1.01 | 1.03 | 1.10 | 1.05 |
| 35 | S35Y | 0.64 | 0.97 | 0.85 | 0.87 | 0.79 |
| 38 | L38A | 0.64 | 0.86 | 0.96 | 1.06 | 1.00 |
| 38 | L38E | 0.65 | 0.94 | 0.98 | 0.95 | 1.02 |
| 38 | L38P | 0.22 | 0.23 | 0.42 | 0.91 | 0.72 |
| 38 | L38S | 0.53 | 0.84 | 0.71 | 0.99 | 0.91 |
| 38 | L38W | 0.30 | 0.51 | 0.77 | 0.84 | 0.53 |
| 63 | R63A | 1.21 | 1.03 | 0.94 | 0.97 | 1.00 |
| 63 | R63C | 1.47 | 1.02 | 1.05 | 0.96 | 1.06 |
| 63 | R63D | 0.12 | 0.11 | 0.19 | 0.05 | 1.02 |
| 63 | R63E | 0.88 | 0.94 | 0.98 | 0.96 | 1.05 |
| 63 | R63F | 0.91 | 0.95 | 0.85 | 0.94 | 1.09 |
| 63 | R63G | 0.71 | 0.96 | 0.95 | 1.08 | 1.20 |
| 63 | R63H | 0.68 | 0.94 | 0.92 | 1.04 | 1.00 |
| 63 | R63I | 0.81 | 0.93 | 1.11 | 1.03 | 1.09 |
| 63 | R63K | 0.23 | 0.53 | 0.77 | 0.81 | 0.91 |
| 63 | R63L | 0.94 | 0.96 | 0.91 | 1.06 | 1.29 |
| 63 | R63M | 1.22 | 0.99 | 1.10 | 1.05 | 1.09 |
| 63 | R63N | 1.23 | 1.02 | 1.11 | 1.03 | 1.07 |
| 63 | R63P | 0.96 | 0.99 | 1.17 | 1.04 | 1.09 |
| 63 | R63Q | 0.87 | 0.99 | 1.01 | 0.99 | 1.13 |
| 63 | R63S | 0.59 | 0.92 | 1.09 | 1.00 | 0.94 |
| 63 | R63T | 0.43 | 0.87 | 0.94 | 0.91 | 0.84 |
| 63 | R63V | 1.00 | 0.99 | 0.89 | 1.03 | 1.06 |
| 63 | R63W | 0.98 | 0.97 | 0.91 | 1.08 | 1.10 |
| 63 | R63Y | 1.29 | 1.03 | 0.99 | 1.06 | 1.07 |
| 77 | R77F | 0.25 | 0.81 | 0.58 | 0.92 | 0.81 |
| 77 | R77G | 0.41 | 1.02 | 0.75 | 1.00 | 0.93 |
| 77 | R77L | 0.14 | 0.53 | 0.36 | 0.94 | 0.79 |
| 77 | R77N | 0.83 | 0.99 | 0.87 | 1.00 | 1.02 |
| 79 | P79C | 0.96 | 1.09 | 0.93 | 1.15 | 0.92 |
| 79 | P79D | 0.33 | 1.08 | 1.17 | 1.02 | 0.94 |
| 79 | P79E | 0.64 | 1.11 | 0.96 | 1.05 | 0.98 |
| 79 | P79F | 0.27 | 0.79 | 0.74 | 1.00 | 0.91 |
| 79 | P79H | 0.21 | 0.76 | 0.68 | 0.92 | 0.77 |
| 79 | P79I | 0.37 | 0.91 | 0.98 | 0.93 | 0.93 |
| 79 | P79K | 0.16 | 1.09 | 0.62 | 0.79 | 0.70 |
| 79 | P79L | 0.66 | 1.12 | 0.97 | 1.10 | 1.09 |
| 79 | P79M | 0.74 | 0.94 | 1.04 | 1.06 | 1.06 |
| 79 | P79N | 0.74 | 1.10 | 0.94 | 1.04 | 0.96 |
| 79 | P79R | 0.41 | 1.11 | 0.86 | 1.04 | 0.97 |
| 79 | P79S | 0.89 | 1.04 | 0.86 | 1.20 | 1.02 |
| 79 | P79V | 0.32 | 0.87 | 0.84 | 0.97 | 0.99 |
| 79 | P79W | 0.53 | 1.02 | 1.09 | 1.05 | 0.98 |
| 80 | P80C | 0.85 | 1.11 | 1.04 | 1.14 | 0.92 |
| 80 | P80D | 1.19 | 1.07 | 1.14 | 1.26 | 1.08 |
| 80 | P80E | 0.41 | 0.88 | 0.86 | 1.14 | 0.88 |
| 80 | P80F | 0.25 | 1.07 | 0.85 | 0.97 | 0.92 |
| 80 | P80G | 0.87 | 1.10 | 1.05 | 1.14 | 0.97 |
| 80 | P80H | 0.33 | 0.83 | 0.83 | 1.11 | 0.90 |
| 80 | P80I | 0.30 | 0.84 | 0.74 | 0.90 | 0.88 |
| 80 | P80K | 0.52 | 0.71 | 0.53 | 1.06 | 1.01 |
| 80 | P80L | 1.23 | 1.09 | 0.96 | 1.09 | 1.05 |
| 80 | P80Q | 0.77 | 1.10 | 0.87 | 1.06 | 1.05 |
| 80 | P80R | 0.25 | 1.04 | 1.23 | 1.06 | 0.96 |
| 80 | P80T | 0.90 | 0.88 | 0.99 | 1.94 | 1.80 |
| 80 | P80V | 0.36 | 0.99 | 1.06 | 0.93 | 0.92 |
| 80 | P80W | 1.13 | 1.01 | 0.95 | 1.21 | 1.08 |
| 89 | S89A | 0.19 | 0.70 | 1.04 | 0.73 | 0.50 |
| 89 | S89C | 0.27 | 0.82 | 1.09 | 0.83 | 0.90 |
| 89 | S89D | 1.45 | 1.06 | 1.13 | 1.05 | 1.02 |
| 89 | S89E | 0.28 | 0.87 | 0.87 | 0.94 | 0.74 |
| 89 | S89F | 0.26 | 0.79 | 0.79 | 0.97 | 0.84 |
| 89 | S89G | 0.27 | 0.82 | 0.82 | 0.88 | 0.78 |
| 89 | S89H | 1.57 | 1.03 | 0.86 | 1.02 | 1.04 |
| 89 | S89I | 0.51 | 1.01 | 0.92 | 1.03 | 1.07 |
| 89 | S89K | 0.51 | 0.93 | 0.76 | 0.99 | 0.96 |
| 89 | S89L | 0.69 | 1.02 | 0.97 | 0.90 | 0.87 |
| 89 | S89M | 0.22 | 0.77 | 1.02 | 0.85 | 0.92 |
| 89 | S89N | 0.28 | 0.85 | 0.68 | 0.83 | 0.88 |
| 89 | S89P | 0.64 | 0.98 | 1.18 | 0.99 | 0.92 |
| 89 | S89Q | 0.51 | 0.80 | 0.53 | 0.98 | 1.15 |
| 89 | S89R | 0.57 | 1.00 | 0.83 | 1.03 | 0.94 |
| 89 | S89T | 0.88 | 1.03 | 0.95 | 1.02 | 1.03 |
| 89 | S89V | 0.16 | 0.65 | 1.02 | 0.73 | 0.61 |
| 89 | S89W | 0.82 | 1.03 | 1.02 | 0.92 | 0.79 |
| 89 | S89Y | 0.70 | 1.02 | 0.97 | 1.00 | 1.00 |
| 94 | V94A | 1.18 | 0.98 | 1.45 | 1.11 | 1.06 |
| 94 | V94C | 0.38 | 0.79 | 0.66 | 0.97 | 0.76 |
| 94 | V94D | 1.13 | 0.99 | 0.92 | 1.10 | 0.97 |
| 94 | V94F | 0.28 | 0.73 | 0.55 | 0.89 | 0.89 |
| 94 | V94G | 0.25 | 0.68 | 0.43 | 0.93 | 0.79 |
| 94 | V94H | 0.23 | 0.64 | 0.52 | 1.03 | 0.97 |
| 94 | V94K | 0.50 | 0.98 | 0.73 | 1.07 | 1.08 |
| 94 | V94P | 0.13 | 0.14 | 0.17 | 0.16 | 1.34 |
| 94 | V94R | 0.22 | 0.90 | 0.58 | 0.76 | 1.03 |
| 94 | V94S | 0.24 | 0.76 | 0.44 | 0.85 | 0.77 |
| 94 | V94T | 0.22 | 0.80 | 0.37 | 0.71 | 0.86 |
| 98 | P98A | 0.90 | 1.09 | 0.94 | 1.01 | 0.99 |
| 98 | P98C | 0.53 | 1.01 | 1.23 | 1.06 | 1.03 |
| 98 | P98D | 0.28 | 0.26 | 0.35 | 1.32 | 2.58 |
| 98 | P98E | 0.30 | 0.54 | 0.35 | 0.99 | 1.28 |
| 98 | P98F | 0.30 | 0.77 | 0.79 | 0.67 | 0.75 |
| 98 | P98G | 0.61 | 0.97 | 0.71 | 0.92 | 1.00 |
| 98 | P98H | 0.29 | 0.67 | 0.35 | 0.62 | 0.87 |
| 98 | P98I | 0.51 | 1.05 | 0.84 | 1.15 | 0.88 |
| 98 | P98K | 0.29 | 0.30 | 0.23 | 1.06 | 2.07 |
| 98 | P98L | 0.80 | 1.12 | 0.89 | 1.16 | 1.45 |
| 98 | P98M | 0.58 | 1.03 | 0.91 | 1.05 | 0.92 |
| 98 | P98N | 0.33 | 0.42 | 0.38 | 1.00 | 1.12 |
| 98 | P98Q | 0.50 | 1.03 | 0.90 | 1.14 | 1.46 |
| 98 | P98R | 0.28 | 0.30 | 0.05 | 0.93 | 1.55 |
| 98 | P98S | 0.32 | 0.27 | 0.16 | 1.23 | 1.36 |
| 98 | P98T | 0.19 | 0.32 | 0.05 | 1.31 | 1.98 |
| 98 | P98V | 0.60 | 1.06 | 1.08 | 1.05 | 1.08 |
| 98 | P98W | 0.37 | 0.38 | 0.34 | 0.82 | 1.01 |
| 98 | P98Y | 0.25 | 0.65 | 0.19 | 0.87 | 0.93 |
| 100 | A100C | 0.37 | 0.91 | 0.83 | 0.71 | 0.61 |
| 100 | A100D | 0.14 | 0.38 | 0.27 | 0.09 | 0.39 |
| 100 | A100E | 0.18 | 0.67 | 0.48 | 0.51 | 0.22 |
| 100 | A100F | 0.11 | 0.34 | 0.27 | 0.42 | 0.74 |
| 100 | A100G | 0.26 | 0.79 | 0.54 | 0.36 | 0.18 |
| 100 | A100H | 0.11 | 0.09 | 0.14 | 1.53 | 0.51 |
| 100 | A100K | 0.16 | 0.97 | 0.59 | 0.71 | 0.65 |
| 100 | A100L | 0.25 | 0.78 | 0.49 | 0.62 | 0.42 |
| 100 | A100N | 0.31 | 0.92 | 0.70 | 0.53 | 0.26 |
| 100 | A100P | 0.14 | 0.65 | 0.53 | 0.63 | 0.44 |
| 100 | A100R | 0.14 | 0.37 | 0.26 | 0.53 | 0.81 |
| 100 | A100S | 0.33 | 0.90 | 0.64 | 0.68 | 0.48 |
| 100 | A100T | 0.39 | 0.87 | 0.70 | 0.86 | 0.89 |
| 100 | A100V | 0.13 | 0.77 | 0.48 | 0.93 | 0.61 |
| 100 | A100W | 0.59 | 0.92 | 0.60 | 0.62 | 0.29 |
| 100 | A100Y | 0.25 | 0.65 | 0.62 | 0.81 | 0.42 |
| 102 | A102C | 0.11 | 0.05 | 0.20 | 1.02 | 5.64 |
| 102 | A102D | 0.60 | 0.98 | 1.01 | 0.82 | 0.64 |
| 102 | A102E | 0.77 | 0.98 | 0.69 | 1.01 | 1.01 |
| 102 | A102F | 0.57 | 0.97 | 0.86 | 0.91 | 0.81 |
| 102 | A102G | 0.55 | 1.00 | 0.90 | 0.93 | 0.89 |
| 102 | A102H | 0.96 | 1.05 | 0.87 | 0.91 | 0.96 |
| 102 | A102I | 0.43 | 0.88 | 0.73 | 0.77 | 0.75 |
| 102 | A102K | 0.50 | 0.97 | 0.91 | 0.95 | 1.02 |
| 102 | A102L | 0.58 | 0.99 | 0.82 | 0.91 | 0.86 |
| 102 | A102M | 0.56 | 0.94 | 0.75 | 0.93 | 0.87 |
| 102 | A102N | 0.62 | 1.01 | 0.75 | 0.93 | 0.92 |
| 102 | A102P | 0.45 | 0.87 | 0.63 | 0.80 | 0.50 |
| 102 | A102Q | 0.10 | 0.09 | 0.14 | 1.47 | 2.14 |
| 102 | A102R | 0.55 | 1.02 | 0.83 | 0.99 | 1.02 |
| 102 | A102S | 0.51 | 0.99 | 0.84 | 0.95 | 0.96 |
| 102 | A102T | 0.49 | 0.96 | 0.81 | 0.69 | 0.54 |
| 102 | A102V | 0.49 | 0.95 | 0.74 | 0.73 | 0.55 |
| 102 | A102W | 0.11 | 0.06 | 0.05 | 44.39 | 31.37 |
| 102 | A102Y | 0.55 | 0.97 | 0.87 | 0.84 | 0.72 |
| 103 | Y103A | 0.89 | 1.01 | 1.02 | 0.64 | 0.45 |
| 103 | Y103C | 0.38 | 0.76 | 0.55 | 0.63 | 0.64 |
| 103 | Y103D | 0.62 | 0.97 | 0.40 | 0.21 | 0.10 |
| 103 | Y103E | 0.90 | 0.95 | 0.92 | 0.92 | 0.61 |
| 103 | Y103F | 1.32 | 0.93 | 0.88 | 1.01 | 0.98 |
| 103 | Y103G | 0.54 | 0.85 | 0.50 | 0.47 | 0.12 |
| 103 | Y103H | 1.18 | 0.96 | 0.98 | 1.12 | 1.15 |
| 103 | Y103I | 0.09 | 0.12 | 0.05 | 0.31 | 1.44 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 103 | Y103K | 0.83 | 0.90 | 0.54 | 0.96 | 0.99 |
| 103 | Y103L | 1.03 | 1.02 | 0.94 | 0.88 | 0.66 |
| 103 | Y103M | 0.08 | 0.09 | 0.09 | 0.53 | 0.91 |
| 103 | Y103P | 0.51 | 0.85 | 0.47 | 0.44 | 0.21 |
| 103 | Y103Q | 0.81 | 0.96 | 0.48 | 0.90 | 0.66 |
| 103 | Y103R | 0.82 | 0.88 | 0.67 | 1.00 | 0.99 |
| 103 | Y103S | 0.42 | 0.85 | 0.56 | 0.50 | 0.17 |
| 103 | Y103T | 0.41 | 0.74 | 0.33 | 0.44 | 0.42 |
| 103 | Y103V | 1.02 | 0.93 | 0.63 | 0.95 | 0.87 |
| 103 | Y103W | 0.93 | 0.96 | 0.72 | 0.75 | 0.56 |
| 104 | Y104A | 0.36 | 0.82 | 0.27 | 0.32 | 0.17 |
| 104 | Y104C | 0.19 | 0.51 | *0.05* | 0.31 | 0.18 |
| 104 | Y104D | 0.23 | 0.44 | 0.14 | 0.40 | 0.22 |
| 104 | Y104E | 0.12 | 0.05 | *0.05* | 4.53 | 29.82 |
| 104 | Y104F | 0.92 | 1.02 | 0.66 | 0.49 | 0.12 |
| 104 | Y104G | 0.28 | 0.50 | *0.05* | 0.35 | 0.28 |
| 104 | Y104H | 0.12 | 0.10 | *0.05* | 2.55 | 1.45 |
| 104 | Y104I | 0.27 | 0.61 | 0.14 | 0.35 | 0.16 |
| 104 | Y104K | 0.38 | 0.45 | 0.15 | 0.24 | 0.21 |
| 104 | Y104L | 0.50 | 0.87 | 0.23 | 0.23 | 0.13 |
| 104 | Y104M | 0.41 | 0.73 | 0.26 | 0.27 | 0.15 |
| 104 | Y104N | 0.22 | 0.15 | 0.14 | 1.06 | 1.75 |
| 104 | Y104P | 0.22 | 0.52 | 0.11 | 0.60 | 0.25 |
| 104 | Y104Q | 0.20 | 0.08 | *0.05* | 1.63 | 1.16 |
| 104 | Y104R | 0.37 | 0.80 | 0.45 | 0.15 | 0.14 |
| 104 | Y104S | 0.38 | 0.48 | 0.26 | 0.46 | 0.17 |
| 104 | Y104T | 0.21 | 0.51 | 0.18 | 0.31 | 0.21 |
| 104 | Y104V | 0.23 | 0.28 | 0.09 | 0.15 | 0.47 |
| 104 | Y104W | 0.77 | 0.91 | 0.60 | 0.37 | 0.16 |
| 105 | A105D | 0.17 | 0.36 | 0.58 | 0.20 | 0.05 |
| 105 | A105G | 0.21 | 0.55 | 0.64 | 0.89 | 0.52 |
| 105 | A105P | 0.11 | 0.16 | 0.30 | 0.14 | 0.71 |
| 105 | A105R | 0.42 | 0.97 | 0.89 | 1.02 | 1.01 |
| 105 | A105T | 0.34 | 0.92 | 0.72 | 0.51 | 0.18 |
| 105 | A105V | 0.35 | 0.78 | 0.74 | 0.60 | 0.24 |
| 105 | A105Y | 0.44 | 0.56 | 0.41 | 0.09 | 0.13 |
| 107 | E107D | 0.19 | 0.27 | 0.40 | 0.07 | 0.23 |
| 107 | E107I | 0.78 | 0.82 | 0.40 | 0.15 | 0.10 |
| 107 | E107K | 0.23 | 0.46 | 0.53 | 0.57 | 0.31 |
| 107 | E107N | 0.38 | 0.62 | 0.60 | 0.09 | 0.16 |
| 107 | E107P | 0.26 | 0.42 | 0.25 | *0.05* | 0.26 |
| 107 | E107Q | 1.19 | 0.94 | 0.54 | 0.58 | 0.14 |
| 107 | E107R | 0.25 | 0.53 | 0.21 | *0.05* | 0.08 |
| 107 | E107S | 0.89 | 0.90 | 0.39 | 0.06 | 0.12 |
| 107 | E107T | 0.53 | 0.72 | 0.55 | *0.05* | 0.09 |
| 107 | E107V | 1.46 | 1.00 | 0.47 | 0.06 | 0.08 |
| 107 | E107W | 0.69 | 0.73 | 0.37 | 0.06 | 0.18 |
| 107 | E107Y | 0.88 | 0.82 | 0.37 | *0.05* | 0.08 |
| 111 | L111A | 1.36 | 1.06 | 1.25 | 0.84 | 0.30 |
| 111 | L111C | 0.57 | 0.81 | 0.99 | 1.00 | 0.93 |
| 111 | L111D | 0.28 | 0.65 | 0.54 | 0.67 | 0.48 |
| 111 | L111E | 0.69 | 1.35 | 1.34 | 0.91 | 0.75 |
| 111 | L111F | 0.52 | 0.67 | 0.49 | 1.02 | 0.76 |
| 111 | L111G | 0.52 | 1.18 | 0.88 | 0.58 | 0.19 |
| 111 | L111H | 0.55 | 0.90 | 0.80 | 0.86 | 0.82 |
| 111 | L111I | 0.93 | 0.77 | 0.90 | 0.86 | 0.80 |
| 111 | L111K | 0.43 | 0.90 | 0.68 | 0.94 | 0.68 |
| 111 | L111M | 1.99 | 1.19 | 0.97 | 1.00 | 0.82 |
| 111 | L111N | 0.26 | 0.76 | 0.80 | 0.73 | 0.53 |
| 111 | L111P | 0.19 | 0.49 | 0.29 | *0.05* | *0.05* |
| 111 | L111Q | 0.96 | 1.34 | 1.11 | 0.95 | 0.82 |
| 111 | L111R | 0.52 | 1.11 | 0.84 | 0.84 | 0.56 |
| 111 | L111S | 0.61 | 0.92 | 0.92 | 1.00 | 1.04 |
| 111 | L111T | 0.66 | 1.17 | 0.84 | 0.81 | 0.55 |
| 111 | L111V | 0.73 | 0.76 | 0.62 | 0.53 | 0.23 |
| 111 | L111W | 0.52 | 0.89 | 0.77 | 0.68 | 0.41 |
| 111 | L111Y | 0.45 | 0.75 | 0.57 | 1.11 | 0.84 |
| 117 | T117A | 0.96 | 1.07 | 0.80 | 0.85 | 0.85 |
| 117 | T117C | 0.61 | 0.94 | 0.94 | 0.87 | 0.96 |
| 117 | T117D | 0.95 | 0.99 | 1.08 | 0.94 | 0.85 |
| 117 | T117E | 0.62 | 1.14 | 0.97 | 1.01 | 1.03 |
| 117 | T117F | 0.51 | 1.14 | 0.82 | 0.88 | 0.90 |
| 117 | T117G | 0.63 | 1.01 | 0.81 | 0.73 | 0.64 |
| 117 | T117H | 0.12 | 0.23 | 0.51 | 3.12 | 8.65 |
| 117 | T117K | 0.69 | 1.03 | 0.82 | 0.95 | 1.05 |
| 117 | T117L | 0.51 | 0.99 | 1.00 | 0.80 | 0.77 |
| 117 | T117M | 0.62 | 0.99 | 1.02 | 0.92 | 0.88 |
| 117 | T117N | 1.35 | 1.03 | 0.84 | 0.99 | 0.98 |
| 117 | T117P | 0.32 | 0.88 | 0.62 | 0.69 | 0.46 |
| 117 | T117Q | 0.28 | 0.93 | 0.71 | 0.95 | 0.99 |
| 117 | T117R | 0.60 | 1.04 | 0.78 | 0.94 | 0.93 |
| 117 | T117S | 0.95 | 1.03 | 0.93 | 1.06 | 1.16 |
| 117 | T117V | 1.00 | 1.03 | 0.70 | 0.92 | 0.94 |
| 117 | T117W | 0.72 | 1.01 | 0.66 | 0.80 | 0.74 |
| 117 | T117Y | 1.18 | 1.05 | 0.84 | 0.95 | 0.91 |
| 119 | A119C | 0.28 | 1.02 | 0.98 | 0.86 | 0.61 |
| 119 | A119D | 0.31 | 0.84 | 0.79 | 0.67 | 0.57 |
| 119 | A119E | 0.25 | 1.16 | 0.99 | 0.86 | 0.84 |
| 119 | A119F | 0.28 | 0.89 | 0.60 | 0.68 | 0.58 |
| 119 | A119G | 0.69 | 0.97 | 0.86 | 0.89 | 0.73 |
| 119 | A119H | 0.49 | 1.03 | 0.85 | 0.91 | 0.71 |
| 119 | A119I | 0.31 | 0.74 | 0.62 | 0.77 | 0.62 |
| 119 | A119K | 0.33 | 0.89 | 0.65 | 1.00 | 0.72 |
| 119 | A119L | 0.55 | 1.11 | 0.94 | 0.84 | 0.59 |
| 119 | A119M | 0.30 | 0.71 | 0.36 | 0.69 | 0.77 |
| 119 | A119N | 0.85 | 1.04 | 0.66 | 1.00 | 0.84 |
| 119 | A119P | 0.71 | 1.02 | 1.10 | 1.07 | 0.97 |
| 119 | A119Q | 0.58 | 1.17 | 0.82 | 1.09 | 0.88 |
| 119 | A119R | 0.56 | 0.80 | 0.42 | 0.92 | 0.88 |
| 119 | A119S | 1.44 | 0.99 | 0.97 | 1.05 | 0.53 |
| 119 | A119T | 0.80 | 0.86 | 0.76 | 0.94 | 0.68 |
| 119 | A119V | 0.36 | 0.89 | 0.45 | 0.90 | 0.91 |
| 119 | A119W | 0.38 | 0.95 | 0.78 | 0.61 | 0.52 |
| 119 | A119Y | 0.38 | 0.54 | 0.47 | 0.79 | 0.99 |
| 120 | M120A | 0.51 | 1.00 | 0.73 | 0.51 | 0.28 |
| 120 | M120C | 0.52 | 0.88 | 0.74 | 0.66 | 0.58 |
| 120 | M120D | 0.31 | 0.95 | 0.76 | 0.32 | 0.31 |
| 120 | M120E | 0.18 | 0.43 | 0.09 | 1.51 | 1.97 |
| 120 | M120F | 0.53 | 1.04 | 0.70 | 0.87 | 0.80 |
| 120 | M120G | 0.35 | 0.49 | 0.30 | 0.92 | 1.21 |
| 120 | M120H | 0.34 | 0.70 | 0.54 | 0.77 | 1.16 |
| 120 | M120I | 0.27 | 0.85 | 0.44 | 0.74 | 0.70 |
| 120 | M120K | 0.34 | 1.10 | 0.49 | 0.72 | 0.76 |
| 120 | M120L | 1.64 | 1.08 | 0.68 | 1.07 | 1.17 |
| 120 | M120N | 0.17 | 0.35 | *0.05* | 0.40 | 0.62 |
| 120 | M120P | 0.28 | 0.53 | 0.33 | 0.65 | 0.71 |
| 120 | M120Q | 0.30 | 0.61 | 0.34 | 1.36 | 1.41 |
| 120 | M120R | 0.31 | 0.80 | 0.14 | 0.31 | 0.28 |
| 120 | M120S | 0.40 | 1.04 | 0.58 | 0.64 | 0.31 |
| 120 | M120T | 0.35 | 0.95 | 0.52 | 0.67 | 0.45 |
| 120 | M120V | 0.30 | 0.60 | 0.47 | 0.91 | 1.12 |
| 120 | M120W | 0.53 | 1.06 | 0.77 | 1.01 | 0.98 |
| 120 | M120Y | 0.70 | 0.84 | 0.47 | 0.91 | 0.81 |
| 121 | A121C | 0.17 | 0.79 | 0.59 | 0.64 | 0.38 |
| 121 | A121D | 0.08 | 1.27 | 0.35 | 0.31 | 0.22 |
| 121 | A121E | 0.11 | 0.30 | *0.05* | 0.99 | 1.43 |
| 121 | A121F | 0.23 | 0.68 | 0.56 | 0.30 | 0.24 |
| 121 | A121G | 0.13 | 0.49 | 0.37 | 14.85 | 14.78 |
| 121 | A121H | 0.08 | 0.39 | 0.49 | 0.36 | 0.28 |
| 121 | A121I | 0.12 | 0.39 | 0.32 | 1.82 | 1.58 |
| 121 | A121K | 0.23 | 0.78 | 0.62 | 0.95 | 0.91 |
| 121 | A121L | 0.40 | 0.66 | 0.46 | 0.76 | 0.76 |
| 121 | A121M | 0.11 | 0.85 | 0.48 | 0.85 | 0.53 |
| 121 | A121N | 0.09 | 0.54 | 0.15 | 0.56 | 0.59 |
| 121 | A121P | 0.10 | 0.30 | 0.18 | 1.03 | 1.05 |
| 121 | A121Q | *0.05* | *0.05* | *0.05* | *0.05* | *0.05* |
| 121 | A121R | 0.52 | 1.10 | 0.85 | 0.98 | 1.01 |
| 121 | A121S | 0.14 | 0.74 | 0.85 | 0.60 | 0.24 |
| 121 | A121T | 0.25 | 0.62 | 0.46 | 0.49 | 0.27 |
| 121 | A121V | 0.15 | 0.73 | 0.57 | 0.81 | 0.75 |
| 121 | A121W | 0.33 | 0.46 | 0.45 | 0.26 | 0.31 |
| 121 | A121Y | 0.35 | 0.77 | 0.57 | 0.36 | 0.16 |
| 125 | A125C | 0.50 | 0.37 | 0.23 | 0.39 | 0.71 |
| 125 | A125D | 0.13 | 0.46 | 0.21 | 1.24 | 2.42 |
| 125 | A125E | 0.70 | 0.66 | 0.40 | 0.96 | 1.07 |
| 125 | A125F | 0.42 | 0.86 | 0.50 | 0.29 | 0.39 |
| 125 | A125G | 0.17 | 0.50 | 0.10 | 1.45 | 2.19 |
| 125 | A125H | 0.46 | 1.06 | 0.44 | 0.39 | 0.30 |
| 125 | A125I | 0.31 | 0.60 | 0.37 | 0.91 | 1.27 |
| 125 | A125K | 0.60 | 1.12 | 0.76 | 0.71 | 0.62 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 125 | A125L | 0.36 | 1.09 | 0.38 | 0.69 | 0.60 |
| 125 | A125M | 0.60 | 1.01 | 0.64 | 0.79 | 0.71 |
| 125 | A125N | 0.40 | 0.97 | 0.49 | 0.46 | 0.34 |
| 125 | A125P | 0.43 | 0.55 | 0.33 | 0.31 | 0.45 |
| 125 | A125Q | 0.29 | 0.74 | 0.34 | 0.78 | 0.73 |
| 125 | A125R | 0.56 | 1.09 | 0.82 | 0.74 | 0.69 |
| 125 | A125S | 0.65 | 0.93 | 0.47 | 0.87 | 0.71 |
| 125 | A125T | 0.50 | 1.00 | 0.43 | 0.50 | 0.28 |
| 125 | A125V | 0.46 | 0.94 | 0.60 | 0.54 | 0.50 |
| 125 | A125W | 0.50 | 0.94 | 0.49 | 0.28 | 0.13 |
| 125 | A125Y | 0.34 | 0.63 | 0.43 | 0.61 | 0.91 |
| 126 | A126D | 0.22 | 0.80 | 0.45 | 0.23 | 0.31 |
| 126 | A126E | 1.46 | 1.02 | 0.84 | 1.06 | 1.04 |
| 126 | A126F | 0.61 | 0.88 | 0.89 | 0.89 | 0.66 |
| 126 | A126G | 0.19 | 0.46 | 0.67 | 0.80 | 0.67 |
| 126 | A126H | 0.27 | 0.86 | 1.16 | 0.84 | 0.75 |
| 126 | A126I | 0.23 | 0.65 | 0.41 | 0.37 | 0.26 |
| 126 | A126K | 0.80 | 1.00 | 0.86 | 1.10 | 1.15 |
| 126 | A126L | 0.44 | 1.10 | 0.89 | 0.88 | 0.63 |
| 126 | A126M | 0.30 | 0.67 | 0.71 | 0.95 | 0.83 |
| 126 | A126N | 0.79 | 0.92 | 0.78 | 1.04 | 0.75 |
| 126 | A126P | 0.17 | 0.26 | 0.62 | 1.39 | 0.83 |
| 126 | A126Q | 1.31 | 0.96 | 0.97 | 1.11 | 1.05 |
| 126 | A126R | 0.82 | 0.88 | 0.82 | 0.97 | 0.95 |
| 126 | A126S | 0.58 | 0.95 | 0.80 | 1.11 | 1.00 |
| 126 | A126T | 0.59 | 0.49 | 0.60 | 0.65 | 0.56 |
| 126 | A126V | 0.62 | 0.96 | 0.68 | 0.97 | 0.70 |
| 126 | A126W | 0.50 | 0.85 | 0.95 | 0.65 | 0.52 |
| 126 | A126Y | 0.75 | 0.96 | 0.80 | 0.82 | 0.68 |
| 129 | K129A | 0.23 | 1.03 | 0.81 | 0.74 | 0.57 |
| 129 | K129L | 0.80 | 0.94 | 0.80 | 0.82 | 0.71 |
| 129 | K129N | 0.15 | 0.93 | 0.65 | 0.73 | 0.61 |
| 129 | K129Q | 0.41 | 1.30 | 0.89 | 1.01 | 0.99 |
| 129 | K129S | 0.37 | 1.05 | 0.92 | 0.84 | 0.84 |
| 129 | K129T | 0.16 | 0.87 | 0.37 | 0.81 | 0.69 |
| 129 | K129V | 0.17 | 0.93 | 0.91 | 0.63 | 0.45 |
| 129 | K129Y | 0.35 | 0.95 | 0.82 | 0.68 | 0.46 |
| 133 | F133A | 0.19 | 0.25 | 0.13 | 0.84 | 0.80 |
| 133 | F133C | 0.15 | 0.20 | 0.09 | 0.71 | 1.32 |
| 133 | F133D | 0.16 | 0.16 | 0.20 | 0.26 | 2.20 |
| 133 | F133G | 0.17 | 0.12 | 0.19 | 0.87 | 5.31 |
| 133 | F133H | 0.14 | 0.22 | 0.06 | 0.90 | 0.76 |
| 133 | F133K | 0.11 | 0.16 | *0.05* | 0.64 | 8.77 |
| 133 | F133P | 0.12 | 0.24 | *0.05* | 0.33 | 0.41 |
| 133 | F133Q | 0.12 | 0.26 | 0.16 | 0.58 | 1.12 |
| 133 | F133S | 0.12 | 0.27 | 0.05 | 1.08 | 2.34 |
| 133 | F133T | 0.11 | 0.24 | *0.05* | 0.21 | 0.52 |
| 133 | F133W | 0.13 | 0.52 | 0.27 | 0.42 | 0.21 |
| 133 | F133Y | 0.13 | 0.60 | 0.25 | 0.53 | 0.74 |
| 134 | M134A | 1.09 | 0.96 | 1.06 | 0.79 | 0.76 |
| 134 | M134C | 0.91 | 1.01 | 0.84 | 0.80 | 1.20 |
| 134 | M134D | 0.42 | 0.69 | 0.50 | 0.89 | 1.52 |
| 134 | M134E | 0.82 | 1.10 | 0.94 | 0.88 | 0.97 |
| 134 | M134F | 1.53 | 1.12 | 0.91 | 1.02 | 1.19 |
| 134 | M134G | 0.33 | 1.11 | 0.80 | 1.16 | 1.47 |
| 134 | M134H | 0.93 | 1.17 | 0.66 | 0.79 | 0.53 |
| 134 | M134I | 1.16 | 1.13 | 0.72 | 1.20 | 1.10 |
| 134 | M134K | 0.53 | 0.56 | 0.38 | 2.39 | 3.02 |
| 134 | M134L | 1.45 | 1.15 | 0.75 | 1.67 | 1.64 |
| 134 | M134N | 0.90 | 1.25 | 0.93 | 1.09 | 0.76 |
| 134 | M134P | 0.37 | 0.40 | 0.28 | 2.37 | 3.64 |
| 134 | M134Q | 0.57 | 1.27 | 0.83 | 0.99 | 0.93 |
| 134 | M134R | 0.84 | 1.54 | 0.86 | 1.74 | 1.18 |
| 134 | M134S | 0.55 | 1.15 | 0.70 | 1.31 | 1.40 |
| 134 | M134T | 0.65 | 1.54 | 0.64 | 1.33 | 1.29 |
| 134 | M134V | 1.50 | 1.24 | 0.69 | 1.74 | 1.84 |
| 134 | M134W | 0.39 | 0.93 | 0.57 | 0.98 | 1.47 |
| 134 | M134Y | 0.93 | 1.15 | 0.68 | 1.48 | 0.96 |
| 137 | D137A | 0.56 | 0.95 | 0.80 | 1.06 | 1.06 |
| 137 | D137C | 0.35 | 0.31 | 0.30 | 0.92 | 1.04 |
| 137 | D137E | 0.48 | 0.85 | 0.50 | 1.00 | 0.93 |
| 137 | D137F | 0.28 | 0.46 | 0.44 | 0.80 | 0.88 |
| 137 | D137G | 0.23 | 0.49 | 0.39 | 1.24 | 1.25 |
| 137 | D137H | 0.14 | 0.24 | *0.05* | 1.77 | 1.76 |
| 137 | D137I | 0.20 | 0.28 | 0.19 | 0.96 | 0.85 |
| 137 | D137K | 0.29 | 0.30 | 0.17 | 0.72 | 1.06 |
| 137 | D137L | 0.23 | 0.21 | 0.31 | 0.90 | 1.53 |
| 137 | D137M | 0.23 | 0.34 | 0.21 | 0.72 | 1.06 |
| 137 | D137N | 2.26 | 0.75 | 0.52 | 1.03 | 1.13 |
| 137 | D137P | 0.41 | 1.22 | 0.48 | 1.03 | 1.23 |
| 137 | D137Q | 0.31 | 0.49 | 0.25 | 0.82 | 0.82 |
| 137 | D137R | 0.25 | 0.24 | 0.34 | 4.67 | 1.96 |
| 137 | D137S | 0.37 | 0.94 | 0.77 | 0.91 | 1.05 |
| 137 | D137T | 0.55 | 0.85 | 0.47 | 1.01 | 1.10 |
| 137 | D137V | 0.24 | 0.27 | 0.15 | 1.14 | 1.33 |
| 137 | D137W | 0.34 | 0.42 | 0.15 | 0.99 | 0.72 |
| 137 | D137Y | 0.36 | 0.50 | 0.28 | 0.83 | 0.91 |
| 138 | T138A | 3.42 | 1.04 | 1.06 | 1.05 | 1.26 |
| 138 | T138C | 2.40 | 0.97 | 0.95 | 1.03 | 1.30 |
| 138 | T138D | 0.23 | 0.11 | *0.05* | 0.76 | 1.68 |
| 138 | T138E | 2.03 | 0.49 | 0.56 | 0.78 | 1.58 |
| 138 | T138F | 0.64 | 0.53 | 0.37 | 1.42 | 4.28 |
| 138 | T138G | 0.51 | 0.75 | 0.63 | 0.99 | 0.94 |
| 138 | T138H | 0.58 | 0.51 | 0.47 | 1.14 | 1.06 |
| 138 | T138I | 0.54 | 0.86 | 0.75 | 0.95 | 0.99 |
| 138 | T138K | 0.40 | 0.39 | 0.18 | 0.86 | 1.68 |
| 138 | T138L | 1.26 | 1.01 | 0.90 | 1.01 | 1.19 |
| 138 | T138M | 0.75 | 0.97 | 0.97 | 1.09 | 1.14 |
| 138 | T138N | 0.51 | 0.52 | 0.43 | 2.14 | 2.93 |
| 138 | T138P | 0.40 | 0.66 | 0.71 | 1.23 | 1.63 |
| 138 | T138Q | 0.91 | 0.98 | 0.85 | 0.96 | 1.01 |
| 138 | T138R | 0.40 | 0.67 | 0.57 | 0.71 | 1.00 |
| 138 | T138S | 1.29 | 0.95 | 1.05 | 1.13 | 1.25 |
| 138 | T138V | 0.99 | 0.98 | 0.74 | 1.04 | 1.20 |
| 138 | T138W | 0.67 | 0.81 | 0.83 | 0.95 | 0.84 |
| 138 | T138Y | 0.34 | 0.83 | 0.54 | 1.37 | 1.26 |
| 139 | L139A | 0.40 | 1.16 | 0.39 | 0.97 | 0.82 |
| 139 | L139C | 1.15 | 1.04 | 0.89 | 0.95 | 1.04 |
| 139 | L139D | 1.03 | 0.94 | 0.95 | 0.98 | 1.07 |
| 139 | L139E | 0.17 | 0.74 | 0.78 | 1.07 | 0.99 |
| 139 | L139F | 0.46 | 0.77 | 0.48 | 1.04 | 1.25 |
| 139 | L139G | 0.60 | 1.04 | 0.95 | 1.07 | 1.06 |
| 139 | L139H | 0.45 | 0.40 | 0.50 | 0.73 | 0.94 |
| 139 | L139I | 0.19 | 0.87 | 0.93 | 0.89 | 0.98 |
| 139 | L139K | 0.65 | 1.03 | 0.97 | 0.97 | 1.10 |
| 139 | L139M | 0.29 | 0.77 | 0.76 | 0.88 | 0.43 |
| 139 | L139N | 0.30 | 0.94 | 0.85 | 0.97 | 1.02 |
| 139 | L139P | 0.18 | 0.19 | 0.29 | 40.66 | 1.02 |
| 139 | L139Q | 0.76 | 0.96 | 0.98 | 1.05 | 1.25 |
| 139 | L139R | 0.51 | 0.98 | 0.68 | 1.00 | 0.96 |
| 139 | L139S | 0.46 | 1.19 | 1.02 | 1.09 | 1.07 |
| 139 | L139T | 0.37 | 1.32 | 1.05 | 1.00 | 1.13 |
| 139 | L139V | 0.73 | 1.04 | 0.64 | 0.95 | 1.05 |
| 139 | L139W | 0.50 | 0.85 | 0.69 | 1.05 | 0.84 |
| 139 | L139Y | 1.51 | 1.00 | 0.50 | 2.68 | 1.87 |
| 140 | D140A | 0.98 | 1.14 | 1.00 | 1.01 | 1.09 |
| 140 | D140C | 0.24 | 0.71 | 0.75 | 0.73 | 0.90 |
| 140 | D140E | 0.47 | 0.87 | 0.63 | 0.85 | 0.87 |
| 140 | D140F | 0.38 | 0.75 | 0.45 | 0.85 | 0.73 |
| 140 | D140G | 0.25 | 0.87 | 0.63 | 0.72 | 0.72 |
| 140 | D140H | 0.26 | 0.77 | 0.72 | 0.86 | 0.94 |
| 140 | D140I | 0.45 | 0.96 | 0.84 | 1.09 | 1.05 |
| 140 | D140K | 0.48 | 0.75 | 0.62 | 0.77 | 1.01 |
| 140 | D140L | 0.28 | 0.80 | 0.81 | 0.95 | 0.91 |
| 140 | D140M | 0.34 | 1.08 | 0.89 | 1.08 | 1.00 |
| 140 | D140N | 0.29 | 0.58 | 0.37 | 0.81 | 1.02 |
| 140 | D140P | 0.10 | 0.14 | 0.17 | 10.60 | 12.72 |
| 140 | D140Q | 1.14 | 1.06 | 0.94 | 1.06 | 1.10 |
| 140 | D140R | 0.36 | 0.75 | 0.47 | 1.09 | 1.02 |
| 140 | D140S | 0.65 | 1.06 | 0.92 | 1.04 | 1.05 |
| 140 | D140T | 0.16 | 0.34 | 0.20 | 1.64 | 1.96 |
| 140 | D140V | 0.24 | 0.85 | 0.55 | 0.88 | 1.11 |
| 140 | D140W | 0.94 | 0.98 | 0.92 | 0.98 | 1.09 |
| 140 | D140Y | 0.34 | 0.78 | 0.64 | 0.91 | 1.01 |
| 141 | K141A | 0.83 | 0.94 |  | 0.54 | 0.54 |
| 141 | K141C | 1.16 | 1.10 |  | 0.56 | 0.51 |
| 141 | K141D | 0.72 | 0.61 |  | 1.39 | 0.68 |
| 141 | K141E | 0.65 | 0.29 |  | 2.54 | 2.73 |
| 141 | K141F | 0.52 | 0.51 |  | 2.02 | 1.67 |
| 141 | K141G | 0.49 | 0.58 |  | 1.62 | 1.45 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 141 | K141H | 1.32 | 1.17 | | 0.67 | 0.83 |
| 141 | K141I | 1.18 | 0.57 | | 1.58 | 1.16 |
| 141 | K141L | 0.87 | 0.35 | | 2.74 | 1.77 |
| 141 | K141M | 0.45 | 0.51 | | 1.93 | 1.54 |
| 141 | K141N | 0.54 | 0.60 | | 2.08 | 1.22 |
| 141 | K141R | 0.63 | 1.11 | | 1.14 | 0.32 |
| 141 | K141S | 0.81 | 0.72 | | 1.14 | 1.63 |
| 141 | K141T | 0.45 | 0.60 | | 2.03 | 1.72 |
| 141 | K141V | 0.40 | 0.46 | | 2.92 | 2.99 |
| 141 | K141Y | 0.65 | 0.07 | | 1.05 | 3.34 |
| 143 | P143A | 0.46 | 1.10 | 0.93 | 1.04 | 0.83 |
| 143 | P143C | 2.28 | 0.75 | 0.82 | 0.68 | 0.66 |
| 143 | P143D | 0.29 | 0.30 | 0.14 | 5.14 | 4.04 |
| 143 | P143E | 1.87 | 0.96 | 0.98 | 1.05 | 1.14 |
| 143 | P143F | 0.57 | 1.29 | 0.70 | 0.98 | 0.90 |
| 143 | P143G | 0.67 | 0.71 | 1.06 | 0.92 | 1.04 |
| 143 | P143H | 0.49 | 0.92 | 0.76 | 0.97 | 0.97 |
| 143 | P143I | 0.86 | 1.06 | 1.03 | 1.02 | 1.10 |
| 143 | P143K | 0.30 | 0.78 | 0.93 | 0.93 | 0.79 |
| 143 | P143L | 1.12 | 0.74 | 0.84 | 1.08 | 1.09 |
| 143 | P143M | 0.18 | 0.06 | 0.14 | 3.72 | 1.81 |
| 143 | P143N | 0.56 | 1.16 | 1.03 | 1.06 | 0.91 |
| 143 | P143Q | 1.57 | 1.09 | 0.90 | 1.09 | 1.16 |
| 143 | P143R | 0.36 | 0.77 | 0.97 | 0.99 | 0.77 |
| 143 | P143S | 1.92 | 1.11 | 1.05 | 1.06 | 1.25 |
| 143 | P143T | 0.49 | 1.33 | 0.96 | 0.86 | 0.85 |
| 143 | P143V | 0.51 | 0.73 | 0.68 | 0.81 | 0.90 |
| 143 | P143W | 1.09 | 0.91 | 1.02 | 0.95 | 0.99 |
| 143 | P143Y | 1.06 | 0.82 | 0.70 | 0.95 | 0.98 |
| 144 | L144A | 1.88 | 1.05 | 1.15 | 0.95 | 0.67 |
| 144 | L144C | 0.36 | 1.10 | 1.11 | 0.75 | 0.75 |
| 144 | L144D | 0.37 | 0.79 | 0.76 | 0.76 | 0.72 |
| 144 | L144E | 1.08 | 1.06 | 0.99 | 0.90 | 0.77 |
| 144 | L144F | 0.77 | 1.03 | 0.93 | 0.96 | 0.85 |
| 144 | L144G | 0.33 | 0.88 | 0.76 | 0.76 | 0.67 |
| 144 | L144H | 0.81 | 1.04 | 0.75 | 0.89 | 0.87 |
| 144 | L144I | 0.68 | 1.03 | 0.95 | 0.93 | 0.72 |
| 144 | L144K | 0.34 | 1.02 | 0.72 | 0.82 | 0.76 |
| 144 | L144M | 0.32 | 1.09 | 0.96 | 0.94 | 0.85 |
| 144 | L144N | 0.44 | 0.81 | 0.59 | 0.86 | 0.81 |
| 144 | L144P | 0.26 | 0.50 | 0.16 | 0.71 | 1.07 |
| 144 | L144Q | 0.36 | 1.00 | 0.77 | 1.00 | 1.31 |
| 144 | L144S | 0.35 | 0.19 | 0.24 | 1.57 | 2.43 |
| 144 | L144T | 0.27 | 0.93 | 0.63 | 0.74 | 0.78 |
| 144 | L144V | 0.32 | 0.83 | 0.70 | 0.76 | 0.77 |
| 144 | L144W | 0.33 | 1.15 | 1.00 | 0.84 | 0.98 |
| 144 | L144Y | 1.02 | 1.05 | 0.85 | 0.99 | 0.96 |
| 147 | Q147A | 0.09 | 0.94 | 0.82 | 0.91 | 0.87 |
| 147 | Q147C | 0.14 | 0.68 | 0.48 | 0.92 | 0.81 |
| 147 | Q147E | 0.86 | 1.00 | 0.88 | 1.07 | 1.05 |
| 147 | Q147F | 0.10 | 0.65 | 0.66 | 1.03 | 1.11 |
| 147 | Q147G | 0.39 | 1.01 | 0.93 | 1.02 | 1.00 |
| 147 | Q147I | 0.14 | 0.88 | 0.54 | 0.96 | 0.75 |
| 147 | Q147K | 0.13 | 0.85 | 0.61 | 0.87 | 0.89 |
| 147 | Q147L | 0.11 | 0.77 | 0.47 | 1.08 | 0.91 |
| 147 | Q147M | 0.23 | 0.85 | 0.56 | 0.75 | 0.69 |
| 147 | Q147N | 0.67 | 1.04 | 0.83 | 0.99 | 0.97 |
| 147 | Q147P | 0.20 | 0.25 | 0.26 | 0.66 | 1.19 |
| 147 | Q147R | 0.46 | 1.01 | 0.80 | 0.97 | 0.85 |
| 147 | Q147S | 0.63 | 0.97 | 0.79 | 1.12 | 1.02 |
| 147 | Q147T | 0.83 | 0.97 | 0.85 | 1.10 | 1.09 |
| 147 | Q147V | 0.19 | 0.71 | 0.59 | 0.89 | 0.94 |
| 147 | Q147W | 0.20 | 0.61 | 0.63 | 0.74 | 0.82 |
| 150 | A150C | 0.15 | 0.40 | 0.42 | 0.61 | 0.90 |
| 150 | A150D | 0.71 | 0.82 | 0.92 | 0.98 | 0.98 |
| 150 | A150E | 0.37 | 1.09 | 0.90 | 1.05 | 1.03 |
| 150 | A150F | 0.33 | 1.10 | 0.87 | 1.01 | 0.93 |
| 150 | A150G | 0.72 | 0.95 | 0.87 | 1.11 | 1.07 |
| 150 | A150H | 1.02 | 1.02 | 0.92 | 1.14 | 1.21 |
| 150 | A150I | 0.28 | 0.83 | 0.92 | 1.03 | 1.05 |
| 150 | A150K | 0.66 | 1.00 | 0.87 | 1.07 | 1.07 |
| 150 | A150L | 0.46 | 0.59 | 0.45 | 1.12 | 1.92 |
| 150 | A150M | 0.51 | 0.80 | 0.70 | 1.05 | 1.05 |
| 150 | A150N | 0.82 | 0.98 | 0.81 | 1.09 | 1.14 |
| 150 | A150P | 0.14 | 0.44 | 0.42 | 1.18 | 1.65 |
| 150 | A150Q | 0.64 | 1.02 | 0.86 | 1.17 | 1.15 |
| 150 | A150R | 0.36 | 0.91 | 0.87 | 0.94 | 1.05 |
| 150 | A150S | 0.53 | 1.05 | 0.95 | 0.99 | 1.05 |
| 150 | A150T | 0.13 | 0.96 | 0.67 | 0.99 | 0.83 |
| 150 | A150V | 0.35 | 0.81 | 0.87 | 0.99 | 0.98 |
| 150 | A150W | 0.61 | 0.82 | 0.77 | 1.01 | 0.99 |
| 150 | A150Y | 0.45 | 0.54 | 0.49 | 0.74 | 0.76 |
| 153 | R153A | 0.23 | 0.50 | 0.72 | 0.63 | 0.64 |
| 153 | R153C | 0.26 | 0.51 | 0.86 | 0.94 | 0.88 |
| 153 | R153D | 0.35 | 0.35 | 0.54 | 0.75 | 0.72 |
| 153 | R153E | 0.27 | 0.69 | 0.75 | 0.79 | 0.80 |
| 153 | R153F | 0.21 | 0.38 | 0.69 | 0.68 | 0.58 |
| 153 | R153G | 0.21 | 0.31 | 0.59 | 0.62 | 0.92 |
| 153 | R153H | 0.39 | 0.71 | 0.79 | 0.97 | 0.97 |
| 153 | R153I | 0.22 | 0.28 | 0.37 | 0.63 | 1.09 |
| 153 | R153K | 0.26 | 0.39 | 0.54 | 0.78 | 0.92 |
| 153 | R153L | 0.19 | 0.30 | 0.40 | 0.94 | 0.44 |
| 153 | R153M | 0.31 | 0.70 | 0.86 | 0.92 | 1.05 |
| 153 | R153N | 0.22 | 0.20 | 0.42 | 1.12 | 1.23 |
| 153 | R153P | 0.23 | 0.14 | 0.10 | 0.39 | 2.17 |
| 153 | R153Q | 0.24 | 0.52 | 0.99 | 0.77 | 1.05 |
| 153 | R153S | 0.41 | 0.78 | 0.99 | 0.93 | 0.93 |
| 153 | R153T | 0.31 | 0.63 | 0.74 | 0.84 | 0.94 |
| 153 | R153V | 0.23 | 0.28 | 0.59 | 0.63 | 0.81 |
| 153 | R153W | 0.42 | 0.77 | 1.07 | 0.90 | 0.87 |
| 153 | R153Y | 0.32 | 0.60 | 0.73 | 0.84 | 0.90 |
| 154 | T154A | 0.73 | 1.06 | 0.86 | 0.98 | 1.00 |
| 154 | T154C | 0.05 | 0.96 | 0.94 | 1.36 | 1.39 |
| 154 | T154D | 0.64 | 0.68 | 0.82 | 1.26 | 1.90 |
| 154 | T154E | 0.35 | 0.83 | 0.65 | 0.96 | 0.91 |
| 154 | T154F | 0.21 | 0.88 | 0.86 | 0.94 | 0.84 |
| 154 | T154G | 0.61 | 0.92 | 0.94 | 0.99 | 0.94 |
| 154 | T154H | 0.46 | 0.97 | 0.86 | 1.03 | 1.02 |
| 154 | T154I | 0.43 | 0.84 | 0.69 | 0.94 | 0.94 |
| 154 | T154K | 0.43 | 0.93 | 0.85 | 0.98 | 0.89 |
| 154 | T154L | 0.34 | 0.70 | 0.67 | 0.98 | 0.89 |
| 154 | T154M | 0.32 | 0.90 | 0.77 | 1.08 | 1.05 |
| 154 | T154N | 0.05 | 0.23 | 0.25 | 2.37 | 3.90 |
| 154 | T154P | 0.30 | 0.46 | 0.34 | 0.78 | 0.37 |
| 154 | T154Q | 0.17 | 0.71 | 1.01 | 0.87 | 0.93 |
| 154 | T154R | 0.40 | 0.96 | 1.10 | 1.04 | 0.95 |
| 154 | T154S | 0.79 | 1.03 | 0.91 | 1.05 | 1.06 |
| 154 | T154V | 0.33 | 0.86 | 0.99 | 1.01 | 0.96 |
| 154 | T154W | 0.43 | 0.97 | 0.98 | 0.93 | 0.94 |
| 154 | T154Y | 0.59 | 0.80 | 0.80 | 0.78 | 1.13 |
| 157 | K157A | 0.68 | 1.04 | 0.93 | 1.01 | 0.91 |
| 157 | K157D | 0.69 | 0.96 | 1.01 | 1.12 | 0.90 |
| 157 | K157E | 0.10 | 0.92 | 0.75 | 1.03 | 0.73 |
| 157 | K157F | 0.40 | 1.01 | 0.94 | 1.07 | 0.95 |
| 157 | K157G | 0.50 | 0.98 | 0.76 | 1.04 | 0.93 |
| 157 | K157H | 0.46 | 1.01 | 0.85 | 1.08 | 0.94 |
| 157 | K157I | 0.71 | 1.00 | 0.81 | 1.05 | 0.94 |
| 157 | K157L | 0.18 | 0.88 | 0.60 | 1.04 | 0.75 |
| 157 | K157M | 0.33 | 0.99 | 0.77 | 0.99 | 0.88 |
| 157 | K157P | 0.11 | 0.57 | 0.63 | 3.04 | 1.86 |
| 157 | K157Q | 0.50 | 1.00 | 0.70 | 1.00 | 0.88 |
| 157 | K157R | 0.82 | 1.02 | 1.19 | 0.98 | 0.92 |
| 157 | K157T | 0.14 | 0.79 | 0.47 | 1.02 | 0.83 |
| 157 | K157V | 0.46 | 0.99 | 0.86 | 0.99 | 0.91 |
| 157 | K157W | 1.06 | 0.95 | 0.84 | 1.04 | 0.93 |
| 157 | K157Y | 0.77 | 0.98 | 0.92 | 1.00 | 0.84 |
| 158 | N158A | 0.43 | 0.95 | 0.80 | 0.94 | 1.03 |
| 158 | N158C | 0.25 | 0.77 | 0.68 | 1.03 | 0.92 |
| 158 | N158D | 0.55 | 0.99 | 0.86 | 1.01 | 0.90 |
| 158 | N158E | 0.54 | 0.93 | 0.88 | 0.94 | 1.18 |
| 158 | N158F | 0.36 | 0.90 | 0.70 | 1.02 | 0.89 |
| 158 | N158G | 0.24 | 1.06 | 0.66 | 0.89 | 0.75 |
| 158 | N158H | 0.43 | 0.93 | 0.72 | 0.98 | 0.89 |
| 158 | N158I | 0.92 | 1.06 | 0.91 | 1.13 | 1.09 |
| 158 | N158L | 0.62 | 1.12 | 0.81 | 0.97 | 0.99 |
| 158 | N158M | 0.19 | 0.38 | 0.27 | 0.40 | 0.88 |
| 158 | N158P | 0.19 | 0.81 | 0.43 | 0.85 | 1.12 |
| 158 | N158Q | 0.41 | 1.05 | 0.95 | 0.93 | 1.06 |
| 158 | N158R | 0.23 | 0.74 | 0.43 | 0.76 | 0.74 |
| 158 | N158S | 0.61 | 0.92 | 0.61 | 0.88 | 0.84 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 158 | N158T | 0.18 | 0.63 | 0.85 | 0.80 | 2.47 |
| 158 | N158V | 0.65 | 0.92 | 0.75 | 1.00 | 0.87 |
| 158 | N158W | 0.28 | 0.90 | 0.65 | 0.80 | 0.73 |
| 158 | N158Y | 0.19 | 0.90 | 0.92 | *0.05* | 0.32 |
| 161 | N161A | 0.39 | 1.43 | 1.91 | 0.99 | 0.97 |
| 161 | N161C | 0.62 | 0.95 | 1.12 | 1.05 | 1.06 |
| 161 | N161E | 0.76 | 1.03 | 1.07 | 1.12 | 1.12 |
| 161 | N161F | 0.62 | 1.07 | 1.07 | 1.01 | 1.05 |
| 161 | N161G | 0.55 | 0.99 | 1.02 | 0.99 | 0.95 |
| 161 | N161H | 0.55 | 0.92 | 0.83 | 1.04 | 1.02 |
| 161 | N161I | 0.51 | 0.89 | 0.68 | 1.03 | 1.01 |
| 161 | N161K | 0.43 | 0.84 | 0.67 | 1.03 | 1.20 |
| 161 | N161L | 0.32 | 0.59 | 0.92 | 2.18 | 1.90 |
| 161 | N161M | 0.53 | 1.01 | 1.11 | 0.98 | 1.09 |
| 161 | N161P | 1.06 | 1.03 | 0.98 | 1.12 | 1.24 |
| 161 | N161Q | 0.68 | 1.02 | 0.97 | 1.04 | 1.07 |
| 161 | N161R | 0.40 | 0.75 | 0.34 | 0.41 | 0.44 |
| 161 | N161S | 0.58 | 1.01 | 1.06 | 0.90 | 0.90 |
| 161 | N161T | 1.06 | 1.05 | 0.96 | 1.01 | 1.18 |
| 161 | N161V | 0.59 | 1.00 | 0.97 | 1.00 | 1.12 |
| 161 | N161W | 0.46 | 0.91 | 1.31 | 1.02 | 0.95 |
| 161 | N161Y | 0.83 | 1.03 | 1.09 | 1.04 | 1.05 |
| 162 | Y162A | 0.15 | 0.78 | 0.73 | 0.97 | 1.11 |
| 162 | Y162C | 0.15 | 0.64 | 0.50 | 0.73 | 1.57 |
| 162 | Y162D | 0.11 | 0.39 | 0.61 | 1.14 | 1.90 |
| 162 | Y162E | 0.14 | 0.28 | 0.37 | 1.44 | 2.01 |
| 162 | Y162F | 0.76 | 1.04 | 0.87 | 1.11 | 1.03 |
| 162 | Y162G | 0.29 | 1.05 | 0.87 | 0.97 | 0.84 |
| 162 | Y162H | 0.61 | 1.04 | 0.91 | 1.12 | 1.16 |
| 162 | Y162I | 0.21 | 0.77 | 0.85 | 0.91 | 0.66 |
| 162 | Y162K | 0.16 | 0.83 | 0.93 | 1.06 | 0.89 |
| 162 | Y162L | 0.17 | 0.59 | 0.52 | 0.78 | 0.83 |
| 162 | Y162M | 0.17 | 0.66 | 0.61 | 0.79 | 0.81 |
| 162 | Y162N | 0.28 | 0.92 | 1.02 | 1.04 | 0.99 |
| 162 | Y162P | 0.14 | 0.33 | 0.21 | 0.95 | 1.01 |
| 162 | Y162Q | 0.18 | 0.93 | 0.81 | 0.86 | 0.75 |
| 162 | Y162R | 0.20 | 0.82 | 0.86 | 1.04 | 0.91 |
| 162 | Y162S | 0.20 | 1.05 | 0.67 | 1.01 | 0.91 |
| 162 | Y162T | 0.14 | 0.52 | 0.33 | 0.63 | 0.96 |
| 162 | Y162V | 0.20 | 0.67 | 0.89 | 1.02 | 0.87 |
| 162 | Y162W | 0.54 | 1.03 | 0.77 | 0.92 | 0.81 |
| 177 | A177C | 0.27 | 0.42 | 0.53 | 1.74 | 1.01 |
| 177 | A177D | 2.02 | 0.95 | 0.98 | 0.93 | 1.04 |
| 177 | A177E | 0.36 | 0.59 | 0.67 | 1.03 | 1.02 |
| 177 | A177F | 0.21 | 0.48 | 0.31 | 0.87 | 0.69 |
| 177 | A177G | 0.80 | 0.73 | 0.66 | 0.95 | 1.11 |
| 177 | A177H | 0.12 | 0.32 | 0.30 | 0.99 | 4.79 |
| 177 | A177I | 0.25 | 0.35 | 0.23 | 0.68 | 0.79 |
| 177 | A177K | 0.52 | 0.76 | 0.43 | 1.02 | 1.07 |
| 177 | A177L | 0.33 | 0.26 | 0.27 | 0.89 | 1.00 |
| 177 | A177M | 0.36 | 0.66 | 0.64 | 0.82 | 0.91 |
| 177 | A177N | 0.66 | 0.92 | 0.92 | 1.09 | 1.32 |
| 177 | A177P | 0.51 | 0.52 | 0.36 | 0.70 | 0.61 |
| 177 | A177Q | 0.21 | 0.46 | 0.42 | 1.40 | 1.12 |
| 177 | A177R | 0.25 | 0.54 | 0.42 | 1.04 | 1.04 |
| 177 | A177S | 1.45 | 1.01 | 0.84 | 1.06 | 1.31 |
| 177 | A177T | 0.45 | 0.62 | 0.46 | 0.86 | 0.74 |
| 177 | A177V | 0.30 | 0.58 | 0.42 | 0.78 | 0.63 |
| 177 | A177W | 0.37 | 0.56 | 0.28 | 1.22 | 0.85 |
| 177 | A177Y | 0.84 | 0.76 | 0.53 | 0.95 | 1.04 |
| 178 | A178C | 0.26 | 0.31 | 0.17 | 0.89 | 1.15 |
| 178 | A178D | 1.60 | 0.63 | 0.68 | 0.96 | 1.03 |
| 178 | A178E | 0.92 | 0.61 | 0.44 | 1.03 | 1.23 |
| 178 | A178F | 0.56 | 0.40 | 0.23 | 0.93 | 0.91 |
| 178 | A178G | 1.18 | 0.73 | 0.61 | 0.84 | 0.81 |
| 178 | A178H | 0.11 | 0.71 | 0.33 | 1.21 | 1.02 |
| 178 | A178I | 0.40 | 0.27 | 0.15 | 1.50 | 1.40 |
| 178 | A178K | 0.76 | 0.10 | 0.12 | 1.15 | 2.62 |
| 178 | A178L | 0.29 | 0.25 | 0.23 | 1.61 | 1.99 |
| 178 | A178M | 0.69 | 0.40 | 0.37 | 1.23 | 1.43 |
| 178 | A178N | 1.80 | 0.36 | 0.48 | 0.95 | 1.39 |
| 178 | A178P | 0.11 | 0.18 | 0.14 | 2.14 | 1.65 |
| 178 | A178Q | 1.22 | 0.51 | 0.49 | 1.17 | 1.36 |
| 178 | A178R | 0.43 | 0.19 | 0.23 | 1.45 | 1.85 |
| 178 | A178S | 0.35 | 0.80 | 0.62 | 1.05 | 0.93 |
| 178 | A178T | 0.21 | 0.39 | 0.30 | 2.08 | 1.42 |
| 178 | A178V | 1.07 | 0.46 | 0.36 | 1.10 | 1.21 |
| 178 | A178W | 0.88 | 0.16 | *0.05* | 1.65 | 2.37 |
| 178 | A178Y | 0.73 | 0.44 | *0.05* | 1.02 | 1.30 |
| 179 | L179A | 1.02 | 1.03 | 1.26 | 1.04 | 0.97 |
| 179 | L179C | 1.06 | 0.87 | 1.01 | 1.09 | 1.04 |
| 179 | L179D | 0.29 | 0.75 | 0.43 | 0.93 | 0.84 |
| 179 | L179E | 0.14 | 0.16 | 0.32 | 0.59 | 0.79 |
| 179 | L179F | 0.27 | 0.77 | 0.42 | 1.01 | 0.93 |
| 179 | L179G | 1.02 | 0.98 | 0.93 | 1.05 | 0.98 |
| 179 | L179H | 0.95 | 0.95 | 0.61 | 1.10 | 0.93 |
| 179 | L179K | 0.76 | 0.89 | 0.70 | 0.99 | 0.87 |
| 179 | L179M | 0.30 | 0.82 | 0.61 | 1.12 | 1.11 |
| 179 | L179N | 0.94 | 0.76 | 0.75 | 1.11 | 0.99 |
| 179 | L179P | 0.24 | 0.32 | 0.26 | 0.91 | 0.85 |
| 179 | L179Q | 0.34 | 0.85 | 1.03 | 1.18 | 1.19 |
| 179 | L179R | 0.13 | 0.17 | *0.05* | 0.27 | 0.92 |
| 179 | L179S | 0.78 | 0.95 | 1.02 | 1.08 | 1.10 |
| 179 | L179T | 0.79 | 0.90 | 0.86 | 1.11 | 1.00 |
| 179 | L179V | 0.82 | 0.96 | 0.79 | 1.06 | 1.03 |
| 179 | L179W | 0.40 | 0.94 | 0.54 | 0.85 | 0.71 |
| 179 | L179Y | 0.24 | 0.67 | 0.56 | 0.79 | 0.73 |
| 180 | A180C | 0.50 | 0.80 | 0.11 | 0.78 | 0.57 |
| 180 | A180D | 0.66 | 0.21 | 0.09 | 0.61 | 0.10 |
| 180 | A180E | 1.04 | 0.53 | 0.24 | 0.76 | 0.74 |
| 180 | A180F | 0.72 | 0.15 | *0.05* | 0.38 | 1.72 |
| 180 | A180G | 0.35 | 0.68 | 0.22 | 0.75 | 0.58 |
| 180 | A180H | 0.58 | 0.11 | 0.07 | 0.56 | 0.25 |
| 180 | A180I | 0.62 | 0.26 | 0.09 | 0.64 | 0.86 |
| 180 | A180K | 0.88 | 0.12 | *0.05* | 0.57 | 0.55 |
| 180 | A180L | 0.82 | 0.20 | 0.08 | 0.59 | 0.83 |
| 180 | A180M | 0.94 | 0.15 | *0.05* | 13.63 | 0.81 |
| 180 | A180N | 0.08 | 0.10 | 0.26 | *0.05* | 4.24 |
| 180 | A180P | 0.50 | 0.53 | 0.10 | 0.72 | 0.59 |
| 180 | A180Q | 0.85 | 0.35 | 0.13 | 0.58 | 0.58 |
| 180 | A180R | 0.69 | 0.05 | 0.11 | 4.95 | 3.56 |
| 180 | A180S | 1.32 | 0.89 | 0.77 | 1.04 | 1.01 |
| 180 | A180T | 0.76 | 0.44 | 0.18 | 0.60 | 0.55 |
| 180 | A180V | 0.32 | 0.19 | 0.23 | 0.85 | 0.84 |
| 180 | A180W | 1.14 | 0.09 | *0.05* | 0.65 | 1.85 |
| 180 | A180Y | 0.63 | 0.09 | *0.05* | 2.52 | 1.23 |
| 181 | S181A | 0.56 | 0.39 | 0.35 | 0.81 | 0.73 |
| 181 | S181C | 0.84 | 0.12 | 0.08 | 1.86 | 1.46 |
| 181 | S181D | 0.84 | 0.12 | 0.16 | 1.32 | 0.90 |
| 181 | S181E | 0.54 | 0.11 | *0.05* | 0.96 | 1.23 |
| 181 | S181F | 0.54 | 0.10 | *0.05* | 1.34 | 1.42 |
| 181 | S181G | 0.90 | 0.42 | 0.18 | 0.89 | 0.84 |
| 181 | S181K | 0.53 | 0.06 | *0.05* | 1.81 | 4.72 |
| 181 | S181L | 0.34 | 0.15 | *0.05* | 0.99 | 1.53 |
| 181 | S181M | 0.45 | 0.11 | 0.13 | 0.55 | 2.09 |
| 181 | S181N | 0.71 | 0.17 | 0.08 | 1.30 | 0.58 |
| 181 | S181P | 0.57 | 0.11 | 0.05 | 1.37 | 0.79 |
| 181 | S181Q | 0.42 | 0.11 | 0.08 | 2.41 | 1.67 |
| 181 | S181R | 0.58 | 0.07 | *0.05* | 0.18 | 1.33 |
| 181 | S181T | 1.01 | 0.17 | 0.09 | 1.53 | 1.19 |
| 181 | S181V | 0.58 | 0.13 | 0.09 | 1.76 | 1.08 |
| 181 | S181W | 0.76 | 0.05 | *0.05* | 0.96 | 3.23 |
| 181 | S181Y | 0.64 | 0.61 | 0.36 | 0.71 | 0.88 |
| 182 | N182A | 0.56 | 1.21 | 0.96 | 0.92 | 1.05 |
| 182 | N182C | 1.24 | 0.96 | 0.80 | 0.91 | 0.89 |
| 182 | N182D | 1.58 | 1.02 | 0.89 | 0.93 | 0.87 |
| 182 | N182E | 0.21 | 0.17 | *0.05* | 0.63 | 1.74 |
| 182 | N182G | 0.93 | 0.86 | 0.83 | 1.21 | 1.26 |
| 182 | N182H | 1.45 | 1.06 | 0.65 | 0.87 | 0.85 |
| 182 | N182I | 0.94 | 0.59 | 0.54 | 1.06 | 1.13 |
| 182 | N182K | 0.99 | 0.59 | 0.43 | 0.87 | 0.80 |
| 182 | N182L | 0.78 | 0.98 | 0.78 | 1.01 | 1.13 |
| 182 | N182M | 1.74 | 0.90 | 0.84 | 1.12 | 1.28 |
| 182 | N182P | 0.87 | 0.63 | 0.50 | 0.85 | 0.85 |
| 182 | N182Q | 0.18 | 0.13 | *0.05* | 1.70 | 1.48 |
| 182 | N182R | 0.69 | 0.73 | 0.46 | 1.03 | 1.03 |
| 182 | N182S | 1.09 | 1.07 | 0.98 | 0.91 | 0.92 |
| 182 | N182T | 1.06 | 0.95 | 0.89 | 0.94 | 0.99 |
| 182 | N182V | 1.10 | 0.74 | 0.59 | 0.76 | 0.77 |
| 182 | N182W | 2.82 | 1.06 | 1.36 | 1.10 | 1.26 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 182 | N182Y | 1.20 | 0.87 | 0.90 | 1.03 | 1.15 |
| 185 | Y185A | 0.07 | *0.05* | 0.29 | 2.19 | 1.88 |
| 185 | Y185C | 0.14 | 0.18 | 0.21 | *0.05* | 0.13 |
| 185 | Y185D | 0.17 | 0.08 | 0.16 | 0.55 | 1.10 |
| 185 | Y185E | 0.59 | 0.08 | 0.12 | 0.09 | 1.45 |
| 185 | Y185F | 0.86 | 1.08 | 0.91 | 1.06 | 1.05 |
| 185 | Y185G | 0.15 | 0.12 | 0.06 | *0.05* | 0.22 |
| 185 | Y185H | 0.59 | 0.88 | 0.34 | 0.64 | 0.46 |
| 185 | Y185I | 0.21 | 0.68 | 0.54 | 0.66 | 0.64 |
| 185 | Y185L | 1.88 | 1.19 | 1.11 | 1.02 | 1.09 |
| 185 | Y185M | 0.35 | 0.74 | 0.41 | 0.97 | 0.78 |
| 185 | Y185P | 0.22 | 0.10 | 0.20 | 0.33 | 0.89 |
| 185 | Y185Q | 0.12 | 0.22 | 0.14 | *0.05* | 0.62 |
| 185 | Y185R | 0.12 | 0.08 | 0.05 | 3.65 | 4.42 |
| 185 | Y185S | 0.16 | 0.41 | 0.16 | 0.32 | 0.26 |
| 185 | Y185T | 0.15 | 0.35 | 0.25 | 0.19 | 0.38 |
| 185 | Y185V | 0.24 | 0.16 | 0.15 | 0.60 | 0.37 |
| 185 | Y185W | 0.28 | 0.80 | 0.77 | 0.83 | 0.97 |
| 186 | S186A | 0.87 | 0.88 | 0.89 | 0.96 | 1.06 |
| 186 | S186C | 0.27 | 0.64 | 0.67 | 1.22 | 2.83 |
| 186 | S186D | 1.73 | 0.97 | 0.96 | 1.04 | 1.19 |
| 186 | S186E | 2.57 | 0.82 | 0.72 | 1.06 | 1.19 |
| 186 | S186F | 0.33 | 0.64 | 0.48 | 1.42 | 1.61 |
| 186 | S186G | 0.49 | 1.02 | 0.59 | 1.01 | 1.09 |
| 186 | S186H | 2.18 | 0.96 | 0.70 | 1.09 | 1.40 |
| 186 | S186I | 3.18 | 0.88 | 0.86 | 1.09 | 1.27 |
| 186 | S186K | 1.22 | 0.95 | 0.61 | 1.03 | 1.00 |
| 186 | S186L | 1.03 | 1.06 | 0.92 | 1.13 | 1.31 |
| 186 | S186M | 1.21 | 0.88 | 0.73 | 1.06 | 1.27 |
| 186 | S186N | 0.16 | 0.65 | 0.43 | 0.91 | 1.04 |
| 186 | S186P | 0.19 | 0.78 | 0.22 | 0.77 | 0.82 |
| 186 | S186Q | 0.69 | 1.10 | 0.95 | 1.07 | 1.21 |
| 186 | S186R | 2.78 | 0.90 | 0.73 | 0.89 | 1.07 |
| 186 | S186T | 0.48 | 1.08 | 0.87 | 1.14 | 1.21 |
| 186 | S186V | 0.92 | 1.03 | 0.91 | 1.03 | 1.26 |
| 186 | S186W | 0.64 | 0.94 | 0.61 | 1.01 | 1.14 |
| 186 | S186Y | 0.21 | 0.24 | *0.05* | 2.68 | 4.96 |
| 188 | A188C | 0.67 | 0.57 | 0.62 | 0.99 | 1.05 |
| 188 | A188D | 0.74 | 0.55 | 0.69 | 1.10 | 1.38 |
| 188 | A188E | 0.42 | 0.79 | 0.62 | 1.41 | 1.06 |
| 188 | A188F | 0.48 | 0.88 | 0.50 | 0.93 | 0.80 |
| 188 | A188H | 0.79 | 0.64 | 0.60 | 1.32 | 1.39 |
| 188 | A188I | 0.41 | 0.52 | 0.37 | 1.60 | 1.05 |
| 188 | A188K | 0.72 | 0.43 | 0.31 | 0.79 | 0.58 |
| 188 | A188L | 0.82 | 0.63 | 0.53 | 1.41 | 0.92 |
| 188 | A188M | 0.39 | 0.60 | 0.52 | 3.51 | 3.70 |
| 188 | A188N | 0.33 | 0.39 | 0.42 | 2.28 | 1.14 |
| 188 | A188P | 0.36 | 1.06 | 0.82 | 1.01 | 0.89 |
| 188 | A188Q | 0.12 | 0.85 | 0.72 | 0.88 | 0.79 |
| 188 | A188R | 0.36 | 0.87 | 0.49 | 0.93 | 0.83 |
| 188 | A188S | 0.63 | 1.21 | 1.17 | 1.05 | 1.00 |
| 188 | A188T | 1.02 | 0.67 | 0.60 | 1.24 | 1.29 |
| 188 | A188V | 0.55 | 0.92 | 0.63 | 0.96 | 0.94 |
| 188 | A188W | 0.53 | 0.61 | 0.57 | 0.90 | 1.02 |
| 188 | A188Y | 0.54 | 0.45 | 0.30 | 1.00 | 0.98 |
| 189 | D189A | 0.29 | 0.77 | 0.73 | 0.79 | 0.69 |
| 189 | D189C | 0.38 | 0.89 | 0.82 | 0.90 | 0.76 |
| 189 | D189E | 0.44 | 0.98 | 0.84 | 0.94 | 0.89 |
| 189 | D189F | 0.39 | 0.82 | 0.64 | 0.94 | 0.99 |
| 189 | D189G | 0.27 | 0.87 | 0.86 | 0.88 | 0.71 |
| 189 | D189H | 0.39 | 0.91 | 0.52 | 0.91 | 0.83 |
| 189 | D189I | 0.16 | 0.52 | 0.39 | 0.63 | 0.61 |
| 189 | D189K | 0.37 | 0.96 | 0.78 | 0.89 | 0.73 |
| 189 | D189L | 0.33 | 1.04 | 0.82 | 0.89 | 0.85 |
| 189 | D189N | 0.55 | 0.95 | 1.05 | 1.00 | 0.96 |
| 189 | D189P | 0.12 | 0.30 | 0.22 | 0.72 | 0.76 |
| 189 | D189Q | 0.73 | 0.98 | 0.72 | 0.93 | 0.86 |
| 189 | D189R | 0.38 | 0.96 | 0.82 | 0.94 | 0.88 |
| 189 | D189S | 0.14 | 0.60 | 0.32 | 0.86 | 1.22 |
| 189 | D189T | 0.21 | 0.84 | 0.84 | 0.85 | 0.76 |
| 189 | D189V | 0.36 | 1.03 | 0.99 | 1.03 | 0.91 |
| 189 | D189W | 0.13 | 0.18 | 0.34 | 0.45 | 1.06 |
| 189 | D189Y | 0.32 | 0.52 | 0.46 | 1.30 | 1.34 |
| 190 | G190A | 0.79 | 0.81 | 0.62 | 0.86 | 0.77 |
| 190 | G190C | 0.35 | 0.80 | 0.87 | 0.78 | 0.83 |
| 190 | G190D | 0.54 | 0.95 | 0.82 | 0.93 | 0.92 |
| 190 | G190E | 0.18 | 0.71 | 0.49 | 0.89 | 1.05 |
| 190 | G190H | 0.11 | 0.40 | 0.24 | 0.35 | 0.80 |
| 190 | G190I | 0.13 | 0.45 | 0.39 | 0.49 | 0.55 |
| 190 | G190K | 0.27 | 0.87 | 0.58 | 0.91 | 0.94 |
| 190 | G190L | 0.74 | 0.89 | 0.60 | 0.82 | 1.04 |
| 190 | G190M | 0.45 | 0.58 | 0.45 | 0.93 | 1.39 |
| 190 | G190N | 0.56 | 1.00 | 0.73 | 0.93 | 0.98 |
| 190 | G190P | 0.14 | 0.09 | 0.26 | 26.00 | 3.19 |
| 190 | G190Q | 0.59 | 1.04 | 0.80 | 0.95 | 1.04 |
| 190 | G190R | 0.49 | 0.74 | 0.44 | 0.74 | 1.10 |
| 190 | G190S | 0.86 | 1.15 | 0.96 | 0.99 | 1.13 |
| 190 | G190T | 0.50 | 0.84 | 0.79 | 1.06 | 1.15 |
| 190 | G190V | 0.25 | 0.90 | 0.57 | 0.88 | 0.83 |
| 190 | G190W | 0.53 | 0.79 | 0.42 | 0.90 | 0.89 |
| 190 | G190Y | 0.38 | 0.95 | 0.83 | 0.84 | 0.91 |
| 191 | G191C | 0.14 | 0.17 | 0.20 | 0.82 | 1.34 |
| 191 | G191D | 0.20 | 0.39 | 0.27 | 0.28 | 0.13 |
| 191 | G191E | 0.15 | 0.22 | 0.10 | 0.75 | 0.79 |
| 191 | G191F | 0.17 | 0.19 | 0.25 | 0.51 | 0.94 |
| 191 | G191I | 0.14 | 0.18 | 0.22 | 0.55 | 0.95 |
| 191 | G191L | 0.15 | 0.24 | 0.18 | 0.95 | 0.91 |
| 191 | G191M | 0.13 | 0.23 | 0.40 | 0.46 | 0.88 |
| 191 | G191P | 0.12 | 0.19 | 0.29 | 0.56 | 1.20 |
| 191 | G191Q | 0.19 | 0.65 | 0.51 | 0.89 | 0.74 |
| 191 | G191R | 0.13 | 0.21 | 0.24 | 0.62 | 1.52 |
| 191 | G191S | 0.09 | 0.38 | 0.05 | 0.75 | 1.30 |
| 191 | G191T | 0.12 | 0.23 | 0.10 | 0.47 | 1.18 |
| 191 | G191V | 0.13 | 0.21 | 0.17 | 0.51 | 1.34 |
| 191 | G191W | 0.12 | 0.18 | 0.12 | 0.07 | 1.08 |
| 192 | V192A | 0.42 | 0.95 | 0.73 | 1.00 | 0.80 |
| 192 | V192C | 0.87 | 0.68 | 0.52 | 0.88 | 0.73 |
| 192 | V192D | 0.38 | 0.39 | 0.34 | 0.48 | 0.50 |
| 192 | V192E | 0.69 | 1.02 | 0.82 | 0.98 | 0.98 |
| 192 | V192F | 0.20 | 0.19 | 0.06 | *0.05* | 0.08 |
| 192 | V192G | 0.16 | 0.46 | 0.21 | 0.47 | 0.53 |
| 192 | V192H | 0.30 | 0.75 | 0.40 | 0.83 | 0.86 |
| 192 | V192K | 0.34 | 0.58 | 0.32 | 0.77 | 0.72 |
| 192 | V192L | 0.76 | 1.04 | 0.55 | 1.03 | 1.00 |
| 192 | V192M | 0.46 | 0.96 | 0.44 | 1.01 | 0.95 |
| 192 | V192P | 0.35 | 0.80 | 0.29 | 0.93 | 0.83 |
| 192 | V192R | 0.60 | 1.01 | 0.76 | 1.02 | 0.99 |
| 192 | V192S | 0.29 | 0.76 | 0.46 | 0.93 | 0.85 |
| 192 | V192T | 0.34 | 0.47 | 0.22 | 0.75 | 0.87 |
| 192 | V192W | 0.25 | 0.53 | 0.25 | 0.72 | 0.65 |
| 192 | V192Y | 0.25 | 0.64 | 0.25 | 0.81 | 0.75 |
| 193 | A193C | 0.31 | 0.99 | 0.93 | 0.94 | 0.71 |
| 193 | A193D | 0.49 | 1.07 | 1.02 | 1.11 | 0.90 |
| 193 | A193E | 0.31 | 1.05 | 0.89 | 1.01 | 0.72 |
| 193 | A193F | 0.35 | 1.06 | 0.75 | 0.99 | 0.80 |
| 193 | A193G | 0.17 | 0.68 | 0.41 | 1.32 | 1.04 |
| 193 | A193I | 0.37 | 1.12 | 0.88 | 0.97 | 0.82 |
| 193 | A193K | 0.32 | 0.85 | 0.71 | 0.99 | 0.85 |
| 193 | A193L | 0.31 | 1.10 | 0.88 | 0.90 | 0.81 |
| 193 | A193M | 0.44 | 1.12 | 0.82 | 0.94 | 0.90 |
| 193 | A193N | 0.74 | 0.96 | 0.84 | 1.05 | 0.97 |
| 193 | A193P | 0.23 | 0.99 | 0.79 | 0.95 | 0.79 |
| 193 | A193Q | 0.48 | 1.11 | 0.82 | 1.02 | 0.96 |
| 193 | A193R | 0.37 | 1.06 | 0.73 | 0.98 | 0.89 |
| 193 | A193S | 0.48 | 0.98 | 0.81 | 0.95 | 0.85 |
| 193 | A193T | 0.10 | 0.40 | 0.31 | 1.16 | 0.77 |
| 193 | A193V | 0.45 | 1.06 | 0.85 | 0.99 | 0.87 |
| 193 | A193W | 0.49 | 1.11 | 1.05 | 0.98 | 0.87 |
| 193 | A193Y | 0.40 | 0.78 | 0.63 | 0.88 | 0.79 |
| 194 | K194A | 0.30 | 0.67 | 0.86 | 0.95 | 1.00 |
| 194 | K194C | 0.22 | 1.08 | 1.72 | 0.88 | 0.88 |
| 194 | K194D | 0.61 | 0.98 | 1.07 | 1.00 | 1.03 |
| 194 | K194E | 0.44 | 1.00 | 1.14 | 1.02 | 1.14 |
| 194 | K194F | 0.67 | 1.03 | 0.94 | 1.04 | 1.13 |
| 194 | K194G | 0.43 | 0.92 | 0.65 | 0.92 | 0.96 |
| 194 | K194H | 0.60 | 0.99 | 0.92 | 1.05 | 1.15 |
| 194 | K194I | 0.24 | 0.38 | 0.49 | 0.50 | 0.59 |
| 194 | K194L | 0.61 | 0.98 | 0.90 | 1.01 | 1.22 |
| 194 | K194M | 0.61 | 1.02 | 0.86 | 1.03 | 1.17 |
| 194 | K194N | 0.54 | 0.99 | 1.02 | 1.04 | 1.17 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 194 | K194P | 0.32 | 0.39 | 0.55 | 0.46 | 0.38 |
| 194 | K194Q | 0.64 | 1.00 | 1.00 | 1.03 | 1.17 |
| 194 | K194R | 0.66 | 1.04 | 0.88 | 1.01 | 1.23 |
| 194 | K194S | 0.66 | 1.00 | 0.83 | 1.12 | 1.03 |
| 194 | K194T | 0.08 | 0.11 | 1.09 | 1.17 | 9.80 |
| 194 | K194V | 0.23 | 0.30 | 0.71 | 0.55 | 0.62 |
| 194 | K194W | 0.43 | 0.93 | 0.98 | 0.98 | 1.01 |
| 194 | K194Y | 0.08 | 0.11 | 0.36 | 0.60 | 2.65 |
| 196 | K196A | 0.43 | 0.98 | 0.81 | 0.91 | 0.85 |
| 196 | K196F | 0.52 | 1.02 | 0.93 | 1.02 | 1.04 |
| 196 | K196G | 0.13 | 0.71 | 0.30 | 0.96 | 0.86 |
| 196 | K196H | 0.26 | 1.02 | 0.77 | 1.00 | 1.03 |
| 196 | K196L | 0.63 | 0.95 | 0.71 | 1.00 | 1.00 |
| 196 | K196M | 0.84 | 0.98 | 0.94 | 0.97 | 1.02 |
| 196 | K196Q | 0.67 | 0.98 | 0.74 | 0.97 | 1.05 |
| 196 | K196W | 0.31 | 0.84 | 0.51 | 0.92 | 0.86 |
| 196 | K196Y | 0.07 | 1.23 | 0.50 | 0.94 | 0.96 |
| 197 | N197A | 0.56 | 1.22 | 1.12 | 0.98 | 0.96 |
| 197 | N197C | 0.30 | 0.98 | 0.72 | 1.09 | 1.02 |
| 197 | N197D | 1.50 | 1.12 | 1.08 | 1.06 | 1.07 |
| 197 | N197F | 0.29 | 0.99 | 0.69 | 0.91 | 0.85 |
| 197 | N197G | 1.53 | 1.10 | 0.92 | 1.07 | 1.10 |
| 197 | N197H | 1.02 | 1.07 | 0.80 | 1.08 | 1.10 |
| 197 | N197I | 0.60 | 1.10 | 0.74 | 1.03 | 1.02 |
| 197 | N197K | 0.45 | 1.00 | 0.48 | 0.89 | 0.94 |
| 197 | N197L | 0.29 | 0.97 | 0.60 | 0.97 | 0.95 |
| 197 | N197M | 0.53 | 1.14 | 0.82 | 1.05 | 1.05 |
| 197 | N197P | 0.41 | 1.01 | 0.79 | 0.93 | 0.93 |
| 197 | N197Q | 0.39 | 0.95 | 0.72 | 0.98 | 0.98 |
| 197 | N197R | 0.26 | 0.98 | 0.74 | 0.93 | 1.05 |
| 197 | N197T | 0.68 | 1.07 | 0.78 | 1.04 | 1.00 |
| 197 | N197V | 0.67 | 1.12 | 0.87 | 0.97 | 1.04 |
| 197 | N197W | 0.46 | 0.99 | 0.77 | 0.98 | 1.01 |
| 197 | N197Y | 0.18 | 0.56 | 0.06 | 0.63 | 1.17 |
| 201 | T201A | 0.54 | 0.61 | 0.61 | 0.87 | 0.83 |
| 201 | T201C | 0.34 | 0.79 | 0.62 | 0.92 | 0.99 |
| 201 | T201D | 0.30 | 1.00 | 1.08 | 0.89 | 0.73 |
| 201 | T201E | 0.18 | 0.84 | 0.43 | 0.87 | 0.71 |
| 201 | T201F | 0.32 | 0.81 | 0.61 | 0.85 | 0.89 |
| 201 | T201G | 0.33 | 1.06 | 0.93 | 0.90 | 0.86 |
| 201 | T201H | 0.33 | 0.96 | 0.75 | 0.86 | 0.86 |
| 201 | T201I | 0.20 | 0.86 | 0.58 | 0.89 | 0.70 |
| 201 | T201K | 0.25 | 1.12 | 0.87 | 0.87 | 0.74 |
| 201 | T201L | 0.40 | 0.98 | 0.63 | 0.93 | 0.89 |
| 201 | T201M | 0.43 | 0.97 | 0.66 | 0.90 | 0.95 |
| 201 | T201N | 0.29 | 0.85 | 0.66 | 0.85 | 0.85 |
| 201 | T201P | 0.22 | 0.63 | 0.42 | 0.94 | 1.41 |
| 201 | T201Q | 0.42 | 0.95 | 0.70 | 0.86 | 0.95 |
| 201 | T201R | 0.33 | 0.56 | 0.39 | 1.28 | 1.26 |
| 201 | T201S | 0.38 | 1.01 | 0.70 | 0.90 | 0.83 |
| 201 | T201V | 0.28 | 0.56 | 0.53 | 1.07 | 1.11 |
| 201 | T201W | 0.23 | 0.66 | 0.50 | 0.92 | 0.93 |
| 201 | T201Y | 0.24 | 0.55 | 0.40 | 1.05 | 2.18 |
| 203 | R203A | 0.71 | 0.93 | 0.75 | 0.69 | 0.88 |
| 203 | R203F | 0.85 | 0.92 | 0.99 | 0.67 | 0.87 |
| 203 | R203G | 0.60 | 1.07 | 1.13 | 0.66 | 1.39 |
| 203 | R203H | 0.81 | 1.04 | 1.24 | 2.57 | 3.09 |
| 203 | R203I | 0.39 | 0.70 | 0.64 | 1.46 | 3.02 |
| 203 | R203K | 0.96 | 0.84 | 0.99 | 0.55 | 0.75 |
| 203 | R203L | 0.46 | 1.14 | 0.54 | 1.08 | 1.24 |
| 203 | R203M | 0.58 | 0.88 | 0.91 | 0.99 | 1.25 |
| 203 | R203N | 0.36 | 1.08 | 0.82 | 1.06 | 1.20 |
| 203 | R203P | 0.29 | 0.49 | 0.28 | 2.85 | 4.58 |
| 203 | R203Q | 0.80 | 0.99 | 0.78 | 0.84 | 0.86 |
| 203 | R203S | 0.54 | 1.19 | 0.53 | 1.99 | 1.96 |
| 203 | R203T | 0.66 | 1.04 | 0.82 | 0.99 | 0.91 |
| 203 | R203V | 0.85 | 0.94 | 0.89 | 0.73 | 0.78 |
| 203 | R203W | 0.39 | 1.10 | 0.63 | 2.28 | 2.42 |
| 203 | R203Y | 0.57 | 1.09 | 1.03 | 1.03 | 1.18 |
| 204 | Q204A | 0.91 | 0.98 | 0.98 | 0.99 | 0.99 |
| 204 | Q204C | 1.03 | 1.13 | 0.91 | 1.00 | 0.89 |
| 204 | Q204D | 1.23 | 1.04 | 0.73 | 1.00 | 1.00 |
| 204 | Q204E | 1.08 | 1.12 | 1.05 | 0.93 | 1.04 |
| 204 | Q204F | 0.48 | 0.74 | 0.94 | 1.13 | 0.94 |
| 204 | Q204G | 1.14 | 1.08 | 0.87 | 0.77 | 0.75 |
| 204 | Q204H | 1.30 | 1.12 | 0.84 | 1.16 | 0.91 |
| 204 | Q204I | 0.86 | 0.68 | 0.88 | 1.33 | 1.57 |
| 204 | Q204K | 1.13 | 0.75 | 0.91 | 1.61 | 1.28 |
| 204 | Q204L | 0.45 | 0.82 | 0.81 | 0.98 | 0.96 |
| 204 | Q204M | 0.44 | 0.85 | 0.87 | 0.78 | 0.76 |
| 204 | Q204N | 0.59 | 0.96 | 0.96 | 1.04 | 0.83 |
| 204 | Q204P | 0.36 | 0.50 | 0.83 | 1.09 | 1.19 |
| 204 | Q204R | 0.95 | 0.87 | 0.89 | 1.36 | 1.06 |
| 204 | Q204S | 0.68 | 0.53 | 1.00 | 0.97 | 1.95 |
| 204 | Q204T | 1.94 | 1.08 | 0.93 | 1.07 | 1.18 |
| 204 | Q204V | 0.85 | 0.78 | 0.74 | 1.29 | 1.32 |
| 204 | Q204W | 0.13 | 0.07 | 0.22 | 0.11 | 0.15 |
| 206 | V206C | 0.46 | 0.83 | 0.43 | 1.52 | 1.48 |
| 206 | V206D | 0.38 | 0.24 | 0.10 | 3.69 | 7.75 |
| 206 | V206E | 0.35 | 0.45 | 0.39 | 1.54 | 3.44 |
| 206 | V206F | 0.76 | 1.00 | 0.74 | 2.06 | 2.29 |
| 206 | V206G | 0.33 | 0.94 | 0.79 | 1.56 | 1.54 |
| 206 | V206I | 0.35 | 1.56 | 0.83 | 1.97 | 1.61 |
| 206 | V206L | 0.82 | 1.44 | 0.87 | 0.70 | 0.84 |
| 206 | V206M | 0.42 | 1.41 | 0.49 | 1.75 | 1.64 |
| 206 | V206P | 0.48 | 0.24 | 0.30 | 3.72 | 7.12 |
| 206 | V206Q | 0.27 | 1.35 | 0.40 | 2.88 | 2.34 |
| 206 | V206R | 0.24 | 0.72 | 0.45 | 7.05 | 6.46 |
| 206 | V206S | 0.44 | 0.48 | 0.44 | 1.64 | 2.37 |
| 206 | V206T | 0.71 | 1.30 | 0.69 | 1.07 | 1.06 |
| 206 | V206W | 0.77 | 0.50 | 0.29 | 0.71 | 2.48 |
| 206 | V206Y | 0.66 | 1.19 | 0.57 | 1.17 | 1.58 |
| 207 | V207A | 0.72 | 1.09 | 0.93 | 0.94 | 1.01 |
| 207 | V207C | 0.69 | 1.07 | 0.83 | 0.94 | 0.99 |
| 207 | V207D | 0.11 | *0.05* | *0.05* | 1.44 | 1.05 |
| 207 | V207E | 0.56 | 1.04 | 0.70 | 0.79 | 1.01 |
| 207 | V207F | 0.78 | 1.11 | 0.67 | 0.87 | 1.09 |
| 207 | V207G | 0.83 | 0.98 | 0.90 | 1.12 | 1.01 |
| 207 | V207I | 0.69 | 1.06 | 0.84 | 0.94 | 1.03 |
| 207 | V207K | 0.75 | 0.97 | 0.67 | 1.03 | 1.04 |
| 207 | V207L | 0.64 | 1.01 | 0.73 | 0.70 | 1.09 |
| 207 | V207M | 0.58 | 0.92 | 0.62 | 1.00 | 1.03 |
| 207 | V207N | 0.68 | 0.84 | 0.53 | 1.01 | 1.03 |
| 207 | V207P | 0.20 | 0.10 | *0.05* | 1.83 | 2.90 |
| 207 | V207Q | 0.62 | 1.04 | 0.72 | 0.89 | 1.01 |
| 207 | V207R | 0.99 | 0.93 | 0.69 | 0.86 | 1.10 |
| 207 | V207S | 0.18 | *0.05* | *0.05* | 11.51 | 0.58 |
| 207 | V207W | 0.96 | 0.95 | 0.58 | 1.13 | 1.06 |
| 207 | V207Y | 0.78 | 0.95 | 0.62 | 1.06 | 1.01 |
| 210 | S210A | 0.69 | 0.94 | 0.87 | 0.94 | 0.91 |
| 210 | S210E | 0.28 | 0.80 | 0.64 | 0.85 | 0.76 |
| 210 | S210F | 0.43 | 0.80 | 0.53 | 0.92 | 0.81 |
| 210 | S210G | 0.39 | 0.70 | 0.49 | 0.94 | 0.83 |
| 210 | S210H | 0.32 | 0.90 | 0.80 | 0.93 | 0.72 |
| 210 | S210I | 0.78 | 0.72 | 0.56 | 0.91 | 0.84 |
| 210 | S210L | 0.06 | 1.45 | 1.58 | 0.93 | 0.86 |
| 210 | S210N | 0.45 | 0.93 | 1.02 | 0.93 | 0.92 |
| 210 | S210P | 0.31 | 0.78 | 0.80 | 0.86 | 0.77 |
| 210 | S210R | 0.38 | 0.91 | 0.62 | 0.94 | 0.88 |
| 210 | S210T | 0.55 | 0.95 | 0.76 | 0.96 | 0.89 |
| 210 | S210V | 0.33 | 0.82 | 0.65 | 0.99 | 0.93 |
| 210 | S210W | 0.38 | 1.02 | 0.97 | 1.00 | 0.89 |
| 210 | S210Y | 0.28 | 0.77 | 0.58 | 0.96 | 0.87 |
| 214 | T214A | 0.23 | 1.00 | 0.60 | 0.84 | 1.11 |
| 214 | T214C | 0.95 | 1.08 | 0.98 | 0.92 | 0.94 |
| 214 | T214D | 0.13 | 0.57 | 0.55 | 0.65 | 1.29 |
| 214 | T214E | 0.16 | 0.54 | 0.32 | 0.90 | 1.02 |
| 214 | T214F | 0.19 | 0.89 | 0.57 | 0.62 | 0.84 |
| 214 | T214G | 0.11 | 0.62 | 0.47 | 0.61 | 0.75 |
| 214 | T214H | 0.88 | 1.05 | 0.97 | 1.04 | 1.13 |
| 214 | T214I | 1.00 | 1.08 | 1.00 | 1.06 | 1.03 |
| 214 | T214K | 0.25 | 0.41 | 0.25 | 0.87 | 0.74 |
| 214 | T214L | 0.33 | 1.07 | 0.31 | 0.61 | 0.40 |
| 214 | T214N | 1.80 | 1.04 | 1.04 | 1.10 | 1.20 |
| 214 | T214P | 0.62 | 0.99 | 0.90 | 1.03 | 0.95 |
| 214 | T214Q | 0.86 | 1.05 | 0.78 | 1.03 | 1.08 |
| 214 | T214R | 0.37 | 0.17 | *0.05* | 0.48 | 1.29 |
| 214 | T214S | 0.54 | 1.03 | 0.86 | 0.94 | 1.08 |
| 214 | T214V | 1.01 | 1.13 | 1.03 | 1.01 | 0.97 |
| 214 | T214W | 0.32 | 0.29 | 0.32 | 0.87 | 1.07 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 214 | T214Y | 0.36 | 0.50 | 0.47 | 0.68 | 0.62 |
| 225 | N225A | 0.26 | 0.36 | 0.51 | 0.54 | 0.38 |
| 225 | N225C | 0.15 | 0.13 | 0.41 | 1.24 | 0.81 |
| 225 | N225D | 0.34 | 0.36 | 0.47 | 0.54 | 0.25 |
| 225 | N225E | 0.15 | 0.11 | 0.21 | 0.87 | 0.31 |
| 225 | N225F | 0.13 | 0.17 | 0.29 | 0.77 | 0.42 |
| 225 | N225G | 0.10 | 0.31 | 0.20 | 0.70 | 0.69 |
| 225 | N225H | 0.12 | 0.13 | 0.17 | 0.80 | 0.30 |
| 225 | N225I | 0.08 | 0.17 | 0.22 | 0.80 | 0.37 |
| 225 | N225K | 0.26 | 0.12 | 0.17 | 0.98 | 2.90 |
| 225 | N225L | 0.11 | 0.24 | 0.36 | 0.87 | 1.11 |
| 225 | N225M | 0.12 | 0.74 | 0.47 | 0.99 | 0.78 |
| 225 | N225P | 0.14 | 0.29 | 0.44 | 0.58 | 0.74 |
| 225 | N225Q | 0.14 | 0.44 | 0.25 | 0.60 | 0.41 |
| 225 | N225R | 0.11 | 0.13 | 0.21 | 1.69 | 1.02 |
| 225 | N225S | 0.14 | 0.40 | 0.45 | 0.68 | 0.82 |
| 225 | N225T | 0.21 | 0.50 | 0.34 | 0.56 | 0.76 |
| 225 | N225V | 0.20 | 0.38 | 0.30 | 0.84 | 0.33 |
| 225 | N225W | 0.20 | 0.13 | 0.20 | 1.87 | 1.45 |
| 225 | N225Y | 0.19 | 0.20 | 0.17 | 0.75 | 0.52 |
| 226 | L226C | 0.15 | 0.65 | 0.39 | 0.73 | 0.56 |
| 226 | L226D | 0.16 | 0.18 | 0.31 | 0.68 | 1.08 |
| 226 | L226E | 0.20 | 0.29 | 0.31 | 0.93 | 1.23 |
| 226 | L226F | 0.21 | 0.57 | 0.34 | 0.80 | 0.74 |
| 226 | L226G | 0.16 | 0.29 | 0.15 | 0.41 | 0.51 |
| 226 | L226H | 0.19 | 0.32 | 0.29 | 0.81 | 0.95 |
| 226 | L226M | 0.67 | 1.02 | 0.80 | 1.12 | 1.05 |
| 226 | L226N | 0.12 | 0.35 | 0.21 | 0.64 | 0.81 |
| 226 | L226P | 0.21 | 0.21 | 0.26 | 1.02 | 1.62 |
| 226 | L226R | 0.14 | 0.24 | 0.16 | 0.73 | 1.18 |
| 226 | L226S | 0.23 | 0.59 | 0.27 | 0.70 | 0.80 |
| 226 | L226T | 0.14 | 0.46 | 0.15 | 0.71 | 0.68 |
| 226 | L226V | 0.26 | 0.86 | 0.43 | 0.85 | 0.83 |
| 226 | L226W | 0.18 | 0.26 | 0.24 | 0.71 | 1.94 |
| 226 | L226Y | 0.15 | 0.28 | 0.35 | 0.53 | 1.17 |
| 228 | T228A | 0.22 | 0.48 | 0.87 | 0.29 | 0.49 |
| 228 | T228C | 0.12 | 0.37 | 0.79 | 0.49 | 0.81 |
| 228 | T228F | 0.22 | 0.14 | 0.23 | 0.92 | 1.09 |
| 228 | T228G | 0.25 | 0.46 | 0.67 | 0.32 | 0.44 |
| 228 | T228H | 0.14 | 0.24 | 0.73 | 0.46 | 1.00 |
| 228 | T228I | 0.23 | 0.23 | 0.36 | 0.76 | 0.88 |
| 228 | T228K | 0.19 | 0.11 | 0.31 | 0.54 | 1.35 |
| 228 | T228M | 0.28 | 0.34 | 0.41 | 0.55 | 0.62 |
| 228 | T228N | 0.23 | 0.49 | 0.28 | 0.54 | 0.49 |
| 228 | T228P | 0.14 | 0.25 | 0.42 | 0.26 | 0.78 |
| 228 | T228R | 0.38 | 0.11 | 0.74 | 0.90 | 1.70 |
| 228 | T228S | 0.22 | 0.63 | 0.41 | 0.55 | 0.52 |
| 228 | T228V | 0.56 | 0.69 | 0.13 | 0.90 | 0.67 |
| 228 | T228W | 0.18 | 0.08 | 0.42 | 9.87 | 33.17 |
| 228 | T228Y | 0.28 | 0.12 | 0.43 | *0.05* | 1.28 |
| 229 | N229A | 0.56 | 0.88 | 0.80 | 0.75 | 0.68 |
| 229 | N229C | 0.19 | 1.06 | 0.65 | 0.90 | 1.09 |
| 229 | N229D | 0.16 | 0.36 | *0.05* | 0.87 | 0.78 |
| 229 | N229E | 0.42 | 0.73 | 0.54 | 0.89 | 0.69 |
| 229 | N229F | 0.24 | 0.44 | 0.50 | 0.97 | 0.90 |
| 229 | N229G | 0.52 | 0.77 | 0.78 | 0.77 | 0.70 |
| 229 | N229H | 0.66 | 0.76 | 0.60 | 0.95 | 1.00 |
| 229 | N229I | 0.49 | 0.78 | 0.81 | 0.89 | 0.93 |
| 229 | N229K | 0.84 | 0.81 | 0.64 | 0.90 | 0.86 |
| 229 | N229L | 0.39 | 0.48 | 0.20 | 0.61 | 0.61 |
| 229 | N229M | 0.54 | 0.77 | 0.43 | 0.90 | 0.86 |
| 229 | N229P | 0.35 | 0.67 | 0.34 | 0.80 | 0.85 |
| 229 | N229Q | 0.17 | 0.48 | 0.33 | 0.94 | 1.72 |
| 229 | N229R | 0.42 | 0.81 | 0.53 | 0.93 | 0.81 |
| 229 | N229S | 0.49 | 0.92 | 0.69 | 0.84 | 0.72 |
| 229 | N229T | 0.36 | 0.67 | 0.53 | 0.64 | 0.60 |
| 229 | N229V | 0.48 | 0.56 | 0.44 | 0.74 | 0.90 |
| 229 | N229W | 0.33 | 0.64 | 0.60 | 0.75 | 0.73 |
| 229 | N229Y | 0.30 | 0.90 | 0.66 | 0.96 | 0.93 |
| 230 | L230A | 0.18 | 0.85 | 0.43 | 0.54 | 0.28 |
| 230 | L230C | 0.27 | 0.77 | 0.51 | 0.62 | 0.39 |
| 230 | L230D | 0.23 | 0.45 | 0.26 | 0.55 | 0.43 |
| 230 | L230E | 0.30 | 0.85 | 0.45 | 0.85 | 0.51 |
| 230 | L230F | 0.46 | 0.88 | 0.42 | 0.80 | 0.62 |
| 230 | L230G | 0.33 | 0.70 | 0.35 | 0.84 | 0.39 |
| 230 | L230H | 0.37 | 0.57 | 0.17 | 3.13 | 1.86 |
| 230 | L230I | 0.22 | 0.63 | 0.48 | 0.71 | 0.62 |
| 230 | L230K | 0.11 | 1.05 | 0.15 | 0.86 | 0.52 |
| 230 | L230M | 0.14 | 0.65 | 0.59 | 0.80 | 0.76 |
| 230 | L230N | 0.55 | 0.97 | 0.50 | 0.71 | 0.51 |
| 230 | L230P | 0.26 | 0.71 | 0.32 | 0.49 | 0.40 |
| 230 | L230Q | 0.30 | 0.78 | 0.37 | 0.79 | 0.51 |
| 230 | L230R | 0.87 | 1.03 | 0.42 | 0.92 | 0.79 |
| 230 | L230S | 0.36 | 0.63 | 0.43 | 1.04 | 0.66 |
| 230 | L230T | 0.42 | 1.04 | 0.52 | 0.78 | 0.67 |
| 230 | L230V | 0.29 | 0.82 | 0.36 | 0.72 | 0.62 |
| 230 | L230W | 0.14 | 0.28 | 0.16 | 0.80 | 0.81 |
| 230 | L230Y | 0.65 | 0.92 | 0.72 | 0.87 | 0.79 |
| 231 | G231A | 1.45 | 0.98 | 1.13 | 1.00 | 0.98 |
| 231 | G231C | 0.43 | 0.72 | 0.24 | 0.89 | 0.66 |
| 231 | G231E | 0.13 | 0.15 | 0.10 | 0.67 | 1.05 |
| 231 | G231F | 0.54 | 0.82 | 0.22 | 0.86 | 0.70 |
| 231 | G231H | 0.39 | 0.78 | 0.32 | 0.88 | 0.80 |
| 231 | G231I | 0.17 | 0.14 | 0.56 | 1.07 | 1.44 |
| 231 | G231K | 0.33 | 0.75 | 0.62 | 0.84 | 0.74 |
| 231 | G231L | 0.45 | 0.92 | 0.65 | 0.74 | 0.58 |
| 231 | G231M | 0.16 | 0.24 | 0.60 | 0.81 | 1.41 |
| 231 | G231N | 0.58 | 0.87 | 0.93 | 0.97 | 0.98 |
| 231 | G231P | 0.16 | 0.21 | 0.45 | 0.72 | 0.81 |
| 231 | G231Q | 0.29 | 0.13 | 0.22 | 0.77 | 1.25 |
| 231 | G231R | 0.33 | 0.43 | 0.36 | 0.79 | 0.79 |
| 231 | G231S | 0.81 | 1.01 | 0.62 | 1.01 | 0.96 |
| 231 | G231T | 0.96 | 0.66 | 0.44 | 0.89 | 0.68 |
| 231 | G231V | 0.19 | 0.55 | 0.55 | 0.54 | 0.42 |
| 231 | G231W | 0.73 | 0.80 | 0.16 | 0.91 | 0.74 |
| 231 | G231Y | 0.75 | 0.85 | 0.58 | 0.83 | 0.65 |
| 232 | T232A | 0.31 | 0.67 | 0.99 | 1.00 | 0.83 |
| 232 | T232C | 0.36 | 0.63 | 1.16 | 0.71 | 0.97 |
| 232 | T232E | 0.34 | 0.64 | 0.88 | 0.91 | 0.85 |
| 232 | T232F | 0.31 | 0.62 | 0.87 | 0.90 | 0.97 |
| 232 | T232I | 0.23 | 0.49 | 0.81 | 0.94 | 0.96 |
| 232 | T232K | 0.63 | 0.76 | 0.66 | 0.97 | 1.02 |
| 232 | T232L | 0.20 | 0.55 | 0.96 | 0.91 | 0.85 |
| 232 | T232N | 0.22 | 0.21 | 0.52 | 0.47 | 0.65 |
| 232 | T232P | 0.52 | 0.79 | 0.95 | 0.89 | 1.02 |
| 232 | T232Q | 0.33 | 0.57 | 0.89 | 0.83 | 0.98 |
| 232 | T232S | 0.34 | 0.72 | 0.76 | 0.94 | 1.06 |
| 232 | T232V | 0.50 | 0.67 | 0.89 | 1.42 | 1.42 |
| 232 | T232W | 0.25 | 0.43 | 0.47 | 0.73 | 0.59 |
| 232 | T232Y | 0.43 | 0.72 | 0.71 | 1.05 | 1.00 |
| 233 | P233A | 0.56 | 1.06 | 1.15 | 0.85 | 0.77 |
| 233 | P233C | 0.28 | 0.92 | 1.01 | 0.85 | 0.72 |
| 233 | P233D | 0.41 | 0.89 | 1.49 | 0.87 | 0.84 |
| 233 | P233E | 0.52 | 1.02 | 1.34 | 0.91 | 0.88 |
| 233 | P233F | 0.30 | 1.01 | 0.89 | 0.85 | 0.81 |
| 233 | P233G | 0.40 | 1.07 | 1.22 | 0.79 | 0.69 |
| 233 | P233H | 0.38 | 1.01 | 0.64 | 0.90 | 0.84 |
| 233 | P233I | 0.43 | 1.04 | 0.87 | 0.90 | 0.81 |
| 233 | P233K | 0.33 | 0.85 | 0.76 | 0.91 | 0.86 |
| 233 | P233L | 0.45 | 1.03 | 0.89 | 0.90 | 0.87 |
| 233 | P233M | 0.26 | 0.99 | 0.92 | 0.92 | 0.88 |
| 233 | P233N | 0.17 | 0.70 | 1.15 | 0.94 | 0.82 |
| 233 | P233Q | 0.35 | 1.03 | 1.19 | 0.94 | 0.87 |
| 233 | P233R | 0.27 | 0.77 | 0.47 | 0.77 | 0.96 |
| 233 | P233S | 0.32 | 0.60 | 0.62 | 0.98 | 1.01 |
| 233 | P233T | 0.27 | 0.77 | 0.84 | 0.87 | 0.90 |
| 233 | P233V | 0.33 | 0.76 | 0.80 | 0.78 | 0.92 |
| 233 | P233W | 0.21 | 0.75 | 0.70 | 0.98 | 0.82 |
| 233 | P233Y | 0.27 | 0.73 | 0.91 | 0.87 | 0.91 |
| 234 | K234A | 1.16 | 0.90 | 0.81 | 0.91 | 1.46 |
| 234 | K234C | 0.60 | 0.94 | 0.48 | 0.94 | 1.36 |
| 234 | K234D | 0.61 | 0.74 | 0.44 | 0.93 | 1.46 |
| 234 | K234F | 0.36 | 0.82 | 0.05 | 0.98 | 2.17 |
| 234 | K234G | 0.84 | 0.91 | 0.56 | 0.50 | 1.41 |
| 234 | K234H | 0.59 | 0.98 | 0.45 | 1.00 | 1.83 |
| 234 | K234L | 0.27 | 1.08 | 0.42 | 2.09 | 1.93 |
| 234 | K234M | 0.39 | 0.84 | 0.44 | 1.18 | 1.85 |
| 234 | K234N | 0.51 | 0.97 | 0.59 | 1.23 | 1.19 |
| 234 | K234S | 0.17 | 0.94 | 0.43 | 3.50 | 3.17 |
| 234 | K234T | 0.77 | 0.92 | 0.57 | 0.75 | 1.27 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 234 | K234V | 0.32 | 1.01 | 0.22 | 1.43 | 2.47 |
| 234 | K234Y | 0.28 | 1.01 | 0.39 | 1.29 | 1.86 |
| 236 | A236C | 0.12 | 0.18 | 0.33 | 3.03 | 3.16 |
| 236 | A236D | 0.39 | 0.97 | 0.91 | 1.03 | 0.61 |
| 236 | A236E | 0.45 | 1.02 | 0.79 | 0.94 | 0.82 |
| 236 | A236F | 0.42 | 0.96 | 0.62 | 0.95 | 0.93 |
| 236 | A236G | 0.58 | 0.84 | 0.59 | 0.88 | 0.68 |
| 236 | A236H | 0.62 | 0.97 | 0.54 | 0.93 | 0.90 |
| 236 | A236I | 0.22 | 0.86 | 0.50 | 0.89 | 0.49 |
| 236 | A236K | 0.34 | 1.08 | 0.56 | 0.95 | 0.69 |
| 236 | A236L | 0.32 | 0.94 | 0.74 | 0.99 | 0.79 |
| 236 | A236M | 0.41 | 1.01 | 0.71 | 0.88 | 0.90 |
| 236 | A236N | 0.30 | 0.97 | 0.72 | 0.94 | 0.88 |
| 236 | A236P | 0.14 | 0.29 | 0.22 | 0.38 | 0.87 |
| 236 | A236Q | 0.43 | 1.07 | 0.74 | 0.93 | 0.78 |
| 236 | A236R | 0.48 | 1.03 | 0.56 | 0.97 | 0.96 |
| 236 | A236S | 0.38 | 0.83 | 0.71 | 1.01 | 0.80 |
| 236 | A236T | 0.35 | 0.97 | 0.60 | 0.85 | 0.71 |
| 236 | A236V | 0.32 | 0.88 | 0.55 | 0.87 | 0.63 |
| 236 | A236W | 0.30 | 0.58 | 0.45 | 13.41 | 5.08 |
| 236 | A236Y | 0.42 | 0.54 | 0.53 | 3.39 | 1.31 |
| 237 | N237A | 0.75 | 1.02 | 0.91 | 0.80 | 0.88 |
| 237 | N237C | 0.43 | 1.26 | 0.77 | 1.02 | 1.28 |
| 237 | N237F | 0.52 | 0.91 | 0.17 | 0.76 | 1.34 |
| 237 | N237G | 0.71 | 1.06 | 0.38 | 1.02 | 0.95 |
| 237 | N237H | 0.57 | 0.98 | 0.56 | 0.99 | 1.03 |
| 237 | N237I | 0.66 | 0.96 | 0.23 | 0.68 | 1.05 |
| 237 | N237K | 0.63 | 1.04 | 0.38 | 1.17 | 1.31 |
| 237 | N237L | 0.76 | 1.04 | 0.58 | 0.64 | 1.40 |
| 237 | N237P | 0.24 | 0.59 | 0.07 | 1.96 | 3.82 |
| 237 | N237Q | 0.93 | 1.06 | 1.05 | 0.92 | 1.39 |
| 237 | N237R | 0.65 | 1.02 | 0.34 | 1.19 | 1.69 |
| 237 | N237S | 0.91 | 0.99 | 0.75 | 0.98 | 1.25 |
| 237 | N237T | 1.39 | 0.95 | 0.92 | 0.68 | 1.15 |
| 237 | N237V | 0.80 | 1.07 | 0.45 | 0.83 | 1.69 |
| 237 | N237W | 0.46 | 1.12 | 0.24 | 0.97 | 1.62 |
| 237 | N237Y | 0.30 | 0.63 | 0.16 | 2.26 | 3.41 |
| 239 | Q239A | 1.09 | 0.96 | 0.82 | 0.94 | 1.05 |
| 239 | Q239C | 0.63 | 0.99 | 0.94 | 0.98 | 0.97 |
| 239 | Q239D | 0.59 | 0.98 | 0.91 | 0.92 | 0.92 |
| 239 | Q239E | 0.70 | 1.10 | 1.16 | 1.00 | 1.04 |
| 239 | Q239F | 0.83 | 0.99 | 0.63 | 0.99 | 0.98 |
| 239 | Q239G | 0.39 | 1.21 | 0.58 | 0.91 | 0.97 |
| 239 | Q239H | 0.96 | 1.08 | 0.84 | 0.92 | 0.99 |
| 239 | Q239I | 0.59 | 1.07 | 0.43 | 0.88 | 0.90 |
| 239 | Q239L | 0.71 | 0.98 | 0.70 | 0.82 | 0.88 |
| 239 | Q239M | 0.85 | 1.08 | 0.77 | 0.97 | 0.99 |
| 239 | Q239N | 0.70 | 1.05 | 0.65 | 0.99 | 0.96 |
| 239 | Q239P | 0.31 | 0.51 | 0.40 | 0.47 | 0.90 |
| 239 | Q239R | 1.06 | 1.02 | 0.70 | 1.01 | 0.96 |
| 239 | Q239S | 0.88 | 1.08 | 1.04 | 0.90 | 1.02 |
| 239 | Q239T | 0.54 | 1.01 | 0.73 | 0.84 | 0.74 |
| 239 | Q239V | 0.84 | 0.97 | 0.71 | 1.03 | 0.92 |
| 239 | Q239W | 0.94 | 0.96 | 0.64 | 0.87 | 0.80 |
| 239 | Q239Y | 1.18 | 0.96 | 0.75 | 0.92 | 0.95 |
| 240 | S240A | 0.90 | 0.96 | 0.80 | 0.89 | 0.61 |
| 240 | S240C | 0.46 | 0.57 | 0.56 | 0.87 | 0.89 |
| 240 | S240D | 0.18 | *0.05* | 0.12 | 23.73 | 17.94 |
| 240 | S240E | 2.24 | 1.09 | 0.99 | 1.03 | 1.07 |
| 240 | S240F | 0.67 | 1.04 | 0.61 | 0.98 | 0.80 |
| 240 | S240G | 1.27 | 1.04 | 0.91 | 1.06 | 1.09 |
| 240 | S240H | 0.17 | 0.62 | 0.22 | 1.08 | 1.14 |
| 240 | S240I | 0.56 | 0.95 | 0.58 | 0.92 | 0.91 |
| 240 | S240K | 0.66 | 1.04 | 0.51 | 0.94 | 0.74 |
| 240 | S240L | 1.77 | 1.05 | 0.69 | 1.08 | 1.10 |
| 240 | S240M | 0.57 | 1.07 | 0.57 | 0.94 | 0.83 |
| 240 | S240N | 0.28 | 0.68 | 0.45 | 0.78 | 1.01 |
| 240 | S240P | 1.00 | 0.99 | 0.62 | 1.00 | 0.97 |
| 240 | S240Q | 0.73 | 0.96 | 0.68 | 0.94 | 0.74 |
| 240 | S240R | 0.66 | 0.68 | 0.48 | 0.98 | 1.67 |
| 240 | S240T | 0.17 | 0.31 | 0.24 | 0.95 | 1.11 |
| 240 | S240V | 1.16 | 1.08 | 0.73 | 0.95 | 0.97 |
| 240 | S240W | 0.56 | 0.69 | 0.44 | 1.15 | 1.33 |
| 240 | S240Y | 0.50 | 0.82 | 0.50 | 0.97 | 0.84 |
| 243 | L243A | 0.86 | 0.07 | 0.19 | 5.39 | 5.71 |
| 243 | L243C | 0.84 | 0.47 | 0.52 | 1.60 | 1.93 |
| 243 | L243D | 0.61 | 0.56 | 0.65 | 0.78 | 0.75 |
| 243 | L243E | 0.49 | 0.49 | 0.41 | 2.61 | 3.15 |
| 243 | L243F | 0.59 | 0.80 | 0.67 | 0.87 | 0.75 |
| 243 | L243G | 0.75 | 0.44 | 0.36 | 0.85 | 0.96 |
| 243 | L243H | *0.05* | *0.05* | *0.05* | *0.05* | *0.05* |
| 243 | L243I | 0.40 | 0.76 | 0.81 | 0.90 | 0.89 |
| 243 | L243K | 0.84 | 0.64 | 0.47 | 0.91 | 0.97 |
| 243 | L243M | 0.49 | 0.72 | 0.54 | 0.91 | 0.82 |
| 243 | L243N | 0.17 | 0.63 | 0.52 | 0.78 | 0.73 |
| 243 | L243P | 0.11 | 0.23 | 0.37 | 0.93 | 1.19 |
| 243 | L243Q | 0.58 | 0.75 | 0.67 | 1.04 | 0.95 |
| 243 | L243R | 0.74 | 0.58 | 0.46 | 1.01 | 0.96 |
| 243 | L243S | 0.95 | 0.58 | 0.44 | 0.86 | 0.74 |
| 243 | L243T | 0.44 | 0.67 | 0.50 | 0.91 | 0.82 |
| 243 | L243V | 0.34 | 0.36 | 0.42 | 0.75 | 0.80 |
| 243 | L243W | 0.48 | 0.47 | 0.31 | 0.89 | 0.99 |
| 243 | L243Y | 0.56 | 0.87 | 0.91 | 0.92 | 0.92 |
| 245 | C245A | 0.27 | 0.97 | 0.62 | 0.74 | 0.64 |
| 245 | C245D | 0.15 | 0.42 | 0.54 | 0.56 | 0.58 |
| 245 | C245E | 0.15 | 0.24 | 0.13 | 0.39 | 0.91 |
| 245 | C245F | 0.18 | 0.14 | 0.13 | 0.56 | 1.88 |
| 245 | C245G | 0.26 | 0.83 | 0.78 | 0.85 | 0.79 |
| 245 | C245H | 0.08 | 0.62 | *0.05* | 0.85 | 1.44 |
| 245 | C245K | 0.13 | 0.28 | 0.39 | 0.80 | 1.34 |
| 245 | C245L | 0.13 | 0.26 | 0.08 | 0.91 | 1.68 |
| 245 | C245M | 0.12 | 0.49 | 0.13 | 0.66 | 0.89 |
| 245 | C245N | 0.12 | 0.47 | 0.38 | 0.45 | 0.77 |
| 245 | C245P | 0.09 | 0.13 | 0.12 | 0.73 | 1.96 |
| 245 | C245Q | 0.11 | 0.22 | 0.22 | 0.75 | 1.30 |
| 245 | C245R | 0.14 | 0.20 | 0.35 | 0.40 | 1.61 |
| 245 | C245S | 0.26 | 0.63 | 0.37 | 0.57 | 0.95 |
| 245 | C245T | 0.13 | 0.46 | 0.28 | 0.74 | 0.88 |
| 245 | C245V | 0.14 | 0.50 | 0.45 | 0.43 | 0.72 |
| 245 | C245W | 0.15 | 0.14 | 0.20 | 1.16 | 1.54 |
| 245 | C245Y | 0.09 | 0.17 | 0.38 | 1.45 | 1.94 |
| 247 | N247A | 1.18 | 0.36 | *0.05* | 1.64 | 1.68 |
| 247 | N247C | 1.46 | 0.82 | 0.79 | 0.71 | 0.83 |
| 247 | N247D | 1.18 | 0.76 | 0.67 | 0.58 | 0.96 |
| 247 | N247E | 1.32 | 0.77 | 0.18 | 0.81 | 0.76 |
| 247 | N247F | 0.76 | 0.81 | 0.29 | 1.10 | 1.27 |
| 247 | N247G | 0.49 | 0.89 | 0.54 | 1.83 | 2.30 |
| 247 | N247H | 1.70 | 0.87 | 0.55 | 0.86 | 0.61 |
| 247 | N247I | 1.53 | 0.88 | 0.66 | 0.77 | 0.85 |
| 247 | N247K | 0.79 | 0.64 | 0.22 | 1.38 | 1.54 |
| 247 | N247L | 1.05 | 0.60 | 0.52 | 1.10 | 1.25 |
| 247 | N247M | 0.73 | 0.76 | 0.34 | 1.39 | 1.37 |
| 247 | N247P | 0.77 | 0.43 | *0.05* | 2.01 | 2.69 |
| 247 | N247Q | 0.49 | 0.60 | 0.41 | 1.77 | 1.71 |
| 247 | N247R | 0.71 | 0.46 | 0.16 | 1.64 | 1.85 |
| 247 | N247S | 0.73 | 0.52 | *0.05* | 2.08 | 1.91 |
| 247 | N247T | 0.62 | 0.88 | 0.68 | 1.16 | 1.39 |
| 247 | N247V | 0.49 | 0.67 | 0.34 | 2.16 | 1.64 |
| 247 | N247Y | 0.71 | 0.85 | 0.28 | 1.55 | 1.56 |
| 251 | T251A | 0.41 | 0.86 | 0.74 | 0.92 | 0.70 |
| 251 | T251C | 0.37 | 1.08 | 1.28 | 0.92 | 0.77 |
| 251 | T251D | 0.27 | 0.72 | 0.75 | 0.89 | 0.79 |
| 251 | T251E | 0.72 | 1.07 | 0.85 | 0.98 | 0.86 |
| 251 | T251F | 0.36 | 0.98 | 0.55 | 0.87 | 0.68 |
| 251 | T251G | 0.40 | 1.02 | 0.79 | 0.95 | 0.82 |
| 251 | T251H | 0.30 | 1.09 | 0.72 | 0.83 | 0.80 |
| 251 | T251I | 0.38 | 0.67 | 0.54 | 1.11 | 0.82 |
| 251 | T251K | 0.27 | 0.81 | 0.55 | 0.87 | 0.80 |
| 251 | T251L | 0.57 | 1.14 | 0.81 | 0.92 | 0.86 |
| 251 | T251M | 0.44 | 1.05 | 0.63 | 0.94 | 0.87 |
| 251 | T251N | 0.50 | 0.83 | 0.59 | 0.90 | 0.97 |
| 251 | T251P | 0.12 | 0.19 | *0.05* | 1.25 | 1.26 |
| 251 | T251Q | 0.48 | 1.01 | 0.77 | 0.95 | 0.92 |
| 251 | T251R | 0.58 | 1.02 | 0.62 | 0.96 | 0.89 |
| 251 | T251S | 0.67 | 1.05 | 0.78 | 0.89 | 0.87 |
| 251 | T251V | 0.91 | 1.04 | 0.77 | 0.99 | 0.98 |
| 251 | T251W | 0.30 | 0.83 | 0.54 | 0.97 | 0.90 |
| 251 | T251Y | 0.10 | 0.18 | 0.14 | 1.18 | 4.59 |
| 252 | Q252A | 0.43 | 0.95 | 0.85 | 0.95 | 0.73 |
| 252 | Q252C | 0.89 | 0.98 | 0.84 | 0.94 | 0.79 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 252 | Q252D | 0.21 | 0.65 | 0.65 | 1.00 | 0.61 |
| 252 | Q252E | 0.31 | 1.01 | 0.80 | 0.90 | 0.74 |
| 252 | Q252F | 0.39 | 0.82 | 0.52 | 1.15 | 0.72 |
| 252 | Q252G | 0.41 | 0.96 | 0.64 | 0.92 | 0.76 |
| 252 | Q252H | 0.78 | 0.97 | 0.63 | 0.98 | 0.84 |
| 252 | Q252I | 0.93 | 1.04 | 0.89 | 1.00 | 0.94 |
| 252 | Q252K | 0.60 | 0.63 | 0.53 | 1.53 | 1.18 |
| 252 | Q252L | 0.47 | 1.02 | 0.77 | 0.91 | 0.88 |
| 252 | Q252M | 0.54 | 1.04 | 0.69 | 0.94 | 0.86 |
| 252 | Q252N | 0.24 | 0.83 | 0.64 | 0.97 | 0.80 |
| 252 | Q252P | 0.16 | 0.12 | 0.09 | 1.25 | 1.12 |
| 252 | Q252R | 0.59 | 0.68 | 0.51 | 1.15 | 0.91 |
| 252 | Q252S | 0.53 | 1.01 | 0.82 | 0.92 | 0.88 |
| 252 | Q252T | 0.32 | 0.69 | 0.33 | 0.55 | 0.62 |
| 252 | Q252V | 0.52 | 0.83 | 0.40 | 1.12 | 1.12 |
| 252 | Q252W | 0.34 | 0.66 | 0.60 | 1.18 | 0.85 |
| 252 | Q252Y | 0.51 | 0.98 | 0.72 | 0.95 | 0.85 |
| 254 | N254A | 0.28 | 0.88 | 0.69 | 0.91 | 0.88 |
| 254 | N254C | 0.26 | 0.88 | 0.82 | 0.83 | 0.91 |
| 254 | N254E | 0.20 | 0.84 | 0.56 | 0.76 | 0.91 |
| 254 | N254F | 0.15 | 0.33 | 0.10 | 0.72 | 1.71 |
| 254 | N254G | 0.28 | 0.37 | 0.29 | 0.73 | 1.31 |
| 254 | N254I | 0.36 | 0.18 | 0.15 | 0.57 | 1.14 |
| 254 | N254K | 0.24 | 0.24 | 0.44 | 0.45 | 1.18 |
| 254 | N254L | 0.23 | 0.30 | 0.11 | 0.49 | 0.64 |
| 254 | N254M | 0.18 | 0.33 | 0.33 | 0.89 | 1.34 |
| 254 | N254P | 0.36 | 0.22 | 0.05 | 0.98 | 1.35 |
| 254 | N254Q | 0.39 | 0.26 | 0.14 | 0.85 | 1.07 |
| 254 | N254R | 0.36 | 0.14 | 0.08 | 1.49 | 1.94 |
| 254 | N254S | 0.29 | 0.49 | 0.19 | 0.87 | 1.24 |
| 254 | N254T | 0.22 | 0.53 | 0.50 | 0.97 | 1.34 |
| 254 | N254V | 1.22 | 0.98 | 0.90 | 1.05 | 1.08 |
| 254 | N254W | 0.26 | 0.17 | 0.12 | 1.05 | 1.02 |
| 254 | N254Y | 0.21 | 0.40 | 0.05 | 0.88 | 1.30 |
| 258 | V258A | 0.56 | 0.63 | 0.72 | 1.10 | 1.08 |
| 258 | V258C | 0.52 | 0.74 | 0.68 | 1.09 | 1.41 |
| 258 | V258D | 0.20 | 0.28 | 0.55 | 1.07 | 1.24 |
| 258 | V258E | 0.18 | 0.17 | 0.29 | 1.03 | 1.45 |
| 258 | V258F | 0.12 | 0.19 | 0.24 | 0.87 | 2.94 |
| 258 | V258G | 0.18 | 0.50 | 0.48 | 0.83 | 0.88 |
| 258 | V258H | 0.16 | 0.20 | 0.43 | 1.16 | 1.55 |
| 258 | V258I | 0.26 | 0.87 | 0.79 | 0.85 | 0.78 |
| 258 | V258K | 0.17 | 0.32 | 0.42 | 0.49 | 0.89 |
| 258 | V258L | 0.34 | 0.92 | 1.10 | 0.88 | 0.82 |
| 258 | V258M | 0.33 | 0.91 | 1.11 | 0.87 | 0.86 |
| 258 | V258N | 0.22 | 0.47 | 0.46 | 0.95 | 0.88 |
| 258 | V258P | 0.21 | 0.13 | 0.19 | 1.53 | 1.46 |
| 258 | V258Q | 0.18 | 0.23 | 0.38 | 0.53 | 1.08 |
| 258 | V258R | 0.23 | 0.15 | *0.05* | 0.33 | 1.69 |
| 258 | V258S | 0.34 | 0.73 | 0.83 | 0.90 | 0.89 |
| 258 | V258T | 0.64 | 0.98 | 1.01 | 0.94 | 0.91 |
| 258 | V258W | 0.21 | 0.16 | 0.37 | 0.88 | 1.85 |
| 258 | V258Y | 0.18 | 0.14 | 0.14 | 1.13 | 1.36 |
| 266 | H266A | 0.26 | 0.41 | 0.39 | 0.42 | 0.57 |
| 266 | H266C | 0.08 | 0.15 | 0.28 | 1.20 | 2.86 |
| 266 | H266D | 0.17 | 0.24 | 0.23 | 1.06 | 1.47 |
| 266 | H266E | 0.20 | 0.20 | 0.30 | 2.06 | 3.59 |
| 266 | H266I | 0.21 | 0.14 | 0.16 | 3.49 | 1.64 |
| 266 | H266K | 0.18 | 0.25 | 0.13 | 1.55 | 0.94 |
| 266 | H266L | 0.24 | 0.14 | 0.20 | 0.85 | 1.74 |
| 266 | H266M | 0.18 | 0.19 | 0.29 | 6.85 | 0.91 |
| 266 | H266N | 0.49 | 0.73 | 0.48 | 0.79 | 0.63 |
| 266 | H266P | 0.14 | 0.14 | 0.26 | 0.98 | 1.25 |
| 266 | H266R | 0.30 | 0.17 | 0.23 | 1.16 | 1.30 |
| 266 | H266S | 0.19 | 0.29 | 0.26 | 0.68 | 0.87 |
| 266 | H266T | 0.20 | 0.27 | 0.18 | 2.35 | 1.95 |
| 266 | H266V | 0.21 | 0.20 | 0.30 | 0.67 | 1.54 |
| 266 | H266W | 0.22 | 0.27 | 0.11 | 0.86 | 0.32 |
| 266 | H266Y | 0.24 | 0.30 | 0.22 | 0.50 | 0.54 |
| 267 | A267C | 0.85 | 0.97 | 0.75 | 0.99 | 0.83 |
| 267 | A267D | 0.23 | 0.23 | 0.07 | 0.76 | 0.91 |
| 267 | A267E | 0.34 | 0.52 | 0.44 | 0.56 | 0.41 |
| 267 | A267F | 0.21 | 0.12 | *0.05* | 1.58 | 0.93 |
| 267 | A267G | 0.86 | 1.00 | 0.36 | 0.44 | 0.13 |
| 267 | A267H | 0.38 | 0.35 | *0.05* | 0.52 | 0.34 |
| 267 | A267I | 0.21 | 0.11 | *0.05* | 0.82 | 0.86 |
| 267 | A267K | 0.20 | 0.21 | *0.05* | 1.20 | 1.07 |
| 267 | A267L | 0.21 | 0.19 | 0.08 | 0.84 | 1.56 |
| 267 | A267M | 0.23 | 0.22 | 0.06 | 0.71 | 0.73 |
| 267 | A267N | 0.29 | 0.49 | *0.05* | 0.47 | 0.45 |
| 267 | A267P | 0.21 | 0.28 | 0.14 | 0.72 | 0.95 |
| 267 | A267R | 0.18 | 0.16 | 0.20 | 1.08 | 0.95 |
| 267 | A267S | 0.80 | 0.93 | 0.67 | 0.83 | 0.55 |
| 267 | A267T | 0.34 | 0.68 | 0.17 | 0.46 | 0.24 |
| 267 | A267V | 0.23 | 0.52 | 0.21 | 0.28 | 0.31 |
| 267 | A267W | 0.25 | 0.22 | 0.16 | 0.91 | 0.83 |
| 267 | A267Y | 0.21 | 0.19 | 0.05 | 0.80 | 0.85 |
| 268 | G268A | 4.40 | 0.33 | 0.14 | 1.65 | 1.34 |
| 268 | G268C | 0.53 | 0.49 | 0.19 | 1.23 | 1.99 |
| 268 | G268D | 0.61 | 0.74 | 0.80 | 0.73 | 0.55 |
| 268 | G268E | 0.55 | 0.17 | 0.07 | 1.42 | 1.95 |
| 268 | G268F | 1.01 | 0.47 | 0.41 | 0.94 | 1.00 |
| 268 | G268H | 1.25 | *0.05* | 0.35 | *0.05* | *0.05* |
| 268 | G268I | 0.76 | 0.65 | 0.80 | 1.21 | 0.84 |
| 268 | G268K | 0.86 | 0.75 | 0.77 | 0.83 | 0.75 |
| 268 | G268L | 0.76 | 0.44 | 0.27 | 1.10 | 1.31 |
| 268 | G268M | 0.55 | 0.36 | 0.14 | 0.49 | 0.31 |
| 268 | G268N | 0.62 | 0.37 | 0.33 | 0.86 | 1.32 |
| 268 | G268P | 0.49 | 0.53 | 0.53 | 1.16 | 1.29 |
| 268 | G268Q | 1.37 | 0.53 | 0.42 | 0.85 | 0.94 |
| 268 | G268R | 1.09 | 0.40 | 0.37 | 0.95 | 0.82 |
| 268 | G268S | 0.81 | 0.70 | 0.36 | 0.53 | 0.52 |
| 268 | G268T | 0.69 | 0.42 | 0.29 | 0.76 | 0.74 |
| 268 | G268V | 1.23 | 0.47 | 0.33 | 0.97 | 0.98 |
| 268 | G268W | 0.69 | 0.47 | 0.47 | 1.71 | 2.59 |
| 268 | G268Y | 0.61 | 0.25 | 0.06 | 0.76 | 1.28 |
| 272 | W272A | 0.93 | 0.52 | 0.20 | 0.59 | 0.33 |
| 272 | W272C | 0.57 | 0.43 | 0.13 | 0.40 | 0.34 |
| 272 | W272D | 0.84 | 0.51 | 0.24 | 0.41 | 0.10 |
| 272 | W272E | 0.67 | 0.47 | 0.12 | 0.55 | 0.41 |
| 272 | W272F | 0.59 | 0.73 | 0.23 | 0.72 | 0.46 |
| 272 | W272G | 0.89 | 0.54 | 0.13 | 0.74 | 0.43 |
| 272 | W272H | 0.07 | 0.27 | *0.05* | 1.91 | 0.37 |
| 272 | W272I | 0.67 | 0.55 | 0.16 | 0.44 | 0.20 |
| 272 | W272K | 0.74 | 0.31 | *0.05* | 0.35 | 0.53 |
| 272 | W272L | 0.67 | 0.59 | 0.20 | 0.53 | 0.42 |
| 272 | W272M | 1.42 | 0.62 | 0.14 | 0.61 | 0.32 |
| 272 | W272N | 0.92 | 0.51 | 0.10 | 0.48 | 0.33 |
| 272 | W272P | 0.61 | 0.49 | 0.14 | 0.62 | 0.44 |
| 272 | W272Q | 0.14 | 0.07 | 0.11 | 0.63 | 0.92 |
| 272 | W272R | 0.89 | 0.36 | *0.05* | 0.58 | 0.44 |
| 272 | W272S | 1.03 | 0.51 | 0.32 | 0.75 | 0.43 |
| 272 | W272T | 0.85 | 0.49 | 0.18 | 0.52 | 0.31 |
| 272 | W272V | 0.74 | 0.53 | 0.07 | 0.27 | 0.15 |
| 272 | W272Y | 0.85 | 0.67 | 0.28 | 0.50 | 0.45 |
| 274 | A274C | 0.23 | 0.47 | 0.52 | 2.95 | 0.43 |
| 274 | A274D | 0.16 | 0.58 | 0.55 | 0.79 | 0.43 |
| 274 | A274E | 0.32 | 0.99 | 0.87 | 0.98 | 0.80 |
| 274 | A274F | 0.33 | 0.85 | 0.42 | 0.91 | 0.89 |
| 274 | A274G | 0.34 | 1.02 | 0.53 | 0.82 | 0.65 |
| 274 | A274H | 0.40 | 0.83 | 0.37 | 0.91 | 0.67 |
| 274 | A274I | 0.26 | 0.88 | 0.34 | 0.84 | 0.71 |
| 274 | A274K | 0.26 | 0.78 | 0.33 | 0.91 | 0.85 |
| 274 | A274L | 0.42 | 0.88 | 0.49 | 0.96 | 0.75 |
| 274 | A274M | 0.31 | 0.63 | 0.48 | 1.23 | 0.84 |
| 274 | A274N | 0.41 | 0.97 | 0.67 | 0.95 | 0.89 |
| 274 | A274P | 0.26 | 0.74 | 0.43 | 0.95 | 0.51 |
| 274 | A274Q | 0.44 | 0.86 | 0.73 | 0.97 | 0.98 |
| 274 | A274R | 0.51 | 0.99 | 0.38 | 0.97 | 0.91 |
| 274 | A274S | 0.46 | 0.96 | 0.71 | 0.97 | 0.84 |
| 274 | A274T | 0.41 | 0.55 | 0.47 | 1.14 | 1.03 |
| 274 | A274V | 0.38 | 0.87 | 0.51 | 0.96 | 0.85 |
| 274 | A274W | 0.56 | 0.70 | 0.37 | 1.03 | 0.88 |
| 274 | A274Y | 0.11 | 0.07 | 0.10 | 1.25 | 0.33 |
| 275 | N275A | 1.11 | 0.93 | 0.87 | 1.02 | 0.97 |
| 275 | N275C | 0.74 | 0.76 | 0.71 | 1.01 | 0.95 |
| 275 | N275D | 0.40 | 0.78 | 0.68 | 0.97 | 1.00 |
| 275 | N275E | 0.65 | 0.90 | 0.57 | 1.02 | 0.96 |
| 275 | N275F | 1.34 | 0.86 | 0.71 | 0.98 | 0.98 |
| 275 | N275G | 0.20 | 0.67 | 0.17 | 0.31 | 0.18 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 275 | N275K | 0.27 | 0.84 | 0.34 | 0.91 | 0.94 |
| 275 | N275L | 0.98 | 0.90 | 0.70 | 0.92 | 1.00 |
| 275 | N275M | 0.65 | 0.87 | 0.63 | 1.04 | 0.98 |
| 275 | N275Q | 0.58 | 0.88 | 0.56 | 1.03 | 0.95 |
| 275 | N275R | 0.64 | 0.68 | 0.27 | 0.96 | 1.04 |
| 275 | N275S | 0.61 | 0.99 | 0.57 | 0.91 | 0.87 |
| 275 | N275T | 0.70 | 0.85 | 0.53 | 0.96 | 1.01 |
| 275 | N275V | 0.81 | 0.89 | 0.53 | 0.95 | 0.97 |
| 275 | N275W | 1.07 | 0.92 | 0.69 | 1.00 | 1.02 |
| 275 | N275Y | 0.37 | 0.64 | 0.43 | 0.94 | 0.96 |
| 281 | Q281A | 1.53 | 0.81 | 0.66 | 0.85 | 0.32 |
| 281 | Q281C | 1.70 | 0.88 | 0.70 | 0.73 | 0.43 |
| 281 | Q281D | 1.10 | 0.60 | 0.43 | 1.33 | 0.95 |
| 281 | Q281E | 2.50 | 0.89 | 0.85 | 1.10 | 0.63 |
| 281 | Q281F | 0.76 | 0.72 | 0.15 | 1.31 | 0.97 |
| 281 | Q281G | 1.04 | 0.75 | 0.46 | 1.02 | 1.35 |
| 281 | Q281I | 0.62 | 0.63 | 0.08 | 1.74 | 1.66 |
| 281 | Q281L | 0.78 | 0.68 | 0.31 | 1.79 | 1.51 |
| 281 | Q281N | 1.38 | 0.85 | 0.46 | 1.09 | 0.85 |
| 281 | Q281T | 0.59 | 0.72 | 0.22 | 1.64 | 1.10 |
| 281 | Q281V | 1.46 | 0.94 | 0.69 | 1.22 | 0.86 |
| 285 | N285A | 0.88 | 1.01 | 0.71 | 0.50 | 0.62 |
| 285 | N285C | 0.46 | 1.02 | 0.70 | 1.22 | 1.23 |
| 285 | N285D | 0.35 | 0.70 | 0.59 | 1.99 | 2.24 |
| 285 | N285F | 0.27 | 0.67 | 0.15 | 2.16 | 1.85 |
| 285 | N285G | 0.47 | 1.24 | 0.62 | 1.02 | 0.92 |
| 285 | N285H | 0.60 | 1.04 | 0.30 | 0.93 | 1.11 |
| 285 | N285K | 0.36 | 0.76 | 0.25 | 1.49 | 2.79 |
| 285 | N285L | 0.46 | 1.15 | 0.68 | 1.16 | 1.05 |
| 285 | N285P | 0.18 | 0.27 | 0.18 | 6.33 | 7.75 |
| 285 | N285S | 0.26 | 0.77 | 0.21 | 2.14 | 2.16 |
| 285 | N285T | 0.40 | 0.78 | 0.33 | 1.66 | 2.14 |
| 285 | N285V | 0.19 | 0.84 | 0.18 | 2.84 | 3.86 |
| 285 | N285W | 0.39 | 1.21 | 0.38 | 1.60 | 2.07 |
| 285 | N285Y | 0.72 | 1.15 | 1.19 | 1.15 | 0.91 |
| 288 | K288A | 0.41 | 0.61 | 0.68 | 1.52 | 2.84 |
| 288 | K288C | 0.41 | 0.95 | 0.63 | 0.72 | 1.49 |
| 288 | K288D | 0.23 | 0.23 | *0.05* | 5.77 | 5.10 |
| 288 | K288E | 0.38 | 0.89 | 0.81 | 0.65 | 1.60 |
| 288 | K288F | 0.36 | 0.75 | 0.29 | 1.53 | 2.74 |
| 288 | K288G | 0.23 | 0.40 | 0.12 | 2.22 | 4.09 |
| 288 | K288H | 0.32 | 0.90 | 0.48 | 1.09 | 1.54 |
| 288 | K288I | 0.40 | 0.75 | 0.37 | 1.51 | 2.48 |
| 288 | K288L | 0.80 | 0.96 | 0.81 | 0.60 | 0.82 |
| 288 | K288N | 0.71 | 0.98 | 0.84 | 1.08 | 1.68 |
| 288 | K288P | 0.26 | 0.34 | *0.05* | 5.00 | 5.39 |
| 288 | K288Q | 0.23 | 0.80 | 0.18 | 1.23 | 2.51 |
| 288 | K288R | 0.27 | 0.42 | *0.05* | 2.13 | 3.33 |
| 288 | K288S | 0.19 | 0.71 | 0.21 | 2.02 | 2.72 |
| 288 | K288T | 0.25 | 0.71 | 0.35 | 1.27 | 2.96 |
| 288 | K288V | 0.31 | 0.84 | 0.38 | 1.67 | 1.87 |
| 289 | N289A | 0.39 | 0.70 | 0.90 | 0.98 | 0.87 |
| 289 | N289C | 0.21 | 0.10 | 0.50 | 6.35 | 7.25 |
| 289 | N289D | 0.84 | 0.96 | 0.87 | 0.93 | 0.92 |
| 289 | N289E | 0.13 | 0.26 | 0.63 | 1.03 | 1.48 |
| 289 | N289F | 0.14 | 0.27 | 0.39 | 0.85 | 0.78 |
| 289 | N289G | 0.17 | 0.42 | 0.79 | 0.72 | 0.58 |
| 289 | N289H | 0.15 | 0.54 | 0.66 | 0.94 | 0.91 |
| 289 | N289I | 0.16 | 0.20 | *0.05* | 0.64 | 0.68 |
| 289 | N289K | 0.31 | 0.79 | 0.66 | 0.88 | 0.85 |
| 289 | N289L | 0.16 | 0.39 | 0.48 | 0.92 | 1.00 |
| 289 | N289M | 0.18 | 0.52 | 0.14 | 0.80 | 0.74 |
| 289 | N289Q | 0.18 | 0.49 | 0.45 | 0.63 | 0.66 |
| 289 | N289R | 0.41 | 0.87 | 0.23 | 0.91 | 0.84 |
| 289 | N289S | 0.44 | 1.05 | 0.85 | 0.84 | 0.88 |
| 289 | N289T | 0.20 | 0.58 | 0.79 | 0.90 | 0.86 |
| 289 | N289V | 0.22 | 0.64 | 0.33 | 0.92 | 0.83 |
| 289 | N289W | 0.19 | 0.43 | 0.59 | 0.95 | 0.98 |
| 289 | N289Y | 0.24 | 0.62 | 0.47 | 0.78 | 0.91 |
| 291 | S291A | 1.22 | 2.27 | 2.57 | 0.90 | 1.26 |
| 291 | S291C | 2.02 | 2.57 | 3.26 | 0.99 | 1.96 |
| 291 | S291D | 0.40 | 0.28 | 0.24 | 1.20 | 5.19 |
| 291 | S291E | 2.53 | 2.54 | 3.48 | 1.02 | 1.91 |
| 291 | S291F | 1.57 | 2.22 | 1.63 | 1.02 | 1.89 |
| 291 | S291G | 0.60 | 0.24 | 0.25 | 1.08 | 0.92 |
| 291 | S291H | 2.52 | 2.45 | 2.33 | 1.06 | 1.94 |
| 291 | S291I | 0.81 | 0.95 | 0.53 | 1.09 | 1.32 |
| 291 | S291K | 1.26 | 2.23 | 1.10 | 1.05 | 1.58 |
| 291 | S291L | 1.28 | 1.99 | 1.50 | 0.91 | 1.23 |
| 291 | S291M | 1.88 | 2.50 | 2.13 | 1.01 | 1.91 |
| 291 | S291N | 0.46 | 0.21 | *0.05* | 2.48 | 2.00 |
| 291 | S291P | 0.75 | 0.72 | 0.88 | 1.18 | 1.19 |
| 291 | S291T | 1.56 | 2.62 | 2.22 | 1.11 | 2.02 |
| 291 | S291V | 0.99 | 0.61 | 0.24 | 1.25 | 1.24 |
| 291 | S291W | 1.09 | 2.20 | 1.87 | 1.01 | 1.50 |
| 291 | S291Y | 0.90 | 1.18 | 0.85 | 0.95 | 1.48 |
| 292 | S292A | 0.96 | 0.97 | 1.12 | 0.99 | 0.94 |
| 292 | S292C | 0.44 | 0.53 | 0.61 | 1.35 | 1.67 |
| 292 | S292D | 0.65 | 0.79 | 0.74 | 0.91 | 1.11 |
| 292 | S292E | 0.50 | 0.73 | 0.47 | 1.14 | 1.40 |
| 292 | S292F | 0.74 | 0.87 | 0.48 | 0.86 | 1.05 |
| 292 | S292G | 0.67 | 0.99 | 0.68 | 0.74 | 0.80 |
| 292 | S292H | 0.35 | 0.67 | 0.63 | 1.16 | 1.90 |
| 292 | S292I | 0.41 | 0.79 | 0.46 | 0.62 | 0.83 |
| 292 | S292K | 0.85 | 0.84 | 0.72 | 0.78 | 0.75 |
| 292 | S292L | 0.31 | 0.61 | 0.65 | 0.59 | 0.60 |
| 292 | S292M | 0.75 | 0.99 | 0.74 | 0.72 | 0.87 |
| 292 | S292N | 0.69 | 0.99 | 0.75 | 0.90 | 1.06 |
| 292 | S292P | 0.42 | 0.52 | 0.34 | 0.53 | 0.85 |
| 292 | S292Q | 0.55 | 0.87 | 0.58 | 0.97 | 0.79 |
| 292 | S292R | 1.12 | 0.98 | 0.45 | 0.84 | 0.85 |
| 292 | S292T | 0.84 | 1.01 | 0.65 | 0.86 | 0.92 |
| 292 | S292V | 0.44 | 0.70 | 0.51 | 0.95 | 1.25 |
| 292 | S292W | 0.91 | 1.10 | 0.82 | 0.83 | 0.64 |
| 292 | S292Y | 1.20 | 0.94 | 0.62 | 1.00 | 0.91 |
| 293 | P293A | 0.34 | 0.93 | 0.85 | 0.94 | 0.76 |
| 293 | P293C | 0.21 | 0.46 | 0.51 | 0.96 | 0.58 |
| 293 | P293D | 0.30 | 0.14 | 0.25 | 0.25 | 0.54 |
| 293 | P293E | 0.13 | 0.14 | 0.23 | 0.94 | 1.08 |
| 293 | P293F | 0.16 | 0.18 | 0.22 | 0.64 | 0.94 |
| 293 | P293G | 0.19 | 0.40 | 0.59 | 0.72 | 0.53 |
| 293 | P293H | 0.17 | 0.14 | 0.14 | 0.62 | 1.01 |
| 293 | P293I | 0.17 | 0.29 | 0.30 | 0.65 | 0.92 |
| 293 | P293K | 0.13 | 0.21 | 0.53 | 4.29 | 0.89 |
| 293 | P293L | 0.16 | 0.27 | 0.21 | 0.80 | 0.51 |
| 293 | P293M | 0.15 | 0.24 | 0.12 | 5.43 | 0.67 |
| 293 | P293N | 0.16 | 0.31 | 0.24 | 0.63 | 0.92 |
| 293 | P293Q | 0.22 | 0.16 | 0.17 | 0.29 | 0.54 |
| 293 | P293R | 0.15 | 0.31 | 0.62 | 1.31 | 0.86 |
| 293 | P293S | 0.18 | 0.38 | 0.24 | 1.04 | 0.74 |
| 293 | P293T | 0.18 | 0.28 | 0.12 | 0.44 | 0.78 |
| 293 | P293V | 0.17 | 0.77 | 0.60 | 0.93 | 0.73 |
| 293 | P293W | 0.18 | 0.11 | 0.16 | 2.77 | 9.61 |
| 293 | P293Y | 0.13 | 0.08 | 0.11 | 0.31 | 1.24 |
| 294 | R294A | 0.97 | 1.06 | 0.89 | 0.92 | 0.77 |
| 294 | R294C | 0.70 | 1.15 | 0.74 | 1.01 | 1.16 |
| 294 | R294D | 0.75 | 0.94 | 0.85 | 0.94 | 1.09 |
| 294 | R294E | 0.73 | 0.82 | 0.66 | 1.02 | 1.20 |
| 294 | R294F | 0.37 | 0.52 | 0.54 | 0.90 | 1.56 |
| 294 | R294G | 1.25 | 0.93 | 0.84 | 0.71 | 0.87 |
| 294 | R294H | 0.96 | 0.93 | 0.55 | 0.97 | 1.18 |
| 294 | R294I | 0.77 | 0.84 | 0.72 | 0.98 | 1.01 |
| 294 | R294K | 1.34 | 0.94 | 0.69 | 1.04 | 1.20 |
| 294 | R294L | 0.54 | 1.06 | 1.03 | 1.05 | 1.22 |
| 294 | R294M | 0.34 | 0.76 | 0.78 | 0.81 | 1.78 |
| 294 | R294N | 0.50 | 0.80 | 0.64 | 1.30 | 1.06 |
| 294 | R294P | 0.48 | 0.86 | 0.74 | 0.74 | 0.99 |
| 294 | R294Q | 0.50 | 0.79 | 0.75 | 1.23 | 1.30 |
| 294 | R294S | 0.64 | 1.00 | 0.57 | 1.32 | 1.47 |
| 294 | R294T | 1.12 | 1.03 | 0.97 | 1.02 | 1.10 |
| 294 | R294V | 0.83 | 0.96 | 0.83 | 0.82 | 1.03 |
| 294 | R294W | 1.08 | 1.01 | 0.57 | 0.56 | 0.58 |
| 294 | R294Y | 0.26 | 0.43 | 0.31 | 2.39 | 3.19 |
| 303 | V303A | 0.30 | 0.46 | 0.33 | 0.40 | 0.38 |
| 303 | V303E | 0.21 | 0.12 | 0.24 | 2.70 | 4.92 |
| 303 | V303F | 0.22 | 0.14 | 0.16 | 0.70 | 0.93 |
| 303 | V303G | 0.23 | 0.24 | 0.29 | 0.48 | 0.86 |
| 303 | V303H | 0.29 | 0.13 | 0.31 | 0.84 | 2.17 |
| 303 | V303I | 0.85 | 1.07 | 0.68 | 0.67 | 0.37 |
| 303 | V303K | 0.24 | 0.15 | 0.31 | 1.05 | 1.94 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 303 | V303L | 0.29 | 0.69 | 0.19 | 0.17 | 0.16 |
| 303 | V303M | 0.18 | 0.29 | 0.13 | 0.47 | 44.68 |
| 303 | V303N | 0.25 | 0.30 | 0.25 | 0.46 | 0.65 |
| 303 | V303P | 0.30 | 0.13 | 0.13 | 1.31 | 2.70 |
| 303 | V303Q | 0.32 | 0.16 | 0.20 | 1.08 | 1.32 |
| 303 | V303R | 0.19 | 0.14 | 0.21 | 1.74 | 1.78 |
| 303 | V303S | 0.26 | 0.37 | 0.14 | 1.00 | 0.83 |
| 303 | V303T | 0.39 | 0.98 | 0.48 | 0.70 | 0.45 |
| 303 | V303W | 0.18 | 0.15 | 0.23 | 1.50 | 1.97 |
| 303 | V303Y | 0.23 | 0.19 | 0.15 | 2.71 | 1.26 |
| 304 | A304C | 0.76 | 0.47 | 0.36 | 0.62 | 0.39 |
| 304 | A304D | 1.25 | 0.13 | 0.16 | 15.46 | 16.85 |
| 304 | A304E | 0.32 | 0.08 | 0.30 | 3.56 | 3.07 |
| 304 | A304F | 0.49 | 0.08 | 0.15 | 1.43 | 1.58 |
| 304 | A304G | 1.16 | 0.65 | 0.42 | 0.80 | 0.66 |
| 304 | A304H | 0.73 | 0.09 | 0.28 | 0.97 | 1.38 |
| 304 | A304I | 0.66 | 0.15 | 0.39 | 1.93 | 1.79 |
| 304 | A304K | 0.82 | 0.15 | 0.17 | 1.63 | 1.59 |
| 304 | A304L | 0.52 | 0.10 | 0.25 | 1.55 | 2.80 |
| 304 | A304M | 0.82 | 0.11 | 0.12 | 1.89 | 1.39 |
| 304 | A304N | 0.65 | 0.11 | 0.14 | 5.49 | 17.77 |
| 304 | A304P | 0.31 | 0.11 | 0.14 | 1.16 | 2.23 |
| 304 | A304Q | 0.66 | 0.13 | 0.22 | 2.05 | 1.82 |
| 304 | A304R | 1.17 | 0.14 | 0.22 | 1.45 | 1.27 |
| 304 | A304S | 0.42 | 0.83 | 0.82 | 0.83 | 0.67 |
| 304 | A304T | 0.58 | 0.19 | 0.22 | 1.08 | 1.33 |
| 304 | A304V | 0.53 | 0.20 | 0.31 | 0.80 | 1.47 |
| 304 | A304W | 0.50 | 0.12 | 0.23 | 1.41 | 2.07 |
| 304 | A304Y | 0.54 | *0.05* | 0.32 | 3.22 | 4.73 |
| 306 | Y306A | 0.35 | 0.77 | 0.39 | 0.10 | 0.15 |
| 306 | Y306C | 0.16 | 0.49 | 0.27 | 0.21 | 0.91 |
| 306 | Y306D | 0.18 | 0.39 | 0.31 | 0.15 | 0.30 |
| 306 | Y306E | 0.15 | 0.45 | 0.22 | 0.15 | 0.46 |
| 306 | Y306G | 0.16 | 0.45 | 0.18 | 0.32 | 0.59 |
| 306 | Y306H | 0.32 | 0.60 | 0.19 | 0.07 | 0.39 |
| 306 | Y306I | 0.34 | 0.81 | 0.23 | 0.09 | 0.17 |
| 306 | Y306K | 0.19 | 0.17 | 0.28 | 0.41 | 0.58 |
| 306 | Y306L | 0.16 | 0.55 | 0.29 | 0.16 | 0.47 |
| 306 | Y306N | 0.22 | 0.60 | 0.13 | 0.08 | 0.21 |
| 306 | Y306P | 0.21 | 0.28 | 0.22 | 0.34 | 0.74 |
| 306 | Y306Q | 0.23 | 0.70 | 0.17 | 0.11 | 0.25 |
| 306 | Y306R | 0.20 | 0.51 | 0.23 | 0.18 | 0.35 |
| 306 | Y306S | 0.35 | 0.80 | 0.26 | 0.06 | 0.15 |
| 306 | Y306T | 0.60 | 0.91 | 0.17 | 0.09 | 0.13 |
| 306 | Y306V | 0.35 | 0.82 | 0.17 | 0.09 | 0.12 |
| 306 | Y306W | 0.50 | 0.78 | 0.68 | 0.56 | 0.75 |
| 307 | N307A | 0.13 | 0.23 | 0.25 | 0.54 | 0.73 |
| 307 | N307C | 0.17 | 0.34 | 0.22 | 0.19 | 0.38 |
| 307 | N307D | 0.20 | 0.77 | 0.57 | 0.15 | 0.24 |
| 307 | N307E | 0.11 | 0.56 | 0.16 | 0.53 | 0.82 |
| 307 | N307F | 0.13 | 0.24 | 0.20 | 0.43 | 0.88 |
| 307 | N307G | 0.25 | 0.59 | 0.25 | 0.20 | 0.52 |
| 307 | N307H | 0.15 | 0.22 | 0.23 | 0.40 | 0.61 |
| 307 | N307I | 0.23 | 0.42 | 0.20 | 0.15 | 0.33 |
| 307 | N307K | 0.14 | 0.21 | 0.26 | 0.38 | 1.07 |
| 307 | N307L | 0.12 | 0.30 | 0.21 | 0.34 | 0.69 |
| 307 | N307M | 0.15 | 0.33 | 0.17 | 0.33 | 0.77 |
| 307 | N307P | 0.14 | 0.15 | 0.23 | 0.83 | 2.18 |
| 307 | N307Q | 0.17 | 0.44 | 0.25 | 0.19 | 0.59 |
| 307 | N307R | 0.18 | 0.21 | 0.17 | 0.56 | 0.85 |
| 307 | N307S | 0.27 | 0.70 | 0.24 | 0.14 | 0.25 |
| 307 | N307T | 0.14 | 0.31 | 0.12 | 0.53 | 0.74 |
| 307 | N307V | 0.15 | 0.29 | 0.25 | 0.27 | 0.82 |
| 307 | N307W | 0.20 | 0.21 | 0.11 | 0.61 | 0.99 |
| 307 | N307Y | 0.20 | 0.18 | 0.19 | 0.30 | 1.06 |
| 312 | T312A | 1.35 | 2.81 | 1.85 | 0.20 | 0.23 |
| 312 | T312C | 0.80 | 0.73 | 0.48 | 0.67 | 0.88 |
| 312 | T312D | 1.09 | 1.51 | 0.93 | 0.22 | 0.28 |
| 312 | T312E | 1.39 | 2.50 | 1.93 | 0.31 | 0.13 |
| 312 | T312F | 1.07 | 1.90 | 0.98 | 0.25 | 0.05 |
| 312 | T312G | 1.17 | 2.33 | 0.47 | 0.16 | 0.27 |
| 312 | T312H | 0.98 | 1.48 | 0.64 | 0.70 | 0.46 |
| 312 | T312I | 1.21 | 2.10 | 0.21 | 0.20 | 0.06 |
| 312 | T312K | 0.78 | 2.31 | 0.87 | 0.36 | 0.24 |
| 312 | T312L | 0.76 | 0.69 | 0.23 | 1.03 | *0.05* |
| 312 | T312N | 0.66 | 0.82 | 0.30 | 0.80 | 0.22 |
| 312 | T312P | 1.18 | 2.16 | 0.42 | 0.29 | 0.14 |
| 312 | T312Q | 0.81 | 1.81 | 0.48 | 0.43 | 0.25 |
| 312 | T312R | 1.20 | 2.32 | 0.76 | 0.32 | 0.32 |
| 312 | T312S | 1.32 | 2.02 | 1.79 | 0.92 | 1.28 |
| 312 | T312V | 0.35 | 0.31 | 0.10 | 1.17 | 2.92 |
| 312 | T312W | 1.11 | 1.34 | 0.32 | 0.19 | 0.38 |
| 312 | T312Y | 1.05 | 1.62 | 0.71 | 0.24 | 0.13 |
| 313 | S313A | 0.34 | 1.08 | 0.85 | 0.77 | 0.60 |
| 313 | S313C | 0.34 | 0.94 | 0.58 | 0.79 | 0.84 |
| 313 | S313D | 0.43 | 1.04 | 1.32 | 1.01 | 0.99 |
| 313 | S313E | 0.46 | 1.20 | 0.90 | 0.99 | 0.88 |
| 313 | S313F | 0.59 | 1.02 | 0.54 | 0.82 | 0.78 |
| 313 | S313G | 0.73 | 1.05 | 0.30 | 0.30 | 0.13 |
| 313 | S313I | 0.69 | 1.06 | 0.69 | 0.90 | 0.90 |
| 313 | S313K | 1.64 | 1.07 | 0.53 | 1.04 | 1.16 |
| 313 | S313L | 0.86 | 1.08 | 0.55 | 0.62 | 0.29 |
| 313 | S313M | 0.50 | 1.12 | 0.72 | 0.74 | 0.57 |
| 313 | S313P | 1.00 | 0.95 | 0.55 | 0.56 | 0.31 |
| 313 | S313Q | 0.74 | 1.04 | 0.81 | 0.93 | 1.01 |
| 313 | S313R | 0.55 | 1.05 | 0.37 | 0.83 | 0.76 |
| 313 | S313T | 0.98 | 1.15 | 1.21 | 1.00 | 1.16 |
| 313 | S313V | 0.53 | 1.05 | 0.81 | 0.87 | 0.82 |
| 313 | S313W | 0.70 | 1.00 | 0.63 | 0.78 | 0.46 |
| 313 | S313Y | 0.52 | 0.97 | 0.49 | 0.67 | 0.31 |
| 316 | S316A | 0.59 | 0.96 | 1.36 | 1.49 | 1.15 |
| 316 | S316C | 0.77 | 0.87 | 1.10 | 1.43 | 1.15 |
| 316 | S316D | 0.85 | 0.98 | 1.18 | 0.63 | 0.46 |
| 316 | S316E | 0.13 | 0.12 | *0.05* | 1.22 | 1.85 |
| 316 | S316F | 0.65 | 0.99 | 0.68 | 1.06 | 0.83 |
| 316 | S316G | 0.69 | 0.97 | 0.60 | 0.71 | 0.79 |
| 316 | S316H | 0.63 | 1.05 | 0.48 | 1.28 | 0.80 |
| 316 | S316I | 0.50 | 0.90 | 0.51 | 1.62 | 0.91 |
| 316 | S316K | 0.78 | 0.99 | 0.66 | 0.97 | 0.85 |
| 316 | S316L | 1.27 | 1.00 | 1.19 | 0.99 | 0.88 |
| 316 | S316M | 0.15 | 0.07 | 0.15 | 14.10 | 22.76 |
| 316 | S316N | 0.73 | 1.06 | 0.92 | 0.76 | 0.70 |
| 316 | S316P | 0.98 | 0.95 | 1.46 | 1.74 | 1.48 |
| 316 | S316Q | 0.82 | 0.97 | 0.91 | 0.85 | 0.74 |
| 316 | S316R | 1.18 | 0.93 | 0.78 | 1.20 | 0.76 |
| 316 | S316T | 0.92 | 0.92 | 0.89 | 0.89 | 0.68 |
| 316 | S316V | 0.76 | 0.98 | 0.88 | 1.12 | 0.94 |
| 316 | S316W | 1.13 | 0.92 | 1.16 | 1.54 | 1.39 |
| 316 | S316Y | 0.85 | 0.93 | 0.60 | 0.56 | 0.87 |
| 319 | Q319A | 0.55 | 1.03 | 0.96 | 1.06 | 1.00 |
| 319 | Q319C | 0.52 | 0.95 | 0.76 | 1.04 | 0.91 |
| 319 | Q319D | 0.78 | 1.01 | 0.86 | 0.95 | 0.80 |
| 319 | Q319E | 0.83 | 1.08 | 0.92 | 1.03 | 0.88 |
| 319 | Q319F | 0.71 | 0.98 | 0.40 | 1.06 | 0.94 |
| 319 | Q319G | 0.81 | 0.98 | 0.41 | 0.78 | 0.56 |
| 319 | Q319I | 0.71 | 1.04 | 0.60 | 1.03 | 1.01 |
| 319 | Q319K | 0.84 | 1.00 | 0.45 | 1.04 | 1.12 |
| 319 | Q319L | 0.48 | 1.03 | 0.61 | 1.10 | 1.13 |
| 319 | Q319M | 0.52 | 1.03 | 0.89 | 0.96 | 0.98 |
| 319 | Q319N | 0.81 | 1.05 | 0.70 | 0.96 | 0.92 |
| 319 | Q319P | 0.44 | 0.91 | *0.05* | 0.26 | 0.30 |
| 319 | Q319R | 0.71 | 1.01 | 0.49 | 1.06 | 1.14 |
| 319 | Q319S | 1.06 | 1.03 | 0.69 | 0.99 | 1.00 |
| 319 | Q319T | 0.93 | 1.06 | 0.77 | 0.97 | 0.95 |
| 319 | Q319V | 0.65 | 1.02 | 0.69 | 1.00 | 1.02 |
| 319 | Q319W | 0.50 | 0.85 | 0.59 | 1.06 | 0.99 |
| 319 | Q319Y | 1.02 | 1.01 | 0.81 | 1.01 | 1.05 |
| 322 | A322C | 0.52 | 0.98 | 0.98 | 0.95 | 0.85 |
| 322 | A322E | 0.56 | 1.02 | 1.05 | 0.99 | 0.98 |
| 322 | A322F | 0.58 | 0.99 | 0.64 | 0.81 | 0.69 |
| 322 | A322G | 0.68 | 0.94 | 0.70 | 0.97 | 0.78 |
| 322 | A322H | 0.48 | 0.97 | 0.50 | 0.91 | 0.84 |
| 322 | A322I | 0.58 | 0.98 | 0.79 | 0.96 | 0.94 |
| 322 | A322K | 0.56 | 1.00 | 0.56 | 0.95 | 1.02 |
| 322 | A322L | 0.57 | 1.00 | 0.57 | 0.94 | 0.93 |
| 322 | A322M | 0.81 | 1.05 | 0.97 | 1.00 | 0.96 |
| 322 | A322N | 0.45 | 0.98 | 0.73 | 0.92 | 0.96 |
| 322 | A322P | 0.88 | 1.02 | 1.06 | 1.09 | 1.21 |
| 322 | A322Q | *0.05* | *0.05* | *0.05* | *0.05* | *0.05* |
| 322 | A322R | 0.51 | 1.01 | 0.33 | 1.01 | 1.01 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 322 | A322S | 0.53 | 1.00 | 1.00 | 1.03 | 1.01 |
| 322 | A322T | 0.91 | 1.03 | 0.91 | 0.99 | 1.01 |
| 322 | A322V | 0.62 | 1.02 | 0.93 | 0.93 | 1.00 |
| 322 | A322W | 0.47 | 0.91 | 0.44 | 0.87 | 0.76 |
| 322 | A322Y | 0.45 | 0.93 | 0.56 | 0.90 | 0.82 |
| 323 | V323A | 0.89 | 1.01 | 0.80 | 0.61 | 0.62 |
| 323 | V323C | 0.73 | 1.05 | 1.21 | 1.51 | 0.84 |
| 323 | V323D | 0.48 | 0.79 | 0.46 | 0.88 | 0.81 |
| 323 | V323E | 0.49 | 0.76 | 0.59 | 0.80 | 0.79 |
| 323 | V323F | 0.68 | 0.92 | 0.86 | 1.09 | 0.85 |
| 323 | V323G | 0.30 | 0.84 | 0.27 | 1.23 | 1.27 |
| 323 | V323H | 0.67 | 0.90 | 0.27 | 0.66 | 0.56 |
| 323 | V323I | 0.70 | 1.07 | 1.04 | 0.53 | 0.73 |
| 323 | V323K | 0.38 | 0.93 | 0.51 | 1.34 | 1.11 |
| 323 | V323L | 0.57 | 0.99 | 0.22 | 0.60 | 0.68 |
| 323 | V323N | 0.47 | 1.01 | 0.38 | 0.88 | 1.04 |
| 323 | V323Q | 0.42 | 0.97 | 0.47 | 0.72 | 1.05 |
| 323 | V323R | 0.23 | 0.69 | 0.26 | 2.20 | 2.25 |
| 323 | V323S | 0.30 | 0.80 | 0.09 | 1.00 | 1.42 |
| 323 | V323T | 0.60 | 0.80 | *0.05* | 0.66 | 1.05 |
| 323 | V323W | 0.45 | 0.90 | 0.20 | 0.71 | 1.06 |
| 323 | V323Y | 0.35 | 1.00 | 0.39 | 0.82 | 1.16 |
| 327 | K327A | 0.86 | 1.03 | 0.98 | 0.76 | 0.76 |
| 327 | K327C | 0.42 | 0.93 | 1.25 | 1.28 | 1.02 |
| 327 | K327D | 0.31 | 0.73 | 0.76 | 1.13 | 1.81 |
| 327 | K327E | 0.73 | 0.84 | 0.85 | 1.05 | 0.87 |
| 327 | K327F | 0.24 | 0.61 | 0.44 | 1.91 | 2.14 |
| 327 | K327G | 0.24 | 0.83 | 0.16 | 1.65 | 1.30 |
| 327 | K327H | 0.58 | 1.05 | 1.22 | 0.66 | 0.80 |
| 327 | K327I | 0.31 | 0.74 | 0.23 | 1.44 | 1.37 |
| 327 | K327L | 0.26 | 0.94 | 0.60 | 0.89 | 1.30 |
| 327 | K327M | 0.41 | 0.90 | 0.90 | 0.87 | 1.44 |
| 327 | K327N | 0.41 | 0.90 | 1.04 | 0.74 | 1.33 |
| 327 | K327P | 0.21 | 0.58 | *0.05* | 1.65 | 2.77 |
| 327 | K327Q | 1.32 | 1.06 | 1.42 | 1.15 | 0.77 |
| 327 | K327R | 0.56 | 0.85 | 0.89 | 1.07 | 1.16 |
| 327 | K327S | 0.20 | 0.63 | 0.58 | 2.39 | 2.92 |
| 327 | K327T | 0.21 | 0.29 | 0.09 | 3.69 | 7.57 |
| 327 | K327V | 0.28 | 0.86 | 0.58 | 0.66 | 1.26 |
| 327 | K327W | 0.28 | 1.05 | 0.74 | 0.93 | 1.57 |
| 327 | K327Y | 0.93 | 1.04 | 1.08 | 0.49 | 0.60 |
| 328 | L328A | 0.91 | 1.11 | 0.89 | 0.49 | 0.18 |
| 328 | L328C | *0.05* | *0.05* | *0.05* | *0.05* | *0.05* |
| 328 | L328D | 0.95 | 1.01 | 0.55 | 0.21 | 0.06 |
| 328 | L328E | 0.97 | 0.97 | 0.54 | 0.31 | 0.10 |
| 328 | L328F | 0.53 | 0.92 | 0.27 | 0.47 | 0.21 |
| 328 | L328G | 0.68 | 0.96 | 0.55 | 0.61 | 0.30 |
| 328 | L328H | 0.62 | 1.05 | 0.27 | 0.22 | 0.16 |
| 328 | L328I | 0.67 | 1.01 | 0.72 | 0.82 | 0.58 |
| 328 | L328K | 0.91 | 1.02 | 0.45 | 0.88 | 0.77 |
| 328 | L328M | 0.91 | 0.95 | 0.61 | 0.89 | 0.82 |
| 328 | L328N | 0.86 | 0.90 | 0.44 | 0.49 | 0.22 |
| 328 | L328P | 0.25 | 0.58 | 0.17 | 0.24 | 0.29 |
| 328 | L328Q | 2.73 | 1.07 | 0.86 | 0.85 | 0.76 |
| 328 | L328R | 0.74 | 0.92 | 0.34 | 0.81 | 0.62 |
| 328 | L328S | 0.40 | 0.90 | 0.42 | 0.38 | 0.18 |
| 328 | L328T | 0.57 | 0.93 | 0.50 | 0.30 | 0.13 |
| 328 | L328V | 0.40 | 0.74 | 0.20 | 0.14 | 0.10 |
| 328 | L328W | 0.45 | 0.88 | 0.27 | 0.12 | 0.14 |
| 328 | L328Y | *0.05* | *0.05* | *0.05* | *0.05* | *0.05* |
| 331 | H331A | 0.31 | 0.58 | 0.60 | 0.52 | 0.18 |
| 331 | H331C | 0.36 | 0.17 | 0.32 | 0.70 | 0.09 |
| 331 | H331D | 0.46 | 0.79 | 0.66 | 0.50 | 0.15 |
| 331 | H331E | 0.34 | 0.66 | 0.60 | 0.64 | 0.36 |
| 331 | H331F | 0.29 | 0.23 | 0.13 | 0.33 | *0.05* |
| 331 | H331G | 0.29 | 0.68 | 0.51 | 0.57 | 0.24 |
| 331 | H331I | 0.25 | 0.14 | 0.26 | 0.06 | 12.66 |
| 331 | H331K | 0.39 | 0.79 | 0.60 | 0.50 | 0.14 |
| 331 | H331L | 0.24 | 0.36 | 0.31 | 0.37 | 0.20 |
| 331 | H331M | 0.25 | 0.41 | 0.29 | 0.18 | 0.07 |
| 331 | H331N | 0.58 | 0.98 | 1.06 | 0.82 | 0.64 |
| 331 | H331P | 0.25 | 0.09 | 0.30 | 0.26 | 1.41 |
| 331 | H331Q | 0.40 | 0.84 | 0.92 | 0.62 | 0.35 |
| 331 | H331R | 0.38 | 0.67 | 0.43 | 0.53 | 0.21 |
| 331 | H331S | 0.33 | 0.56 | 0.55 | 0.74 | 0.35 |
| 331 | H331T | 0.24 | 0.64 | 0.58 | 0.57 | 0.27 |
| 331 | H331V | 0.22 | 0.25 | 0.30 | 0.16 | 0.22 |
| 331 | H331W | 0.32 | 0.69 | 0.69 | 0.66 | 0.44 |
| 331 | H331Y | 0.58 | 0.81 | 0.72 | 0.68 | 0.36 |
| 338 | A338C | 0.79 | 0.94 | 0.81 | 0.93 | 0.91 |
| 338 | A338D | 1.11 | 0.97 | 0.90 | 1.03 | 1.06 |
| 338 | A338E | 0.71 | 0.97 | 0.74 | 0.95 | 0.93 |
| 338 | A338F | 0.56 | 0.90 | 0.72 | 0.92 | 0.88 |
| 338 | A338G | 0.71 | 0.98 | 0.75 | 0.93 | 0.92 |
| 338 | A338H | 0.85 | 1.05 | 0.57 | 0.94 | 1.02 |
| 338 | A338I | 0.74 | 0.97 | 0.87 | 1.00 | 1.14 |
| 338 | A338K | 0.90 | 1.05 | 0.67 | 0.98 | 1.02 |
| 338 | A338L | 0.36 | 0.68 | 0.71 | 1.02 | 0.97 |
| 338 | A338M | 0.72 | 0.88 | 0.84 | 1.10 | 1.15 |
| 338 | A338N | 0.87 | 1.02 | 0.81 | 0.97 | 1.04 |
| 338 | A338P | 0.48 | 0.88 | 0.85 | 0.97 | 1.03 |
| 338 | A338Q | 0.34 | 0.66 | 0.57 | 0.92 | 0.86 |
| 338 | A338R | 0.70 | 1.09 | 0.79 | 0.95 | 0.97 |
| 338 | A338S | 0.70 | 0.94 | 0.86 | 1.00 | 1.05 |
| 338 | A338T | 0.21 | 0.68 | 0.68 | 0.83 | 0.88 |
| 338 | A338V | 0.48 | 1.00 | 1.01 | 0.92 | 1.01 |
| 338 | A338W | 0.30 | 0.83 | 0.75 | 0.87 | 0.94 |
| 339 | N339A | 0.67 | 1.03 | 1.24 | 1.06 | 1.10 |
| 339 | N339C | 0.60 | 0.98 | 1.09 | 0.96 | 0.96 |
| 339 | N339D | 0.92 | 1.04 | 1.05 | 1.04 | 1.10 |
| 339 | N339E | 0.94 | 1.03 | 0.83 | 1.08 | 1.13 |
| 339 | N339F | 0.53 | 1.02 | 0.56 | 1.08 | 1.12 |
| 339 | N339G | 0.57 | 1.01 | 0.63 | 1.09 | 1.00 |
| 339 | N339H | 0.66 | 1.05 | 0.58 | 1.00 | 1.11 |
| 339 | N339I | 0.66 | 1.09 | 0.77 | 1.05 | 1.13 |
| 339 | N339K | 0.69 | 1.03 | 0.65 | 1.06 | 1.11 |
| 339 | N339L | 0.61 | 1.13 | 0.74 | 1.05 | 1.15 |
| 339 | N339M | 0.47 | 1.03 | 0.51 | 1.05 | 1.09 |
| 339 | N339P | 0.19 | 0.90 | 0.64 | 0.84 | 0.74 |
| 339 | N339Q | 0.36 | 1.06 | 0.69 | 1.06 | 0.84 |
| 339 | N339R | 0.97 | 1.01 | 0.58 | 1.07 | 1.10 |
| 339 | N339S | 0.74 | 1.04 | 0.85 | 0.97 | 1.02 |
| 339 | N339T | 0.71 | 1.03 | 0.91 | 0.98 | 1.00 |
| 339 | N339V | 0.75 | 1.08 | 0.65 | 1.04 | 1.08 |
| 339 | N339W | 0.17 | 0.46 | 0.44 | 0.83 | 1.26 |
| 339 | N339Y | 0.59 | 0.97 | 0.73 | 0.88 | 0.81 |
| 340 | H340A | 0.25 | 0.18 | 0.44 | 0.23 | *0.05* |
| 340 | H340C | 0.39 | 0.69 | 0.72 | 0.65 | 0.37 |
| 340 | H340D | 0.32 | 0.45 | 0.78 | 0.41 | 0.28 |
| 340 | H340E | 0.39 | 0.73 | 0.79 | 0.80 | 0.51 |
| 340 | H340F | 0.68 | 1.08 | 0.91 | 0.77 | 0.64 |
| 340 | H340G | 0.35 | 0.44 | 0.50 | 0.47 | 0.24 |
| 340 | H340I | 0.28 | 0.29 | 0.44 | 0.51 | 0.14 |
| 340 | H340K | 0.71 | 1.03 | 1.00 | 0.83 | 0.69 |
| 340 | H340L | 0.36 | 0.84 | 0.70 | 0.63 | 0.42 |
| 340 | H340M | 0.36 | 0.73 | 0.68 | 0.81 | 0.52 |
| 340 | H340N | 0.76 | 0.92 | 1.02 | 0.92 | 0.81 |
| 340 | H340P | 0.22 | 0.17 | 0.21 | 0.16 | 0.39 |
| 340 | H340Q | 0.33 | 0.69 | 0.49 | 0.66 | 0.42 |
| 340 | H340R | 0.22 | 0.12 | 0.36 | 0.13 | 0.13 |
| 340 | H340S | 0.36 | 0.81 | 0.83 | 0.65 | 0.46 |
| 340 | H340T | 0.24 | 0.36 | 0.31 | 0.28 | 0.14 |
| 340 | H340V | 0.31 | 0.48 | 0.60 | 0.52 | 0.26 |
| 340 | H340W | 1.02 | 1.03 | 0.97 | 0.88 | 0.80 |
| 340 | H340Y | 0.38 | 0.85 | 1.01 | 0.83 | 0.66 |
| 343 | S343A | 1.40 | 2.48 | 2.75 | 0.94 | 1.77 |
| 343 | S343C | 3.71 | 2.52 | 3.51 | 1.02 | 2.16 |
| 343 | S343D | 1.37 | 2.87 | 3.53 | 0.95 | 1.67 |
| 343 | S343E | 4.68 | 2.37 | 3.30 | 1.09 | 2.31 |
| 343 | S343F | 1.52 | 2.15 | 1.82 | 0.95 | 1.59 |
| 343 | S343G | 0.51 | 0.48 | 0.19 | 3.20 | 5.39 |
| 343 | S343H | 0.66 | 0.73 | 0.33 | 0.97 | 2.31 |
| 343 | S343I | 1.19 | 2.45 | 1.98 | 1.09 | 1.76 |
| 343 | S343K | 2.34 | 2.56 | 3.03 | 1.19 | 2.04 |
| 343 | S343L | 1.32 | 2.65 | 2.59 | 1.00 | 1.83 |
| 343 | S343M | 0.18 | 0.57 | 0.73 | 6.24 | 57.92 |
| 343 | S343P | 2.09 | 2.50 | 2.38 | 1.01 | 2.03 |
| 343 | S343Q | 3.31 | 2.39 | 2.38 | 1.12 | 2.29 |
| 343 | S343R | 1.02 | 2.73 | 1.69 | 1.22 | 1.75 |
| 343 | S343T | 4.19 | 2.37 | 3.08 | 1.15 | 2.26 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 343 | S343V | 0.47 | 0.49 | 0.17 | 1.38 | 2.43 |
| 343 | S343W | 2.83 | 2.47 | 2.53 | 1.12 | 2.19 |
| 343 | S343Y | 2.20 | 2.50 | 2.89 | 1.07 | 2.01 |
| 344 | N344A | 0.58 | 1.02 | 1.17 | 1.13 | 1.12 |
| 344 | N344C | 0.46 | 0.96 | 1.31 | 0.84 | 0.96 |
| 344 | N344D | 0.29 | 0.85 | 1.10 | 1.43 | 1.31 |
| 344 | N344F | 0.31 | 0.87 | 0.42 | 1.03 | 1.08 |
| 344 | N344G | 0.73 | 1.02 | 1.25 | 1.17 | 1.25 |
| 344 | N344H | 0.64 | 0.96 | 0.36 | 0.81 | 0.90 |
| 344 | N344I | 0.26 | 0.78 | 0.60 | 1.33 | 1.49 |
| 344 | N344K | 0.89 | 1.04 | 0.91 | 0.90 | 0.72 |
| 344 | N344L | 0.23 | 0.69 | 0.40 | 1.49 | 2.90 |
| 344 | N344M | 0.53 | 0.99 | 0.79 | 0.60 | 0.75 |
| 344 | N344P | 0.33 | 0.87 | 0.61 | 1.62 | 1.82 |
| 344 | N344Q | 0.69 | 1.01 | 0.68 | 1.07 | 1.06 |
| 344 | N344R | 0.28 | 0.87 | 0.30 | 1.45 | 1.62 |
| 344 | N344S | 0.84 | 0.94 | 0.77 | 0.98 | 0.92 |
| 344 | N344T | 0.27 | 0.67 | 0.39 | 1.51 | 2.53 |
| 344 | N344V | 0.26 | 0.82 | 0.42 | 1.44 | 1.84 |
| 344 | N344W | 0.22 | 0.64 | *0.05* | 1.86 | 2.16 |
| 344 | N344Y | 0.32 | 0.91 | 0.43 | 0.89 | 1.49 |
| 346 | F346A | 0.70 | 1.02 | 1.25 | 0.95 | 0.99 |
| 346 | F346C | 0.48 | 0.90 | 0.99 | 0.82 | 0.87 |
| 346 | F346D | 0.18 | 0.26 | 0.35 | 1.22 | 2.13 |
| 346 | F346E | 0.21 | 0.31 | 0.30 | 1.53 | 2.18 |
| 346 | F346G | 0.60 | 1.01 | 0.72 | 0.97 | 1.10 |
| 346 | F346H | 1.05 | 1.02 | 0.91 | 1.06 | 1.22 |
| 346 | F346I | 0.20 | 0.62 | 0.31 | 1.42 | 1.75 |
| 346 | F346K | 1.01 | 0.98 | 0.78 | 1.00 | 1.21 |
| 346 | F346L | 0.28 | 0.66 | 0.63 | 0.96 | 1.13 |
| 346 | F346M | 0.63 | 0.98 | 0.77 | 1.03 | 1.04 |
| 346 | F346N | 0.43 | 0.82 | 0.61 | 0.92 | 1.14 |
| 346 | F346P | 0.31 | 0.24 | 0.22 | 1.16 | 2.49 |
| 346 | F346Q | 0.89 | 0.93 | 0.71 | 1.26 | 1.70 |
| 346 | F346R | 1.02 | 0.94 | 0.69 | 1.07 | 1.30 |
| 346 | F346S | 0.78 | 0.95 | 0.94 | 1.01 | 0.99 |
| 346 | F346T | 0.27 | 0.85 | 0.58 | 0.76 | 0.98 |
| 346 | F346V | 0.30 | 0.69 | 0.60 | 0.89 | 1.09 |
| 346 | F346W | 0.41 | 0.91 | 0.87 | 0.96 | 1.00 |
| 346 | F346Y | 0.91 | 1.02 | 0.85 | 1.10 | 1.31 |
| 356 | K356A | 1.22 | 1.03 | 0.88 | 0.23 | 0.25 |
| 356 | K356C | 0.62 | 0.92 | 0.98 | 0.29 | 0.45 |
| 356 | K356D | 0.42 | 0.87 | 0.57 | 0.22 | 0.42 |
| 356 | K356E | 0.43 | 0.98 | 0.71 | 0.28 | 0.43 |
| 356 | K356F | 0.69 | 0.99 | 0.45 | 0.15 | 0.39 |
| 356 | K356G | 0.97 | 0.98 | 0.20 | 0.20 | 0.40 |
| 356 | K356H | 0.70 | 0.88 | 0.63 | 0.52 | 0.52 |
| 356 | K356I | 0.76 | 0.96 | 0.60 | 0.26 | 0.46 |
| 356 | K356L | 0.67 | 1.00 | 0.68 | 0.45 | 0.39 |
| 356 | K356M | 0.68 | 0.99 | 0.88 | 0.54 | 0.53 |
| 356 | K356N | 0.98 | 1.04 | 0.72 | 0.19 | 0.37 |
| 356 | K356P | 0.23 | 0.52 | 0.33 | 1.09 | 0.99 |
| 356 | K356Q | 0.77 | 0.99 | 0.77 | 0.41 | 0.43 |
| 356 | K356R | 0.70 | 0.98 | 0.62 | 0.95 | 0.76 |
| 356 | K356S | 0.58 | 0.88 | 0.48 | 0.22 | 0.41 |
| 356 | K356T | 0.63 | 1.00 | 0.49 | 0.28 | 0.43 |
| 356 | K356V | 0.91 | 0.90 | 0.75 | 0.35 | 0.31 |
| 356 | K356W | 0.39 | 0.90 | 0.42 | 0.24 | 0.47 |
| 356 | K356Y | 0.52 | 0.96 | 0.47 | 0.20 | 0.51 |
| 360 | G360A | 0.56 | 0.89 | 0.47 | 0.08 | *0.05* |
| 360 | G360E | 0.62 | 0.88 | 0.45 | *0.05* | *0.05* |
| 360 | G360F | 0.24 | 0.45 | 0.08 | 0.08 | *0.05* |
| 360 | G360H | 0.51 | 0.84 | 0.21 | 0.07 | *0.05* |
| 360 | G360I | 0.41 | 0.83 | 0.19 | 0.07 | *0.05* |
| 360 | G360K | 0.19 | 0.46 | 0.07 | *0.05* | 0.08 |
| 360 | G360L | 0.69 | 0.93 | 0.33 | *0.05* | *0.05* |
| 360 | G360M | 0.84 | 1.06 | 0.47 | 0.07 | 0.05 |
| 360 | G360N | 0.60 | 0.93 | 0.23 | *0.05* | *0.05* |
| 360 | G360Q | 0.68 | 1.01 | 0.58 | *0.05* | *0.05* |
| 360 | G360R | 0.77 | 1.01 | 0.29 | *0.05* | *0.05* |
| 360 | G360S | 0.73 | 0.96 | 0.47 | *0.05* | *0.05* |
| 360 | G360T | 0.58 | 0.97 | 0.13 | *0.05* | *0.05* |
| 360 | G360V | 0.10 | 0.07 | 0.14 | 4.46 | 16.21 |
| 360 | G360W | 0.61 | 0.92 | 0.27 | *0.05* | 0.07 |
| 360 | G360Y | 0.11 | *0.05* | 0.06 | 0.78 | 6.25 |
| 361 | Q361A | 0.93 | 1.02 | 0.18 | 0.13 | 0.14 |
| 361 | Q361C | 0.45 | 0.91 | 0.18 | 0.21 | 0.20 |
| 361 | Q361D | 0.43 | 0.65 | 0.10 | 0.19 | 0.29 |
| 361 | Q361E | 0.07 | 1.37 | *0.05* | 1.01 | 0.93 |
| 361 | Q361F | 0.34 | 0.40 | *0.05* | 0.31 | 0.49 |
| 361 | Q361G | 0.33 | 1.01 | 0.10 | 0.23 | 0.24 |
| 361 | Q361H | 0.25 | 0.87 | 0.20 | 0.74 | 0.59 |
| 361 | Q361I | 0.19 | 0.49 | 0.19 | 0.91 | 1.00 |
| 361 | Q361K | 0.66 | 0.73 | 0.07 | 0.27 | 0.34 |
| 361 | Q361L | 0.86 | 0.86 | 0.21 | 0.20 | 0.19 |
| 361 | Q361M | 0.59 | 0.86 | 0.10 | 0.27 | 0.25 |
| 361 | Q361N | 0.06 | 0.05 | *0.05* | 0.36 | 4.82 |
| 361 | Q361P | 0.26 | 0.21 | *0.05* | 0.80 | 0.86 |
| 361 | Q361R | 0.69 | 0.75 | 0.10 | 0.13 | 0.18 |
| 361 | Q361S | 0.55 | 0.90 | 0.13 | 0.27 | 0.22 |
| 361 | Q361T | 0.57 | 0.83 | 0.12 | 0.25 | 0.26 |
| 361 | Q361V | 0.44 | 0.80 | 0.09 | 0.08 | 0.12 |
| 361 | Q361W | 0.49 | 0.66 | 0.27 | 0.41 | 0.38 |
| 361 | Q361Y | 0.31 | 0.39 | 0.22 | 0.79 | 0.58 |
| 362 | Q362A | 0.81 | 0.98 | 0.90 | 0.83 | 0.69 |
| 362 | Q362C | 0.68 | 0.95 | 0.83 | 0.90 | 0.98 |
| 362 | Q362D | 1.15 | 1.02 | 0.95 | 0.85 | 0.78 |
| 362 | Q362E | 0.93 | 0.95 | 0.70 | 0.86 | 0.81 |
| 362 | Q362F | 0.73 | 0.97 | 0.54 | 0.75 | 0.66 |
| 362 | Q362G | 0.70 | 0.99 | 0.34 | 0.31 | 0.44 |
| 362 | Q362H | 1.00 | 0.96 | 0.41 | 0.96 | 0.96 |
| 362 | Q362I | 0.86 | 0.99 | 1.04 | 1.30 | 1.81 |
| 362 | Q362K | 0.17 | 0.44 | 0.28 | 0.64 | 3.22 |
| 362 | Q362L | 0.71 | 0.96 | 0.89 | 1.29 | 1.86 |
| 362 | Q362M | 0.75 | 0.96 | 0.88 | 1.10 | 1.45 |
| 362 | Q362N | 0.78 | 0.98 | 0.74 | 0.96 | 0.99 |
| 362 | Q362P | 0.55 | 0.86 | 0.71 | 0.90 | 0.90 |
| 362 | Q362R | 0.96 | 0.96 | 0.53 | 1.03 | 1.15 |
| 362 | Q362S | 0.68 | 0.98 | 0.61 | 0.78 | 0.80 |
| 362 | Q362T | 0.73 | 0.99 | 0.60 | 0.85 | 0.73 |
| 362 | Q362V | 1.05 | 0.96 | 0.77 | 0.98 | 1.00 |
| 362 | Q362W | 0.94 | 0.97 | 0.54 | 0.75 | 0.60 |
| 362 | Q362Y | 0.78 | 1.05 | 0.76 | 0.71 | 0.61 |
| 363 | Q363A | 1.26 | 1.00 | 0.95 | 1.07 | 1.25 |
| 363 | Q363C | 0.27 | 0.69 | 0.50 | 0.50 | 1.16 |
| 363 | Q363D | 0.30 | 0.83 | 0.94 | 0.98 | 1.30 |
| 363 | Q363E | 0.91 | 1.00 | 0.87 | 0.97 | 1.03 |
| 363 | Q363F | 1.37 | 0.95 | 0.72 | 0.56 | 1.15 |
| 363 | Q363G | 0.17 | 0.31 | 0.23 | 1.14 | 2.30 |
| 363 | Q363H | 0.39 | 0.92 | 0.39 | 1.05 | 1.40 |
| 363 | Q363I | 0.43 | 0.92 | 0.28 | 0.31 | 0.56 |
| 363 | Q363K | 0.44 | 0.95 | 0.60 | 0.63 | 1.22 |
| 363 | Q363L | 0.21 | 0.80 | 0.38 | 0.93 | 0.93 |
| 363 | Q363M | 0.65 | 0.95 | 0.62 | 0.90 | 0.84 |
| 363 | Q363N | 3.15 | 0.98 | 1.15 | 1.31 | 1.70 |
| 363 | Q363P | 0.37 | 0.63 | 0.20 | 0.48 | 0.82 |
| 363 | Q363R | 0.94 | 0.94 | 0.55 | 1.11 | 1.22 |
| 363 | Q363S | 0.62 | 1.00 | 0.85 | 1.05 | 1.40 |
| 363 | Q363T | 1.10 | 0.98 | 0.74 | 0.99 | 0.86 |
| 363 | Q363V | 0.18 | 0.88 | 0.50 | 0.86 | 1.24 |
| 363 | Q363W | 0.70 | 0.88 | 0.45 | 0.68 | 0.61 |
| 363 | Q363Y | 0.75 | 0.91 | 0.75 | 1.05 | 1.08 |
| 364 | W364A | 0.95 | 0.85 | 0.19 | 0.13 | 0.18 |
| 364 | W364C | 0.81 | 0.69 | 0.50 | 0.77 | 0.65 |
| 364 | W364D | 1.65 | 0.88 | 0.31 | 0.11 | 0.11 |
| 364 | W364E | 0.69 | 0.93 | 0.27 | 0.18 | 0.22 |
| 364 | W364F | 0.54 | 0.77 | 0.08 | 0.28 | 0.30 |
| 364 | W364G | 0.70 | 0.83 | 0.21 | 0.18 | 0.13 |
| 364 | W364I | 0.46 | 0.82 | 0.18 | 0.14 | 0.19 |
| 364 | W364K | 0.69 | 0.50 | 0.12 | 0.21 | 0.09 |
| 364 | W364L | 0.35 | 0.83 | 0.13 | 0.10 | 0.19 |
| 364 | W364M | 0.63 | 0.93 | 0.17 | 0.19 | 0.12 |
| 364 | W364N | 0.54 | 0.83 | 0.23 | 0.11 | 0.11 |
| 364 | W364P | 0.72 | 0.81 | 0.08 | 0.20 | 0.23 |
| 364 | W364Q | 0.55 | 0.92 | 0.16 | 0.17 | 0.20 |
| 364 | W364R | 1.01 | 0.61 | 0.09 | 0.14 | 0.16 |
| 364 | W364S | 0.65 | 0.82 | 0.10 | 0.20 | 0.24 |
| 364 | W364T | 0.83 | 0.79 | 0.11 | 0.06 | 0.13 |
| 364 | W364V | 0.52 | 0.85 | 0.51 | 0.12 | 0.20 |
| 364 | W364Y | 0.66 | 0.68 | 0.14 | 0.21 | 0.29 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 365 | G365C | 0.48 | 0.59 | 0.37 | 0.87 | 0.88 |
| 365 | G365E | 0.96 | 0.83 | 0.57 | 0.92 | 0.92 |
| 365 | G365F | 0.38 | 0.66 | 0.18 | 0.64 | 0.53 |
| 365 | G365H | 0.47 | 0.72 | 0.21 | 0.74 | 0.66 |
| 365 | G365I | 0.38 | 0.52 | 0.09 | 0.68 | 0.61 |
| 365 | G365K | 0.74 | 0.72 | 0.28 | 0.85 | 0.79 |
| 365 | G365L | 0.40 | 0.57 | 0.29 | 0.86 | 0.86 |
| 365 | G365M | 0.62 | 0.66 | 0.39 | 0.97 | 1.08 |
| 365 | G365N | 0.30 | 0.66 | 0.29 | 0.84 | 0.86 |
| 365 | G365P | 0.37 | 0.64 | 0.23 | 0.53 | 0.26 |
| 365 | G365Q | 0.25 | 0.15 | 0.21 | 0.82 | 1.38 |
| 365 | G365R | 0.64 | 0.72 | 0.26 | 0.83 | 0.86 |
| 365 | G365S | 0.71 | 0.80 | 0.74 | 1.01 | 1.14 |
| 365 | G365T | 0.85 | 0.66 | 0.36 | 0.94 | 1.11 |
| 365 | G365V | 0.65 | 0.55 | 0.17 | 0.68 | 0.78 |
| 365 | G365W | 0.80 | 0.77 | 0.36 | 0.66 | 0.58 |
| 365 | G365Y | 0.06 | 1.15 | 0.15 | 0.99 | 1.15 |
| 371 | I371A | 0.34 | 1.05 | 1.25 | 0.75 | 0.57 |
| 371 | I371C | 0.34 | 0.87 | 0.84 | 0.88 | 0.59 |
| 371 | I371D | 0.62 | 0.99 | 0.88 | 0.90 | 0.79 |
| 371 | I371E | 0.36 | 0.98 | 0.73 | 0.81 | 0.54 |
| 371 | I371F | 0.21 | 0.24 | 0.07 | 0.70 | 0.49 |
| 371 | I371G | 0.54 | 0.98 | 0.57 | 0.88 | 0.70 |
| 371 | I371H | 0.24 | 0.08 | *0.05* | 0.63 | 0.94 |
| 371 | I371K | 0.11 | 0.07 | *0.05* | 0.86 | 1.24 |
| 371 | I371L | 0.29 | 0.64 | 0.55 | 0.54 | 0.28 |
| 371 | I371M | 0.28 | 0.87 | 0.53 | 0.68 | 0.40 |
| 371 | I371N | 0.64 | 1.06 | 0.74 | 0.93 | 0.82 |
| 371 | I371P | 0.21 | 0.18 | *0.05* | 1.78 | 1.31 |
| 371 | I371Q | 0.31 | 0.81 | 0.67 | 0.77 | 0.57 |
| 371 | I371R | 0.21 | 0.43 | 0.13 | 0.63 | 0.55 |
| 371 | I371S | 1.05 | 1.00 | 1.10 | 1.14 | 1.12 |
| 371 | I371T | 0.95 | 1.00 | 0.80 | 1.08 | 1.00 |
| 371 | I371V | 0.28 | 0.59 | 0.37 | 0.73 | 0.52 |
| 371 | I371W | 0.23 | 0.18 | 0.10 | 0.74 | 0.73 |
| 371 | I371Y | 0.24 | 0.42 | 0.27 | 0.56 | 0.45 |
| 378 | R378A | 0.21 | 0.76 | 0.79 | 0.25 | 0.54 |
| 378 | R378C | 0.25 | 0.34 | 0.42 | 0.74 | 1.01 |
| 378 | R378D | 0.19 | 0.23 | 0.33 | 0.49 | 0.58 |
| 378 | R378E | 0.17 | 0.18 | 0.30 | 0.92 | 0.94 |
| 378 | R378F | 0.13 | 0.39 | 1.34 | 0.12 | 0.38 |
| 378 | R378G | 0.08 | 0.22 | 1.48 | 0.19 | 0.82 |
| 378 | R378H | 0.13 | 0.22 | 0.82 | 0.62 | 1.22 |
| 378 | R378I | 0.19 | 0.42 | 0.33 | 0.38 | 0.69 |
| 378 | R378K | 0.15 | 0.45 | 0.27 | 0.61 | 0.98 |
| 378 | R378L | 0.21 | 0.75 | 0.79 | 0.33 | 0.53 |
| 378 | R378M | 0.14 | 0.52 | 0.77 | 0.37 | 0.47 |
| 378 | R378N | 0.12 | 0.19 | 0.48 | 0.38 | 0.81 |
| 378 | R378P | 0.17 | 0.65 | 0.54 | 0.48 | 0.62 |
| 378 | R378Q | 0.20 | 0.82 | 0.94 | 0.56 | 0.59 |
| 378 | R378S | 0.18 | 0.65 | 0.47 | 0.45 | 0.64 |
| 378 | R378T | 0.18 | 0.52 | 1.03 | 0.25 | 0.43 |
| 378 | R378V | 0.36 | 1.01 | 0.98 | 1.06 | 1.19 |
| 378 | R378W | 0.09 | 0.10 | 0.64 | 0.34 | 0.30 |
| 378 | R378Y | 0.24 | 0.60 | 0.62 | 0.23 | 0.53 |
| 380 | S380A | 0.95 | 0.99 | 0.48 | 0.31 | 0.10 |
| 380 | S380C | 0.52 | 1.03 | 0.63 | 0.57 | 0.37 |
| 380 | S380D | 0.61 | 1.12 | 0.45 | 0.12 | 0.16 |
| 380 | S380E | 0.52 | 0.94 | 0.29 | 0.41 | 0.20 |
| 380 | S380F | 0.60 | 1.05 | 0.22 | 0.08 | 0.10 |
| 380 | S380G | 0.68 | 1.05 | 0.20 | 0.17 | 0.21 |
| 380 | S380H | 0.68 | 1.09 | 0.37 | 0.42 | 0.14 |
| 380 | S380I | 0.73 | 1.06 | 0.66 | 0.99 | 0.96 |
| 380 | S380K | 0.80 | 1.08 | 0.42 | 0.94 | 0.94 |
| 380 | S380L | 1.04 | 1.07 | 0.57 | 0.78 | 0.60 |
| 380 | S380M | 1.02 | 1.03 | 0.43 | 0.85 | 0.69 |
| 380 | S380N | 0.81 | 1.09 | 0.58 | 0.95 | 0.89 |
| 380 | S380P | 0.73 | 1.04 | 0.08 | 0.07 | 0.11 |
| 380 | S380Q | 0.69 | 1.02 | 0.44 | 0.45 | 0.17 |
| 380 | S380R | 0.83 | 1.04 | 0.38 | 0.86 | 0.73 |
| 380 | S380T | 0.30 | 0.70 | 0.17 | 0.56 | 0.35 |
| 380 | S380V | 0.98 | 1.02 | 0.79 | 0.99 | 0.96 |
| 380 | S380W | 0.85 | 1.00 | 0.11 | *0.05* | 0.06 |
| 380 | S380Y | 1.01 | 1.01 | 0.25 | 0.14 | 0.10 |
| 381 | A381C | 0.67 | 1.05 | 0.94 | 0.89 | 0.83 |
| 381 | A381D | 0.67 | 1.05 | 0.96 | 0.90 | 0.79 |
| 381 | A381E | 0.52 | 1.08 | 0.84 | 0.85 | 0.75 |
| 381 | A381F | 0.69 | 1.07 | 0.66 | 0.89 | 0.82 |
| 381 | A381G | 0.36 | 0.98 | 0.76 | 0.76 | 0.65 |
| 381 | A381H | 0.14 | 0.15 | *0.05* | 1.39 | 0.95 |
| 381 | A381I | 1.12 | 1.09 | 0.84 | 0.89 | 0.83 |
| 381 | A381K | 0.13 | 0.11 | *0.05* | 0.27 | 1.00 |
| 381 | A381L | 0.52 | 0.95 | 0.62 | 0.78 | 0.62 |
| 381 | A381M | 0.47 | 1.05 | 0.68 | 0.82 | 0.75 |
| 381 | A381N | 0.38 | 0.89 | 0.62 | 0.84 | 0.76 |
| 381 | A381P | 0.54 | 1.00 | 0.72 | 0.94 | 1.02 |
| 381 | A381Q | 0.48 | 1.01 | 0.60 | 0.87 | 0.75 |
| 381 | A381R | 0.39 | 0.95 | 0.59 | 0.80 | 0.75 |
| 381 | A381S | 1.20 | 1.05 | 0.78 | 1.04 | 1.06 |
| 381 | A381T | 0.93 | 0.97 | 0.73 | 0.97 | 1.01 |
| 381 | A381V | 0.54 | 0.97 | 0.59 | 0.90 | 0.81 |
| 381 | A381W | 0.54 | 0.87 | 0.64 | 0.97 | 0.93 |
| 381 | A381Y | 0.61 | 0.92 | 0.60 | 0.92 | 0.87 |
| 382 | N382A | 1.22 | 0.70 | | 2.07 | 0.91 |
| 382 | N382C | 1.11 | 0.57 | | 1.52 | 1.54 |
| 382 | N382D | 0.71 | 0.81 | | 1.17 | 1.15 |
| 382 | N382E | 2.21 | 0.16 | | 6.19 | 5.56 |
| 382 | N382F | 0.91 | 1.23 | | 1.03 | 0.66 |
| 382 | N382G | 0.78 | 0.56 | | 1.73 | 1.31 |
| 382 | N382H | 0.81 | 1.01 | | 1.23 | 1.08 |
| 382 | N382I | 0.48 | 0.80 | | 1.63 | 1.35 |
| 382 | N382K | 1.66 | 0.50 | | 2.10 | 1.85 |
| 382 | N382L | 0.56 | 0.74 | | 1.58 | 1.31 |
| 382 | N382M | 0.50 | 0.66 | | 1.75 | 1.57 |
| 382 | N382Q | 1.08 | 0.65 | | 1.45 | 1.46 |
| 382 | N382T | 0.50 | 1.04 | | 1.31 | 0.99 |
| 382 | N382V | 1.53 | 0.58 | | 1.57 | 1.66 |
| 382 | N382Y | 0.49 | 0.62 | | 1.67 | 1.55 |
| 384 | G384A | 0.58 | 0.72 | 0.68 | 1.26 | 0.79 |
| 384 | G384C | 0.65 | 1.06 | 1.22 | 0.88 | 0.91 |
| 384 | G384D | 1.36 | 1.06 | 1.31 | 0.84 | 0.73 |
| 384 | G384E | 0.52 | 0.92 | 1.05 | 1.33 | 0.96 |
| 384 | G384F | 0.75 | 1.00 | 0.87 | 1.16 | 0.96 |
| 384 | G384H | 0.48 | 0.73 | 0.86 | 1.02 | 1.01 |
| 384 | G384K | 0.50 | 0.60 | | 1.41 | 1.56 |
| 384 | G384L | 0.41 | 0.76 | 1.03 | 0.95 | 0.90 |
| 384 | G384M | 0.61 | 0.70 | 1.01 | 1.19 | 1.24 |
| 384 | G384N | 0.76 | 0.53 | 0.61 | 1.03 | 1.43 |
| 384 | G384Q | 0.57 | 1.15 | 1.19 | 0.92 | 0.85 |
| 384 | G384R | 0.67 | 0.62 | 0.55 | 1.20 | 1.70 |
| 384 | G384S | 0.16 | 0.17 | 0.51 | 0.59 | 1.21 |
| 384 | G384T | 0.87 | 0.06 | | 4.44 | 3.08 |
| 384 | G384V | 0.38 | 0.80 | 0.53 | 0.72 | 0.80 |
| 384 | G384W | 0.69 | 1.12 | 0.71 | 0.97 | 0.95 |
| 384 | G384Y | 0.45 | 0.50 | | 1.83 | 2.73 |
| 386 | S386A | 1.89 | 2.69 | 3.12 | 0.99 | 1.88 |
| 386 | S386C | 2.63 | 2.50 | 3.75 | 1.03 | 2.09 |
| 386 | S386D | 1.57 | 2.52 | 2.56 | 0.92 | 1.79 |
| 386 | S386E | 6.64 | 2.19 | 4.12 | 1.05 | 2.33 |
| 386 | S386F | 2.11 | 3.11 | 2.96 | 1.05 | 2.19 |
| 386 | S386G | 0.45 | 0.51 | 0.43 | 1.78 | 3.74 |
| 386 | S386H | 2.52 | 2.56 | 2.50 | 1.11 | 2.13 |
| 386 | S386I | 2.44 | 2.52 | 2.64 | 1.08 | 2.03 |
| 386 | S386K | 0.93 | 0.36 | 0.30 | 2.91 | 2.66 |
| 386 | S386L | 1.33 | 2.29 | 1.43 | 0.92 | 1.65 |
| 386 | S386M | 0.43 | 0.26 | *0.05* | 1.20 | 7.13 |
| 386 | S386P | 4.61 | 2.34 | 2.31 | 1.10 | 2.27 |
| 386 | S386Q | 0.57 | 2.58 | 0.27 | 0.38 | 0.71 |
| 386 | S386R | 1.16 | 2.27 | 0.76 | 0.91 | 1.58 |
| 386 | S386T | 1.05 | 2.01 | 1.88 | 0.96 | 1.70 |
| 386 | S386V | 3.71 | 2.47 | 3.11 | 1.04 | 2.15 |
| 386 | S386W | 0.88 | 2.31 | 1.52 | 0.97 | 1.32 |
| 394 | V394A | 0.53 | 0.99 | 0.74 | 0.67 | 0.40 |
| 394 | V394C | 0.32 | 0.87 | 0.81 | 0.80 | 0.52 |
| 394 | V394D | 0.11 | 0.18 | 0.31 | 0.98 | 0.85 |
| 394 | V394E | 0.06 | 0.43 | *0.05* | 0.34 | 0.64 |
| 394 | V394F | 0.06 | 0.42 | 0.17 | 0.46 | 0.56 |
| 394 | V394G | 0.27 | 0.76 | 0.56 | 0.48 | 0.28 |
| 394 | V394H | 0.09 | 0.18 | 0.07 | 0.68 | 1.18 |
| 394 | V394I | 0.51 | 1.01 | 0.76 | 0.89 | 0.80 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 394 | V394K | 0.07 | 0.23 | 0.73 | 1.04 | 0.86 |
| 394 | V394L | 0.17 | 0.87 | 0.23 | 0.09 | 0.24 |
| 394 | V394M | 0.71 | 0.94 | 0.31 | 0.11 | 0.11 |
| 394 | V394N | 0.09 | 0.30 | 0.18 | 0.79 | 0.67 |
| 394 | V394P | 0.11 | 0.18 | 0.08 | 0.73 | 1.42 |
| 394 | V394Q | 0.11 | 0.22 | 0.11 | 0.87 | 1.30 |
| 394 | V394R | 0.06 | 0.28 | 0.23 | 0.87 | 1.11 |
| 394 | V394S | 0.12 | 0.58 | 0.19 | 0.21 | 0.37 |
| 394 | V394T | 0.22 | 0.79 | 0.29 | 0.15 | 0.21 |
| 394 | V394W | 0.09 | 0.15 | 0.31 | 0.15 | 1.55 |
| 394 | V394Y | 0.11 | 0.17 | *0.05* | 0.54 | 1.12 |
| 396 | P396A | 0.52 | 0.68 | 1.01 | 0.81 | 0.51 |
| 396 | P396C | 0.29 | 0.24 | 0.73 | 0.76 | 0.73 |
| 396 | P396D | 0.09 | 0.56 | 0.88 | 0.44 | 0.76 |
| 396 | P396E | 0.31 | 0.58 | 0.90 | 0.48 | 0.44 |
| 396 | P396F | 0.29 | 0.48 | 0.48 | 0.29 | 0.30 |
| 396 | P396G | 0.49 | 0.63 | 0.82 | 0.44 | 0.25 |
| 396 | P396H | 0.19 | 0.33 | 0.58 | 0.50 | 0.75 |
| 396 | P396I | 0.34 | 0.57 | 0.52 | 0.11 | 0.35 |
| 396 | P396K | 0.34 | 0.29 | 0.40 | 0.43 | 0.80 |
| 396 | P396L | 0.48 | 0.51 | 0.52 | 0.16 | 0.30 |
| 396 | P396M | 0.40 | 0.66 | 0.52 | 0.12 | 0.31 |
| 396 | P396N | 0.12 | 0.47 | 0.58 | 0.79 | 0.98 |
| 396 | P396Q | 0.06 | *0.05* | 0.32 | 0.65 | 1.26 |
| 396 | P396R | 0.29 | 0.31 | 0.46 | 0.24 | 0.56 |
| 396 | P396S | 0.16 | 0.14 | 0.43 | 0.35 | 1.18 |
| 396 | P396T | 0.48 | 0.60 | 0.50 | 0.22 | 0.26 |
| 396 | P396V | 0.40 | 0.59 | 0.51 | 0.42 | 0.27 |
| 396 | P396W | 0.26 | 0.25 | 0.56 | 0.21 | 0.30 |
| 396 | P396Y | 0.27 | 0.32 | 0.42 | 0.37 | 0.37 |
| 399 | E399A | 0.68 | 0.36 | 0.39 | 0.09 | 0.08 |
| 399 | E399C | 0.31 | 0.11 | 0.26 | 0.24 | 0.19 |
| 399 | E399D | 0.15 | 0.31 | 0.21 | 0.32 | 0.39 |
| 399 | E399F | 1.02 | 0.30 | 0.25 | 0.11 | *0.05* |
| 399 | E399G | 0.75 | 0.32 | 0.20 | 0.13 | *0.05* |
| 399 | E399H | 0.86 | 0.29 | 0.33 | 0.18 | 0.16 |
| 399 | E399I | 0.54 | 0.18 | 0.16 | 0.80 | 0.33 |
| 399 | E399K | 0.43 | 0.21 | 0.21 | 0.35 | 0.22 |
| 399 | E399L | 0.68 | 0.19 | 0.23 | 0.32 | 0.24 |
| 399 | E399M | 0.56 | 0.22 | 0.21 | 0.31 | 0.28 |
| 399 | E399N | 0.50 | 0.33 | 0.33 | 0.20 | 0.19 |
| 399 | E399P | 0.80 | 0.23 | 0.27 | 0.15 | 0.17 |
| 399 | E399Q | 0.69 | 0.68 | 0.40 | 0.30 | 0.09 |
| 399 | E399R | 0.69 | 0.13 | 0.15 | 0.62 | 0.49 |
| 399 | E399S | 0.64 | 0.39 | 0.23 | 0.13 | 0.14 |
| 399 | E399T | 0.12 | 0.31 | *0.05* | 1.16 | 1.26 |
| 399 | E399V | 0.49 | 0.20 | 0.25 | 0.53 | 0.54 |
| 399 | E399W | 1.00 | 0.30 | 0.31 | 0.55 | 0.30 |
| 399 | E399Y | 0.82 | 0.30 | 0.26 | 0.22 | 0.19 |
| 400 | C400A | 1.11 | 0.98 | 0.72 | 0.89 | 0.74 |
| 400 | C400D | 0.42 | 0.76 | 0.48 | 0.48 | 0.48 |
| 400 | C400E | 0.32 | 0.35 | *0.05* | 0.47 | 0.28 |
| 400 | C400F | 0.57 | 0.27 | *0.05* | 0.50 | 0.22 |
| 400 | C400G | 0.75 | 1.01 | 0.47 | 0.32 | 0.11 |
| 400 | C400H | 0.24 | 0.11 | 0.09 | 1.53 | 1.07 |
| 400 | C400I | 0.65 | 0.40 | 0.10 | 0.51 | 0.11 |
| 400 | C400K | 0.63 | 0.36 | 0.08 | 0.32 | 0.33 |
| 400 | C400L | 0.62 | 0.36 | *0.05* | 0.60 | 0.49 |
| 400 | C400M | 0.69 | 0.46 | *0.05* | 0.22 | 0.29 |
| 400 | C400N | 0.11 | *0.05* | 0.09 | 5.30 | 3.48 |
| 400 | C400P | 0.48 | 0.38 | 0.05 | 0.45 | 0.36 |
| 400 | C400Q | 0.45 | 0.21 | 0.05 | 0.87 | 0.61 |
| 400 | C400R | 0.61 | 0.20 | 0.07 | 0.57 | 0.73 |
| 400 | C400S | 0.88 | 0.90 | 1.02 | 1.04 | 1.51 |
| 400 | C400T | 0.93 | 0.75 | 0.14 | 0.20 | 0.21 |
| 400 | C400V | 1.18 | 0.55 | 0.25 | 0.23 | 0.14 |
| 400 | C400W | 0.32 | 0.09 | 0.08 | 0.27 | 0.22 |
| 400 | C400Y | 0.57 | 0.20 | *0.05* | 0.40 | 0.22 |
| 405 | D405A | 1.75 | 0.82 | 0.33 | 0.32 | 0.60 |
| 405 | D405C | 0.45 | 0.63 | 0.57 | 0.72 | 0.97 |
| 405 | D405E | 0.85 | 0.81 | 0.63 | 0.50 | 0.65 |
| 405 | D405F | 0.79 | 0.95 | 0.24 | 0.56 | 0.82 |
| 405 | D405G | 0.77 | 0.87 | 0.16 | 0.56 | 0.86 |
| 405 | D405H | 0.27 | 0.38 | 0.25 | 3.35 | 3.59 |
| 405 | D405I | 0.62 | 1.04 | 0.49 | 0.83 | 1.02 |
| 405 | D405K | 0.63 | 0.65 | 0.24 | 0.43 | 0.72 |
| 405 | D405L | 0.41 | 0.95 | 0.76 | 0.38 | 0.43 |
| 405 | D405M | 0.52 | 1.31 | 0.58 | 0.59 | 0.69 |
| 405 | D405N | 0.74 | 1.04 | 0.78 | 1.34 | 1.32 |
| 405 | D405P | 0.77 | 0.80 | 0.19 | 0.99 | 1.02 |
| 405 | D405Q | 0.71 | 1.12 | 0.39 | 1.10 | 1.21 |
| 405 | D405R | 0.93 | 1.20 | 0.36 | 0.56 | 0.61 |
| 405 | D405S | 0.95 | 1.24 | 0.40 | 0.75 | 0.96 |
| 405 | D405T | 0.74 | 1.17 | 0.32 | 0.64 | 0.83 |
| 405 | D405V | 0.39 | 1.05 | 0.60 | 1.32 | 1.24 |
| 405 | D405W | 1.12 | 1.17 | 0.40 | 0.42 | 0.48 |
| 405 | D405Y | 1.56 | 1.07 | 0.39 | 0.31 | 0.07 |
| 406 | S406A | 1.28 | 1.05 | 1.70 | 1.01 | 0.99 |
| 406 | S406C | 0.57 | 0.86 | 1.05 | 0.66 | 0.71 |
| 406 | S406D | 0.10 | 0.09 | 0.07 | 0.34 | 1.33 |
| 406 | S406E | 1.24 | 1.04 | 0.99 | 0.94 | 0.90 |
| 406 | S406F | 1.01 | 1.04 | 0.72 | 0.56 | 0.38 |
| 406 | S406G | 0.84 | 1.00 | 0.67 | 0.49 | 0.39 |
| 406 | S406H | 0.62 | 0.99 | 0.78 | 0.85 | 0.79 |
| 406 | S406I | 2.11 | 1.06 | 0.70 | 0.83 | 0.63 |
| 406 | S406K | 0.15 | 0.11 | *0.05* | 1.18 | 0.67 |
| 406 | S406L | 0.18 | 0.22 | 0.32 | 0.26 | 0.42 |
| 406 | S406M | 0.89 | 1.01 | 0.78 | 0.85 | 0.75 |
| 406 | S406N | 0.73 | 1.02 | 0.79 | 0.80 | 0.63 |
| 406 | S406P | 1.07 | 1.02 | 1.10 | 1.16 | 1.41 |
| 406 | S406Q | 1.01 | 0.99 | 0.77 | 0.90 | 0.79 |
| 406 | S406R | 1.26 | 0.99 | 0.73 | 1.13 | 1.28 |
| 406 | S406T | 0.83 | 0.98 | 0.77 | 0.80 | 0.72 |
| 406 | S406V | 0.95 | 1.00 | 0.61 | 0.76 | 0.57 |
| 406 | S406W | 0.72 | 0.96 | 1.15 | 1.03 | 1.21 |
| 406 | S406Y | 0.86 | 0.98 | 0.77 | 0.59 | 0.39 |
| 407 | S407A | 0.92 | 1.00 | 1.15 | 0.89 | 0.86 |
| 407 | S407C | 0.55 | 1.03 | 1.19 | 0.80 | 0.87 |
| 407 | S407D | 0.93 | 1.00 | 0.91 | 0.71 | 0.61 |
| 407 | S407E | 0.79 | 1.00 | 1.03 | 0.83 | 0.75 |
| 407 | S407F | 1.19 | 1.05 | 0.57 | 0.61 | 0.39 |
| 407 | S407G | 0.90 | 1.03 | 0.63 | 0.80 | 0.63 |
| 407 | S407H | 1.17 | 1.01 | 0.61 | 1.09 | 1.27 |
| 407 | S407I | 0.23 | 0.13 | 0.21 | 0.57 | 1.16 |
| 407 | S407K | 0.90 | 1.04 | 0.49 | 1.07 | 1.29 |
| 407 | S407L | 1.02 | 1.08 | 0.66 | 0.73 | 0.56 |
| 407 | S407M | 0.11 | 0.13 | 0.09 | 0.37 | 1.24 |
| 407 | S407N | 1.09 | 1.02 | 0.70 | 1.06 | 1.12 |
| 407 | S407P | 0.56 | 0.94 | 0.64 | 0.19 | 0.39 |
| 407 | S407Q | 0.09 | 0.13 | 0.28 | 0.40 | 1.29 |
| 407 | S407R | 1.07 | 1.02 | 0.67 | 1.08 | 1.17 |
| 407 | S407T | 1.26 | 1.06 | 0.98 | 1.11 | 1.21 |
| 407 | S407V | 0.91 | 0.99 | 0.39 | 0.38 | 0.38 |
| 407 | S407W | 0.79 | 0.99 | 0.47 | 0.37 | 0.41 |
| 407 | S407Y | 1.01 | 0.99 | 0.49 | 0.55 | 0.45 |
| 410 | R410A | 0.84 | 0.71 | 0.52 | 0.99 | 1.09 |
| 410 | R410C | 0.43 | 0.74 | 0.99 | 1.09 | 1.15 |
| 410 | R410D | 1.27 | 0.78 | 0.90 | 1.21 | 1.52 |
| 410 | R410E | 0.65 | 0.74 | 0.47 | 1.10 | 1.21 |
| 410 | R410F | 0.54 | 0.65 | 0.43 | 1.04 | 1.23 |
| 410 | R410G | 0.69 | 0.73 | 0.67 | 1.19 | 1.61 |
| 410 | R410H | 0.64 | 0.74 | 0.85 | 1.18 | 1.60 |
| 410 | R410I | 0.49 | 0.53 | 0.38 | 0.77 | 0.82 |
| 410 | R410K | 0.73 | 0.76 | 0.90 | 1.23 | 1.20 |
| 410 | R410L | 0.89 | 0.73 | 0.65 | 0.87 | 0.84 |
| 410 | R410M | 0.53 | 0.71 | 0.70 | 0.90 | 1.03 |
| 410 | R410N | 0.77 | 0.76 | 0.97 | 1.22 | 1.58 |
| 410 | R410P | 0.49 | 0.56 | 0.42 | 0.45 | 0.75 |
| 410 | R410Q | 0.70 | 0.78 | 0.86 | 1.05 | 1.30 |
| 410 | R410S | 0.63 | 1.51 | 1.83 | 1.14 | 1.38 |
| 410 | R410T | 0.68 | 0.61 | 0.57 | 1.00 | 1.29 |
| 410 | R410V | 0.57 | 0.58 | 0.56 | 0.87 | 1.19 |
| 410 | R410W | 0.72 | 0.66 | 0.36 | 0.84 | 0.86 |
| 410 | R410Y | 0.71 | 0.63 | 0.68 | 1.11 | 1.40 |
| 413 | S413A | 0.57 | 1.15 | 1.04 | 1.21 | 1.01 |
| 413 | S413C | 0.58 | 1.03 | 0.72 | 0.98 | 1.05 |
| 413 | S413D | 0.28 | 0.90 | 0.90 | 0.64 | 0.72 |
| 413 | S413E | 0.48 | 0.89 | 0.51 | 0.83 | 1.22 |
| 413 | S413F | 0.96 | 0.80 | 0.61 | 1.71 | 1.87 |
| 413 | S413G | 0.35 | 0.81 | 0.61 | 1.26 | 1.07 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 413 | S413H | 0.71 | 0.81 | 0.45 | 1.10 | 1.02 |
| 413 | S413I | 0.70 | 1.18 | 0.72 | 1.06 | 1.23 |
| 413 | S413K | 0.64 | 0.86 | 0.61 | 0.99 | 0.82 |
| 413 | S413L | 1.00 | 1.05 | 0.72 | 1.10 | 1.46 |
| 413 | S413M | 0.83 | 0.87 | 0.59 | 1.31 | 1.48 |
| 413 | S413N | 0.54 | 1.03 | 0.81 | 0.73 | 0.69 |
| 413 | S413P | 0.27 | 0.76 | 0.62 | 1.71 | 2.11 |
| 413 | S413Q | 0.45 | 1.03 | 0.89 | 0.96 | 1.07 |
| 413 | S413R | 0.58 | 1.07 | 0.56 | 1.12 | 0.90 |
| 413 | S413T | 0.63 | 1.08 | 0.85 | 0.92 | 0.87 |
| 413 | S413V | 1.18 | 0.98 | 0.92 | 0.98 | 1.26 |
| 413 | S413W | 0.40 | 0.96 | 0.78 | 1.61 | 1.47 |
| 413 | S413Y | 0.71 | 0.88 | 0.48 | 1.68 | 1.49 |
| 414 | H414A | 1.38 | 0.98 | 0.99 | 1.04 | 1.08 |
| 414 | H414C | 0.25 | *0.05* | 0.37 | 4.50 | 4.02 |
| 414 | H414D | 0.85 | 0.82 | 0.92 | 1.01 | 0.88 |
| 414 | H414E | 0.50 | 0.91 | 0.43 | 0.05 | 0.11 |
| 414 | H414F | 0.78 | 0.97 | 0.73 | 0.86 | 0.57 |
| 414 | H414G | 0.97 | 0.89 | 0.61 | 0.51 | 0.20 |
| 414 | H414I | 0.57 | 0.94 | 0.56 | 0.34 | 0.20 |
| 414 | H414K | 0.82 | 1.04 | 0.94 | 0.89 | 0.77 |
| 414 | H414L | 0.78 | 0.93 | 0.45 | 0.27 | 0.17 |
| 414 | H414M | 0.46 | 0.97 | 1.09 | 0.95 | 1.06 |
| 414 | H414N | 0.10 | 0.13 | 0.13 | 1.62 | 2.06 |
| 414 | H414P | 0.21 | 0.05 | *0.05* | 3.19 | 0.30 |
| 414 | H414Q | 0.73 | 0.95 | 0.72 | 0.78 | 0.64 |
| 414 | H414R | 0.22 | 0.07 | 0.09 | 1.93 | 2.69 |
| 414 | H414S | 0.67 | 0.92 | 0.93 | 0.83 | 0.84 |
| 414 | H414T | 0.61 | 1.01 | 0.72 | 0.76 | 0.50 |
| 414 | H414V | 0.54 | 0.90 | 0.65 | 0.61 | 0.38 |
| 414 | H414W | 0.28 | 0.48 | 0.47 | 0.58 | 0.24 |
| 414 | H414Y | 1.00 | 0.98 | 0.78 | 0.86 | 0.67 |
| 416 | A416C | 0.49 | 0.73 | 0.49 | 0.58 | 0.23 |
| 416 | A416D | 0.25 | 0.47 | 0.38 | 0.16 | *0.05* |
| 416 | A416E | 0.37 | 0.98 | 0.69 | 0.34 | *0.05* |
| 416 | A416F | 0.38 | 0.97 | 0.28 | *0.05* | 0.10 |
| 416 | A416G | 0.49 | 0.61 | 0.40 | 0.52 | 0.25 |
| 416 | A416H | 0.43 | 0.87 | 0.23 | 0.10 | *0.05* |
| 416 | A416I | 0.59 | 0.98 | 0.68 | 0.67 | 0.29 |
| 416 | A416K | 0.58 | 0.99 | 0.48 | 0.61 | 0.41 |
| 416 | A416L | 0.22 | 0.46 | 0.12 | 0.19 | 0.17 |
| 416 | A416M | 0.32 | 0.92 | 0.49 | 0.42 | 0.19 |
| 416 | A416P | 0.27 | 0.30 | 0.12 | 0.14 | *0.05* |
| 416 | A416Q | 0.37 | 0.98 | 0.50 | 0.56 | 0.33 |
| 416 | A416R | 0.58 | 0.95 | 0.20 | 0.59 | 0.31 |
| 416 | A416S | 0.24 | 0.77 | 0.62 | 0.68 | 0.58 |
| 416 | A416T | 0.58 | 0.98 | 0.68 | 0.76 | 0.59 |
| 416 | A416V | 0.59 | 1.10 | 0.56 | 0.66 | 0.33 |
| 416 | A416W | 0.42 | *0.05* | 0.15 | 0.50 | 1.05 |
| 416 | A416Y | 0.38 | 0.84 | 0.17 | 0.07 | *0.05* |
| 417 | L417A | 0.51 | 0.95 | 0.90 | 0.75 | 0.50 |
| 417 | L417C | 0.36 | 0.81 | 0.57 | 0.35 | *0.05* |
| 417 | L417D | 0.49 | 0.90 | 0.49 | 0.10 | *0.05* |
| 417 | L417E | 0.22 | 0.62 | 0.50 | 0.36 | 0.11 |
| 417 | L417F | 0.45 | 0.96 | 0.74 | 0.67 | 0.49 |
| 417 | L417G | 0.57 | 0.99 | 0.42 | 0.54 | 0.21 |
| 417 | L417H | 0.76 | 1.02 | 0.24 | 0.12 | 0.10 |
| 417 | L417I | 0.48 | 0.89 | 0.30 | 0.20 | *0.05* |
| 417 | L417K | 0.51 | 1.01 | 0.59 | 0.82 | 0.81 |
| 417 | L417M | 0.53 | 1.02 | 0.73 | 0.78 | 0.59 |
| 417 | L417P | 0.23 | 0.62 | 0.28 | 0.07 | 0.07 |
| 417 | L417R | 0.81 | 1.01 | 0.46 | 0.80 | 0.68 |
| 417 | L417S | 0.80 | 1.01 | 0.74 | 0.61 | 0.39 |
| 417 | L417T | 0.66 | 1.01 | 0.51 | 0.41 | 0.12 |
| 417 | L417V | 0.50 | 0.89 | 0.45 | 0.23 | *0.05* |
| 417 | L417W | 0.80 | 0.98 | 0.28 | *0.05* | *0.05* |
| 417 | L417Y | 0.33 | 0.70 | 0.58 | 0.80 | 0.48 |
| 422 | Q422A | 1.39 | 0.93 | 0.75 | 0.66 | 0.68 |
| 422 | Q422C | 0.84 | 0.94 | 0.40 | 1.04 | 0.86 |
| 422 | Q422D | 0.31 | 1.58 | *0.05* | 0.43 | 0.90 |
| 422 | Q422E | 0.95 | *0.05* | *0.05* | 53.56 | 10.85 |
| 422 | Q422G | 0.33 | 1.32 | 0.10 | 0.89 | 1.23 |
| 422 | Q422H | 1.35 | 0.75 | 0.09 | 0.96 | 1.14 |
| 422 | Q422I | 0.93 | 1.12 | 0.60 | 0.47 | 0.87 |
| 422 | Q422K | 0.64 | 1.08 | 0.55 | 1.07 | 1.09 |
| 422 | Q422L | 0.93 | 0.89 | 0.20 | 1.13 | 0.94 |
| 422 | Q422M | 0.41 | 0.83 | 0.43 | 2.12 | 1.83 |
| 422 | Q422N | 1.12 | 0.37 | *0.05* | 2.24 | 2.42 |
| 422 | Q422P | 0.33 | 1.01 | 0.07 | 1.52 | 1.20 |
| 422 | Q422R | 0.64 | 0.93 | 0.35 | 1.34 | 1.04 |
| 422 | Q422S | 0.58 | 1.20 | 0.19 | 0.79 | 0.75 |
| 422 | Q422T | 0.57 | 1.22 | 0.91 | 0.73 | 0.93 |
| 422 | Q422V | 0.51 | 1.27 | 0.94 | 1.17 | 0.97 |
| 422 | Q422W | 0.32 | *0.05* | 0.11 | 6.62 | 0.06 |
| 422 | Q422Y | 0.71 | 0.70 | 0.11 | 1.26 | 1.39 |
| 426 | Q426A | 0.30 | 0.53 | 0.69 | 0.68 | 0.57 |
| 426 | Q426C | 0.83 | 0.83 | 0.81 | 0.78 | 0.78 |
| 426 | Q426D | 0.90 | 0.93 | 1.02 | 0.97 | 0.91 |
| 426 | Q426E | 0.05 | 0.36 | 0.20 | 1.40 | 1.97 |
| 426 | Q426F | 0.47 | 0.76 | 0.56 | 0.58 | 0.31 |
| 426 | Q426G | 0.75 | 0.82 | 0.69 | 0.87 | 0.66 |
| 426 | Q426H | 0.82 | 0.81 | 0.46 | 0.70 | 0.38 |
| 426 | Q426I | 0.59 | 0.72 | 0.75 | 1.01 | 0.89 |
| 426 | Q426K | 0.63 | 0.65 | 0.44 | 1.29 | 1.23 |
| 426 | Q426L | 0.86 | 0.87 | 0.56 | 0.74 | 0.54 |
| 426 | Q426M | 0.52 | 0.71 | 0.67 | 0.96 | 1.00 |
| 426 | Q426N | 0.51 | 0.77 | 0.49 | 1.06 | 0.98 |
| 426 | Q426P | 0.60 | 0.85 | 0.76 | 0.98 | 1.02 |
| 426 | Q426R | 0.51 | 0.87 | 0.43 | 0.79 | 0.79 |
| 426 | Q426S | 0.67 | 0.84 | 0.75 | 0.88 | 0.73 |
| 426 | Q426T | 0.63 | 0.88 | 0.71 | 0.81 | 0.64 |
| 426 | Q426V | 0.51 | 0.91 | 0.44 | 0.53 | 0.40 |
| 426 | Q426W | 0.38 | 0.72 | 0.44 | 0.49 | 0.23 |
| 426 | Q426Y | 0.44 | 0.72 | 0.64 | 0.67 | 0.33 |
| 427 | A427C | 1.03 | 0.36 | 0.31 | 0.88 | 0.54 |
| 427 | A427D | 1.06 | 0.48 | 0.31 | 0.16 | 0.23 |
| 427 | A427F | 0.65 | 0.80 | 0.52 | 1.08 | 0.97 |
| 427 | A427G | 0.84 | 0.78 | 0.44 | 0.37 | 0.29 |
| 427 | A427H | 0.92 | 0.39 | 0.14 | 0.59 | 0.36 |
| 427 | A427I | 0.92 | 0.33 | 0.14 | 0.62 | 0.50 |
| 427 | A427L | 0.62 | 0.20 | 0.16 | 0.76 | 0.40 |
| 427 | A427M | 0.70 | 0.12 | 0.08 | 1.76 | 1.63 |
| 427 | A427N | 1.34 | 0.77 | 0.42 | 0.36 | 0.16 |
| 427 | A427P | 0.79 | 0.59 | 0.35 | 0.60 | 0.51 |
| 427 | A427Q | 0.14 | 0.10 | *0.05* | 10.42 | 3.80 |
| 427 | A427R | 0.96 | 0.16 | 0.23 | 1.03 | 1.68 |
| 427 | A427S | 0.88 | 1.00 | 0.47 | 0.66 | 0.46 |
| 427 | A427T | 0.67 | 0.75 | 0.61 | 0.58 | 0.47 |
| 427 | A427V | 1.14 | 0.59 | 0.46 | 0.83 | 0.61 |
| 427 | A427W | 0.95 | 0.07 | 0.08 | 1.67 | 2.16 |
| 427 | A427Y | 0.11 | 0.43 | *0.05* | 0.40 | 0.97 |
| 429 | A429C | 0.39 | 0.69 | 0.69 | 0.88 | 0.82 |
| 429 | A429D | 0.70 | 0.88 | 1.07 | 1.07 | 0.90 |
| 429 | A429E | 1.11 | 0.90 | 0.90 | 1.10 | 1.11 |
| 429 | A429F | 0.54 | 1.08 | 0.65 | 0.72 | 0.45 |
| 429 | A429G | 0.62 | 0.88 | 0.61 | 0.66 | 0.41 |
| 429 | A429H | 0.41 | 0.76 | 0.26 | 0.19 | 0.41 |
| 429 | A429I | 0.59 | 0.92 | 0.55 | 0.61 | 0.34 |
| 429 | A429K | 0.89 | 1.03 | 0.69 | 0.83 | 0.84 |
| 429 | A429L | 0.46 | 0.91 | 0.74 | 0.92 | 0.67 |
| 429 | A429M | 0.99 | 1.07 | 1.05 | 0.93 | 0.97 |
| 429 | A429N | 0.13 | 0.18 | 0.22 | 0.38 | 1.99 |
| 429 | A429P | 0.46 | 0.48 | 0.24 | 0.17 | 0.48 |
| 429 | A429Q | 0.36 | 1.10 | 0.60 | 0.82 | 0.73 |
| 429 | A429R | 0.75 | 1.04 | 0.54 | 0.87 | 0.75 |
| 429 | A429S | 1.34 | 1.04 | 0.85 | 0.90 | 0.84 |
| 429 | A429T | 0.66 | 1.03 | 0.74 | 0.87 | 0.81 |
| 429 | A429V | 0.20 | 0.32 | 0.42 | 0.53 | 0.53 |
| 429 | A429W | 0.29 | 0.87 | 0.32 | *0.05* | 0.16 |
| 429 | A429Y | 0.66 | 1.04 | 0.74 | 0.76 | 0.61 |
| 431 | F431A | 0.40 | 0.97 | 0.35 | 0.22 | 0.18 |
| 431 | F431C | 0.10 | 3.60 | 0.09 | 1.05 | 1.36 |
| 431 | F431D | 0.52 | 0.94 | 0.41 | 0.13 | 0.14 |
| 431 | F431E | 0.33 | 0.59 | 0.37 | 0.23 | 0.28 |
| 431 | F431G | 0.33 | 0.37 | 0.61 | 0.44 | 0.59 |
| 431 | F431H | 0.71 | 0.91 | 0.43 | 0.17 | 0.21 |
| 431 | F431I | 0.93 | 0.92 | 0.36 | 0.06 | 0.18 |
| 431 | F431K | 0.25 | 0.22 | 0.29 | 0.99 | 1.10 |
| 431 | F431L | 0.61 | 1.04 | 0.32 | 0.09 | 0.13 |
| 431 | F431M | 0.46 | 0.94 | 0.53 | 0.12 | 0.17 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 431 | F431P | 0.16 | 0.20 | 0.36 | 1.11 | 1.82 |
| 431 | F431Q | 0.33 | 1.06 | 0.45 | 0.12 | 0.26 |
| 431 | F431S | 0.30 | 0.97 | 0.28 | 0.19 | 0.27 |
| 431 | F431T | 0.10 | 1.39 | 0.30 | 0.27 | 0.36 |
| 431 | F431V | 0.38 | 1.04 | 0.58 | 0.20 | 0.18 |
| 431 | F431W | 0.36 | 0.92 | 0.15 | 0.10 | 0.22 |
| 431 | F431Y | 0.57 | 0.98 | 0.40 | 0.48 | 0.14 |
| 433 | A433C | 0.42 | 0.96 | 0.69 | 0.55 | 0.33 |
| 433 | A433D | 1.23 | 1.06 | 0.93 | 0.78 | 0.63 |
| 433 | A433E | 0.35 | 1.00 | *0.05* | 0.10 | 0.15 |
| 433 | A433F | 0.57 | 1.01 | 0.13 | 0.10 | 0.09 |
| 433 | A433G | 1.08 | 1.08 | 0.84 | 0.56 | 0.25 |
| 433 | A433H | 0.10 | 0.09 | *0.05* | 1.01 | 4.13 |
| 433 | A433I | 0.40 | 0.98 | 0.49 | 0.27 | 0.10 |
| 433 | A433K | 0.53 | 0.98 | 0.70 | 0.82 | 0.66 |
| 433 | A433L | 0.46 | 1.07 | 0.57 | 0.71 | 0.51 |
| 433 | A433M | 0.70 | 1.00 | 0.72 | 0.71 | 0.54 |
| 433 | A433N | 0.60 | 0.93 | 0.86 | 0.69 | 0.49 |
| 433 | A433P | 0.52 | 1.00 | 0.66 | 0.71 | 0.50 |
| 433 | A433Q | 0.85 | 1.06 | 0.71 | 0.81 | 0.68 |
| 433 | A433R | 1.25 | 1.00 | 0.82 | 0.85 | 0.67 |
| 433 | A433S | 0.81 | 1.03 | 0.70 | 0.72 | 0.54 |
| 433 | A433T | 0.57 | 1.01 | 0.65 | 0.50 | 0.28 |
| 433 | A433V | 0.46 | 0.94 | 0.90 | 0.21 | 0.14 |
| 433 | A433W | 0.28 | 0.55 | 0.28 | 0.16 | 0.20 |
| 433 | A433Y | 0.59 | 0.90 | 0.52 | 0.08 | 0.09 |
| 436 | V436A | 0.87 | 1.02 | 0.91 | 0.41 | 0.17 |
| 436 | V436C | 0.73 | 0.96 | 0.76 | 0.73 | 0.48 |
| 436 | V436D | 0.98 | 0.99 | 0.77 | 0.35 | 0.14 |
| 436 | V436E | 1.11 | 1.04 | 0.75 | 0.76 | 0.58 |
| 436 | V436F | 0.64 | 0.99 | 0.53 | 0.45 | 0.15 |
| 436 | V436G | 0.37 | 0.93 | 0.26 | 0.15 | 0.20 |
| 436 | V436H | 0.55 | 0.99 | 0.45 | 0.10 | 0.09 |
| 436 | V436I | 0.58 | 1.02 | 0.76 | 0.93 | 0.87 |
| 436 | V436K | 0.29 | 0.67 | 0.15 | 0.35 | 0.29 |
| 436 | V436L | 0.66 | 1.02 | 0.77 | 0.80 | 0.68 |
| 436 | V436M | 0.53 | 0.99 | 0.74 | 0.69 | 0.42 |
| 436 | V436N | 0.30 | 0.76 | 0.31 | 0.29 | 0.14 |
| 436 | V436P | 0.28 | 0.18 | *0.05* | 0.59 | 0.99 |
| 436 | V436Q | 0.53 | 0.90 | 0.49 | 0.47 | 0.20 |
| 436 | V436R | 0.87 | 0.98 | 0.47 | 0.28 | 0.10 |
| 436 | V436S | 0.47 | 0.49 | 0.13 | 0.28 | 0.14 |
| 436 | V436T | 0.74 | 1.03 | 0.68 | 0.53 | 0.26 |
| 436 | V436W | 0.59 | 0.94 | 0.56 | 0.11 | 0.13 |
| 436 | V436Y | *0.05* | *0.05* | *0.05* | *0.05* | *0.05* |
| 440 | T440A | 1.17 | 1.02 | 0.84 | 0.99 | 0.92 |
| 440 | T440C | 0.60 | 0.93 | 0.92 | 1.08 | 1.07 |
| 440 | T440D | 0.86 | 0.97 | 0.85 | 0.90 | 0.79 |
| 440 | T440E | 0.77 | 1.01 | 0.85 | 1.04 | 1.12 |
| 440 | T440F | 0.65 | 1.01 | 0.50 | 0.91 | 0.82 |
| 440 | T440G | 0.40 | 0.91 | 0.51 | 0.66 | 0.51 |
| 440 | T440H | 1.01 | 1.06 | 0.52 | 0.85 | 0.80 |
| 440 | T440I | 0.43 | 1.00 | 0.68 | 1.07 | 1.12 |
| 440 | T440K | 0.82 | 1.02 | 0.64 | 1.01 | 1.07 |
| 440 | T440L | 0.56 | 0.75 | 0.48 | 1.06 | 1.08 |
| 440 | T440M | 0.62 | 1.03 | 0.72 | 1.02 | 1.06 |
| 440 | T440N | 0.68 | 0.91 | 0.24 | 0.11 | 0.13 |
| 440 | T440P | 0.25 | 0.26 | 0.10 | 0.72 | 0.77 |
| 440 | T440Q | 1.26 | 1.02 | 0.82 | 1.05 | 1.12 |
| 440 | T440R | 0.40 | 0.73 | 0.15 | 0.86 | 0.89 |
| 440 | T440S | 0.88 | 1.01 | 0.91 | 0.94 | 0.93 |
| 440 | T440V | 0.27 | 0.40 | *0.05* | 0.28 | 0.27 |
| 440 | T440W | 0.78 | 0.89 | 0.47 | 0.95 | 0.90 |
| 440 | T440Y | 1.22 | 1.01 | 0.93 | 0.90 | 0.91 |
| 441 | N441A | 0.16 | 0.07 | 0.71 | 0.26 | 1.16 |
| 441 | N441C | 0.28 | 0.78 | 1.16 | 0.27 | 0.12 |
| 441 | N441D | 0.09 | *0.05* | 0.21 | 1.89 | 3.43 |
| 441 | N441E | 0.48 | 0.89 | 0.96 | 0.44 | 0.10 |
| 441 | N441F | 0.42 | 0.86 | 0.91 | 0.88 | 0.61 |
| 441 | N441G | 0.42 | 0.87 | 0.79 | 0.33 | 0.09 |
| 441 | N441H | 0.11 | 0.06 | 0.15 | 3.38 | 1.88 |
| 441 | N441I | 0.17 | 0.39 | 0.52 | 0.10 | 0.10 |
| 441 | N441K | 0.29 | 0.84 | 0.72 | 0.30 | 0.21 |
| 441 | N441L | 0.46 | 0.89 | 0.92 | 0.83 | 0.67 |
| 441 | N441M | 0.38 | 0.87 | 0.66 | 0.41 | 0.10 |
| 441 | N441P | 0.20 | 0.37 | 0.40 | 0.17 | 0.28 |
| 441 | N441Q | 0.37 | 0.90 | 0.71 | 0.28 | 0.14 |
| 441 | N441R | 0.28 | 0.81 | 0.57 | 0.26 | 0.18 |
| 441 | N441S | 0.39 | 0.89 | 0.88 | 0.52 | 0.31 |
| 441 | N441T | 0.26 | 0.70 | 0.55 | *0.05* | 0.14 |
| 441 | N441V | 0.18 | 0.55 | 0.49 | 0.15 | 0.23 |
| 441 | N441W | 0.31 | 0.79 | 0.72 | 0.70 | 0.36 |
| 441 | N441Y | 0.33 | 0.83 | 0.88 | 0.80 | 0.68 |
| 443 | N443C | 0.34 | 1.74 | 1.69 | 1.22 | 0.94 |
| 443 | N443D | 0.24 | 1.85 | 1.21 | 1.01 | 0.73 |
| 443 | N443E | 0.30 | 1.75 | 0.76 | 1.19 | 0.89 |
| 443 | N443F | 0.79 | 0.68 | 0.42 | 1.14 | 1.02 |
| 443 | N443G | 0.26 | 1.00 | 0.23 | 1.15 | 1.43 |
| 443 | N443I | 0.38 | 1.07 | 0.53 | 1.40 | 1.20 |
| 443 | N443L | 0.83 | 0.37 | 0.40 | 1.88 | 2.31 |
| 443 | N443M | 0.49 | 0.96 | 0.62 | 1.13 | 1.29 |
| 443 | N443P | 0.48 | 0.16 | 0.13 | 1.56 | 4.87 |
| 443 | N443Q | 0.34 | 1.36 | 0.89 | 0.46 | 1.02 |
| 443 | N443R | 0.31 | 1.34 | 0.40 | 0.50 | 0.91 |
| 443 | N443S | 0.51 | 1.21 | 0.77 | 0.93 | 0.76 |
| 443 | N443T | 0.54 | 0.33 | 0.12 | 3.61 | 2.60 |
| 443 | N443V | 0.47 | 1.22 | 0.43 | 1.20 | 0.86 |
| 443 | N443W | 0.97 | *0.05* | 0.10 | 2.57 | 0.94 |
| 443 | N443Y | 0.60 | *0.05* | *0.05* | 0.33 | *0.05* |
| 444 | P444A | 0.85 | 0.40 | 0.34 | 2.29 | 1.44 |
| 444 | P444C | 0.42 | 0.61 | 0.74 | 2.47 | 2.22 |
| 444 | P444D | 2.18 | 0.53 | 0.54 | 0.82 | 1.78 |
| 444 | P444E | 0.93 | 0.53 | 0.29 | 12.61 | 4.67 |
| 444 | P444F | 0.42 | 0.58 | 0.52 | 3.38 | 2.94 |
| 444 | P444G | 0.48 | 0.53 | 0.42 | 2.38 | 1.50 |
| 444 | P444H | 0.27 | 0.63 | 0.25 | 1.19 | 1.66 |
| 444 | P444I | 0.25 | 0.54 | 0.40 | 1.39 | 1.77 |
| 444 | P444K | 0.53 | 0.47 | 0.51 | 1.53 | 1.73 |
| 444 | P444L | 0.20 | 0.58 | 0.45 | 1.57 | 1.57 |
| 444 | P444M | 0.33 | 0.39 | 0.45 | 2.24 | 2.88 |
| 444 | P444N | 0.33 | 0.42 | 0.43 | 1.63 | 1.88 |
| 444 | P444Q | 0.40 | 0.66 | 0.49 | 1.74 | 1.66 |
| 444 | P444R | 0.38 | 0.43 | 0.54 | 1.98 | 1.85 |
| 444 | P444S | 0.98 | 0.49 | 0.33 | 1.47 | 2.17 |
| 444 | P444T | 0.78 | 0.65 | 0.52 | 0.68 | 1.08 |
| 444 | P444V | 0.33 | 0.54 | 0.41 | 1.80 | 1.60 |
| 444 | P444W | 0.75 | 0.49 | 0.31 | 1.85 | 2.13 |
| 444 | P444Y | 0.33 | 0.84 | 0.59 | 0.50 | 0.69 |
| 445 | S445A | 0.27 | 0.68 | 0.52 | 0.85 | 0.73 |
| 445 | S445D | 0.35 | 0.88 | 0.90 | 0.57 | 0.22 |
| 445 | S445E | 0.49 | 0.95 | 0.74 | 0.75 | 0.54 |
| 445 | S445F | 0.40 | 0.54 | 0.33 | 0.24 | 0.17 |
| 445 | S445G | 0.37 | 0.67 | 0.61 | 0.76 | 0.64 |
| 445 | S445H | 0.07 | 0.16 | *0.05* | 0.71 | 1.15 |
| 445 | S445I | 0.41 | 0.61 | 0.34 | 0.34 | 0.20 |
| 445 | S445L | 0.51 | 0.68 | 0.35 | 0.36 | 0.27 |
| 445 | S445N | 0.58 | 1.03 | 0.77 | 0.72 | 0.51 |
| 445 | S445P | 0.65 | 1.00 | 0.67 | 1.01 | 1.09 |
| 445 | S445Q | 0.32 | 0.83 | 0.57 | 0.78 | 0.60 |
| 445 | S445R | 0.75 | 1.01 | 0.85 | 0.86 | 0.83 |
| 445 | S445T | 0.41 | 0.90 | 0.74 | 0.85 | 0.82 |
| 445 | S445V | 0.53 | 0.83 | 0.62 | 0.57 | 0.38 |
| 445 | S445W | 0.32 | 0.55 | 0.14 | 0.17 | 0.26 |
| 445 | S445Y | 0.33 | 0.70 | 0.29 | 0.27 | 0.13 |
| 447 | L447A | 0.46 | 0.92 | 0.97 | 0.67 | 0.39 |
| 447 | L447C | 0.47 | 0.94 | 0.96 | 0.84 | 0.70 |
| 447 | L447D | 0.51 | 0.96 | 1.27 | 0.64 | 0.40 |
| 447 | L447E | 0.45 | 0.92 | 0.98 | 0.77 | 0.57 |
| 447 | L447F | 0.40 | 0.91 | 0.92 | 0.99 | 1.10 |
| 447 | L447G | 0.37 | 0.83 | 0.94 | 0.71 | 0.42 |
| 447 | L447H | 0.11 | 0.09 | 0.14 | 1.66 | 2.62 |
| 447 | L447I | 0.29 | 0.39 | 0.37 | 0.57 | 0.59 |
| 447 | L447K | 0.34 | 0.93 | 0.94 | 0.63 | 0.45 |
| 447 | L447M | 0.76 | 1.02 | 0.99 | 0.93 | 0.97 |
| 447 | L447N | 0.58 | 0.97 | 0.86 | 0.80 | 0.52 |
| 447 | L447P | 0.44 | 0.97 | 0.98 | 0.74 | 0.50 |
| 447 | L447Q | 0.49 | 0.97 | 0.68 | 0.72 | 0.51 |
| 447 | L447R | 0.41 | 0.95 | 1.02 | 0.64 | 0.43 |
| 447 | L447S | 0.50 | 0.95 | 0.59 | 0.70 | 0.42 |
| 447 | L447T | 0.51 | 0.99 | 0.93 | 0.78 | 0.59 |

TABLE 3-1-continued

Performance Index Values for CBH2 Variants

| Position | Variant | HPLC | PASC Sp. Ac. | PCS Sp. Ac. | Res. EtOH | Res. Heat |
|---|---|---|---|---|---|---|
| 447 | L447V | 0.72 | 0.99 | 1.02 | 0.86 | 0.76 |
| 447 | L447W | 0.60 | 0.96 | 0.85 | 0.89 | 0.79 |
| 447 | L447Y | 0.69 | 0.97 | 0.89 | 0.92 | 0.89 |

Non Combinable variants are those for which all Pi values are ≤0.05. For *Hypocrea jecorina* CBH2, of the 2,828 variants, 6 are non-combinable. They are A121Q, L243H, A322Q, L328C, L328Y, V436Y. Any CBH2 which has one of the above substitutions relative to *Hypocrea jecorina* CBH2 can be improved by mutating that amino acid to one of the combinable substitutions at that position, or to the amino acid present in *Hypocrea jecorina* CBH2 at position 121, 243, 322, 328, or 463.

TABLE 3-2

| CBH2 Combinatorial Variant | HPLC | Act. CC | Act. PASC | Act. PCS | EtOH ratio | Heat ratio |
|---|---|---|---|---|---|---|
| CBH2.L111S/L144W/T154C/Y162N | 0.17 | 0.61 | 0.67 | 1.45 | 1.05 | 1.16 |
| CBH2.L111S/L144W/T154V/Y162N/S413Y | 0.39 | 0.39 | 0.73 | 0.97 | 0.97 | 1.05 |
| CBH2.L144W/T154C/S413Y | 0.39 | 0.32 | 0.88 | 1.07 | 1.02 | 1.09 |
| CBH2.L111S/T154V | 0.10 | 0.72 | 0.49 | 0.92 | 1.06 | 1.12 |
| CBH2.T154C | 0.47 | 0.44 | 1.02 | 1.05 | 0.92 | 0.89 |
| CBH2.L144Q/T154V/Y162N/R410S/S413Y | 0.15 | 0.31 | 0.50 | 0.81 | 0.95 | 0.96 |
| CBH2.L111S/T154C/Y162N | 0.13 | 5.44 | 1.11 | 6.50 | 0.91 | 0.82 |
| CBH2.L111S/L144W/Y162N/R410S/S413W | 0.12 | 1.03 | 0.50 | 0.94 | 0.97 | 1.07 |
| CBH2.L111S/L144W/T154C/R410S/S413Y | 0.08 | 0.79 | 0.48 | 0.85 | 0.88 | 0.85 |
| CBH2.L144W/T154C/Y162N/R410S/S413W | 0.12 | 1.52 | 0.43 | 0.23 | 0.95 | 0.55 |
| CBH2.Y162N/R410S/S413Y | 0.57 | 0.55 | 0.77 | 0.89 | 1.09 | 1.42 |
| CBH2.L144W/T154C/R410S/S413Y | 0.52 | 0.72 | 0.85 | 0.97 | 1.05 | 1.32 |
| CBH2.L144Q | 0.61 | 0.41 | 0.75 | 0.98 | 1.10 | 1.39 |
| CBH2.L111S/L144W/R410S/S413Y | 0.66 | 0.46 | 0.70 | 0.67 | 1.11 | 1.43 |
| No Sequence | 0.20 | 0.23 | 0.54 | 1.06 | 1.07 | 1.19 |
| CBH2.L144Q/Y162N/R410S/S413Y | 0.20 | 0.62 | 0.69 | 0.84 | 1.02 | 1.42 |
| CBH2.L144W/T154V/R410S/S413Y | | | | | | |
| CBH2.L144W/T154C/S413W | 0.14 | 1.09 | 0.44 | 0.78 | 1.17 | 1.23 |
| CBH2.R410S/S413Y | 0.12 | 0.92 | 0.68 | 1.10 | 0.89 | 1.06 |
| CBH2.L111S/L144Q/T154V/Y162N/R410S/S413Y | 0.12 | 1.23 | 0.54 | 1.02 | 0.95 | 1.20 |
| CBH2.L111S/T154C/R410S/S413W | 0.39 | 0.64 | 0.54 | 0.64 | 1.15 | 1.13 |
| CBH2.L144W/R410S/S413Y | 0.27 | 0.99 | 0.63 | 0.74 | 1.03 | 1.39 |
| CBH2.L144Q/T154C/Y162N/S413Y | 0.09 | 1.72 | 0.54 | 1.35 | 1.01 | 1.21 |
| CBH2.L144Q/Y162N/R410S/S413W | 0.13 | 1.65 | 0.64 | 1.27 | 1.04 | 1.20 |
| CBH2.L111S/L144W/T154C/Y162N/R410S/S413Y | 0.11 | 1.15 | 0.46 | 0.91 | 1.16 | 1.15 |
| CBH2.L144W/T154V/Y162N | 0.19 | 0.95 | 0.80 | 1.00 | 0.94 | 0.72 |
| CBH2.L111S/T154C/Y162N/R410S/S413Y | 0.23 | 0.50 | 0.56 | 0.79 | 1.03 | 1.31 |
| CBH2.L144Q/T154C/S413W | 0.32 | 0.95 | 0.75 | 0.79 | 1.06 | 1.32 |
| CBH2.L144W/T154V/S413Y | 0.20 | 1.18 | 0.73 | 0.72 | 0.84 | 0.53 |
| CBH2.T154V/Y162N/R410S/S413Y | 0.65 | 0.69 | 0.78 | 0.96 | 1.15 | 1.51 |
| CBH2.L111S | 0.61 | 1.25 | 0.95 | 1.02 | 1.00 | 1.14 |
| CBH2.T154V/R410S/S413W | 0.17 | 1.28 | 0.44 | 0.75 | 1.06 | 1.28 |
| CBH2.L111S/L144W/T154V/R410S/S413W | 0.15 | 3.33 | 0.52 | 0.68 | 0.93 | 1.45 |
| CBH2.T154C/Y162N/S413Y | 0.15 | 1.01 | 0.70 | 1.12 | 1.09 | 1.16 |
| CBH2.L111S/L144W/R410S/S413W | 0.08 | 1.75 | 0.43 | 0.94 | 0.99 | 1.16 |
| CBH2.L144W/T154C/Y162N/S413Y | 0.12 | 2.38 | 0.67 | 1.43 | 0.92 | 0.96 |
| CBH2.L144W/Y162N | 0.16 | 0.80 | 0.83 | 1.13 | 0.93 | 0.72 |
| CBH2.T154C/Y162N/R410S/S413W | 0.25 | 1.88 | 0.59 | 0.96 | 1.10 | 1.43 |
| CBH2.L111S/L144Q/T154C/R410S/S413Y | 0.12 | 0.00 | 0.09 | 0.36 | 0.43 | 0.36 |
| CBH2.L111S/L144W/Y162N/R410S | | | | | | |
| CBH2.L144W/T154C | 0.13 | 2.35 | 0.56 | 0.99 | 0.94 | 1.13 |
| CBH2.L111S/L144W/T154C/S413Y | 0.54 | 0.95 | 0.89 | 0.99 | 1.08 | 1.26 |
| CBH2.L111S/L144W/Y162N/R410S/S413Y | 0.20 | 1.01 | 0.57 | 0.88 | 1.12 | 1.31 |
| CBH2.L111S/R410S/S413W | 0.62 | 0.43 | 0.69 | 0.66 | 1.12 | 1.39 |
| CBH2.L111S/L144Q/T154V/R410S/S413Y | 0.50 | 0.74 | 0.68 | 0.75 | 1.15 | 1.45 |
| CBH2.L111S/L144Q/R410S | 0.61 | 1.00 | 0.76 | 0.83 | 0.99 | 1.03 |
| CBH2.L111S/L144Q/T154C/S413Y | 0.54 | 0.88 | 0.81 | 0.89 | 1.07 | 1.29 |
| CBH2.L111S/L144Q/T154V/R410S | | | | | | |
| CBH2.L111S/L144W/Y162N/S413Y | 0.18 | 3.03 | 0.63 | 1.01 | 1.03 | 1.18 |
| CBH2.L111S/L144Q/T154C/Y162N/R410S | 0.13 | 4.55 | 0.55 | 0.79 | 0.65 | 0.75 |
| CBH2.T154V/R410S/S413Y | 0.51 | 0.88 | 0.71 | 0.82 | 1.10 | 1.38 |
| CBH2.L144W/T154V/Y162N/R410S/S413Y | 0.22 | 2.00 | 0.58 | 0.85 | 1.15 | 1.33 |
| CBH2.L144W/T154V/Y162N/S413Y | 0.02 | 4.80 | 0.12 | 0.13 | 1.26 | 1.41 |
| CBH2.L111S/L144Q/R410S/S413W | 0.45 | 0.42 | 0.66 | 0.85 | 1.12 | 1.30 |
| CBH2.L111S/L144W/T154V/R410S/S413Y | 0.70 | 0.58 | 0.75 | 0.82 | 1.10 | 1.43 |
| CBH2.L111S/L144W/Y162N | 0.13 | 2.62 | 0.64 | 0.58 | 0.92 | 0.80 |
| CBH2.L144Q/T154C/Y162N/R410S/S413Y | | | | | | |
| CBH2.L111S/T154V/S413Y | 0.59 | 0.66 | 0.90 | 1.00 | 1.10 | 1.43 |
| CBH2.L111S/T154V/Y162N/S413W | 0.09 | 5.39 | 0.46 | 0.80 | 0.83 | 1.58 |
| CBH2.L111S/Y162N/S413W | 0.15 | 2.13 | 0.48 | 0.77 | 0.95 | 1.12 |
| CBH2.L111S/L144W/T154C | 0.57 | 1.70 | 0.94 | 0.97 | 0.92 | 1.02 |
| CBH2.L111S/L144Q/Y162N/R410S | 0.17 | 2.48 | 0.54 | 0.93 | 0.96 | 0.95 |
| CBH2.L111S/T154V/Y162N | 0.29 | 1.41 | 0.90 | 0.96 | 0.89 | 0.97 |

TABLE 3-2-continued

| CBH2 Combinatorial Variant | HPLC | Act. CC | Act. PASC | Act. PCS | EtOH ratio | Heat ratio |
|---|---|---|---|---|---|---|
| CBH2.L111S/L144W/S413Y | 0.80 | 0.78 | 0.90 | 0.86 | 1.07 | 1.43 |
| CBH2.T154V/Y162N | | | | | | |
| CBH2.L111S/T154C/S413Y | 0.65 | 0.89 | 0.89 | 1.19 | 1.16 | 1.36 |
| CBH2.L111S/L144W/T154V/S413Y | 0.60 | 0.98 | 0.90 | 0.93 | 1.11 | 1.32 |
| CBH2.L111S/L144W/T154V/R410S | 0.52 | 0.88 | 0.74 | 0.81 | 1.04 | 1.27 |
| CBH2.L111S/L144W/T154C/S413W | 0.42 | 0.81 | 0.76 | 0.78 | 1.10 | 1.39 |
| CBH2.L111S/L144W/T154V/Y162N/R410S | 0.24 | 1.65 | 0.65 | 0.95 | 0.95 | 1.09 |
| CBH2.L111S/L144Q | 0.74 | 1.29 | 0.95 | 0.95 | 0.93 | 0.92 |
| CBH2.L111S/L144Q/T154V/S413Y | 0.54 | 1.49 | 0.90 | 1.01 | 1.06 | 1.24 |
| CBH2.L111S/L144Q/S413Y | 0.77 | 1.20 | 0.92 | 0.89 | 1.01 | 1.17 |
| CBH2.L144Q/R410S/S413Y | 0.32 | 0.44 | 0.83 | 1.29 | 1.10 | 1.26 |
| CBH2.L111F/L144W/T154V/Y162N/S413Y | 0.12 | 0.88 | 0.59 | 1.30 | 0.96 | 1.19 |
| CBH2.L111S/L144Q/T154C/Y162N/S413W | 0.12 | 0.04 | 0.26 | 0.82 | 1.05 | 1.05 |
| CBH2.S313T/S316P/G384Q | 1.01 | | 1.08 | 1.22 | 1.12 | 1.41 |
| CBH2.P98L/S316P/G384Q | 0.48 | | 1.01 | 1.31 | 1.15 | 1.56 |
| CBH2.P98L/S313T/G384Q/N443I | 0.14 | | 0.94 | 1.08 | 0.90 | 0.31 |
| CBH2.K194E/S313T/S316P/G384C | 0.27 | | 0.90 | 0.83 | 1.11 | 1.60 |
| CBH2.P98L/K194E/S313T/S316F/G384Q | 0.12 | | 1.25 | 1.77 | 1.03 | 1.36 |
| CBH2.P98L/K194C/G384Q | | | | | | |
| CBH2.K194E/S316P | 0.23 | | 1.12 | 1.14 | 0.96 | 1.16 |
| CBH2.K194E | 0.41 | | 1.05 | 0.97 | 0.92 | 0.91 |
| CBH2.P98L/K194C/S313T/G384Q/N443I | | | | | | |
| CBH2.K194C/S313T/S316P/G384Q/N443I | 0.08 | | 1.08 | 1.37 | 0.53 | 0.50 |
| CBH2.P98L/G384C | 0.36 | | 1.18 | 0.95 | 0.98 | 1.17 |
| CBH2.K194C | 0.27 | | 1.16 | 1.00 | 0.76 | 0.80 |
| CBH2.K194E/G384C | 0.21 | | 0.79 | 0.78 | 1.05 | 1.10 |
| CBH2.P98L/K194E/S313T/S316P/G384C/N443I | | | | | | |
| CBH2.P98L/S313T/S316P/G384Q | 0.50 | | 1.01 | 1.11 | 1.21 | 1.61 |
| CBH2.P98L/K194E/S316P/G384C/N443I | | | | | | |
| CBH2.P98L/K194E/S316P | 0.27 | | 1.15 | 1.14 | 1.11 | 1.39 |
| CBH2.S316P/G384Q/N443I | 0.16 | | 0.89 | 0.72 | 0.66 | 0.42 |
| CBH2.P98L/K194E/S316P/G384Q | 0.15 | | 1.14 | 1.56 | 1.05 | 1.37 |
| CBH2.P98L/S313T/N443I | 0.19 | | 0.99 | 1.11 | 0.71 | 0.29 |
| CBH2.K194E/G384C/N443I | 0.05 | | 0.63 | 0.91 | 0.10 | 0.73 |
| CBH2.P98L/K194C/G384C/N443I | | | | | | |
| CBH2.K194E/S313T | 0.38 | | 1.12 | 0.99 | 0.87 | 1.04 |
| CBH2.P98L/K194E/G384C | 0.08 | | 1.14 | 1.75 | 0.87 | 1.21 |
| CBH2.K194E/S313T/S316P/G384Q | 0.47 | | 0.98 | 1.37 | 1.14 | 1.55 |
| CBH2.K194C/G384C/N443I | | | | | | |
| CBH2.K194C/S313T/S316P/G384Q/N443I | 0.05 | | 0.78 | 0.78 | 0.07 | 0.32 |
| CBH2.P98L/K194E/S313T/G384Q/N443I | 0.05 | | 0.83 | 1.08 | 0.50 | 0.53 |
| CBH2.K194C/S313T/N443I | 0.09 | | 1.07 | 0.72 | 0.44 | 0.09 |
| CBH2.P98L/K194C/S316P/N443I | 0.07 | | 1.12 | 0.99 | 0.61 | 0.85 |
| CBH2.P98L/K194C/S313T/G384C/N443I | | | | | | |
| CBH2.P98L/S316P/G384C | 0.33 | | 1.10 | 1.20 | 1.05 | 1.35 |
| CBH2.P98L/K194C/S316P/G384Q/N443I | | | | | | |
| CBH2.K194E/S313T/G384Q/N443I | 0.08 | | 0.83 | 1.07 | 0.20 | 0.34 |
| CBH2.K194C/S313T/S316P/N443I | 0.11 | | 1.15 | 0.92 | 0.52 | 0.53 |
| CBH2.P98L/K194E/N443I | 0.08 | | 1.37 | 1.40 | 0.25 | 0.48 |
| CBH2.P98L/G384Q | 0.54 | | 0.99 | 1.14 | 1.12 | 1.36 |
| CBH2.P98L/S313T/S316P/G384Q/N443I | 0.19 | | 0.99 | 1.23 | 1.04 | 1.03 |
| CBH2.S316P/G384C/N443I | 0.07 | | 0.63 | 0.83 | 0.63 | 0.42 |
| CBH2.K194E/N443I | | | | | | |
| CBH2.P98L/K194E/S313T/N443I | 0.08 | | 1.17 | 1.46 | 0.56 | 0.44 |
| CBH2.P98L/K194E/S316P/N443I | 0.11 | | 1.04 | 1.26 | 0.84 | 0.94 |
| CBH2.G384Q/N443I | 0.16 | | 0.99 | 0.80 | 0.42 | 0.27 |
| CBH2.P98L/K194E/S313T/S316P | | | | | | |
| CBH2.K194C/S313T/G384Q/N443I | 0.06 | | 0.87 | 0.91 | 0.18 | 0.36 |
| CBH2.P98L/G384Q/N443I | 0.13 | | 1.15 | 1.18 | 0.41 | 0.37 |
| CBH2.G384C/N443I | 0.06 | | 0.75 | 0.72 | 0.23 | 0.44 |
| CBH2.K194E/S316P/G384Q/N443I | 0.10 | | 0.88 | 1.30 | 0.75 | 0.65 |
| CBH2.K194E/S316P/G384C/N443I | 0.05 | | 0.69 | 0.83 | 0.59 | 0.45 |
| CBH2.P98L/K194C/N443I | 0.07 | | 0.90 | 1.19 | 0.42 | 0.40 |
| CBH2.K194E/S316P/G384Q | 0.33 | | 1.06 | 1.40 | 1.07 | 1.37 |
| CBH2.K194E/S313T/S316P/N443I | 0.16 | | 1.09 | 1.18 | 0.78 | 0.54 |
| CBH2.K194C/S316P/N443I | 0.09 | | 0.99 | 1.11 | 0.60 | 0.40 |
| CBH2.K194E/S313T/N443I | 0.13 | | 1.10 | 1.10 | 0.40 | 0.06 |
| CBH2.K194E/S313T/G384Q | 0.54 | | 1.12 | 1.16 | 0.97 | 1.06 |
| CBH2.K194C/S313T/G384Q | 0.28 | | 0.99 | 0.85 | 0.86 | 1.01 |
| CBH2.P98L/S316P/G384Q/N443I | | | | | | |
| CBH2.P98L/K194C/S313T/G384C | 0.06 | | 1.14 | 1.49 | 0.92 | 1.17 |
| CBH2.S316P | 1.26 | | 0.94 | 1.13 | 1.19 | 1.39 |
| CBH2.P98L/K194C/G384Q/N443I | | | | | | |
| CBH2.P98L/K194E/S313T/S316P/G384Q/N443I | 0.07 | | 0.94 | 1.21 | 1.03 | 1.03 |
| CBH2.K194E/S313T/G384C/N443I | 0.05 | | 0.65 | 1.37 | 0.30 | 0.35 |
| CBH2.K194E/S316P/N443I | 0.17 | | 1.02 | 1.07 | 0.74 | 0.49 |

TABLE 3-2-continued

| CBH2 Combinatorial Variant | HPLC | Act. CC | Act. PASC | Act. PCS | EtOH ratio | Heat ratio |
|---|---|---|---|---|---|---|
| CBH2.P98L/S313T/S316P/G384C | 0.37 | | 1.00 | 1.43 | 1.09 | 1.50 |
| CBH2.S313T/S316P | | | | | | |
| CBH2.P98L/K194E/S313T/S316P/G384Q | 0.11 | | 1.01 | 1.54 | 0.98 | 1.40 |
| CBH2.K194C/G384Q/N443I | 0.06 | | 0.92 | 1.13 | 0.24 | 0.57 |
| CBH2.P98L/K194C/S313T/S316P/G384Q | 0.08 | | 1.29 | 1.45 | 1.01 | 1.52 |
| CBH2.P98L/K194C/S313T/G384Q | 0.10 | | 1.37 | 1.77 | 0.86 | 1.17 |
| CBH2.P98L/K194E/S313T/S316P/N443I | 0.14 | | 1.02 | 1.44 | 1.04 | 1.15 |
| CBH2.G384Q | | | | | | |
| CBH2.P98L | 0.68 | | 1.03 | 1.29 | 1.08 | 1.27 |
| CBH2.P98L/S313T/S316P/N443I | 0.29 | | 1.02 | 1.10 | 0.94 | 0.88 |
| CBH2.K194C/S313T/S316P/G384Q | 0.37 | | 0.99 | 1.15 | 1.08 | 1.40 |
| CBH2.P98L/K194E/S313T/G384Q | 0.22 | | 1.19 | 1.28 | 0.93 | 1.18 |
| CBH2.P98L/K194C/S316P | 0.19 | | 0.98 | 1.09 | 1.04 | 1.42 |
| CBH2.R153Q/N161W/Q422V | 0.05 | 3.70 | 0.66 | 1.20 | 0.39 | 0.66 |
| CBH2.N161W/P233D/Q422V | 0.06 | 0.57 | 0.87 | 0.93 | 0.42 | 0.41 |
| CBH2.R203H/Q422V/P444Q | | | | | | |
| CBH2.R153Q/N161A/R203H/P444Q | | | | | | |
| CBH2.R153Q/R203H/P444Q | | | | | | |
| CBH2.N161W/R203H/P233D/Q422V/P444Q | | | | | | |
| CBH2.R153Q/N161A/P444Q | | | | | | |
| CBH2.N161W/R203H/P233D/P444Q | | | | | | |
| CBH2.N161A/R203H/Q422V/P444Q | | | | | | |
| CBH2.R153Q/N161A/R203H/P233D/Q422V/P444Q | | | | | | |
| CBH2.R153Q/R203H/Q422V | 0.16 | 1.07 | 0.75 | 0.70 | 0.45 | 0.42 |
| CBH2.R153Q/P233D/P444Q | | | | | | |
| CBH2.N161A/R203H/P233D/Q422V/P444Q | | | | | | |
| CBH2.N161W/R203H/P233D/Q422V | | | | | | |
| CBH2.N161W/R203H/P444Q | | | | | | |
| CBH2.N161A/P233D/Q422V/P444Q | | | | | | |
| CBH2.R153Q/R203H/P233D/Q422V/P444Q | | | | | | |
| CBH2.N161A/Q422V/P444Q | | | | | | |
| CBH2.R153Q/N161A/R203H/P233D | | | | | | |
| CBH2.R153Q/N161W/R203H/P233D/Q422V | | | | | | |
| CBH2.N161W/P233D/Q422V/P444Q | | | | | | |
| CBH2.R203H/P444Q | | | | | | |
| CBH2.N161A/Q422V | 0.58 | 0.73 | 1.04 | 0.65 | 0.60 | 0.27 |
| CBH2.R203H/P233D/P444Q | | | | | | |
| CBH2.N161A/R203H/P444Q | | | | | | |
| CBH2.N161A/R203H/P233D/Q422V | 0.18 | 0.51 | 0.73 | 0.57 | 0.24 | 0.26 |
| CBH2.N161W/P233D | 0.21 | 0.69 | 0.86 | 1.02 | 0.87 | 0.72 |
| CBH2.R153Q/N161W/R203H/Q422V/P444Q | | | | | | |
| CBH2.R153Q/N161A/P233D | 0.15 | 0.81 | 0.65 | 0.73 | 0.80 | 0.75 |
| CBH2.R153Q/N161A/R203H/P233D/Q422V | | | | | | |
| CBH2.N161W/R203H/P233D | | | | | | |
| CBH2.P233D/P444Q | | | | | | |
| CBH2.P233D | 0.84 | 0.49 | 1.00 | 0.82 | 1.01 | 1.00 |
| CBH2.R153Q/P233D/Q422V/P444Q | | | | | | |
| CBH2.N161A/P233D/Q422V | 0.28 | 1.19 | 0.87 | 0.48 | 0.37 | 0.23 |
| CBH2.N161A | 0.83 | 1.01 | 1.05 | 1.05 | 1.16 | 1.13 |
| CBH2.N161W/P444Q | | | | | | |
| CBH2.N161W/Q422F/P444Q | | | | | | |
| CBH2.N161A/P233D | 0.45 | 0.97 | 0.96 | 0.90 | 0.95 | 0.89 |
| CBH2.Q422V/P444Q | | | | | | |
| CBH2.R153Q/N161A/R203H/Q422V | | | | | | |
| CBH2.R153Q/N161A/R203H/Q422V/P444Q | | | | | | |
| CBH2.R153Q/N161A/P233D/Q422V | 0.12 | 0.00 | 0.50 | 0.20 | 0.24 | 0.62 |
| CBH2.Q422V | 0.79 | 1.00 | 1.02 | 0.61 | 0.67 | 0.37 |
| CBH2.R153Q/N161A/R203H | 0.15 | 1.28 | 0.59 | 0.48 | 0.79 | 0.81 |
| CBH2.R153Q/R203H/P233D/P444Q | | | | | | |
| CBH2.R153Q/N161W/P233D/Q422V/P444Q | | | | | | |
| CBH2.N161A/R203H/P233D/P444Q | | | | | | |
| CBH2.N161A/R203H/P233D | 0.23 | 0.57 | 0.79 | 0.82 | 0.86 | 0.68 |
| CBH2.R203H/Q422V | | | | | | |
| CBH2.R153Q/N161A/Q422V/P444Q | | | | | | |
| CBH2.R153Q/R203H/P233D | 0.10 | 1.11 | 0.52 | 0.87 | 0.81 | 0.88 |
| CBH2.N161W/P233D/P444Q | | | | | | |
| CBH2.R153Q/R203H/P233D/Q422V | 0.13 | 0.65 | 0.42 | 0.35 | 0.40 | 0.38 |
| CBH2.R203H/P233D/Q422V/P444Q | | | | | | |
| CBH2.R153Q/N161W/R203H | | | | | | |
| CBH2.N161A/P233D/P444Q | | | | | | |
| CBH2.R203H/P233D | 0.46 | 0.94 | 0.91 | 0.78 | 0.98 | 0.79 |
| CBH2.P233D/Q422V/P444Q | | | | | | |
| CBH2.R203H/P233D/Q422V | | | | | | |
| CBH2.R203H | 0.59 | 1.02 | 0.92 | 0.86 | 1.05 | 1.07 |
| CBH2.N161A/P444Q | | | | | | |
| CBH2.R153Q/N161W/R203H/P233D | | | | | | |
| CBH2.N161A/R203H/Q422V | 0.26 | 1.17 | 0.94 | 0.80 | 0.46 | 0.26 |

TABLE 3-2-continued

| CBH2 Combinatorial Variant | HPLC | Act. CC | Act. PASC | Act. PCS | EtOH ratio | Heat ratio |
|---|---|---|---|---|---|---|
| CBH2.P233D/Q422V | 0.56 | 1.36 | 0.91 | 0.58 | 0.22 | 0.19 |
| CBH2.R153Q/N161A/Q422V | | | | | | |
| CBH2.P444Q | | | | | | |
| CBH2.N161W/R203H | 0.22 | 0.53 | 0.74 | 0.90 | 0.90 | 0.76 |
| CBH2.N161W/Q422V | 0.37 | 1.16 | 0.92 | 0.69 | 0.48 | 0.22 |
| CBH2.R153Q/P233D | | | | | | |
| CBH2.N161W/R203H/Q422V/P444Q | | | | | | |
| CBH2.P98L/S413W | 0.22 | 1.15 | 0.56 | 0.74 | 0.16 | 0.23 |
| CBH2.L144W/S313T/S316P | 1.30 | 0.70 | 0.96 | 0.99 | 1.40 | 1.12 |
| CBH2.P98L/L144W/S316P/Q422V | 0.51 | 0.67 | 0.97 | 0.94 | 0.75 | 0.82 |
| CBH2.L111S/L144W/S316P | 1.23 | 0.96 | 0.93 | 1.01 | 1.31 | 1.12 |
| CBH2.P98L/L111S/S313T/S316P | | | | | | |
| CBH2.L111S/S316P/S413W | 0.99 | 1.08 | 0.88 | 0.85 | 1.51 | 1.11 |
| CBH2.L111S/L144W/S313T/S316P/S413W/Q422V | 0.66 | 1.31 | 0.89 | 0.92 | 1.31 | 1.04 |
| CBH2.P98L/L144W/S313T/S316P | 0.66 | 1.53 | 1.06 | 1.32 | 1.30 | 1.12 |
| CBH2.L144W/S313T/Q422V | 0.63 | 1.50 | 0.97 | 0.97 | 0.27 | 0.59 |
| CBH2.L111S/S313T/Q422V | 0.72 | 1.71 | 0.98 | 0.92 | 0.44 | 0.61 |
| CBH2.P98L/L111S/L144W/S313T/S316P/S413W | 0.40 | 1.80 | 1.03 | 1.58 | 1.38 | 1.01 |
| CBH2.S313T/S316P/S413W/Q422V | | | | | | |
| CBH2.P98L/L111S/S316P | 0.08 | 6.48 | 1.20 | 5.02 | 1.39 | 1.09 |
| CBH2.L111S/S313T | | | | | | |
| CBH2.P98L/L111S/S316P/S413W | 0.11 | 2.45 | 0.92 | 3.57 | 1.47 | 1.06 |
| CBH2.L144W/S313T/S413W/Q422V | 0.50 | 0.95 | 0.97 | 1.13 | 0.94 | 0.79 |
| CBH2.L111S/L144W/S316P/Q422V | 0.70 | 1.37 | 0.90 | 0.89 | 0.72 | 0.87 |
| CBH2.L111S/L144W/S413W/Q422V | | | | | | |
| CBH2.Q422V | 0.55 | 1.20 | 1.10 | 0.97 | 0.28 | 0.54 |
| CBH2.P98L/L111S/L144W/S313T/S413W/Q422V | | | | | | |
| CBH2.P98L/L111S/L144W/S413W | 0.21 | 0.42 | 0.55 | 0.40 | 0.26 | 0.25 |
| CBH2.P98L/L111S/S313T | 0.56 | 1.68 | 1.09 | 1.51 | 1.31 | 1.05 |
| CBH2.P98L/L111S/L144W/S413W/Q422V | 0.18 | 2.34 | 1.07 | 1.55 | 0.67 | 0.67 |
| CBH2.L111S/L144W/S313T/S413W/Q422V | 0.33 | 1.64 | 1.08 | 1.22 | 0.80 | 0.74 |
| CBH2.S313T | 1.18 | 0.49 | 0.97 | 0.94 | 1.13 | 1.07 |
| CBH2.L111S/Q422V | | | | | | |
| CBH2.P98L/L111S/L144W/S313T/Q422V | | | | | | |
| CBH2.P98L/L111S/S313T/S413W | 0.42 | 1.17 | 0.89 | 1.21 | 1.52 | 1.07 |
| CBH2.S313T/S413W | | | | | | |
| CBH2.P98L/S313T/S413W | 0.35 | 0.80 | 0.92 | 1.25 | 1.37 | 1.07 |
| CBH2.P98L/L111S/S413W/Q422V | 0.06 | 6.43 | 0.93 | 3.08 | 0.82 | 0.77 |
| CBH2.P98L/L111S/S313T/Q422V | | | | | | |
| CBH2.S316P | 0.92 | 1.17 | 1.02 | 1.15 | 1.34 | 1.12 |
| CBH2.P98L/L144W | 0.54 | 1.54 | 1.07 | 1.19 | 1.11 | 0.94 |
| CBH2.L144W/S413W/Q422V | 0.33 | 1.57 | 0.92 | 0.86 | 0.53 | 0.70 |
| CBH2.L111S/L144W/S313T/S316P/S413W | 0.54 | 1.63 | 1.05 | 1.39 | 1.18 | 1.02 |
| CBH2.L111S | 0.34 | 1.56 | 0.54 | 0.34 | 0.33 | 0.13 |
| CBH2.P98L/L111S | 0.69 | 1.36 | 1.04 | 1.38 | 1.30 | 1.03 |
| CBH2.P98L/L111S/L144W | 0.49 | 1.37 | 1.02 | 1.45 | 1.12 | 1.05 |
| CBH2.P98L/L111S/S313T/S316P/Q422V | 0.54 | 1.38 | 1.03 | 1.22 | 1.07 | 1.00 |
| CBH2.P98L/S316P/S413W | | | | | | |
| CBH2.P98L/S313T/S413W/Q422V | 0.06 | 5.98 | 0.95 | 3.57 | 0.89 | 0.78 |
| CBH2.P98L/L144W/S313T/Q422V | 0.05 | 7.12 | 0.98 | 3.45 | 0.30 | 0.42 |
| CBH2.P98L/S313T/S316P/Q422V | 0.14 | 3.62 | 1.14 | 2.12 | 0.96 | 0.82 |
| CBH2.L111S/L144W/S313T | 0.76 | 0.78 | 0.98 | 1.06 | 1.01 | 0.96 |
| CBH2.L111S/L144W/S316P/S413W/Q422V | 0.81 | 0.82 | 0.79 | 0.77 | 0.93 | 0.85 |
| CBH2.P98L/L111S/L144W/S316P/S413W/Q422V | 0.38 | 1.47 | 0.95 | 1.01 | 0.50 | 0.41 |
| CBH2.L111S/S313T/S316P/Q422V | | | | | | |
| CBH2.P98L/L111S/Q422V | | | | | | |
| CBH2.P98L/L111S/L144W/S313T/S316P/Q422V | 0.07 | 3.16 | 1.06 | 3.78 | 0.75 | 0.75 |
| CBH2.P98L/L111S/L144W/S313T | 0.42 | 1.68 | 0.95 | 1.42 | 1.31 | 1.11 |
| CBH2.L111S/S316P | 0.56 | 2.08 | 0.90 | 1.21 | 1.23 | 1.01 |
| CBH2.P98L/L111S/L144W/S313T/S316P | 0.59 | 1.47 | 0.97 | 1.38 | 1.46 | 1.15 |
| CBH2.L111S/L144W | 0.22 | 0.96 | 0.53 | 0.35 | 0.16 | 0.10 |
| CBH2.L111S/L144W/S413W | 0.77 | 1.22 | 0.82 | 0.86 | 1.36 | 1.12 |
| CBH2.L144W/S313T/S316P/S413W | | | | | | |
| CBH2.P98L/L111S/L144W/S313T/S316P/S413W/Q422V | 0.49 | 0.30 | 0.83 | 0.78 | 1.00 | 0.85 |
| CBH2.P98L/L111S/L144W/S316P/S413W | 0.49 | 1.26 | 0.97 | 1.13 | 1.29 | 0.97 |
| CBH2.L111S/S313T/S413W/Q422V | 0.27 | 2.43 | 1.01 | 1.84 | 0.96 | 0.85 |
| CBH2.P98L/Q422V | 0.56 | 1.65 | 1.06 | 1.05 | 0.59 | 0.79 |
| CBH2.P98L/L144W/S313T/S413W | 0.26 | 1.01 | 0.69 | 0.55 | 0.33 | 0.13 |
| CBH2.L111S/L144W/Q422V | 0.70 | 1.40 | 0.94 | 0.88 | 0.28 | 0.61 |
| CBH2.S313T/Q422V | 0.97 | 0.93 | 1.04 | 0.76 | 0.38 | 0.70 |
| CBH2.P98L/S316P/Q422V | 0.49 | 1.19 | 1.05 | 1.38 | 1.04 | 1.03 |
| CBH2.S313T/S413W/Q422V | 0.16 | 3.56 | 1.05 | 1.87 | 0.77 | 0.67 |
| CBH2.P98L/L111S/L144W/S316P | 0.43 | 1.36 | 0.83 | 0.52 | 0.12 | 0.00 |
| CBH2.P98L/S316P | 0.79 | 1.30 | 1.12 | 1.24 | 1.38 | 1.03 |
| CBH2.P98L/L144W/S413W/Q422V | 0.36 | 1.64 | 0.94 | 0.98 | 0.35 | 0.46 |

TABLE 3-2-continued

| CBH2 Combinatorial Variant | HPLC | Act. CC | Act. PASC | Act. PCS | EtOH ratio | Heat ratio |
|---|---|---|---|---|---|---|
| CBH2.L111S/L144W/S313T/S413W | 0.40 | 1.30 | 0.91 | 0.51 | 0.86 | 0.74 |
| CBH2.P98L/L111S/L144W/Q422V | | | | | | |
| CBH2.P98L/L111S/S316P/Q422V | | | | | | |
| CBH2.P98L/S413W/Q422V | 0.32 | 1.50 | 1.06 | 1.55 | 1.14 | 0.93 |
| CBH2.P98L/S313T/Q422V | 0.27 | 0.65 | 0.88 | 0.23 | 0.08 | 0.08 |
| CBH2.P98L | 0.79 | 1.21 | 1.10 | 1.37 | 1.16 | 1.00 |
| CBH2.L144W/S316P/S413W/Q422V | 0.65 | 1.38 | 0.86 | 0.90 | 1.07 | 0.91 |
| CBH2.L111S/L144W/S313T/S316P | 1.00 | 0.91 | 0.98 | 1.11 | 1.36 | 1.09 |
| CBH2.S413W | 0.45 | 0.48 | 0.32 | 0.17 | 0.69 | 0.31 |
| CBH2.L144W/S316P/S413W | 0.55 | 1.44 | 1.05 | 1.18 | 1.20 | 1.00 |

Example 4

Classification of CBH2 Positions

As described throughout, functionality of cellulase variants was quantified as a performance index (PI), which is the ratio of performance of a variant to a parent or reference cellulase. Various terms set forth below are used to describe the mutation: up mutations have a PI>1; neutral mutations have a PI>0.5, non-deleterious mutations have a PI>0.05; deleterious mutations have a PI=0.05; combinable mutations are those mutations for which the variant has Performance index values=0.5 for at least one property, and >0.05 for all properties. Combinable mutations are mutations that can be combined to deliver proteins with appropriate performance indices for one or more desired properties. Positions at which mutations occur are classed as follows: Non-restrictive positions have ≥20% neutral mutations for at least one property; and Restrictive positions have <20% neutral mutations for activity and stability.

As shown in Table 4-1, for the 162 positions tested in CBH2, all 162 are Non-restrictive. Non-restrictive positions are the positions that are most suitable for use in constructing combinatorial libraries, since they have a large number of combinable mutations.

TABLE 4-1

Non-restrictive Positions of CBH2

| Position | WT AA | # at Position | HPLC PI % >0.50 | PASC Sp. Ac. PI % >0.50 | PCS Sp. Ac. PI % >0.50 | Res. EtOH PI % >0.50 | Res. Heat PI % >0.50 |
|---|---|---|---|---|---|---|---|
| 5 | S | 19 | 47% | 100% | 84% | 100% | 100% |
| 18 | P | 19 | 58% | 84% | 63% | 95% | 95% |
| 19 | T | 17 | 71% | 82% | 76% | 100% | 100% |
| 28 | V | 19 | 74% | 89% | 89% | 100% | 100% |
| 30 | S | 19 | 53% | 89% | 63% | 100% | 100% |
| 32 | D | 19 | 32% | 100% | 89% | 95% | 95% |
| 35 | S | 15 | 67% | 93% | 100% | 100% | 100% |
| 38 | L | 5 | 60% | 80% | 80% | 100% | 100% |
| 63 | R | 19 | 84% | 95% | 95% | 95% | 100% |
| 77 | R | 4 | 25% | 100% | 75% | 100% | 100% |
| 79 | P | 14 | 50% | 100% | 100% | 100% | 100% |
| 80 | P | 14 | 57% | 100% | 100% | 100% | 100% |
| 89 | S | 19 | 58% | 100% | 100% | 100% | 100% |
| 94 | V | 11 | 27% | 91% | 64% | 91% | 100% |
| 98 | P | 19 | 42% | 63% | 47% | 100% | 100% |
| 100 | A | 16 | 6% | 75% | 56% | 81% | 44% |
| 102 | A | 19 | 58% | 84% | 84% | 100% | 95% |
| 103 | Y | 18 | 72% | 89% | 67% | 67% | 67% |
| 104 | Y | 19 | 11% | 58% | 11% | 26% | 21% |
| 105 | A | 7 | 0% | 71% | 71% | 57% | 43% |
| 107 | E | 12 | 58% | 75% | 33% | 17% | 0% |
| 111 | L | 19 | 74% | 95% | 89% | 95% | 68% |

TABLE 4-1-continued

Non-restrictive Positions of CBH2

| Position | WT AA | # at Position | HPLC PI % >0.50 | PASC Sp. Ac. PI % >0.50 | PCS Sp. Ac. PI % >0.50 | Res. EtOH PI % >0.50 | Res. Heat PI % >0.50 |
|---|---|---|---|---|---|---|---|
| 117 | T | 18 | 83% | 94% | 100% | 100% | 94% |
| 119 | A | 19 | 42% | 100% | 79% | 100% | 100% |
| 120 | M | 19 | 32% | 84% | 47% | 84% | 74% |
| 121 | A | 19 | 5% | 63% | 37% | 63% | 53% |
| 125 | A | 19 | 37% | 89% | 26% | 68% | 63% |
| 126 | A | 18 | 61% | 83% | 89% | 89% | 89% |
| 129 | K | 8 | 13% | 100% | 88% | 100% | 75% |
| 133 | F | 12 | 0% | 17% | 0% | 67% | 83% |
| 134 | M | 19 | 79% | 95% | 89% | 100% | 100% |
| 137 | D | 19 | 16% | 37% | 16% | 100% | 100% |
| 138 | T | 19 | 74% | 84% | 74% | 100% | 100% |
| 139 | L | 19 | 42% | 89% | 79% | 100% | 95% |
| 140 | D | 19 | 21% | 89% | 74% | 100% | 100% |
| 141 | K | 16 | 75% | 75% | 0% | 100% | 94% |
| 143 | P | 19 | 63% | 89% | 89% | 100% | 100% |
| 144 | L | 18 | 33% | 94% | 89% | 100% | 100% |
| 147 | Q | 16 | 25% | 94% | 81% | 100% | 100% |
| 150 | A | 19 | 47% | 89% | 79% | 100% | 100% |
| 153 | R | 19 | 0% | 53% | 79% | 95% | 95% |
| 154 | T | 19 | 26% | 89% | 89% | 100% | 95% |
| 157 | K | 16 | 44% | 100% | 94% | 100% | 100% |
| 158 | N | 18 | 33% | 94% | 83% | 89% | 94% |
| 161 | N | 18 | 72% | 100% | 94% | 94% | 94% |
| 162 | Y | 19 | 16% | 84% | 79% | 100% | 100% |
| 177 | A | 19 | 37% | 68% | 42% | 100% | 100% |
| 178 | A | 19 | 58% | 32% | 16% | 100% | 100% |
| 179 | L | 18 | 50% | 83% | 72% | 94% | 100% |
| 180 | A | 19 | 84% | 26% | 5% | 89% | 89% |
| 181 | S | 17 | 82% | 6% | 0% | 94% | 100% |
| 182 | N | 18 | 89% | 89% | 72% | 100% | 100% |
| 185 | Y | 17 | 24% | 35% | 24% | 59% | 65% |
| 186 | S | 19 | 63% | 95% | 79% | 100% | 100% |
| 188 | A | 18 | 56% | 83% | 72% | 100% | 100% |
| 189 | D | 18 | 11% | 89% | 72% | 94% | 100% |
| 190 | G | 18 | 39% | 83% | 61% | 89% | 100% |
| 191 | G | 14 | 0% | 7% | 7% | 71% | 93% |
| 192 | V | 16 | 25% | 75% | 31% | 81% | 94% |
| 193 | A | 18 | 6% | 94% | 89% | 100% | 100% |
| 194 | K | 19 | 47% | 74% | 89% | 89% | 95% |
| 196 | K | 9 | 44% | 100% | 78% | 100% | 100% |
| 197 | N | 17 | 47% | 100% | 88% | 100% | 100% |
| 201 | T | 19 | 5% | 100% | 79% | 100% | 100% |
| 203 | R | 16 | 69% | 94% | 94% | 100% | 100% |
| 204 | Q | 18 | 72% | 94% | 94% | 94% | 94% |
| 206 | V | 15 | 33% | 67% | 40% | 100% | 100% |
| 207 | V | 17 | 82% | 82% | 82% | 100% | 100% |
| 210 | S | 14 | 21% | 100% | 93% | 100% | 100% |
| 214 | T | 18 | 44% | 83% | 61% | 94% | 94% |
| 225 | N | 19 | 0% | 11% | 5% | 100% | 58% |
| 226 | L | 15 | 7% | 33% | 7% | 93% | 100% |
| 228 | T | 15 | 7% | 13% | 33% | 60% | 80% |
| 229 | N | 19 | 26% | 79% | 68% | 100% | 100% |
| 230 | L | 19 | 16% | 89% | 26% | 95% | 74% |
| 231 | G | 18 | 39% | 67% | 50% | 100% | 94% |

TABLE 4-1-continued

Non-restrictive Positions of CBH2

| Position | WT AA | # at Position | HPLC PI % >0.50 | PASC Sp. Ac. PI % >0.50 | PCS Sp Ac. PI % >0.50 | Res. EtOH PI % >0.50 | Res. Heat PI % >0.50 |
|---|---|---|---|---|---|---|---|
| 232 | T | 14 | 21% | 79% | 93% | 93% | 100% |
| 233 | P | 19 | 11% | 100% | 95% | 100% | 100% |
| 234 | K | 13 | 54% | 100% | 31% | 100% | 100% |
| 236 | A | 19 | 11% | 89% | 79% | 95% | 95% |
| 237 | N | 16 | 75% | 100% | 44% | 100% | 100% |
| 239 | Q | 18 | 89% | 100% | 89% | 94% | 100% |
| 240 | S | 19 | 74% | 89% | 63% | 100% | 100% |
| 243 | L | 19 | 53% | 58% | 47% | 95% | 95% |
| 245 | C | 18 | 0% | 22% | 17% | 78% | 100% |
| 247 | N | 18 | 83% | 83% | 39% | 100% | 100% |
| 251 | T | 19 | 26% | 89% | 89% | 100% | 100% |
| 252 | Q | 19 | 47% | 95% | 84% | 100% | 100% |
| 254 | N | 17 | 6% | 29% | 24% | 88% | 100% |
| 258 | V | 19 | 16% | 37% | 42% | 89% | 100% |
| 266 | H | 16 | 0% | 6% | 0% | 88% | 94% |
| 267 | A | 18 | 17% | 33% | 11% | 78% | 67% |
| 268 | G | 19 | 95% | 32% | 21% | 89% | 89% |
| 272 | W | 19 | 89% | 58% | 0% | 63% | 11% |
| 274 | A | 19 | 11% | 89% | 42% | 100% | 84% |
| 275 | N | 16 | 75% | 100% | 75% | 94% | 94% |
| 281 | Q | 11 | 100% | 100% | 36% | 100% | 82% |
| 285 | N | 14 | 21% | 93% | 43% | 100% | 100% |
| 288 | K | 16 | 13% | 75% | 31% | 100% | 100% |
| 289 | N | 18 | 6% | 56% | 50% | 100% | 100% |
| 291 | S | 17 | 88% | 82% | 76% | 100% | 100% |
| 292 | S | 19 | 63% | 100% | 74% | 100% | 100% |
| 293 | P | 19 | 0% | 11% | 32% | 79% | 100% |
| 294 | R | 19 | 79% | 95% | 95% | 100% | 100% |
| 303 | V | 17 | 6% | 18% | 6% | 71% | 76% |
| 304 | A | 19 | 79% | 11% | 5% | 100% | 95% |
| 306 | Y | 17 | 6% | 65% | 6% | 6% | 29% |
| 307 | N | 19 | 0% | 21% | 5% | 32% | 79% |
| 312 | T | 18 | 94% | 94% | 50% | 33% | 17% |
| 313 | S | 17 | 71% | 100% | 82% | 94% | 71% |
| 316 | S | 19 | 84% | 89% | 84% | 100% | 95% |
| 319 | Q | 18 | 89% | 100% | 72% | 94% | 94% |
| 322 | A | 18 | 72% | 94% | 83% | 94% | 94% |
| 323 | V | 17 | 41% | 100% | 35% | 100% | 100% |
| 327 | K | 19 | 32% | 95% | 74% | 95% | 100% |
| 328 | L | 19 | 68% | 89% | 37% | 32% | 26% |
| 331 | H | 19 | 11% | 63% | 58% | 68% | 16% |
| 338 | A | 18 | 67% | 100% | 100% | 100% | 100% |
| 339 | N | 19 | 79% | 95% | 95% | 100% | 100% |
| 340 | H | 19 | 21% | 58% | 68% | 68% | 37% |
| 343 | S | 18 | 89% | 89% | 83% | 100% | 100% |
| 344 | N | 18 | 39% | 100% | 56% | 100% | 100% |
| 346 | F | 19 | 47% | 84% | 79% | 100% | 100% |
| 356 | K | 19 | 79% | 100% | 63% | 21% | 26% |
| 360 | G | 16 | 69% | 75% | 6% | 13% | 13% |
| 361 | Q | 19 | 37% | 74% | 0% | 26% | 32% |
| 362 | Q | 19 | 95% | 95% | 84% | 95% | 95% |
| 363 | Q | 19 | 53% | 95% | 63% | 89% | 100% |
| 364 | W | 18 | 89% | 94% | 6% | 6% | 6% |
| 365 | G | 17 | 47% | 94% | 12% | 100% | 94% |
| 371 | I | 19 | 26% | 63% | 58% | 100% | 79% |
| 378 | R | 19 | 0% | 47% | 63% | 32% | 79% |
| 380 | S | 19 | 95% | 100% | 26% | 47% | 37% |
| 381 | A | 19 | 63% | 89% | 89% | 95% | 100% |
| 382 | N | 15 | 80% | 87% | 0% | 100% | 100% |
| 384 | G | 17 | 65% | 88% | 82% | 100% | 100% |
| 386 | S | 17 | 88% | 88% | 76% | 94% | 100% |
| 394 | V | 19 | 16% | 42% | 26% | 58% | 68% |
| 396 | P | 19 | 5% | 47% | 68% | 26% | 47% |
| 399 | E | 19 | 74% | 5% | 0% | 26% | 11% |
| 400 | C | 19 | 63% | 32% | 11% | 47% | 32% |
| 405 | D | 19 | 79% | 95% | 32% | 74% | 84% |
| 406 | S | 19 | 84% | 84% | 84% | 84% | 79% |
| 407 | S | 19 | 84% | 84% | 63% | 74% | 74% |
| 410 | R | 19 | 84% | 100% | 74% | 95% | 100% |
| 413 | S | 19 | 68% | 100% | 89% | 100% | 100% |
| 414 | H | 19 | 63% | 74% | 63% | 84% | 63% |
| 416 | A | 18 | 28% | 78% | 33% | 50% | 17% |
| 417 | L | 17 | 59% | 100% | 47% | 47% | 18% |
| 422 | Q | 18 | 72% | 83% | 28% | 89% | 94% |
| 426 | Q | 19 | 74% | 95% | 63% | 95% | 74% |
| 427 | A | 17 | 88% | 41% | 12% | 76% | 53% |
| 429 | A | 19 | 58% | 84% | 74% | 79% | 68% |
| 431 | F | 17 | 29% | 82% | 18% | 18% | 24% |
| 433 | A | 19 | 63% | 95% | 74% | 63% | 47% |
| 436 | V | 19 | 68% | 84% | 53% | 37% | 21% |
| 440 | T | 19 | 74% | 89% | 63% | 89% | 89% |
| 441 | N | 19 | 0% | 74% | 79% | 37% | 32% |
| 443 | N | 16 | 38% | 69% | 44% | 88% | 94% |
| 444 | P | 19 | 37% | 63% | 37% | 95% | 100% |
| 445 | S | 16 | 31% | 94% | 63% | 69% | 56% |
| 447 | L | 19 | 37% | 89% | 89% | 100% | 68% |

Example 5

Effect of Charge Change on the Activity of CBH2 Variants

In this example, the effect of charge change on the activity of CBH2 in PCS and PASC assays was assessed. Briefly, the number of PCS and PASC winners in the CBH2 SELs was determined as a property of net charge change. In Tables 5-1 and 5-2, the ratio of observed to expected (o/e) winners was determined in PCS and PASC assays respectively. Values in bold italics are significantly different from the average of 10 random distributions plus or minus the number of standard deviations (sd) listed in the respective columns

TABLE 5-1

Charge Effect on Activity of CBH2 Variants in a PCS Assay

| PCS Charge change | o/e 1 sd | o/e 2 sd | o/e 3 sd | Results |
|---|---|---|---|---|
| −2.00 | *1.20* | 1.20 | 1.20 | >90% confident more than expected |
| −1.00 | *1.40* | *1.40* | *1.40* | >99% confident more than expected |
| 0.00 | 1.03 | 1.03 | 1.03 | as expected |
| 1.00 | *0.46* | *0.46* | *0.46* | >95% confident less than expected |
| 2.00 | 0.00 | 0.00 | 0.00 | as expected |

TABLE 5-2

Charge Effect on Activity of CBH2 Variants in a PASC Assay

| PASC Charge change | o/e 1 sd | o/e 2 sd | o/e 3 sd | Results |
|---|---|---|---|---|
| −2.00 | *0.13* | *0.13* | *0.13* | >99% confident less than expected |
| −1.00 | *0.82* | 0.82 | 0.82 | >90% confident less than expected |
| 0.00 | *1.06* | *1.06* | 1.06 | >95% confident more than expected |
| 1.00 | 1.03 | 1.03 | 1.03 | as expected |
| 2.00 | *0.40* | *0.40* | *0.40* | >95% confident less than expected |

As shown in Table 5-1 and FIG. 2A, decreasing charge (e.g., −1, −2) results in a significantly higher frequency of CBH2 winners in the PCS assay, while increasing charge (e.g., +1) results in a significantly lower frequency of CBH2 winners in the PCS assay. In contrast, as shown in Table 5-2 and FIG. 2B, a significantly higher frequency of CBH2 winners is observed for variants without a charge change (e.g., 0), while a significantly lower frequency of CBH2 winners is observed for charge changes (e.g., −2, −1, +2).

In conclusion, CBH2 activity on PCS correlates with decrease in charge. CBH2 activity on PASC however, shows that this trend does not correlate with cellulose hydrolyzing activity, but is specific for PCS material.

Example 6

Creation of *Trichoderma reesei* Screening Strains

Improved screening strains were created to increase the consistency of CBH2 variant expression in the presence of factors unrelated to the amino acid sequences of the enzyme variants. In particular, *T. reesei* screening strains were developed in combination with a targeting vector to force integration of cbh2 variant genes (e.g., coding region in operable combination with a regulatory sequence). The new strains prepared during development of the present disclosure, combine several mutations that are advantageous for screening variant libraries. A schematic of the genetic engineering steps is shown in FIG. 4.

Deletion of ku80 from the *T. reesei* quad deleted derivative strain. A single orthologue of MUS52, the *N. crassa* orthologue of the human KU80, was identified by TBLASTN search in the genome sequence of *H. jecorina* QM6a (*Trichoderma reesei*) and was consequently named *T. reesei* ku80. protein id 58213; http://genome.jgi-psf.org/Trire2/Trire2.home.html The nucleotide sequence of the *T. reesei* ku80 gene is provided as SEQ ID NO:23:

```
ATGGCGGACAAGGAAGCAACCGTCTTCATCATCGACCTCGGCGCGTCCA

TGGCAGCTGTCAATGGGGGTCGAGAAGAATCCGACCTTGATTGGAGCAT

GAGCTACGTCTGGGACAAGATCAGCAACGTCGTGGCCTCGAATCGCAAG

ACGCTGTGCGTTGGCGTCGTGGGGTTCAGAACCGACGAGACAAACCACA

CGCTGAGCGAGGATGGGTACGAGAACATCTCCATATTGCAGCCCCTGGG

GCCGATGAGCATGTCCAGCCTCAAGGCTCTTCAGCCCAAGGTGAAGCCG

AGCAGGACGGTGGAAGGCGATGCCATCTCGGCGATTGTCATTGCCGTCG

ACATGATTGACAAGTACACGAAGAAGAACAAATGGAAGCGGCAGATTGT

TCTCATTACCGACGGCCAAGGCGAGATTGATCCAGATGATATTGGCGAC

ATTGCTAGAAAGATGCGCGACTCGAATATTGAATTGACAGTCTTGTGAG

TTGGCGAGACCGTTTGGCGGACGGTAATGGTGCTGACGGTGATGCAAGG

GGCGTCGACTTTGATGCTCCCGATTACGGCTTCAAAGAGGAGGACAAAC

CTTCAGTCAAGGTACTCCATATGTTCACTTCTTTTCTTTTTCTTCTTTA

TTTTCTTTTCTTTTGAAGCTTTCATTAACCTCTTCGTTAGAAGCAAAAC

GAAGAGACCCTAAAAAAGCTCGTGGATGGCTGTGGCGACGACTCAAGGT

TCGCCTCCATGGTCGAGGCCATTGACGACTTGAATGAGCCACGAGCAAA

GTCGGTCAAGCCTTACAAAACGTACGAAGGTCTCTTGACCTTGGGAGAT

CCGAAAAACGCTCCCGCAGTGGTGGAAATCCGCGTCGAGAGATACTTCA

AGACCCATCTAGCCAGGCCACCTGCCGCCAGCACCGTGGTGGTCAAGGA
```

```
GGAGCAAGCTGGGCCGTCTCAGGCAGACGAGGACGAACAGATGGACGGA

GCGGAACTTACAGCTGTGAGGCAGGCCAGGACATACAAGGTCAATGATC

CAGATGCCCCTGGCGGTAAGCGTGACGTTGAGTTTGAGTCTCTGGCCAA

AGGGTACGAGTACGGCAGGACGGCAGTCCACATCAGCGAGTCTGATCAA

AACGTCACCAAGCTCGCGACAGAAAAGAGCTTCAAGATCATCGGCTTCG

TCCAGAAAGAAAAGGTATTGGCTTGGCTCTCAGCATTTGACCCGTTGCT

CTTGGCTAACCCTTGTTTAGTATGAAATGCTCCTTAATCTTGGCGAAAC

CTGCGTTACCGTTGCATCCAAGTACGATGAAAAGTCTGAGCTGGCTTTT

AGCTCTCTGGTGTGGGCGCTCTCGGAGCTCGACGCCTACGCCGTGGCCC

GCCTAGTAACTAAGGACCAAAAGGACCCCATGCTGGTGTTACTGATGCC

GTATATGGAGCCTGATTATGTTTGTCTCTATGATGTGCCTCTGCCTTTC

GCAGAGGACATCAGGACGTACCAGTTTCCTCCCTTGGACAGAGTCGTTA

CCGTCAGTGGCCAAACGCTCACCAACCATCGCCTATTGCCATCCGACGA

GCTCAACCAAGCGATGAGCGACTACGTAGATGCCATGGACATTTCAAGT

TATGGTATCGATGAAGATGGGTGAGTATAGAAGATGATTGTTCAAATCT

TTCACTTCTAAGCATTGCTTCTGATCTAGGCAACCGGCTGAATATGCCA

CCATCGATGAGTTATACAACCCTGCGATACATCGCATAGGCCATGCGAT

CAAACAACGAGCGATCCACCCAGAGAAACCCGTGCCCGAGATCCCCCCA

GTCTTGCTTAGATTCGCAGCACCCCCGACAGAACTCGTCGAGACTGTGC

AGCCTCATATCGATGCACTGATTCACGCTGCAGACGTGAAGAAAGGTAC

TGATTCCATTACATATGCTTCTCTGCACACTGATGTTTGATTTGTGCTA

ACGCCCCCCTTAGTGCCGCCCAAGGCCAAGGGCAAGCGCCAAAGAGAAA

CAGTTAAACCCATCTCGGGACTGGATGTGGATGCCCTTCTGGGAGAAGA

GCAGAAAGGTTCCATTAGTCCGGAGAATGCCATTCCGGACTTCAAACGA

GCCCTCAACTCGTCCGAAGAAGTCGAGCAGATTGCCGACGCCACAAAAC

AAATGGGGGCCATTGTGCGGTCTCTCATTACGGACAGCTTCGGGGATAG

CAAATATGCCCAGGCAATGGAAGGCATTGGTGCGATGCGTGAGGAGCTG

ATCAACCTGGAAGAGCCTGGCCTGTACAACGACTTTGTGCGCGACTTGA

AGAAAAGTTTGCTATCTGGAGCCTTGGGTGGTGACAGGCGAGATTTCTG

GTTCAAGATGAGGTGGGCGAAGCTGGGCCTGATTGACAAGAAACAGTCG

GAGGTGTCTTCGGTCACTCTTGAGGAGGCGGACGAGGTGAGTGGTGCAG

CATGCTGTCGGATTATACGGACGTTGTTTGCTAACTTGTGGGATAGTTT

TACAAGTCGAGGTGAGGTATCTACGTTGACCAAGAATGGGACCATGTAT

ATGAGCGGTGTAACAACAGAATCCTGTGCTTTGAGCATTGTATGA
```

The *T. reesei* ku80 gene was deleted from the quad deleted derivative strain using standard methods of the art (WO 2005/001036). Briefly, a ku80 deletion cassette was utilized that employed a selectable marker flanked between 1.3 kb of 5' ku80 sequence and 2.3 kb of 3' ku80 sequence, as schematically shown in FIG. 5. The variant *T. reesei* als, which confers resistance to the herbicide chlorimuron ethyl, was used as selectable marker as described in WO 2008/039370. The nucleotide sequence of the ku80 knockout cassette is 7685 base pairs in length: bases 1-1271 correspond to the 5' ku80 homologous region; bases 1280-7685 correspond to the als-chlorimuron ethyl resistant variant (A190D); and bases 5381-7685 correspond to the 3' ku80 homologous region. The nucleotide sequence of the ku80 knockout cassette is provided as SEQ ID NO:14:

```
ggccgcctcaacacccacactcgaggcacacgagttcatcggcggcaccc
ccacaagctctcggccaacctgctaccggctctctcgcgagacttcccaa
agcctacaaacgaggtcgacgtcaaggaggccctcgagcgccagcccggc
agatggagcctccagggccagatcaaggccaacaacatgagagcccagag
cgccgcactccggctcgacgacaaggagggcaaggcgagagcctttgagg
aggccaagcgcgagctactggcgtatcaccacagcgccctgcggaagcct
tccggcgcaagataatgagcttgatcgcaatgacgagttcacgtacgctt
tgccatattgttgttgcttttttgtttggtcctacatgtacggcgcattgg
ttgggaggatatacccacgagagtgtccgagtggcttctgggatttaga
gcgtcattagcaggatagagatggttggccaggggaatggaattgacttt
tcactacaaggaacttgttcactctggtgttgattcccattgcgtgactg
gtagtagggaggaatgcttttactttgtgccactagaccgcagagaaggg
ttggttgcaagcggggtccgtgtataccgaccaagagtgatgggcataca
gcaacgtttctgaacgacttcattttgtccgagtctactggatgcgagat
gccagcgtgaagccgtacgccaccagggcgacgaactcgacaaggttgac
gagggaggagatgccgtgcagcatgccaaacacttgttgagggcacgcat
ctcatccgactgtgcatccttgtcataccactccttttccgtctcgcttgg
ctggtgggagggacaacaaatccatcgtcagccatccggggtctcaaatc
aatggcgtgcatgcggagtcgggcttgaggctaaccttgtccatggcggt
ccttcatggtcttgacagtggcgggaagcagcacggcgaggttgacgagg
ccgctgacgaacatggttgcgatgggcaccaaggagctccacttgttggg
agcgtcgacgaggccgccgatgccgcccttgatgcccaagagggcgtttc
cggggaacgtgagggcgagcagcgcggggatggccgtctgcatgccaaag
tagatggggaacagcttgctctggatggcggagaaggagggccggctgac
ggtgcggaacatgacgatgccgttgacgaaggactgcagtagcgtagtgt
gatggtaagcagctggccggcgcgcctgagacaatggccggcaatggtaa
aaaggaccaagatgtactaggtagttgcaatgtggcttattacctaccta
ctacctggtaggcacctactaggtacttgggtagacggacaatgaaattt
gaagtcggggttgcaggaaagcagggcgctggacacattgtgcttcaggc
ggtacccgtcgtcatcgtcagccaatgtcgaggcccggcagcccgaggag
cgagacaaccttggccggaggagcccgcaggtacctgccaaagcgcggct
ggtacctctcaaccctctcaggctgttggatgccctatgacatgccctg
ggggatgcagctgttgcccggccccgcactttcgggtgaccgcgaggct
gctgattggctggttgccacgggctgggcggtccctgaagttgttgccat
ctgaactctgtcggcgctggcgtcggctgcgcccaatgggaggcgagaca
actcagggtactagaatcactgacagaagaagagaatcgaaagtaggtag
acagccaattcgttgcatggcaggcaaccgcacaggagaaaaattgacta
ccccacaatcaggcacagtaagtagggcacagtacgtatgtacagacaag
gcgcaagcgatactgcgcgacccggtacctcgccggcttgacacgtgcga
caggctactttactagtattcgcagcggcgggtcgcgcattattacatgt
actgtgccgccatttgatgactgggctgctgcagtattagtagatctgcc
cggcatcgcccttccatgggcgcgacccgggactggaccctctgactcta
cctacatgtacctaggccgggccgggcttggtgacttttgtccgatcagg
tcgttcgcctggctaccattattttctctttcttcttctccatcctgctt
ctggccttgcaattcttcttcgccactcctccctcttcccccgcgatac
ccttgaattcgtcagagaggaaaagacgagaaaaaaagggcagcagaga
cgtcggtctggctcacgtgctgcatctctgcgcactctcattttttttat
tgtccgaccctccctcaaccttctccttcgttgacaggctaagccttgc
ttcgacgctctctctttgaattttctacttctaccttcttttcttgcgt
gttacccaccatagctcgattcacgatgctccgaagtcgccaagtcacag
ccagggcgtccgggctctgggccaggcgcgcgcctttacctcgacgacc
aagcctgtcatgatccagagcagccagaggaaacaggccaacgccagcgc
tgctccgtaagtcgcccattgccattgcatcttctgtttgatatatactt
cctgctgcttgcgtggcgtcgtctctcggttatgcgtgtcaaggaccagg
tgtgttcgcatcgtggttttccagcgccgattaccggggacgaattttt
ggctgctcaactcgcgcgcgcgcattctgattcttcgttttcaatcttga
gcgacaactggctaacataatggccattggcaattgcttcacacagacaa
gtccgccctgtaccgagccctgctttcaacgctgaagacaaagaccgcag
ccatgtgcagcctctggtcaaccgtcgaagcccgacatggatgaatcgt
atgtccacgtccctcgtcccgccctacaaaatgaacacgattacaccag
aatttttgcaacaatcgacacttctataacagaccaattgagctttgttc
tgaccaatcatgttgctctagattcattggcaaaaccggaggcgaaatct
tccacgagatgatgctgcgacagggtgtcaagcacatttgtaggttccga
tgccggccgcccacacgggctccatccttgctccatctctccagctaggc
aaatctcgctaaccttgagtcaccatccagtcggataccctggcggcgct
atcctgcccgtcttcgacgccatctacaactcaaaacacttcgacttcat
cctgccccgtcatgagcagggagctggccatatggccgagggctatgccc
gtgcctcgggcaaaccggtgtcgtcctggtgacttccggcccggtgct
accaatgtcatcacgcccatgcaggatgccctgtcggacggaacgccctt
ggtcgtcttctgcggccaggtccccaccacggccatcggcagcgatgact
tccaagaggccgacgtcgtgggcatctcgcgggcctgcaccaagtggaac
gtcatggtcaagagcgttgctgagctgccgcggagaatcaacgaggcctt
tgagattgccaccagcggccgccctggccccgtcctcgtcgacctgccca
aggatgtcacggctggtatcctgaggagagccatccctacggagactgct
ctgccgtctctgcccagtgccgcctcccgcgccgccatggagctgagctc
caagcagctcaacgcctccatcaagcgtgccgccgacctcatcaacatcg
ccaagaagcccgtcatctacgccggtcagggtgtcatccagtccgagggc
```

```
ggcgttgagctcctgaagcagctggcggacaaggcctccatccccgtcac
caccaccctccatggcctgggtgcctttgatgagctggacgagaagtcgc
tgcacatgctgggcatgcacggctcggcgtatgccaacatggccatgcag
caggccgacctcatcatcgccctcggcagccgattcgacgaccgtgttac
tctgaatgtctccaaatttgcgcctgcagccaggcaagctgctgccgagg
gccgcggcggcatcattcactttgagatcatgcccaagaacatcaacaag
gtcatccaggcgaccgaggccgtcgagggcgacgtcgccaccaacctgaa
gcacctcattccccagattgccgaaaagtccatggcggaccgaggagagt
ggttcggcctcatcaatgagtggaagaagaagtggcccctgtcaaactac
cagcgcgcggagcgggctggcctcatcaagccgcagacggtcatggagga
gattagcaacctgacggccaaccgaaaggacaagacgtacattgccacgg
gtgtcggccagcaccagatgtgggttgcccagcacttccgctggaggcac
cctcgatccatgattacctctggtggtctgggcaccatgggctacggtct
ccccgcggccattggcgccaaggtggcccagcccgacgctctcgtaattg
acgttgatggcgatgcctcgtttaacatgacgctgacggagctgtcgact
gctgcacagttcaacattggcgtcaaggtggttgtgctcaacaacgagga
gcagggcatggtgacgcagtggcagaacctcttttacgaggaccgatatg
cccacacgcaccagaagaaccccgacttcatgaagctggccgacgccatg
ggcgttcagcaccagcgcgtgacggagccggagaagctggtcgatgccct
gacgtggctgatcaacaccgatggcccggccctgttggaggttgtcacgg
acaagaaggtgcctgtcctgcccatggtgcccgccggatcggccctgcac
gagttcctcgtctttgaacctggtgagtctacttcagacatattgcttgc
gcattgcagatactaacactctcacagaaaaggataagcagcgccgtgag
ctgatgaaggagagaacaaagggtgtgcactcctaaagcgatgatgtctg
cgaggggttcttcgttgaaccctagttcaggcaccatcttaccctcttat
ttttcccgtgggctttcattttgtgtcatccgagcatgacgttgtaggg
ttggagtttcttcctttttatcttgtcatttactggtacccataggcgcg
agactaggcttccatgttttgttttgcgactttcaaaaagtacttttagt
ggtttggggcacgacgaggggggcaacctcttctgtcgaaaaaggtggc
tggatggatgagatgagatgagatgagggtgaagatagatacctgcagtg
tttttgacgcgacgggatggcgatcgcagcaccccgacagaactcgtcg
agactgtgcagcctcatatcgatgcactgattcacgctgcagacgtgaag
aaaggtactgattccattacatatgcttctctgcacactgatgtttgatt
tgtgctaacgccccccttagtgccgcccaaggccaagggcaagcgccaaa
gagaaacagttaaacccatctcgggactggatgtggatgcccttctggga
gaagagcagaaaggttccattagtccggagaatgccattccggacttcaa
acgagccctcaactcgtccgaagaagtcgagcagattgccgacgccacaa
aacaaatgggggccattgtgcggtctctcattacggacagcttcggggat
agcaaatatgccaggcaatggaaggcattggtgcgatgcgtgaggagct
gatcaacctggaagagcctggcctgtacaacgactttgtgcgcgacttga
```
```
agaaaagtttgctatctggagccttgggtggtgacaggcgagatttctgg
ttcaagatgaggtgggcgaagctgggcctgattgacaagaaacagtcgga
ggtgtcttcggtcactcttgaggaggcggacgaggtgagtggtgcagcat
gctgtcggattatacgacgttgtttgctaacttgtgggatagttttaca
agtcgaggtgaggtatctacgttgaccaagaatgggaccatgtatatgag
cggtgtaacaacagaatcctgtgctttgagcattgtatgatatgattatt
gatgaaccggacaaaaggggggtaggggattgatgccatcacgaccgattg
accagacctggattctcgcacagcatggctgctgattttgttgaccttgc
gacgtaacatccctgaagaacaacctactattaacctatcatttagcaga
agctctgtaaccttcttgattcttgtattcagcttctgagtctgtcaaat
gtaatcatttcgaggttgtgtaattccggccaagcaggcggccgtctgcc
agcgcctgcctaggctgcaccgcaatctgcccaatcagctgcccttcagt
ttcgtttgaccttgcagctgcccttcatcctttatctgcacacaattatt
ttcctctgctctgcgcattcttctctctctcgtctcccttctcaagctca
acttcacctcatccgctccactacaagccctcccgtcgtcgtctcgcatc
ctcatctcgactgcggccagcaaaacaagcaaagccgtgatcgatcctca
gcatggctaccttcaacctcaccgtccgcctggagatgctcaaagaaatt
ggaatcaccgtccaatacggcgagcatgtagcgaaagaagcagccagcaa
cgaagcagcgatggcattcgaagaagaagaagagttccccgccgttgtgc
cgcccaaggcagaacagcacgcctctgaacacgacgctggccacgatgct
tgggacgcggctgcccacatctcgacttcggcgcaagaacagcagaagcc
ccaggagatggacgactcgtctatcgtgatgccgctggactactccaagt
ttgtcgttggagagcctgcggacgaatccatcagcttttgctcgtggaag
gtcgtcgaggcttatcctgaccagtttatcggcaaggcaaacaggcctcg
tgtatgtagcgattgctttctctgcattatgggaatctcaagagagtatg
gtagaagataactgacaacttgcaggccaagccgtactttgacaagattt
tggaagacagagtctgggatttgtgaggatcttgattgatgtgcatatgg
cgacatgcctgctaatatcattgtagcttctatctctacaaccccgagaa
gcatcagagaagcctcgcgtgctggtgcccactgttcagctcgaaggctt
tctcaaaagcatcaacagagcgctcggtacttctctcaccattccaggag
gggcaaaccaggaccgttttatctgaggttcggccagggagacacccca
aggcctcgatatctacagaggtcgagagaccagaaatccctaaagattga
aacgttccccgattttcaacaggcggactacgacagctttaggaacgcgc
atggcgccatccaggaggactggttgaagaactggcagatgctggtacct
cggccgagtttcgacaagaagaaaatgcagacaaaagagcagccaagag
aaggctcgagcgagagcgaatgcttcacaatacgcaggaatttcttcatt
tggcaggtaagggcaaaggggctgacgtgg.
```

Creation of the Archy2 strain from the *T. reesei* Δku80 quad deleted derivative strain. The pyr2 gene was deleted from the ku80 knockout strain. The pyr2 deletion cassette contains the *T. reesei* cbh1 promoter, a hygromycin resistance gene and a partial amdS selectable marker flanked by 5' and 3' pyr2 sequences, schematically shown in FIG. 6. Use of this vector permits screening for resistance to hygromycin and fluoro-orotic acid of pyr2 knockout transformants. The partial amdS gene contains the 3' portion of the gene, but lacks a promoter and the amino-terminal portion of the coding region, and is consequently non-functional. The nucleotide sequence of the pyr2 knockout cassette is 9259 base pairs in length: bases 1-1994 correspond to the pyr2 3' homologous region; bases 2002-3497 correspond to the *T. reesei* cbh1 promoter; bases 3563-5449 correspond to the hygromycin resistance selectable marker; bases 5450-7440 correspond to the *A. nidulans* amdS 3' partial marker; and bases 7441-9259 correspond to the pyr2 5' homologous region. The nucleotide sequence of the pyr2 knockout cassette is provided as SEQ ID NO:15:

```
atcacgccctcgcataaaagaccctcaagagtccatgtgccctatctgcc
tgatcttcctaacccttatttaacattggccctatcacaacctagttctt
cttcagcctgctttgtcaacacttgtcacggttcaactcaacgtaatcag
caggtagcaggacgaggatagggagagaaacgaagagaagaagaggagag
aggaagaaaaaaaaagaaaagaaagaaaaagggaaaaggaaagaaggag
gaaaagagaagaaagtcagatgaagaagcaagaagacgccatggtagcca
ccgcttgtcagggctccttagcaacgaacaactctagcttggggacttgt
cgatgtgtcgtttccttcctacccatcagcaccaacgatgagttcgatat
agacgaggacctcatggaagtagagaccattgggttcgacaggatctctc
agtttcacttctatgaggtctgtcgctcggatgacttttttgaggagcttc
cccttctgcttcaaccccaaactctattcctgaaaccgcagcacgttggc
acggccgtgttgctggagcagtttgctttcgagcactctcagcgtggttt
cagcagcccactggtgagtggcctcctttgacgtccacaccttgctcctg
tcgcatgcgtatctggtgggaacgactgctccaaggaggattgctaacga
ggttgtaggccgaatatcgcatcagattctccggtaaccttagctacggc
ctcttcaacatctgtgacatgacggagcgcaagtactggtggttggcgac
caagatgcgcggctggaacatcgacggctgccccgaagacgtcaggagac
tcatgtttgttcacatcatcgccaccctgggatgcagcccgtcgtgacg
gatgaagacatggactaccccaagaactgggcggcaattctccacggtag
agacagatatccgagtgaacctgtgggccaccggcctcatgggcgcacca
tctgcctccactcggtggccgtctgccctcgtctccagggcttgggtctc
ggtactgcgactctgaagtcgtatgtgcagcgcatgaacagcctcggcgc
cgcggaccgtgttgctctcgtttgccgcaagcccgagacgagatttttg
aaagatgcggcttcaggaacagcggccggagtagtatcaagactctggtc
ggcgaatactacaacatggtgtgtgatccacatcgacttggccagactct
atacgattttcaaacctcgctatacgtcatattgacttgtttctttaggt
atcgatttgccggcccaaagactttatcgactggaatagcattgccga
cgctgccaagaagatgtgaaccatttgactgatacgatgtgtgctacgca
tgtcgaccttctttgtttgtttctttggcggctcttttgtataccttggga
cacggcagacgcatgtctatgtgaagaaaacgttcacggcgctgtttgca
tcaggaatatgatcattaaacatggagcgtaatggtattaatgatcaact
agaaaaatggtatgtgaagggcgagagggcgatcaacaaagcagcccgggg
```

-continued
```
catagtctggaagcagcaggaattggaagggaaaaggaagctgcacaatg
aagggatatcgtgagcggagtggctcacgagagtatcaacagactggcga
aagcaagcaattgccaacgccggctattaggccataagatggcctgttgt
gagtcccagttgcacgtatccccatatgactgctctgtcgctgacttgaa
aaaaaatagggaggataaaggagaaagaaagtgagacaacccgtgaggga
cttgggggtagtaggagaacacatgggcaaccgggcaatacacgcgatgtg
agacgagttcaacggcgaatggaaaatcttgaaaaacaaaataaaataac
tgccctccatacgggtatcaaattcaagcagttgtacggaggctagctag
agttgtgaagtcggtaatcccgctgtatagtaatacgagtcgcatctaaa
tactccgaagctgctgcgaacccggagaatcgagatgtgctggaaagctt
ctagcgagcggctaaattagcatgaaaggctatgagaaattctggagacg
gcttgagaatcatggcgttccattcttcgacaagcaaagcgttccgtcgc
agtagcaggcactcattcccgaaaaaactcggagattcctaagtagcgat
ggaaccggaataatataataggcaatacattgagttgcctcgacggttgc
aatgcaggggtactgagcttggacataactgttccgtaccccacctcttc
tcaacctttggcgtttccctgattcagcgtacccgtacaagtcgtaatca
ctattaacccagactgaccggacgtgttttgcccttcatttggagaaata
atgtcattgcgatgtgtaatttgcctgcttgaccgactggggctgttcga
agcccgaatgtaggattgttatccgaactctgctcgtagaggcatgagtg
aatctgtgtcgggcaggacacgcctcgaaggttcacggcaagggaaacca
ccgatagcagtgtctagtagcaacctgtaaagccgcaatgcagcatcact
ggaaaatacaaaccaatggctaaaagtacataagttaatgcctaaagaag
tcatataccagcggctaataattgtacaatcaagtggctaaacgtaccgt
aatttgccaacggcttgtggggttgcagaagcaacggcaaagcccactt
ccccacgtttgtttcttcactcagtccaatctcagctggtgatcccccaa
ttgggtcgcttgtttgttccggtgaagtgaaagaagacagaggtaagaat
gtctgactcggagcgttttgcatacaaccaagggcagtgatggaagacag
tgaaatgttgacattcaaggagtatttagccagggatgcttgagtgtatc
gtgtaaggaggtttgtctgccgatacgacgaatactgtatagtcacttct
gatgaagtggtccatattgaaatgtaaagtcggcactgaacaggcaaaag
attgagttgaaactgcctaagatctcgggccctcgggccttcggccttttg
ggtgtacatgtttgtgctccgggcaaatgcaaagtgtggtaggatcgaac
acactgctgcctttaccaagcagctgagggtatgtgataggcaaatgttc
aggggccactgcatggtttcgaatagaaagagaagcttagccaagaacaa
tagccgataaagatagcctcattaaacggaatgagctagtaggcaaagtc
agcgaatgtgtatatataaaggttcgaggtccgtgcctccctcatgctct
ccccatctactcatcaactcagatcctccaggagacttgtacaccatctt
ttgaggcacagaaacccaatagtcaaccgcggactgcgcatcatgtatcg
gaagttggccgtcatctcggccttcttggccacacctcgtgctagactag
gcgcgccaggaagcccggaaggtaagtggattcttcgccgtggctggagc
```

-continued

```
aaccggtggattccagcgtctccgacttggactgagcaattcagcgtcac
ggattcacgatagacagctcagaccgctccacggctggcggcattattgg
ttaacccggaaactcagtctccttggccccgtcccgaagggacccgactt
accaggctgggaaagccagggatagaatacactgtacgggcttcgtacgg
gaggttcggcgtagggttgttcccaagttttacacaccccccaagacagc
tagcgcacgaaagacgcggagggtttggtgaaaaaagggcgaaaattaag
cgggagacgtatttaggtgctagggccggtttcctccccattttttcttcg
gttccctttctctcctggaagactttctctctctctcttcttctcttctt
ccatcctcagtccatcttcctttcccatcatccatctcctcacctccatc
tcaactccatcacatcacaatcgtatgaaaaagcctgaactcaccgcga
cgtctgtcgagaagtttctgatcgaaaagttcgttcagcgtctccgacct
gatgcagctctcggagggcgaagaatctcgtgctttcagcttcgatgtag
gagggcgtggatatgtcctgcgggtaaatagctgcgccgatggtttctac
aaagatcgttatgtttatcggcactttgcatcggccgcgctcccgattcc
ggaagtgcttgacattggggaattcagcgagagcctgacctattgcatct
cccgccgtcacagggtgtcacgttgcaagacctgcctgaaaccgaactg
cccgctgttctgcagccggtcgcggaggccatggatgcgatcgctgcggc
cgatcttagccagacgagcgggttcggcccattcggaccgcaaggaatcg
gtcaatacactacatggcgtgatttcatatgcgcgattgctgatccccat
gtgtatcactggcaaactgtgatggacgacaccgtcagtgcgtccgtcgc
gcaggctctcgatgagctgatgctttgggccgaggactgccccgaagtcc
ggcacctcgtgcacgcggatttcggctccaacaatgtcctgacggacaat
ggccgcataacagcggtcattgactggagcgaggcgatgttcggggattc
ccaatacgaggtcgccaacatcttcttctggaggccgtggttggcttgta
tggagcagcagacgcgctacttcgagcggaggcatccggagcttgcagga
tcgccgcggctccgggcgtatatgctccgcattggtcttgaccaactcta
tcagagcttggttgacggcaatttcgatgatgcagctttgggcgcagggtc
gatgcgacgcaatcgtccgatccggagccgggactgtcgggcgtacacaa
atcgcccgcagaagcgcggccgtctgtgaccgatggctgtgtagaagtact
cgccgatagtggaaaccgacgccccagcactcgtccgagggcaaaggaat
agagtagatgccgaccgggatccacttaacgttactgaaatcatcaaaca
gcttgacgaatctggatataagatcgttggtgtcgatgtcagctccggag
ttgagacaaatggtgttcaggatctcgataagatacgttcatttgtccaa
gcagcaaagagtgccttctagtgatttaatagctccatgtcaacaagaat
aaaacgcgtttcgggtttacctcttccagatacagctcatctgcaatgca
ttaatgcattggacctcgcaacccctagtacgcccttcaggctccggcgaa
gcagaagaatagcttagcagagtctattttcattttcgggagactagcat
tctgtaaacgggcagcaatcgcccagcagttagtagggtcccctctacct
ctcagggagatgtaacaacgccaccttatgggactatcaagctgacgctg
gcttctgtcagacaaactgcgcccacgagttcttccctgacgccgctctc
```

```
gcgcaggcaagggaactcgatgaatactacgcaaagcacaagagacccgt
tggtccactccatggcctcccatctctctcaaagaccagcttcgagtca
aggtacaccgttgcccctaagtcgttagatgtcccttttttgtcagctaac
atatgccaccagggctacgaaacatcaatgggctacatctcatggctaaa
caagtacgacgaagggggactcggttctgacaaccatgctccgcaaagccg
gtgccgtcttctacgtcaagacctctgtcccgcagaccctgatggtctgc
gagacagtcaacaacatcatcgggcgcaccgtcaacccacgcaacaagaa
ctggtcgtgcggcggcagttctggtggtgagggtgcgatcgttgggattc
gtggtggcgtcatcggtgtaggaacggatatcggtggctcgattcgagtg
ccggccgcgttcaacttcctgtacggtctaaggccgagtcatgggcggct
gccgtatgcaaagatggcgaacagcatggagggtcaggagacggtgcaca
gcgttgtcgggccgattacgcactctgttgagggtgagtccttcgcctct
tccttcttttcctgctctataccaggcctccactgtcctcctttcttgct
ttttatactatatacgagaccggcagtcactgatgaagtatgttagacct
ccgcctcttcaccaaatccgtcctcggtcaggagccatggaaatacgact
ccaaggtcatcccatgccctggcgccagtccgagtcggacattattgcc
tccaagatcaagaacggcgggctcaatatcggctactacaacttcgacgg
caatgtccttccacaccctcctatcctgcgcggcgtggaaaccaccgtcg
ccgcactcgccaaagccggtcacaccgtgaccccgtggacgccatacaag
cacgatttcggccacgatctcatctcccatatctacgcggctgacggcag
cgccgacgtaatgcgcgatatcagtgcatccggcgagccggcgattccaa
atatcaaagacctactgaacccgaacatcaaagctgttaacatgaacgag
ctctgggacacgcatctccagaagtggaattaccagatggagtaccttga
gaaatggcgggaggctgaagaaaaggccgggaaggaactggacgccatca
tcgcgccgattacgcctaccgctgcggtacggcatgaccagttccggtac
tatgggtatgcctctgtgatcaacctgctggatttcacgagcgtggttgt
tccggttacctttgcggataagaacatcgataagaagaatgagagtttca
aggcggttagtgagcttgatgccctcgtgcaggaagagtatgatccggag
gcgtaccatggggcaccggttgcagtgcaggttatcggacggagactcag
tgaagagaggacgttggcgattgcagaggaagtggggaagttgctgggaa
atgtggtgactccatagctaataagtgtcagatagcaatttgcacaagaa
atcaataccagcaactgtaaataagcgctgaagtgaccatgccatgctac
gaaagagcagaaaaaacctgccgtagaaccgaagagatatgacacgcttt
ccatctctcaaaggaagaatcccttcagggttgcgtttccagtagtgatt
ttaccgctgatgaaatgactggactccctcctcctgctcttatacgaaaa
attgcctgactctgcaaaggttgtttgtcttggaagatgatgtgcccccc
catcgctcttatctcataccccgccatctttctagattctcatcttcaac
aagaggggcaatccatgatctgcgatccagatgtgcttctggcctcatac
tctgccttcaggttgatgttcacttaattggtgacgaattcagctgattt
gctgcagtatgctttgtgttggttctttccaggcttgtgccagccatgag
```

```
cgctttgagagcatgttgtcacttataaactcgagtaacggccacatatt
gttcactacttgaatcacatacctaattttgatagaattgacatgtttaa
agagctgaggtagctttaatgcctctgaagtattgtgacacagcttctca
cagagtgagaatgaaaagttggactcccctaatgaagtaaaagtttcgt
ctctgaacggtgaagagcatagatccggcatcaactacctggctagacta
cgacgtcaattctgcggccttttgacctttatatatgtccattaatgcaa
tagattcttttttttttttttttttttttttttttttttttttttttgc
ccaatttcgcagatcaaagtggacgttatagcatcataactaagctcagt
tgctgagggaagccgtctactaccttagcccatccatccagctccatacc
ttgatactttagacgtgaagcaattcacactgtacgtctcgcagctctcc
ttcccgctcttgatcccactggggtccatggtgcgtgtatcgtccctc
cacaattctatgccatggtacctccagcttatcaatgcccgctaacaag
tcgcctctttgccttgatagcttatcgataaaacttttttttccgccagaa
aggctccgcccacagacaagaaaaaaaattcaccgcctagcctttggccc
cggcatttggctaaacctcgagcctctctcccgtcttggggtatcaggaa
gaaaagaaaaaaatccatcgccaagggctgttttggcatcaccacccgaa
aacagcacttcctcgatcaaaagttgcccgccatgaagaccacgtggaag
gacatccctccggtgcctacgcaccaggagtttctggacattgtgctgag
caggacccagcgcaaactgccactcagatccgtgccggcttcaagatta
gcagaattcgaggtacgtcgcattgcccatcgcaggatgtctcattatcg
gggtccttggagaacgatcatgattgcatggcgatgctaacacatagaca
gccttctacactcgaaaggtcaagttcacccaggagacgttttccgaaaa
gttcgcctccatcctcgacagcttccctcgcctccaggacatccacccct
tccacaaggaccttctcaacaccctctacgatgccgaccacttcaagatt
gcccttggccagatgtccactgccaagcacctggtcgagaccatctcgcg
cgactacgtccgtctcttgaaatacgcccagtcgctctaccagtgcaagc
agctcaagcgggccgctctcggtcgcatggccacgctggtcaagcgcctc
aaggaccccctgctgtacctggaccaggtccgccagcatctcggccgtct
tccctccatcgaccccaacaccaggaccctgctcatctgcggttaccca
atgttggcaagtccagcttcctgcgaagtatcacccgcgccgatgtggac
gtccagccctatgctttcaccaccaagagtctgtttgtcggccactttga
ctacaagtacctgcgattccaggccattgataccccggtattctggacc
accctcttgaggagatgaacactatcgaaatgcagaggtatgtggcgcgg
cta.
```

Creation of the Archy3 strain from the Archy2 *T. reesei* strain. The Archy 2 strain was transformed with a vector to integrate at the same pyr2 locus and replace the hygromycin resistance gene with the coding region of the pyr2 gene. The hygromycin deletion cassette is shown in FIG. 7. This reintroduction of the pyr2 gene back into the pyr2 locus placed it between the *T. reesei* cbh1 promoter and the partial amdS selectable marker. This strain could be selected for uridine prototrophy and sensitivity to hygromycin. The nucleotide sequence of the hygR knockout cassette is 9088 base pairs in length: bases 1-1994 correspond to the pyr2 3' homologous region; bases 1995-3497 correspond to the *T. reesei* cbh1 promoter; bases 3564-5137 correspond to the pyr2 selectable marker; bases 5280-7270 correspond to the *A. nidulans* amdS 3' partial marker; bases 7271-9088 correspond to the pyr2 5' homologous region. The nucleotide sequence of the hygR knockout cassette is provided as SEQ ID NO:16:

```
atcacgccctcgcataaaagaccctcaagagtccatgtgccctatctgcc
tgatcttcctaacccttatttaacattggccctatcacaacctagttctt
cttcagcctgctttgtcaacacttgtcacggttcaactcaacgtaatcag
caggtagcaggacgaggatagggagagaaacgaagagaagaagaggagag
aggaagaaaaaaaaagaaaagaaagaaaaagggaaaaggaaagaaggag
gaaaagagaagaaagtcagatgaagaagcaagaagacgccatggtagcca
ccgcttgtcagggctccttagcaacgaacaactctagcttggggacttgt
cgatgtgtcgtttccttcctacccatcagcaccaacgatgagttcgatat
agacgaggacctcatggaagtagagaccattgggttcgacaggatctctc
agtttcacttctatgaggtctgtcgctcggatgacttttttgaggagcttc
cccttctgcttcaaccccaaactctcttcctgaaaccgcagcacgttgg
cacggccgtgttgctggagcagtttgctttcgagcactctcagcgtggtt
tcagcagcccactggtgagtggcctcattgacgtccacaccttgctcctg
tcgcatgcgtatctggtgggaacgactgctccaaggaggattgctaacga
ggttgtaggccgaatatcgcatcagattctccggtaaccttagctacggc
ctcttcaacatctgtgacatgacggagcgcaagtactggtggttggcgac
caagatgcgcggctggaacatcgacggctgccccgaagacgtcaggagac
tcatgtttgttcacatcatcgccaccctgggatgcagccccgtcgtgacg
gatgaagacatggactaccccaagaactgggcggcaattctccacggtag
agacagatatccgagtgaacctgtgggccaccgcctcatgggcgcacca
tctgcctccactcggtggccgtctgccctcgtctccagggcttgggtctc
ggtactgcgactctgaagtcgtatgtgcagcgcatgaacagcctcggcgc
cgcggaccgtgttgctctcgtttgccgcaagcccgagacgagattttttg
aaagatgcggcttcaggaacagcggccggagtagtatcaagactctggtc
ggcgaatactacaacatggtgtgtgcttccacatcgacttggccagactc
tatacgattttcaaacctcgctatacgtcatattgacttgtttctttagg
tcttcgatttgcccggcccaaagactttatcgactggaatagcattgcc
gacgctgccaagaagatgtgaaccatttgactgatacgatgtgtgctacg
catgtcgaccttctttgtttgtttctttggcggctctttgtataccttgg
gacacggcagacgcatgtctatgtgaagaaaacgttcacggcgctgtttg
catcaggaatatgatcattaaacatggagcgtaatggtattaatgatcaa
ctagaaaaatggtatggaagggcgagagggcgatcaacaaagcagcccgg
ggcatagtctggaagcagcaggaattggaaggggaaaaggaagctgcacaa
tgaagggatatcgtgagcggagtggctcacgagagtatcaacagactggc
gaaagcaagcaattgccaacgccggctattaggccataagatggcctgtt
gtgagtcccagttgcacgtatccccatatgactgctctgtcgctgacttg
``` aaaaaaaatagggaggataaaggagaaagaaagtgagacaacccgtgagg
gacttggggtagtaggagaacacatgggcaaccgggcaatacacgcgatg
tgagacgagttcaacggcgaatggaaatcttgaaaaacaaaataaaata
actgccctccatacgggtatcaaattcaagcagttgtacggaggctagat
agagttgtgaagtcggtaatcccgctgtatagtaatacgagtcgcatcta
aatactccgaagctgctgcgaacccggagaatcgagatgtgctggaaagc
ttctagcgagcggctaaattagcatgaaaggctatgagaaattctggaga
cggcttgttgaatcatggcgttccattcttcgacaagcaaagcgttccgt
cgcagtagcaggcactcattcccgaaaaaactcggagattcctaagtagc
gatggaaccggaataatataataggcaatacattgagttgcctcgacggt
tgcaatgcaggggtactgagcttggacataactgttccgtaccccacctc
ttctcaacctttggcgtttccctgattcagcgtaccgtacaagtcgtaa
tcactattaacccagactgaccggacgtgttttgcccttcatttggagaa
ataatgtcattgcgatgtgtaatttgcctgcttgaccgactgggggctgtt
cgaagcccgaatgtaggattgttatccgaactctgctcgtagaggcatgt
tgtgaatctgtgtcgggcaggacacgcctcgaaggttcacggcaagggaa
accaccgatagcagtgtctagtagcaacctgtaaagccgcaatgcagcat
cactggaaaatacaaaccaatggctaaaagtacataagttaatgcctaaa
gaagtcatataccagcggctaataattgtacaatcaagtggctaaacgta
ccgtaatttgccaacgcttgtggggttgcagaagcaacggcaaagcccc
acttccccacgtttgtttcttcactcagtccaatctcagctggtgatccc
ccaattgggtcgcttgtttgttccggtgaagtgaaagaagacagaggtaa
gaatgtctgactcggagcgttttgcatacaaccaagggcagtgatggaag
acagtgaaatgttgacattcaaggagtatttagccagggatgcttgagtg
tatcgtgtaaggaggtttgtctgccgatacgacgaatactgtatagtcac
ttctgatgaagtggtccatattgaaatgtaaagtcggcactgaacaggca
aaagattgagttgaaactgcctaagatctcgggccctcgggccttcggcc
tttgggtgtacatgtttgtgctccgggcaaatgcaaagtgtggtaggatc
gaacacactgctgccttaccaagcagctgagggtatgtgataggcaaat
gttcaggggccactgcatggtttcgaatagaaagagaagcttagccaaga
acaatagccgataaagatagcctcattaaacggaatgagctagtaggcaa
agtcagcgaatgtgtatatataaaggttcgaggtccgtgcctccctcatg
ctctccccatctactcatcaactcagatcctccaggagacttgtacacca
tcttttgaggcacagaaacccaatagtcaaccgcggactgcgcatcatgt
atcggaagttggccgtcatctcggccttcttggccacacctcgtgctaga
ctaggcgcgtcaatatgtggccgttactcgagtttataagtgacaacatg
ctctcaaagcgctcatggctggcacaagcctggaaagaaccaacacaaag
catactgcagcaaatcagctgaattcgtcaccaattaagtgaacatcaac
ctgaaggcagagtatgaggccagaagcacatctggatcgcagatcatgga
ttgcccctcttgttgaagatgagaatctagaaagatggcggggtatgaga taagagcgatggggggggcacatcatcttccaagacaaacaacctttgcag
agtcaggcaattttcgtataagagcaggaggagggagtccagtcatttc
atcagcggtaaaatcactctagacaatcttcaagatgagttctgccttgg
gtgacttatagccatcatcatacctagacagaagcttgtgggatactaag
accaacgtacaagctcgcactgtacgctttgacttccatgtgaaaactcg
atacggcgcgcctctaaattttatagctcaaccactccaatccaacctct
gcatccctctcactcgtcctgatctactgttcaaatcagagaataaggac
actatccaaatccaacagaatggctaccacctcccagctgcctgcctaca
agcaggacttcctcaaatccgccatcgacggcggcgtcctcaagtttggc
agcttcgagctcaagtccaagcggatatcccctacttcttcaacgcggg
cgaattccacacggcgcgcctcgccggcgccatcgcctccgcctttgcaa
agaccatcatcgaggcccaggagaaggccggcctagagttcgacatcgtc
ttcggcccggcctacaagggcatcccgctgtgctccgccatcaccatcaa
gctcggcgagctggcgccccagaacctggaccgcgtctcctactcgtttg
accgcaaggaggccaaggaccacggcgagggcggcaacatcgtcggcgct
tcgctcaagggcaagagggtcctgattgtcgacgacgtcatcaccgccgg
caccgccaagagggacgccattgagaagatcaccaaggagggcggcatcg
tcgccggcatcgtcgtggccctggaccgcatggagaagctcccccgctgcg
gatggcgacgactccaagcctggaccgagtgccattggcgagctgaggaa
ggagtacgcatcccatctttgccatcctcactctggatgacattatcg
atggcatgaagggctttgctacccctgaggatatcaagaacacggaggat
taccgtgccaagtacaaggcgactgactgattgaggcgttcaatgtcaga
agggagagaaagactgaaaaggtggaaagaagaggcaaattgttgttatt
attattattctatctcgaatcttctagatcttgtcgtaaataaacaagcg
taactagctagcctccgtacaactgcttgaatttgatacccgtatggagg
gcagttattttattttgatttcaagattttccattcgccgttgaactcgt
ctcacatcgcgtgtattgcccggttgcccatgtgtacgcgtttcgggttt
acctcttccagatacagctcatctgcaatgcattaatgcattggacctcg
caacccctagtacgcccttcaggctccggcgaagcagaagaatagcttagc
agagtctattttcattttcgggagactagcattctgtaaacgggcagcaa
tcgcccagcagttagtagggtcccctctacctctcagggagatgtaacaa
cgccacttatgggactatcaagctgacgctggcttctgtgcagacaaac
tgcgcccacgagttcttccctgacgccgctctcgcgcaggcaagggaact
cgatgaatactacgcaaagcacaagagacccgttggtccactccatggcc
tccccatctctctcaaagaccagcttcgagtcaaggtacaccgttgcccc
taagtcgttagatgtccctttttgtcagctaacatatgccaccagggcta
cgaaacatcaatgggctacatctcatggctaaacaagtacgacgaagggg
actcggttctgacaaccatgctccgcaaagccggtgccgtcttctacgtc
aagacctctgtcccgcagaccctgatggtctgcgagacagtcaacaacat
catcgggcgcaccgtcaacccacgcaacaagaactggtcgtgcggcggca -continued

```
gttctggtggtgagggtgcgatcgttgggattcgtggtggcgtcatcggt
gtaggaacggatatcggtggctcgattcgagtgccggccgcgttcaactt
cctgtacggtctaaggccgagtcatgggcggctgccgtatgcaaagatgg
cgaacagcatggagggtcaggagacggtgcacagcgttgtcgggccgatt
acgcactctgttgagggtgagtccttcgcctcttccttcttttcctgctc
tataccaggcctccactgtcctcctttcttgcttttatactatatacga
gaccggcagtcactgatgaagtatgttagacctccgcctcttcaccaaat
ccgtcctcggtcaggagccatggaaatacgactccaaggtcatccccatg
ccctggcgccagtccgagtcggacattattgcctccaagatcaagaacgg
cgggctcaatatcggctactacaacttcgacggcaatgtccttccacacc
ctcctatcctgcgcggcgtggaaaccaccgtcgccgcactcgccaaagcc
ggtcacaccgtgaccccgtggacgccatacaagcacgatttcggccacga
tctcatctcccatatctacgcggctgacggcagcgccgacgtaatgcgcg
atatcagtgcatccggcgagccggcgattccaaatatcaaagacctactg
aacccgaacatcaaagctgttaacatgaacgagctctgggacacgcatct
ccagaagtggaattaccagatggagtaccttgagaaatggcgggaggctg
aagaaaaggccgggaaggaactggacgccatcatcgcgccgattacgcct
accgctgcggtacggcatgaccagttccggtactatgggtatgcctctgt
gatcaacctgctggatttcacgagcgtggttgttccggttacctttgcgg
ataagaacatcgataagaagaatgagagtttcaaggcggttagtgagctt
gatgccctcgtgcaggaagagtatgatccggaggcgtaccatggggcacc
ggttgcagtgcaggttatcggacggagactcagtgaagagaggacgttgg
cgattgcagaggaagtggggaagttgctgggaaatgtggtgactccatag
ctaataagtgtcagatagcaatttgcacaagaaatcaataccagcaactg
taaataagcgctgaagtgaccatgccatgctacgaaagagcagaaaaaaa
cctgccgtagaaccgaagagatatgacacgcttccatctctcaaaggaag
aatcccttcagggttgcgtttccagtagtgattttaccgctgatgaaatg
actggactccctcctcctgctcttatacgaaaaattgcctgactctgcaa
aggttgtttgtcttggaagatgatgtgcccccccatcgctcttatctcat
accccgccatctttctagattctcatcttcaacaagaggggcaatccatg
atctgcgatccagatgtgcttctggcctcatactctgccttcaggttgat
gttcacttaattggtgacgaattcagctgatttgctgcagtatgctttgt
gttggttctttccaggcttgtgccagccatgagcgctttgagagcatgtt
gtcacttataaactcgagtaacggccacatattgttcactacttgaatca
catacctaattttgatagaattgacatgtttaaagagctgaggtagcttt
aatgcctctgaagtattgtgacacagcttctcacagagtgagaatgaaaa
gttggactcccctaatgaagtaaaagtttcgtctctgaacggtgaagag
catagatccggcatcaactacctggctagactacgacgtcaattctgcgg
cctttgacctttatatatgtccattaatgcaatagattcttttttttt
ttttttttttttttttttttttttttttttgcccaatttcgcagatcaa
agtggacgttatagcatcataactaagctcagttgctgagggaagccgtc
tactaccttagcccatccatccagctccataccttgatactttagacgtg
aagcaattcacactgtacgtctcgcagctctccttcccgctcttgcttcc
ccactggggtccatggtgcgtgtatcgtcccctccacaattctatgccat
ggtacctccagcttatcaatgccccgctaacaagtcgcctctttgccttg
atagcttatcgataaaacttttttttccgccagaaaggctccgcccacaga
caagaaaaaaattcaccgcctagcctttggccccggcatttggctaaac
ctcgagcctctctcccgtcttggggtatcaggaagaaaagaaaaaaatcc
atcgccaagggctgttttggcatcaccacccgaaaacagcacttcctcga
tcaaaagttgcccgccatgaagaccacgtggaaggacatccctccggtgc
ctacgcaccaggagtttctggacattgtgctgagcaggacccagcgcaaa
ctgcccactcagatccgtgccggcttcaagattagcagaattcgaggtac
gtcgcattgcccatcgcaggatgtctcattatcggggtccttggagaacg
atcatgattgcatggcgatgctaacacatagacagccttctacactcgaa
aggtcaagttcacccaggagacgttttccgaaaagttcgcctccatcctc
gacagcttccctcgcctccaggacatccaccccttccacaaggaccttct
caacaccctctacgatgccgaccacttcaagattgcccttggccagatgt
ccactgccaagcacctggtcgagaccatctcgcgcgactacgtccgtctc
ttgaaatacgcccagtcgctctaccagtgcaagcagctcaagcgggccgc
tctcggtcgcatggccacgctggtcaagcgcctcaaggacccctgctgt
acctggaccaggtccgccagcatctcggccgtcttccctccatcgacccc
aacaccaggaccctgctcatctgcggttaccccaatgttggcaagtccag
cttcctgcgaagtatcacccgcgccgatgtggacgtccagcccctatgctt
tcaccaccaagagtctgtttgtcggccactttgactacaagtacctgcga
ttccaggccattgataccccccggtattctggaccaccctcttgaggagat
gaacactatcgaaatgcagaggtatgtggcgcggct.
```

Creation of the A5D Strain from the Archy3 *T. reesei* Strain.

Native *T. reesei* bgl1 was deleted from the Archy 3 strain using a double recombination vector known in the art. Hygromycin resistance was used as the selectable marker for bgl1 deletion. In addition, the hygromycin resistance marker was flanked by loxP sites. The deletion cassette is shown in FIG. 8. Subsequent hygromycin resistant transformants were analyzed for bgl1 deletion. A strain confirmed for deletion of bgl1 was next transformed with a telomeric vector encoding cre recombinase and a functional amdS for selection of transformants to facilitate removal of the hygromycin by cre recombinase expression and loop out of the loxP sites. The telomeric vector encoding the cre recombinase is schematically shown in FIG. 10. Transformants were first obtained on acetamide media, then transferred to potato dextrose agar and replica plated onto hygromycin media to screen for hygromycin sensitivity. Strains sensitive to hygromycin, were again transferred to potato dextrose media and replica plated to acetamide media. A strain was selected which tossed the ability to grow on acetamide, indicative of a loss of the telomeric vector. The nucleotide sequence of the bgl1 knockout cassette is provided as SEQ ID NO:17:

aatggtaggaatgctgggatataggctctgtgctggcaagttgatggatc
ctcgaatgaggccgccctgcaaggggaacatcagagatctaccattgcct
ccttggcccaatccactatcataccttacctcatgatcattcctgcgaagg
tctaccagtaaatatttcctcgtcccgtgtttcatcatgtccagaacctc
atctcgccaaattgactttgccacagtgtctggagctgggtaagcagcgt
gccaaggaattgttgtcgagtctgtgccaggcattgtgcccgacattgtg
aacttcagccaggagaacttttcgatcgcacctatgctgagcaccgtggg
catgcgatggcttcaataatgcagttcgagagggagtgtgtcatgcccta
aagctcattggccacctccacaggctagctctacctgcatctgtagatgg
actttccttgtcctcctccttcagaaaacctcttggtcgctcgcaggtaa
ctgttgttgccgtcattgtttgacagtggatagcaaggcaaaaccgtct
gctttcaacggaagcattcggcggttgtttgtcatcgtgttatcgatcga
ccaggagaacccagacgagtgttgttcgagagaatcatcgacgatgtgaa
gaggcgacgactagtatctagaagattataatcgaacaaatcagcgtttg
tctgtcgggcgtttgagggcgcagttgcccgcaaagcagcgtcgcaata
tataggcagcgagagactgtcaacagccagccgccatgtgatcgatcgta
gccgtcttcccgatcttccctaaaccccttctttggggggcggggcag
cggcgttctaatatttgctggctgtctggataacgtgaatggtagacatg
gtaatgttcggtctgcgaaacatttgtacaattggagtttacgatcgaga
tggaaggaaacgctccacaaactcggtgactgggttgccatcaggtgctc
agggcatagcgttctctgcaaatagaggaaagagaatagcactagtgaaa
gtgtgaatcacaatgaagaggaggttgttgccggaatgctttgagcagcg
tcaaagttgaacttgaagctatcacaaattgcagggtaaagtacatgttg
gtgccagtttgacagcacagtgcgcggagcggaggatgtcgcggaagagg
cgcgacgctaacccgggccttcttctcagtgagcagaactcctgctgcaa
gagttccttctctctgcgagatgacgtgaggcccaatttgcagcttccct
cgaacaaggtgattgaacatctctcttccctcacatttcatcatcactac
ctcctcaattcacttctgcttcggccgtcttcatcattcatgttactgct
ctgatgcctatcctgaagattgtattcctgcagtattcacgccatcccac
cttcggtcctcactcacagtcacaggtcaaccgccttcaccctcctcgcg
atgatgtcggcaatctggtggatcaatgtgcggttgagggccgccgtagt
gaggatgggcatggggaacgaggtcgcccattcgcccacagataacttcg
tatagcatacattatacgaagttatcctgggcttgtgactggtcgcgagc
tgccactaagtggggcagtaccattttatcggacccatccagctatggga
cccactcgcaaattttacatcattttcttttgtcagtaacggccacc
ttttgtaaagcgtaaccagcaaacaaattgcaattggcccgtagcaaggt
agtcagggcttatcgtgatggaggagaaggctatatcagcctcaaaaata
tgttgccagctggcggaagcccggaaggtaagtggattcttcgccgtggc
tggagcaaccggtggattccagcgtctccgacttggactgagcaattcag
cgtcacggattcacgatagacagctcagaccgctccacggctggcggcat
tattggttaacccggaaaactcagtctccttggccccgtcccgaagggacc
cgacttaccaggctgggaaagccagggatagaatacactgtacgggcttc
gtacgggaggttcggcgtagggttgttcccaagttttacacaccccccaa
gacagctagcgcacgaaagacgcggagggtttggtgaaaaagggcgaaa
attaagcgggagacgtatttaggtgctagggccggtttcctccccatttt
tcttcggttccctttctctcctggaagactttctctctctctcttcttct
cttcttccatcctcagtccatcttccttttcccatcatccatctcctcacc
tccatctcaactccatcacatcacaatcgatatgaaaaagcctgaactca
ccgcgacgtctgtcgagaagtttctgatcgaaaagttcgacagcgtctcc
gacctgatgcagctctcggagggcgaagaatctcgtgctttcagcttcga
tgtaggagggcgtggatatgtcctgcgggtaaatagctgcgccgatggtt
tctacaaagatcgttatgtttatcggcactttgcatcggccgcgctcccg
attccgaagtgcttgacattggggaattcagcgagagcctgacctattg
catctcccgccgtgcacagggtgtcacgttgcaagacctgcctgaaaccg
aactgcccgctgttctgcagccggtcgcggaggccatggatgcgatcgct
gcggccgatcttagccagacgagcgggttcggcccattcggaccgcaagg
aatcggtcaatacactacatggcgtgatttcatatgcgcgattgctgatc
cccatgtgtatcactggcaaactgtgatggacgacaccgtcagtgcgtcc
gtcgcgcaggctctcgatgagctgatgctttgggccgaggactgccccga
agtccggcacctcgtgcacgcggatttcggctccaacaatgtcctgacgg
acaatggccgcataacagcggtcattgactggagcgaggcgatgttcggg
gattcccaatacgaggtcgccaacatcttcttctggaggccgtggttggc
ttgtatggagcagcagacgcgctacttcgagcggaggcatccggagcttg
caggatcgccgcggctccgggcgtatatgctccgcattggtcttgaccaa
ctctatcagagcttggttgacggcaatttcgatgatgcagcttgggcgca
gggtcgatgcgacgcaatcgtccgatccggagccgggactgtcgggcgta
cacaaatcgcccgcagaagcgcggccgtctggaccgatggctgtgtagaa
gtactcgccgatagtggaaaccgacgccccagcactcgtccgagggcaaa
ggaatagagtagatgccgaccgggatccacttaacgttactgaaatcatc
aaacagcttgacgaatctggatataagatcgttggtgtcgatgtcagctc
cggagttgagacaaatggtgttcaggatctcgataagatacgttcatttg
tccaagcagcaaagagtgccttctagtgatttaatagctccatgtcaaca
agaataaaacgcgtttcgggtttacctcttccagatacagctcatctgca
atgcattaatgcattggacctcgcaaccctagtacgcccttcaggctccg
gcgaagcagaagaatagcttagcagagtctatttcattttcggagacg
agatcaagcagatcaacggtcgtcaagagacctacgagactgaggaatcc
gctcttggctccacgcgactatatatttgtctctaattgtactttgacat
gctcctcttctttactctgatagcttgactatgaaaattccgtcaccagc
ccctgggttcgcaaagataattgcactgtttcttccttgaactctcaagc
ctacaggacacacattcatcgtaggtataaacctcgaaaatcattcctac
taagatgggtatacaatagtaaccatggttgcctagtgaatgctccgtaa

```
cacccaatacgccggccgataacttcgtatagcatacattatacgaagtt
atacttggcgcgcctagtggaacacgagcacataagcttttacctatggt
tatcgcttgcatctacgcgccgttgatggtggaggatggtggacgttccc
gagaccctacgagctgtggcatcgtcaaactgtgcccacagacctttgt
cttgctttcataacctcgaggagtgtttccagactcatcatccatacaca
agcagtattaatcaaagaaactcggtcgcaatggcaaaaatggtttgcaa
acagaaaactatggcctcttcctattccatcattaactactctaccccgtt
tgtcataacaacatcattaaaacccttatgcgtcaggtgtagcatccttg
atctgttgctcctccaacggccagttctcaatcgttacctcttctcccac
caactcaaactcaagcttcacagactcgtcggtgttcaaggctagctcat
acttgccggggtatacaatccggtttccgtgagaatcaacacgggcgaga
gcactgacagggatggggatgctgagcttggaagagtgaccaggcttgat
gtcggcaagtcggtcgaatccgacgagccacttgttcgggtacgggctg
ggccagcgttgcttgtgcgaacaaacagcatggccgtatatggggactcc
gtcttgcccgagttcttgatgttggcctcgaaggtgaagacgggaatctg
ctcgctgtaagtgtatccggggtgaggagcagagaggatcgatgaggtgt
taacttgaggctcttgggggtggctggcgagagtctccttgaaggtggtgt
agaagagaccactgccaaactcgtagacgggtttgccggtgtaccagatg
taagtctgtccagggtttgactttccatcgggtcggaggttcatgtcatt
ctgggggaattggtgaacatactcagccgggtactgagtggtgaccagtc
ggccggcaggagcacgcttgccagagagaatgtcgaagagggcaacgcct
cccgactggccgggatatccgcccagacgagggagttgaccttcttgtt
gctcttgagcgaggatgagtctacctgaccaccgcccatttgcaggacga
caaggggtttgccgacctcgctgagctgcttgatgagatccagctgatta
ccgggccaagcaatgtccgtgcggtcagcgccctcctgttcaatggtgtt
gtcaattccaccgaggtagatgatggcatccgacttcttggcggcagcaa
tggccttggcaaagccagtggtgctgttgccggcgatctctgtgccgagt
tcaaagttgacgtgatagccggccttcttagcagcttccagagggctgat
gaggtatggggcagggccatagtagttgccttgcatttgggttgtggcat
tggcccatggtccgatcagagcaatgctgcgcaccttcttggacagaggg
agagtgccatcgttcttgagcaggacgatgccctcaacagcagcctcgta
cgagatgtt.
```

The nucleotide sequence of the telomeric vector, pTTT-cre, is provided as SEQ ID NO:18:

```
ttgtacaaagtggtgatcgcgccgcgcgccagctccgtgcgaaagcctga
cgcaccggtagattcttggtgagcccgtatcatgacggcggcgggagcta
catggcccgggtgatttattttttttgtatctacttctgacccttttca
aatatacggtcaactcatcttttcactggagatgcggcctgcttggtattg
cgatgttgtcagcttggcaaattgtggctttcgaaaacacaaaacgattc
cttagtagccatgcatttaagataacggaatagaagaaagaggaaatta
aaaaaaaaaaaaaacaaacatcccgttcataacccgtagaatcgccgct
cttcgtgtatcccagtaccagtttattttgaatagctcgcccgctggaga
gcatcctgaatgcaagtaacaaccgtagaggctgacacggcaggtgttgc
tagggagcgtcgtgttctacaaggccagacgtcttcgcggttgatatata
tgtatgtttgactgcaggctgctcagcgacgacagtcaagttcgccctcg
ctgcttgtgcaataatcgcagtggggaagccacaccgtgactcccatctt
tcagtaaagctctgttggtgtttatcagcaatacacgtaatttaaactcg
ttagcatggggctgatagcttaattaccgtttaccagtgccatggttctg
cagctttccttggcccgtaaaattcggcgaagccagccaatcaccagcta
ggcaccagctaaacccctataattagtctcttatcaacaccatccgctccc
ccgggatcaatgaggagaatgaggggggatgcggggctaaagaagcctaca
taaccctcatgccaactcccagtttacactcgtcgagccaacatcctgac
tataagctaacacagaatgcctcaatcctgggaagaactggccgtgataa
gcgcgcccgcctcgcaaaaaccatccctgatgaatggaaagtccagacgc
tgcctgcggaagacagcgttattgatttcccaaagaaatcggggatcctt
tcagaggccgaactgaagatcacagaggcctccgctgcagatcttgtgtc
caagctggcggccggagagttgacctcggtggaagttacgctagcattct
gtaaacgggcagcaatcgcccagcagttagtagggtcccctctacctctc
agggagatgtaacaacgccaccttatgggactatcaagctgacgctggct
tctgtgcagacaaactgcgcccacgagttcttccctgacgccgctctcgc
gcaggcaagggaactcgatgaatactacgcaaagcacaagagacccgttg
gtccactccatggcctcccatctctctcaaagaccagcttcgagtcaag
gtacaccgttgcccctaagtcgttagatgtccctttttgtcagctaacat
atgccaccagggctacgaaacatcaatgggctacatctcatggctaaaca
agtacgacgaaggggactcggttctgacaaccatgctccgcaaagccggt
gccgtcttctacgtcaagacctctgtcccgcagaccctgatggtctgcga
gacagtcaacaacatcatcggcgcaccgtcaacccacgcaacaagaact
ggtcgtgcggcggcagttctggtggtgagggtgcgatcgttgggattcgt
ggtggcgtcatcggtgtaggaacggatatcggtggctcgattcgagtgcc
ggccgcgttcaacttcctgtacggtctaaggccgagtcatgggcggctgc
cgtatgcaaagatggcgaacagcatggagggtcaggagacggtgcacagc
gttgtcgggccgattacgcactctgttgagggtgagtccttcgcctcttc
cttcttttcctgctctctataccaggcctccactgtcctcctttcttgcttt
ttatactatatacgagaccggcagtcactgatgaagtatgttagacctcc
gcctcttcaccaaatccgtcctcggtcaggagccatggaaatacgactcc
aaggtcatcccatgccctggcgccagtccgagtcggacattattgcctc
caagatcaagaacggcgggctcaatatcggctactacaacttcgacggca
atgtccttccacaccctcctatcctgcgcggcgtggaaaccaccgtcgcc
gcactgccaaagccggtcacaccgtgacccccgtggacgccatacaagca
cgatttcggccacgatctcatctcccatatctacgcggctgacggcagcg
```

-continued

```
ccgacgtaatgcgcgatatcagtgcatccggcgagccggcgattccaaat
atcaaagacctactgaacccgaacatcaaagctgttaacatgaacgagct
ctgggacacgcatctccagaagtggaattaccagatggagtaccttgaga
aatggcgggaggctgaagaaaaggccgggaaggaactggacgccatcatc
gcgccgattacgcctaccgctgcggtacggcatgaccagttccggtacta
tgggtatgcctctgtgatcaacctgctggatttcacgagcgtggttgttc
cggttacctttgcggataagaacatcgataagaagaatgagagtttcaag
gcggttagtgagcttgatgccctcgtgcaggaagagtatgatccggaggc
gtaccatggggcaccggttgcagtgcaggttatcggacggagactcagtg
aagagaggacgttggcgattgcagaggaagtggggaagttgctgggaaat
gtggtgactccatagctaataagtgtcagatagcaatttgcacaagaaat
caataccagcaactgtaaataagcgctgaagtgaccatgccatgctacga
aagagcagaaaaaacctgccgtagaaccgaagagatatgacacgcttcc
atctctcaaaggaagaatcccttcagggttgcgtttccagtctagacacg
tataacggcacaagtgtctctcaccaaatgggttatatctcaaatgtgat
ctaaggatggaaagcccagaatatcgatcgcgcgcagatccatatatagg
gcccgggttataattacctcaggaaatagctttaagtagcttattaagta
ttaaaattatatatatttttaatataactatatttctttaataaataggt
attttaagctttatatataaatataataataaaataatatattatatagc
ttttattaataaataaaatagctaaaaatataaaaaaaatagctttaaa
atacttattataattagaattttatatattttaatatataagatcttt
acttttttataagcttcctaccttaaattaaattttttactttttttact
attttactatatcttaaataaaggcttaaaaatataaaaaaaatcttct
tatatattataagctataaggattatatatatattttttttaatttta
aagtaagtattaaagctagaattaaagttttaattttttaaggctttatt
taaaaaaggcagtaatagcttataaaagaaatttctttttctttatac
taaaagtacttttttttttaataaggttagggttagggttagggttagggt
tagggttagggttagggttagggttagggttagggttagggttagggtta
gggttagggttagggtaaggggtttaaacaaagccacgttgtgtctcaaaa
tctctgatgttacattgcacaagataaaaatatatcatcatgaacaataa
aactgtctgcttacataaacagtaatacaagggggtgttatgagccatatt
caacgggaaacgtcttgctcgaggccgcgattaaattccaacatggatgc
tgatttatatgggtataaatgggctcgcgataatgtcgggcaatcaggtg
cgacaatctatcgattgtatgggaagcccgatgcgccagagttgtttctg
aaacatggcaaaggtagcgttgccaatgatgttacagatgagatggtcag
actaaaactggctgacgaatttatgcctcttccgaccatcaagcatttta
tccgtactcctgatgatgcatggttactcaccactgcgatccccgggaaa
acagcattccaggtattagaagaatatcctgattcaggtgaaaatattgt
tgatgcgctggcagtgttcctgcgccggttgcattcgattcctgtttgta
attgtccttttaacagcgatcgcgtatttcgtctcgctcaggcgcaatca
```

```
cgaatgaataacggtttggttgatgcgagtgattttgatgacgagcgtaa
tggctggcctgagaacaagtctggaaagaaatgcataagcttttgccatt
ctcaccggattcagtcgtcactcatggtgatttctcacttgataaccta
tttttgacgaggggaaattaataggttgtattgatgttggacgagtcgga
atcgcagaccgataccaggatcttgccatcctatggaactgcctcggtga
gttttctccttcattacagaaacggcttttcaaaaatatggtattgata
atcctgatatgaataaattgcagtttcatttgatgctcgatgagttttc
taatcagaattggttaattggttgtaacactggcagagcattacgctgac
ttgacgggacggcggctttgttgaataaatcgaacttttgctgagttgaa
ggatcagatcacgcatcttcccgacaacgcagaccgttccgtggcaaagc
aaaagttcaaaatcaccaactggtccacctacaacaaagctctcatcaac
cgtggctcccctcactttctggctggatgatggggcgattcaggcctggta
tgagtcagcaacaccttcttcacgaggcagacctcagcggtttaaaccta
accctaaccctaaccctaaccctaaccctaaccctaaccctaaccctaac
cctaaccctaaccctaaccctaaccctaaccctaacctaaccctaatggg
gtcgatctgaaccgaggatgagggttctatagactaatctacaggccgta
catggtgtgattgcagatgcgacgggcaaggtgtacagtgtccagaagga
ggagagcggcataggtattgtaatagaccagctttacataataatcgcct
gttgctactgactgatgaccttcttccctaaccagtttcctaattaccac
tgcagtgaggataaccctaactcgctctggggttattattatactgatta
gcaggtggcttatatagtgctgaagtactataagagtttctgcgggagga
ggtggaaggactataaactggacacagttagggatagagtgatgacaaga
cctgaatgttatcctccggtgtggtatagcgaattggctgaccttgcaga
tggtaatggtttaggcagggttttgcagaggggacgagaacgcgttct
gcgatttaacggctgctgccgccaagctttacggttctctaatgggcggc
cgcctcaggtcgacgtcccatggccattcgaattcgtaatcatggtcata
gctgtttcctgtgtgaaattgttatccgctcacaattccacacaacatac
gagccggaagcataaagtgtaaagcctggggtgcctaatgagtgagctaa
ctcacattaattgcgttgcgctcactgcccgctttccagtcgggaaacct
gtcgtgccagctgcattaatgaatcggccaacgcgcggggagaggcggtt
tgcgtattgggcgctcttccgcttcctcgctcactgactcgctgcgctcg
gtcgttcggctgcggcgagcggtatcagctcactcaaaggcggtaatacg
gttatccacagaatcaggggataacgcaggaaagaacatgtgagcaaaag
gccagcaaaaggccaggaaccgtaaaaaggccgcgttgctggcgtttttc
cataggctccgcccccctgacgagcatcacaaaaatcgacgctcaagtca
gaggtggcgaaacccgacaggactataaagataccaggcgtttccccctg
gaagctccctcgtgcgctctcctgttccgaccctgccgcttaccggatac
ctgtccgcctttctcccttcgggaagcgtggcgctttctcatagctcacg
ctgtaggtatctcagttcggtgtaggtcgttcgctccaagctgggctgtg
tgcacgaacccccgttcagcccgaccgctgcgccttatccggtaactat
```

-continued cgtcttgagtccaacccggtaagacacgacttatcgccactggcagcagc
cactggtaacaggattagcagagcgaggtatgtaggcggtgctacagagt
tcttgaagtggtggcctaactacggctacactagaagaacagtatttggt
atctgcgctctgctgaagccagttaccttcggaaaaagagttggtagctc
ttgatccggcaaacaaaccaccgctggtagcggtggttttttttgtttgca
agcagcagattacgcgcagaaaaaaggatctcaagaagatcctttgatc
ttttctacggggtctgacgctcagtggaacgaaaactcacgttaagggat
tttggtcatgagattatcaaaaaggatcttcacctagatcctttaaatt
aaaaatgaagttttaaatcaatctaaagtatatatgagtaaacttggtct
gacagttaccaatgcttaatcagtgaggcacctatctcagcgatctgtct
atttcgttcatccatagttgcctgactcccgtcgtgtagataactacga
tacgggagggcttaccatctggccccagtgctgcaatgataccgcgagac
ccacgctcaccggctccagatttatcagcaataaaccagccagccggaag
ggccgagcgcagaagtggtcctgcaactttatccgcctccatccagtcta
ttaattgttgccgggaagctagagtaagtagttcgccagttaatagtttg
cgcaacgttgttgccattgctacaggcatcgtggtgtcacgctcgtcgtt
tggtatggcttcattcagctccggttcccaacgatcaaggcgagttacat
gatccccatgttgtgcaaaaaagcggttagctccttcggtcctccgatc
gttgtcagaagtaagttggccgcagtgttatcactcatggttatggcagc
actgcataattctcttactgtcatgccatccgtaagatgcttttctgtga
ctggtgagtactcaaccaagtcattctgagaatagtgtatgcggcgaccg
agttgctcttgcccggcgtcaatacgggataataccgcgccacatagcag
aactttaaaagtgctcatcattggaaaacgttcttcggggcgaaaactct
caaggatcttaccgctgttgagatccagttcgatgtaacccactcgtgca
cccaactgatcttcagcatcttttactttcaccagcgtttctgggtgagc
aaaaacaggaaggcaaaatgccgcaaaaaagggaataagggcgacacgga
aatgttgaatactcatactcttcctttttcaatattattgaagcatttat
cagggttattgtctcatgagcggatacatatttgaatgtatttagaaaaa
taaacaaatagggggttccgcgcacatttccccgaaaagtgccacctgacg
tctaagaaaccattattatcatgacattaacctataaaaataggcgtatc
acgaggccctttcgtctcgcgcgtttcggtgatgacggtgaaaacctctg
acacatgcagctcccggagacggtcacagcttgtctgtaagcggatgccg
ggagcagacaagcccgtcagggcgcgtcagcgggtgttggcgggtgtcgg
ggctggcttaactatgcggcatcagagcagattgtactgagagtgcacca
taaaattgtaaacgttaatattttgttaaaattcgcgttaaattttgtt
aaatcagctcatttttaaccaataggccgaaatcggcaaaatcccttat
aaatcaaaagaatagcccgagatagggttgagtgttgttccagtttggaa
caagagtccactattaaagaacgtggactccaacgtcaaagggcgaaaa
ccgtctatcagggcgatggcccactacgtgaaccatcacccaaatcaagt
tttagggttcgaggtgccgtaaagcactaaatcggaaccctaaagggagc -continued ccccgatttagagcttgacggggaaagccggcgaacgtggcgagaaagga
agggaagaaagcgaaaggagcgggcgctagggcgctggcaagtgtagcgg
tcacgctgcgcgtaaccaccaccccgccgcgcttaatgcgccgctacag
ggcgcgtactatggttgctttgacgtatgcggtgtgaaataccgcacaga
tgcgtaaggagaaaataccgcatcaggcgccattcgccattcaggctgcg
caactgttgggaagggcgatcggtgcgggcctcttcgctattacgccagc
tggcgaaaggggatgtgctgcaaggcgattaagttgggtaacgccaggg
ttttcccagtcacgacgttgtaaaacgacggccagtgccaagcttacta
gatgcatgctcgagcggccgccagtgtgatggatatctgcagaattcgcc
cttgactagtgctctctatcctggtggcaggcgtcaagtacccagaggca
gcagcgggcttaggagcggcctgggttgttctccgcaccctctacatgct
gggctatatttatagcgacaagccgaacggcaccggcaggtacaatggtt
cgctgtacttgcttgcgcaagcgggtctttggggattgagcgcatttggt
gttgcaaaggatttgatgtaaatgtagtcgacatcttagcacagagggga
gagttgataaaatgtggtctgtttgaatgatagtcgggttcgtgacctat
attcgtgatagtggagataggtctgcgcctatcttatcgggccggagcaa
aaattccaccgcagcggggtgagttttcgttatacagccatcccacttcc
agcttcaaattgtcagtttaatccagcccaattcaatcattggagaaccg
ccatcatgtcttcgaagtcccacctcccctacgcaattcgcgcaaccaac
catcccaacccctttaacatctaaactcttctccatcgccgaggagaagaa
aaccaacgtcaccgtctccgcagacgttactacttccgccgagctcctcg
atcttgctgaccgtacatcctgcaccaatgcccctccaggataacaaata
gctgatgcgtagtgagtacaggcctaggcccctatatcgcagttctgaaa
acccacatcgacatcctcaccgatctcaccccgtcgaccctttcctcgct
ccaatccctcgcgacaaagcacaacttcctcatctttgaggaccgcaagt
tcatcgacatcggcaacaccgtgcaaaagcagtaccacggtggcgctctc
cgcatctccgaatgggcacacatcatcaactgcgccatcctgccgggcga
agggatcgtcgaggccctcgcacagacaaccaagtctcctgactttaaag
acgcgaatcaacgaggtctcctgattcttgccgagatgacgagtaaggga
tctcttgcgacaggggagtcacaggcacgctcggttgagtacgcgcggaa
gtataaggggtttgtgatgggattcgtgagtacaagggcgttgagtgagg
tgctgcccgaacagaaagaggagagcgaggattttgtcgtctttacgact
ggggtgaatctgtcggataaggggataagctggggcagcagtatcagac
acctgggtcggcggttgggcgaggtgcggactttatcattgcgggtaggg
gcatctataaggcggacgatccagtcgaggcggttcagaggtaccgggag
gaaggctgaaagcttacgagaaaagagttggactttgagtgtgagtgga
aatgtgtaacggtattgactaaaagggatccatatgtttattgcagccag
catagtattaccagaaagagcctcactgacggctctagtagtattcgaac
agatattattgtgaccagctctgaacgatatgctccctaatctggtagac
aagcactgatctaccccttggaacgcagcatctaggctctggctgtgctc

```
taaccctaactagacgattgatcgcagaccatccaatactgaaaagtctc
tatcagaggaaatccccaacattgtagtagtcaggttcctttgtggctgg
gagagaattggttcgctccactgattccagttgagaaagtgggctagaaa
aaagtcttgaagattggagttgggctgtggttatctagtacttctcgagc
tctgtacatgtccggtcgcgacgtacgcgtatcgatggcgccagctgcag
gcggccgctgcagccacttgcagtcccgtggaattctcacggtgaatgt
aggccttttgtagggtaggaattgtcactcaagcaccccaacctccatt
acgcctccccatagagttcccaatcagtgagtcatggcactgttctcaa
atagattggggagaagttgacttccgcccagagctgaaggtcgcacaacc
gcatgatatagggtcggcaacggcaaaaaagcacgtggctcaccgaaaag
caagatgtttgcgatctaacatccaggaacctggatacatccatcatcac
gcacgaccactttgatctgctggtaaactcgtattcgccctaaaccgaag
tgcgtggtaaatctacacgtgggccctttcggtatactgcgtgtgtctt
ctctaggtgccattcttttcccttcctctagtgttgaattgtttgtgttg
gagtccgagctgtaactacctctgaatctctggagaatggtggactaacg
actaccgtgcacctgcatcatgtatataatagtgatcctgagaaggggg
tttggagcaatgtgggactttgatggtcatcaaacaaagaacgaagacgc
ctcttttgcaaagttttgtttcggctacggtgaagaactggatacttgtt
gtgtcttctgtgtattttttgtggcaacaagaggccagagacaatctattc
aaacaccaagcttgctcttttgagctacaagaacctgtggggtatatatc
tagagttgtgaagtcggtaatcccgctgtatagtaatacgagtcgcatct
aaatactccgaagctgctgcgaacccggagaatcgagatgtgctggaaag
cttctagcgagcggctaaattagcatgaaaggctatgagaaattctggag
acggcttgttgaatcatggcgttccattatcgacaagcaaagcgttccgt
cgcagtagcaggcactcattcccgaaaaaactcggagattcctaagtagc
gatggaaccggaataatataataggcaatacattgagttgcctcgacggt
tgcaatgcaggggtactgagcttggacataactgttccgtacccacctc
ttctcaacctttggcgtttccctgattcagcgtacccgtacaagtcgtaa
tcactattaacccagactgaccggacgtgttttgcccttcatttggagaa
ataatgtcattgcgatgtgtaatttgcctgcttgaccgactggggctgtt
cgaagcccgaatgtaggattgttatccgaactctgctcgtagaggcatgt
tgtgaatctgtgtcgggcaggacacgcctcgaaggttcacggcaagggaa
accaccgatagcagtgtctagtagcaacctgtaaagccgcaatgcagcat
cactggaaaatacaaaccaatggctaaaagtacataagttaatgcctaaa
gaagtcatataccagcggctaataattgtacaatcaagtggctaaacgta
ccgtaatttgccaacggcttgtggggttgcagaagcaacggcaaagcccc
acttccccacgtttgtttcttcactcagtccaatctcagctggtgatccc
ccaattgggtcgcttgtttgttccggtgaagtgaaagaagacagaggtaa
gaatgtctgactcggagcgttttgcatacaaccaagggcagtgatggaag
```

```
acagtgaaatgttgacattcaaggagtatttagccagggatgcttgagtg
tatcgtgtaaggaggtttgtctgccgatacgacgaatactgtatagtcac
ttctgatgaagtggtccatattgaaatgtaaagtcggcactgaacaggca
aaagattgagttgaaactgcctaagatctcgggccctcgggccttcggcc
tttgggtgtacatgtttgtgctccgggcaaatgcaaagtgtggtaggatc
gaacacactgctgcctttaccaagcagctgagggtatgtgataggcaaat
gttcaggggccactgcatggtttcgaatagaaagagaagcttagccaaga
acaatagccgataaagatagcctcattaaacggaatgagctagtaggcaa
agtcagcgaatgtgtatatataaaggttcgaggtccgtgcctccctcatg
ctctccccatctactcatcaactcagatcctccaggagacttgtacacca
tcttttgaggcacagaaacccaatagtcaaccatcacaagtttgtacaaa
aaagcaggctcaccatgagcaacctgctcaccgtccaccagaacctccct
gccctcctgtcgacgccacctctgacgaggtccgcaagaacctcatgga
catgttccgcgaccgccaggcctttagcgagcacacctggaagatgctcc
tcagcgtctgccgatcttgggccgcctggtgcaagctcaacaaccgcaag
tggttccccgccgagccggaggacgtccgcgactacctcctctacctgca
ggcccgaggcctggccgtcaagaccatccagcagcacctcggccagctca
acatgctccaccgacgctctggcctgcctcgccctagcgactctaacgcc
gtcagcctggtcatgcgccgcatccgcaaggagaacgtcgacgctggcga
gcgagccaagcaggccctcgccttcgagcgcaccgacttcgaccaggtcc
gcagcctcatggagaacagcgaccgctgccaggatatccgcaacctcgcc
tttctcggcattgcctacaacaccctgctccgcattgccgagatcgcccg
catccgcgtcaaggacatctctcgcaccgacggcggccgcatgctcattc
acatcggccgcaccaagaccctcgtgtctaccgccggcgtcgagaaggcc
ctcagcctcggcgtcaccaagctcgtcgagcgctggatttctgtctccgg
cgtcgctgacgacccaacaactacctcttctgccgcgtccgaaagaacg
gcgtcgccgcccttctgccacctctcagctcagcaccgagccctggag
ggcatctttgaggccacccaccgcctcatctacggcgccaaggacgactc
tggccagcgctacctcgcctggtctggccactctgcccgagtcggcgctg
cccgagacatggcccgagccggcgtcagcatccccgagattatgcaggcc
ggcggctggaccaacgtcaacatcgtcatgaactacatccgcaccctcga
ctctgagaccggcgccatggtccgactcctcgaggacggcgactaaaccc
agctttc.
```

Creation of the MAD6 Strain from A5D *T. reesei* Strain.

Native egl3 was deleted from the A5D strain using the method previously described for bgl1 deletion. A schematic of the deletion cassette is shown in FIG. 9. Hygromycin resistance was used as the selectable marker for egl3 deletion. The hygromycin resistance marker was flanked by loxP sites. A transformant was confirmed with a deletion of the egl3. The hygromycin marker was removed from this strain as described for creation of the A5D strain. The nucleotide sequence of the egl3 deletion cassette is provided as SEQ ID NO:19:

```
gggaggtaggcgcagatacggtgcatgggacccgaacccgtaaccggaac
acgaccttatcagccctccaactcacaccctctcgcctatcactatccta
gatagttcatcggccaactcatgtaacctagctacctacctacctggtaa
gaatgcgggctatcatgtctcacggcgcggtacatgtcggtatctcgctg
cttccccgcaggttgacgtcggaatccatgcaagtactccctgaaatcga
gacgacagagaacaaccaacgcgcttaaacgcttcatgttcatctaag
aggcacattcgaagaactagcttaacacactagacctggcttttcgaccc
cctccgcagaaagccgttttctcctcaatcctcccgggcttggcttttgt
cagtccgtacttgctgcgctaacagagtcttggacgcagcgtttgcgcat
cagtcttgcaggcggttcacgggactaggacaacaggggatgtgacaggc
cggatagtaattatgggttatccggggtaagcaggggaatttacgaggccg
ctttacgtgggggaacagccacttgcgggggggaagaggagtagtaggcga
ctcggtcgatgagctcgaggtgtctggttgacttggactgcagagcgtag
gtaattgagatcgggcaacattatcggtgttcggctcggtatggccgagt
tgcgactgcttggtcattcggcgaagctgatgtcgtggtatcctgaagca
tcgatatcggaaaccatgatggtcagtctatctgacgtgtgcggtgacaa
gcgagtccgattttgtgacatgacgttcaacttcagtcaatgccttagg
gctcgataagattaagattgggactggcagcggtctagaacaccgccaca
aattctgtccattgaggagcgtgatgtctaggcgcatcactaacacggag
ctgtatgaccggcagctcaacggacttctcttcgttcaacggcagtctat
ttgcggtacacgaatggatctttcttcctggtcttgaagtgccgcagtgg
cgtgcgaatgtatagatgtctcgctacctagaaaagctggcttttctgac
agggtcccttccacctctcctaccaacgacaaactgaacaagtatctggc
ggtttccaacgccgaataggccagtcgccaatactccctccagccctga
ttgggcccctcgaagtatcgccatgtctgtgtgttgagattattcgatgg
acgtcactcccccaacctacaggaagagcaaaatgggagcagtgttctgc
aatgagctatataatgatcgctcgatctcatacaaattgtatgctcagt
caatacaacgagcggttccaagatcccttctccaacgaccctcgaaacat
tgcaacccggtgcagcctgaacttgttcgtatagcctagaaagcgacgcc
atcttcatcttttacgcgattagcctcatggctatttgtgccgaagtggg
agttgtatggtagcagtgaggagattgtggctacgacacaggcgggttct
cttgagcggcttacatctccgcattaggcctgcgtacgatccagatcatg
ggaaactttacaatggcttactcgttttatctcaacactgagcttccaat
tcactctatgcattgattaacacgtttggtcatgtggttcttcagctgta
aatcttcagcttcccaagaattgcaacctcgctgattgctaatagtgttg
catgcgttgcatcctggtgcggcagtgcaaaggagagtcaaagtagccgg
cagattaatttaagcttatatcactcaggggtaaacagccgtaaaggacc
ttttgatctaacatgccgatgtgtatgtagatcacgcaatgccaccata
tcttggcagtcagatttgtccgtggcgcgccaagtataacttcgtataat
gtatgctatacgaagttatcggccggcgtattgggtgttacggagcattc
actaggcaaccatggttactattgtatacccatcttagtaggaatgattt
tcgaggtttatacctacgatgaatgtgtgtcctgtaggcttgagagttca
aggaagaaacagtgcaattatctttgcgaacccaggggctggtgacggaa
ttttcatagtcaagctatcagagtaaagaagaggagcatgtcaaagtaca
attagagacaaatatatagtcgcgtggagccaagagcggattcctcagtc
tcgtaggtctcttgacgaccgttgatctgcttgatctcgtctcccgaaaa
tgaaaatagactctgctaagctattcttctgcttcgccggagcctgaagg
gcgtactagggttgcgaggtccaatgcattaatgcattgcagatgagctg
tatctggaagaggtaaacccgaaacgcgttttattcttgttgacatggag
ctattaaatcactagaaggcactctttgctgcttggacaaatgaacgtat
cttatcgagatcctgaacaccatttgtctcaactccggagctgacatcga
caccaacgatcttatatccagattcgtcaagctgtttgatgatttcagta
acgttaagtggatcccggtcggcatctactctattcctttgccctcggac
gagtgctggggcgtcggtttccactatcggcgagtacttctacacagcca
tcggtccagacggccgcgcttctgcgggcgatttgtgtacgcccgacagt
cccggctccggatcggacgattgcgtcgcatcgaccctgcgcccaagctg
catcatcgaaattgccgtcaaccaagctctgatagagttggtcaagacca
atgcggagcatatacgcccggagccgcggcgatcctgcaagctccggatg
cctccgctcgaagtagcgcgtctgctgctccatacaagccaaccacggcc
tccagaagaagatgttggcgacctcgtattgggaatccccgaacatcgcc
tcgctccagtcaatgaccgctgttatgcggccattgtccgtcaggacatt
gttggagccgaaatccgcgtgcacgaggtgccggacttcggggcagtcct
cggcccaaagcatcagctcatcgagagcctgcgcgacgacgcactgacg
gtgtcgtccatcacagtttgccagtgatacacatggggatcagcaatcgc
gcatatgaaatcacgccatgtagtgtattgaccgattccttgcggtccga
atgggccgaacccgctcgtctggctaagatcggccgcagcgatcgcatcc
atgcctccgcgaccggctgcagaacagcgggcagttcggtttcaggcag
gtcttgcaacgtgacaccctgtgcacggcgggagatgcaataggtcaggc
tctcgctgaattccccaatgtcaagcacttccggaatcgggagcgcggcc
gatgcaaagtgccgataaacataacgatctttgtagaaaccatcggcgca
gctatttacccgcaggacatatccacgccctcctacatcgaagctgaaag
cacgagattcttcgccctccgagagctgcatcaggtcggagacgctgtcg
aacttttcgatcagaaacttctcgacagacgtcgcggtgagttcaggctt
tttcatatcgattgtgatgtgatggagttgagatggaggtgaggagatgg
atgatgggaaaggaagatggactgaggatggaagaagagaagaagagaga
gagagaaagtcttccaggagagaaagggaaccgaagaaaaatggggagga
aaccggccctagcacctaaatacgtctcccgcttaattttcgccctttt
tcaccaaaccctccgcgtctttcgtgcgctagctgtcttggggggtgtgt
aaaacttgggaacaacccctacgccgaacctcccgtacgaagcccgtacag
tgtattctatccctggcttcccagcctggtaagtcgggtcccttcggga
cggggccaaggagactgagtttccgggttaaccaataatgccgccagccg
```

-continued

```
tggagcggtctgagctgtctatcgtgaatccgtgacgctgaattgctcag
tccaagtcggagacgctggaatccaccggttgctccagccacggcgaaga
atccacttaccttccgggcttccgccagctggcaacatattttttgaggct
gatatagccttctcctccatcacgataagccctgactaccttgctacggg
ccaattgcaatttgtttgctggttacgctttacaaaaggtggccgttact
gagcaaaaagaaaatgatgtaaaaatttgcgagtgggcccatagctgga
tgggtccgataaaatggtactgccccacttagtggcagctcgcgaccagt
cacaagcccaggataacttcgtataatgtatgctatacgaagttatctgt
gggcgttatgaataatagactggaaccgggccctttgattgacgactcca
tattttgtagatgtagcaactcggcaagagcattatgtgcaatacatttg
ttaccatacaaaggcagctgccagacgacttgtattgcgtacaattctca
cggcaagctttccaggtgttatgcattatgcgcaaatgcttgatgcttac
cgcaggattaatctcggaagaagcgctgcaagctatatgggtgtagtaga
tatgtagatgtaccaaccaatgaagaacatttatggtctagaatgtagtg
atgaaggttttgagtaatttgtatcaagtaagacgatattattgataaa
taccaagcatatattcatgataaattacttggaaccaccccttgcgtccgg
cctcacgagccttctcactgccgggctcgaaggagccactggaggcctgt
ccaccccttggatgcgatttcctgcacctttttccttgggcctgcacgtcga
ttagacatgattcaaatcgagatcttggaatatcttacatgctggcgaag
ccaccggtgtggctggactgtccgcccttctgcgcaatgctttgaacctc
ctccttgggctgtgtagaaaggtttgttagcaacattactacaactctc
aggactcggtggtcgtaccggttggcgaagtttccggggttatcgttgcc
agacattgtgtgattatttggtgtgcaaatgtgtgctatgtgtgttgttg
ctgttggtgatgatgctgaagctgttgaaagcaggctggttctgtgggag
agacttgggatatttatatccaaagttcggtcgtgttccttctggaagct
cttctctactccatacaatcatccaaagttgtcgtcattgagcgttgatc
agtagtagcctctgaggtcatcaccatgatccttccggccaacagtcggc
actcatcaacagcaacaatcagccgccacaaacataggtacagtaaggag
ttagatatcatgtagtcgtcgagtactcgacatcatgacgtacaagcttt
gccagtgtcggtaggtgcaagtatgatgatcgtatccgccgttgttcgat
cgaacagagtgcggtcagattcacggtttctctcaccttgaacattggat
gcaattggattgatccacaatcctggagaatggcttcaagctcactgctc
cagtcgcaagcttcagagcctattactaagggtagagctacctatgtcaa
gagttttcaaggtacctaagctacatgtgatagtcggcaagccattttga
acgcagaccgtgaacggtgatgtaaatccgggatagacgcccaagcgtgc
cgtgtcaatgacgctagatacacctcgatttacgtagagtgaatgccagc
caatggagtcatgcacataacccgcttagactctgctcggggcgatacc
gatcgcagaggcagagccgcttaaacgcgatcgcggtaacctgtaatcag
agccagcgctcgatgaattgcatcatggaagccattgatgtggaatgttg
agcgtataacaacacgaattgaagacgacattgacttgcttcaagtgagt
```

-continued

```
ggagaattgccgggcagacaagataggtaggctcttggtgcgctgtcaca
tcaatccattccttttcctctgttcaatctctatgttgacattctgatag
ggatcattggatgccaatgcaaagaacatgagagtgtggtctgcattcaa
gtatcctggtcgtaagctgtggccatgggcgctgcggtcaaggtcaatcg
cgatgactaatcagtctcggtgactctggggcggtagaggcagtgtcgtg
aaccaaagcttgagccgagggcaaaaacaacggcgcatcaaacaatcaac
gaaagcatcgtcaacagtgtctcttcccagtcaattacttcgcaaaacct
tctcgatagaaccccttcagacgatgaacaggccacgcaaccgtcagccgc
gcccccaggacagactcagcgcccgggaggcagatcgtcacaccttggt
cgacgagctc.
```

Example 7

Analysis of Select Singly-Substituted CBH2 Variants in Activity and Thermostability Assays Protoplasts of a six-fold deleted *T. reesei* strain (Δegl1, Δegl2, Δegl3, Δcbh1, Δcbh2, Δbgl1) were transformed with selected CBH2 SEL variants encoded on the pTTTpyrG vector as described (WO 2009/048488). Spores were harvested, replated on acetamide agar, and incubated at 28° C. for 7 days. Next, CBH2 variants were produced by inoculating 25 ml of YEG culture (5 g/L yeast extract, 20 g/L glucose) with a sporulating *Trichoderma* strain on agar, followed by a two day incubation period at 28° C., 200 rpm. Five ml of the YEG culture was used to inoculate 45 ml of glycine medium containing a 2% glucose sophorose mixture. The culture was dispensed over a 6-well microtiterplate and incubated stationary for five days at 28° C. in an oxygen-enriched atmosphere. Cells were removed by filtration through a 0.2 μm filter. Supernatants were subsequently concentrated using Vivaspin spin cells with a 10 kD molecular weight cutoff. The variants were tested for their ability to hydrolyze phosphoric acid swollen cellulose (PASC) at 50° C., dilute acid pretreated corn stover (PCS) at 50° C., dilute ammonia pretreated corncob (CC) at 50° C. and 57° C. In addition, the variants were tested for thermostability.

PASC 50° C.

Enzyme activity on phosphoric acid swollen cellulose was examined essentially as described in Example 1, Section C, with the following changes. To each well, 10 μl was added containing 4.9 μg protein in supernatant from a CBH2 deleted strain (Δegl1, Δegl2, Δcbh1, Δcbh2). The plate was incubated at 50° C. while shaking at 200 rpm. After 2 hours the plate was put on ice for 5 min and 100 μl of 100 mM glycine pH 10.0 was added. After mixing, the plate was centrifuged at 3000 rpm for 5 min. A volume of 40 μl supernatant was diluted in 160 μl water. Ten μl of the diluted solution was transferred to a new 96-well microtiterplate (Costar Flat Bottom PS) containing 100 μl ABTS glucose assay mixture (2.74 mg/ml 2,2' azino-bis(3-ethylbenzo-thiazoline-6-sulfonic acid, 1 U/ml horseradish peroxidase type VI, 1 U/ml glucose oxidase) and increase in $A_{420}$ was recorded in a microtiterplate spectrophotometer (Spectramax Plus 384, Molecular Devices). A range of glucose concentrations was included as a standard on each plate (0; 0.008; 0.016; 0.031; 0.063; 0.125; 0.25; 0.5; 1 mg/ml). Assays were done in duplicate. A dose response curve was generated for the wild-type CBH2 by fitting the data with a Temkin isotherm equation ($y=a+b(\ln(1+c^*x))$)

and the activities of the CBH2 variants were divided by a calculated activity of wild-type CBH2 of the same plate to yield a performance index.

PCS 50° C.

Enzyme activity on washed dilute acid pretreated cornstover was examined essentially as described in Example 1, Section D, with the following changes. To each well, 10 μl was added containing 49 μg protein in supernatant from a CBH2 deleted strain (Δegl1, Δegl2, Δcbh1, Δcbh2). The plate was incubated at 50° C. while shaking at 200 rpm. After 2 days the plate was put on ice for 5 min and 100 μl of 100 mM glycine pH 10.0 was added. After mixing, the plate was centrifuged at 3000 rpm for 5 min. A volume of 10 μl supernatant was diluted in 190 μl water. Ten μl of the diluted solution was transferred to a new 96-well microtiter plate (Costar Flat Bottom PS) containing 100 μl ABTS glucose assay mixture and assayed and analyzed as described above for the PASC assay.

Corncob 50° C.

Enzyme activity on corncob at 50° C. was performed essentially as described in Example 1, Section E, with the following changes. To each well 10 μl solution was added containing 46.55 μg protein of supernatant from a CBH2 deleted strain (Δegl1, Δegl2, Δcbh1, Δcbh2), supplemented with 4.90 μg T. reesei CBH1, 6.84 μg T. reesei Xyn2 Y5 (Xiong et al, Extremophiles 8:393-400, 2004), 2.28 μg Fusarium verticillioides (Fv) 51A, 5.32 μg Fv3A, 0.76 μg Fv43D, and 2.45 μg T. reesei BGL1. The Fusarium verticillioides enzymes have been described in U.S. 61/245,269 (herein incorporated by reference for the teaching of this method). Different volumes of supernatant of a transformed T. reesei strain expressing a CBH2 variant were added as described in Example 1. The plates were incubated for two days at 50° C. with shaking at 200 rpm.

Corncob 57° C.

Corn cob was ground to pass through a 0.9 mm screen then pretreated as described in Example 4 of WO 2006/110901 (herein incorporated by reference for the teaching of this method). Pretreated corn cob was used as a 7% cellulose suspension in 50 mM sodium acetate pH 5.0. Seventy microliters of the suspension was added per well to a 96-well microtiterplate (Nunc Flat Bottom PS). To each well 10 μl solution containing 46.55 μg protein of supernatant from a CBH2 deleted strain (Δegl1, Δegl2, Δcbh1, Δcbh2), 4.90 μg CBH1 variant (S8P/T41I/N89D/S92T/S113N/S196T/P227L/D249K/T255P/S278P/E295K/T296P/T332Y/V403D/S411F/T462I), 6.84 μg T. reesei Xyn2 Y5 (Xiong et al, Extremophiles 8:393-400, 2004), 2.28 μg Fv51A, 5.32 μg Fv3A, 0.76 μg Fv43D, 2.45 ug Talaromyces emersonii beta-glucosidase were added. Up to twenty microliters of supernatant from H. jecorina cells expressing either wild-type CBH2 or a CBH2 variant was added. Compensating volumes of acetate buffer were added to make up for differences in total volume. The plate was incubated at 57° C. while shaking at 200 rpm. After 2 days the plate was put on ice for 5 min and 100 μl of 100 mM glycine pH 10.0 was added. After mixing, the plate was centrifuged at 3000 rpm for 5 min. A volume of 10 μl supernatant was diluted in 190 μl water. Ten μl of the diluted solution was transferred to a new 96-well microtiterplate (Costar Flat Bottom PS) containing 100 μl ABTS glucose assay mixture and assayed and analyzed as described above.

CBH2 Thermostability Assay 2.

To test the thermostability of the CBH2 variants, 50 μl of supernatant was incubated in a PCR machine across a temperature range of 50-70° C. The remaining activity was determined by incubating 20 μl supernatant with 80 μl 0.625 mg/ml cellotriose in 50 mM sodium acetate buffer pH5.0 with 0.0025% Tween80. After 1 hour, 40 μl of 100 mM glycine pH10 was added. Twenty μl was added to 80 μl ABTS reagent (see above) and color development at OD420 was recorded for 5 min. A pseudo melting temperature (Tm) was calculated by fitting the remaining activity at each temperature with the formula:

$$y=1/(1+\exp(-(a*(1-b/c-\ln(c/b))+d*((1/c)-(1/b)))/e))$$

in which a is the heat capacity ($kcal*mol^{-1}*K^{-1}$), b is the melting temperature (K), c is the assay temperature (K), d is the enthalpy change ($kcal*mol^{-1}*K^{-1}$), and e is the gas constant ($kcal*mol^{-1}*K^{-1}$).

TABLE 7-1

Performance Index and Tm Values for Select CBH2 Variants

| Variant | PASC 50° C. | PCS 50° C. | CC 50° C. | CC 57° C. | Tm (° C.)[1] |
|---|---|---|---|---|---|
| T19K | 0.93 | 0.86 | 0.99 | 0.88 | 55.7 |
| R63L | 0.95 | 0.64 | 1.05 | 0.92 | 56.4 |
| V94A | 0.81 | 0.92 | 0.89 | 0.79 | 56.8 |
| P98Q | 1.19 | 1.07 | 1.06 | 0.98 | 58.8 |
| P98L | 0.96 | 0.52 | 0.80 | 0.77 | 58.3 |
| L111S | 0.97 | 0.96 | 0.98 | 1.03 | 57.8 |
| T138S | 1.09 | 1.02 | 1.03 | 1.05 | 56.5 |
| T138C | 1.13 | 1.09 | 1.07 | 1.08 | 56.3 |
| T138A | 0.90 | 0.93 | 1.03 | 0.75 | 55.6 |
| P143S | 0.76 | 0.69 | 0.92 | 0.68 | 56.5 |
| L144W | 0.88 | 1.07 | 1.03 | 0.90 | 56.5 |
| A150H | 1.01 | 0.95 | 1.04 | 1.02 | 56.9 |
| T154D | 0.96 | 0.97 | 0.97 | 0.82 | 55.9 |
| N161P | 0.93 | 0.88 | 1.00 | 0.87 | 57.0 |
| A177N | 0.81 | 0.81 | 0.94 | 0.74 | 57.3 |
| A177S | 0.94 | 1.41 | 1.07 | 0.89 | 57.1 |
| N182A | 0.89 | 0.80 | 0.94 | 0.79 | 57.4 |
| N182M | 1.02 | 0.97 | 1.08 | 1.11 | 57.5 |
| N182W | 0.92 | 0.33 | 0.70 | 0.57 | 58.8 |
| A188S | 1.16 | 1.30 | 1.20 | 1.05 | 56.4 |
| N197A | 1.03 | 1.16 | 1.16 | 1.18 | 56.1 |
| K288N | 0.90 | 0.80 | 0.93 | 0.96 | 57.4 |
| S291A | 1.01 | 1.03 | 1.06 | 1.15 | 57.1 |
| S291T | 0.88 | 0.73 | 0.94 | 0.92 | 57.0 |
| S291C | 1.53 | 0.95 | 1.02 | 1.06 | 56.3 |
| S291H | 1.07 | 0.87 | 1.11 | 1.00 | 56.6 |
| S291E | 0.85 | 0.61 | 0.84 | 0.95 | 58.0 |
| T312S | 1.08 | 1.07 | 1.09 | 1.11 | 56.7 |
| S313T | 1.01 | 1.08 | 1.20 | 1.21 | 56.4 |
| S316A | 1.03 | 1.03 | 1.17 | 1.04 | 57.0 |
| S316P | 1.05 | 1.09 | 1.03 | 1.06 | 57.1 |
| S316W | 1.02 | 0.94 | 1.11 | 1.05 | 57.0 |
| A322P | 1.04 | 1.05 | 1.16 | 1.13 | 56.7 |
| S343W | 0.80 | 0.60 | 0.92 | 1.00 | 57.1 |
| S343Q | 0.94 | 0.94 | 1.06 | 1.16 | 56.5 |
| S343T | 1.09 | 1.02 | 1.04 | 0.82 | 57.0 |
| S343E | 1.10 | 1.13 | 1.18 | 1.12 | 56.4 |
| F346A | 1.04 | 1.07 | 1.18 | 1.14 | 57.0 |
| F346Y | 1.06 | 1.15 | 1.06 | 1.05 | 56.6 |
| F346H | 1.04 | 0.91 | 1.04 | 1.05 | 57.0 |
| Q362L | 1.24 | 0.99 | 0.95 | 1.14 | 58.1 |
| Q362I | 1.02 | 0.94 | 0.98 | 0.93 | 58.3 |
| Q363S | 1.00 | 1.02 | 1.08 | 1.08 | 57.1 |
| S386D | 0.99 | 0.96 | 1.00 | 1.03 | 55.9 |
| S386A | 1.03 | 1.00 | 1.06 | 1.08 | 55.9 |
| S386F | 1.16 | 0.63 | 0.94 | 0.79 | 52.8 |
| S386I | 0.91 | 0.86 | 0.98 | 0.78 | 56.3 |
| S386C | 1.64 | 1.33 | 1.10 | 1.24 | 56.1 |
| S386V | 1.09 | 0.97 | 1.04 | 1.08 | 56.6 |
| C400S | 0.95 | 0.87 | 0.93 | 0.95 | 64.6 |
| S406P | 1.34 | 1.10 | 1.06 | 1.11 | 57.4 |
| S406A | 1.00 | 1.00 | 1.02 | 1.02 | 57.1 |
| S407T | 1.16 | 1.05 | 1.08 | 1.05 | 57.0 |
| S413W | 0.88 | 0.27 | 0.66 | 0.53 | 59.4 |
| S413Y | 0.98 | 0.91 | 0.94 | 1.01 | 58.0 |
| Q422V | 0.97 | 0.87 | 1.03 | 0.93 | 55.1 |
| Q422T | 1.03 | 1.00 | 1.08 | 1.04 | 55.2 |

[1]As determined by thermostability assay 2. The Tm of the reference CBH2 of SEQ ID NO: 3 was 57.5° C. under the test conditions.

A category of mutations was devised, that is highly combinable mutations, to encompass mutations that have a PI>0.75 for at least one property, and >0.05 for all properties. As illustrated in the succeeding examples, some variants having two highly combinable mutations, have activity and/or stability that is greater than the reference CBH2 enzyme. An accumulation of highly combinable mutations can be used to make a beneficial variant where each individual mutation is not sufficient to confer superior activity, thermostability and/or expression levels to a variant enzyme.

Example 8

CBH2 Combinatorial Library Variants and Activities Thereof

A synthetic CBH2 combinatorial library was produced by GeneOracle (Mountain View, Calif.). Table 8-1 lists the possible substitutions of members of the CBH2 combinatorial library (numbered according to the CBH2 mature amino acid sequence). This library was created by combining substitutions classified as up mutations and/or highly combinable mutations on the basis of their Tm and performance as listed in Table 7-1.

TABLE 8-1

CBH2 Combinatorial Library Design

| Targeted Position | Wild-Type Residue | Substitution |
|---|---|---|
| 98 | P | P, Q, L |
| 111 | L | L, S |
| 182 | N | N, W |
| 291 | S | S, E |
| 316 | S | S, P |
| 362 | Q | Q, I, L |
| 400 | C | C, S |

The library was received from the above-mentioned provider as purified PCR products in which primers GACCGGACGT-GTTTTGCCCTTCAT (SEQ ID NO:20) and GTGTGACCG-GCTTTGGCGAGTG (SEQ ID NO:21) were used to amplify the cbh2 gene flanked upstream by about 1.1 kb of the cbh1 promoter and downstream by about 1.85 kb of the amdS marker for forced integration in the pyr2 locus in the *H. jecorina* host strain. A schematic of the homologous recombination of the expression cassette into the screening strain is shown in FIG. 11. The nucleotide sequence of a PCR fragment (partial cbh1 promoter, cbh2 gene, and partial amdS gene) amplified from pTTTpyrG-CBH2 using the primers of SEQ ID NO:20 and SEQ ID NO:21, is provided below as SEQ ID NO:22:

```
gaccggacgtgttttgcccttcatttggagaaataatgtcattgcgatgt
gtaatttgcctgcttgaccgactggggctgttcgaagcccgaatgtagga
ttgttatccgaactctgctcgtagaggcatgttgtgaatctgtgtcgggc
aggacacgcctcgaaggttcacggcaagggaaaccaccgatagcagtgtc
tagtagcaacctgtaaagccgcaatgcagcatcactggaaaatacaaacc
aatggctaaaagtacataagttaatgcctaaagaagtcatataccagcgg
ctaataattgtacaatcaagtggctaaacgtaccgtaatttgccaacggc
ttgtggggttgcagaagcaacggcaaagcccacttccccacgtttgttt
cttcactcagtccaatctcagctggtgatcccccaattgggtcgcttgtt
tgttccggtgaagtgaaagaagacagaggtaagaatgtctgactcggagc
gttttgcatacaaccaagggcagtgatggaagacagtgaaatgttgacat
tcaaggagtatttagccagggatgcttgagtgtatcgtgtaaggaggttt
gtctgccgatacgacgaatactgtatagtcacttctgatgaagtggtcca
tattgaaatgtaaagtcggcactgaacaggcaaaagattgagttgaaact
gcctaagatctcgggccctcgggccttcggcctttgggtgtacatgtttg
tgctccgggcaaatgcaaagtgtggtaggatcgaacacactgctgccttt
accaagcagctgagggtatgtgataggcaaatgttcaggggccactgcat
ggtttcgaatagaaagagaagcttagccaagaacaatagccgataaagat
agcctcattaaacggaatgagctagtaggcaaagtcagcgaatgtgtata
tataaaggacgaggtccgtgcctccctcatgctctccccatctactcatc
aactcagatcctccaggagacttgtacaccatcttttgaggcacagaaac
ccaatagtcaaccatcacaagtttgtacaaaaaagcaggctccgcggccg
cccccttcacccaccatgattgtcggcattctcaccacgctggctacgct
ggccacactcgcagctagtgtgcctctagaggagcggcaagcttgctcaa
gcgtctggtaattatgtgaaccctctcaagagacccaaatactgagatat
gtcaaggggccaatgtggtggccagaattggtcgggtccgacttgctgtg
atccggaagcacatgcgtctactccaacgactattactcccagtgtcttc
ccggcgctgcaagctcaagctcgtccacgcgcgccgcgtcgacgacttct
cgagtatcccccacaacatcccggtcgagctccgcgacgcctccacctgg
ttctactactaccagagtacctccagtcggatcgggaaccgctacgtatt
caggcaacccttttgttggggtcactccttgggccaatgcatattacgcc
tctgaagttagcagcctcgctattcctagcttgactggagccatggccac
tgctgcagcagctgtcgcaaaggttccctcttttatgtggctgtaggtcc
tcccggaaccaaggcaatctgttactgaaggctcatcattcactgcagag
atactcttgacaagaccctctcatggagcaaaccttggccgacatccgc
accgccaacaagaatggcggtaactatgccggacagtttgtggtgtatga
cttgccggatcgcgattgcgctgcccttgcctcgaatggcgaatactcta
ttgccgatggtggcgtcgccaaatataagaactatatcgacaccattcgt
caaattgtcgtggaatattccgatatccggaccctcctggttattggTAt
gagtttaaacacctgcctcccccccccttccctccttttcccgccggca
tcttgtcgttgtgctaactattgttccctcttccagagcctgactctctt
gccaacctggtgaccaacctcggtactccaaagtgtgccaatgctcagtc
agcctaccttgagtgcatcaactacgccgtcacacagctgaaccttccaa
atgttgcgatgtatttggacgctggccatgcaggatggcttggctggccg
gcaaaccaagacccggccgctcagctatttgcaaatgtttacaagaatgc
atcgtctccgagagctcttcgcggattggcaaccaatgtcgccaactaca
acgggtggaacattaccagcccccatcgtacacgcaaggcaacgctgtc
tacaacgagaagctgtacatccacgctattggacctcttcttgccaatca
```

-continued

```
cggctggtccaacgccttcttcatcactgatcaaggtcgatcgggaaagc
agcctaccggacagcaacagtggggagactggtgcaatgtgatcggcacc
ggatttggtattcgccatccgcaaacactggggactcgttgctggattc
gtttgtctgggtcaagccaggcggcgagtgtgacggcaccagcgacagca
gtgcgccacgatttgactcccactgtgcgctcccagatgccttgcaaccg
gcgcctcaagctggtgcttggttccaagcctactttgtgcagcttctcac
aaacgcaaacccatcgttcctgtaaAagggtgggcgcgccgacccagctt
tcttgtacaaagtggtgatcgcgccgcgcgccagctccgtgcgaaagcct
gacgcaccggtagattcttggtgagcccgtatcatgacggcggcgggagc
tacatggccccgggtgatttatttttttttgtatctacttctgacccttt
caaatatacggtcaactcatctttcactggagatgcggcctgcttggtat
tgcgatgttgtcagcttggcaaattgtggctttcgaaaacacaaaacgat
tccttagtagccatgcattttaagataacggaatagaagaaagaggaaat
taaaaaaaaaaaaaaaacaaacatcccgttcataacccgtagaatcgccg
ctcttcgtgtatcccagtaccagtttattttgaatagctcgcccgctgga
gagcatcctgaatgcaagtaacaaccgtagaggctgacacggcaggtgtt
gctagggagcgtcgtgttctacaaggccagacgtcttcgcggttgatata
tatgtatgtttgactgcaggctgctcagcgacgacagtcaagttcgccct
cgctgcttgtgcaataatcgcagtggggaagccacaccgtgactcccatc
tttcagtaaagctctgttggtgtttatcagcaatacacgtaatttaaact
cgttagcatggggctgatagcttaattaccgtttaccagtgccatggttc
tgcagctttccttggcccgtaaaattcggcgaagccagccaatcaccagc
taggcaccagctaaaccctataattagtctcttatcaacaccatccgctc
ccccgggatcaatgaggagaatgagggggatgcggggctaaagaagccta
cataaccctcatgccaactcccagtttacactcgtcgagccaacatcctg
actataagctaacacagaatgcctcaatcctgggaagaactggccgctga
taagcgcgcccgcctcgcaaaaaccatccctgatgaatggaaagtccaga
cgctgcctgcggaagacagcgttattgatttcccaaagaaatcggggatc
ctttcagaggccgaactgaagatcacagaggcctccgctgcagatcttgt
gtccaagctggcggccggagagttgacctcggtggaagttacgctagcat
tctgtaaacgggcagcaatcgcccagcagttagtagggtcccctctacct
ctcagggagatgtaacaacgccaccttatgggactatcaagctgacgctg
gcttctgtgcagacaaactgcgcccacgagttcttccctgacgccgctct
cgcgcaggcaagggaactcgatgaatactacgcaaagcacaagagacccg
ttggtccactccatggcctcccatctctctcaaagaccagcttcgagtc
aaggtacaccgttgcccctaagtcgttagatgtcccttttttgtcagctaa
catatgccaccagggctacgaaacatcaatgggctacatctcatggctaa
acaagtacgacgaaggggactcggttctgacaaccatgctccgcaaagcc
ggtgccgtcttctacgtcaagacctctgtcccgcagaccctgatggtctg
cgagacagtcaacaacatcatcgggcgcaccgtcaacccacgcaacaaga
actggtcgtgcggcggcagttctggtggtgagggtgcgatcgttgggatt
cgtggtggcgtcatcggtgtaggaacggatatcggtggctcgattcgagt
gccggccgcgttcaacttcctgtacggtctaaggccgagtcatgggcggc
tgccgtatgcaaagatggcgaacagcatggagggtcaggagacggtgcac
agcgttgtcgggccgattacgcactctgttgagggtgagtccttcgcctc
ttccttcttttcctgctctataccaggcctccactgtcctcctttcttgc
ttttatactatatacgagaccggcagtcactgatgaagtatgttagacc
tccgcctcttcaccaaatccgtcctcggtcaggagccatggaaatacgac
tccaaggtcatcccatgccctggcgccagtccgagtcggacattattgc
ctccaagatcaagaacggcgggctcaatatcggctactacaacttcgacg
gcaatgtccttccacaccctcctatcctgcgcggcgtggaaaccaccgtc
gccgcactcgccaaagccggtcacacc.
```

Protoplasts of the AD5 H. jecorina strain (Δegl1, Δegl2, Δcbh1, Δcbh2, Δbgl1) described in Example 6 were transformed with the linear DNA library as described (US 2006/0094080) and grown on selective agar containing acetamide at 28° C. for 7 days (0.6 g/L acetamide, 1.68 g/L CsCl, 20 g/L glucose, 6 g/L KH2PO4, 0.6 g/L MgSO4.7H2O, 0.6 g/L CaCl2.2H2O, 0.5 g/L uridine, trace element salts, 10 g/L low melting point agarose). After 24 hours the agar was overlaid with selective agar supplemented with 1.2 g/L fluoroorotic acid (FOA). A total of 380 colonies were transferred to potato dextrose agar plates containing 1.2 g/L FOA and incubated at 28° C. for 4-5 days. Spores were transferred to fresh potato dextrose agar plates, which were incubated at 28° C. for 3 days. Alternatively, protoplasts of the MAD6 strain described in Example 6 can be employed instead of AD5 for expression of variant library members. Likewise, protoplasts of derivatives of the MAD6 strain in which additional cellulases have been inactivated can be used for this purpose. Such derivatives would exhibit even less background cellulase activity.

For CBH2 variant protein production, spores were transferred using a 96-pin replicator to 200 μl glycine minimal medium supplemented with 2% glucose/sophorose mixture in a PVDF filter plate: 6.0 g/L glycine, 4.7 g/L $(NH_4)_2SO_4$; 5.0 g/L $KH_2PO_4$; 1.0 g/L $MgSO_4.7H_2O$; 33.0 g/L PIPPS; pH 5.5; with sterile addition of a 2% glucose/sophorose mixture as the carbon source, 10 ml/L of 100 g/L of $CaCl_{2, 2.5}$ ml/L of T. reesei trace elements (400×): 175 g/L Citric acid anhydrous; 200 g/L $FeSO_4.7H_2O$; 16 g/L $ZnSO_4.7H_2O$; 3.2 g/L $CuSO_4.5H_2O$; 1.4 g/L $MnSO_4.H_2O$; 0.8 g/L $H_3BO_3$. Each CBH2 variant was grown in quadruplicate. After sealing the plate with an oxygen permeable membrane, the plates were incubated at 28° C. for 6 days, while shaking at 200 rpm. Supernatant was harvested by transferring the culture medium to a microtiter plate under low pressure.

A total of ten variants that showed improved activity on corn cob at 57° C. were isolated. Genomic DNA of these strains was isolated and their cbh2 gene sequences determined. The CBH2 variants were tested for properties of interest. The substitutions and activities of combinatorial library members on corncob and corn stover is shown in Table 8-2. The specific activities for washed dilute acid pretreated corn-stover (PCS 50° C.), for corncob at 50° C. (CC 50° C.), and for corncob at 57° C. (CC 57° C.) were determined as described in Example 7.

TABLE 8-2

CBH2 Combinatorial Variants with Improved Activity on Corncob at 57° C.

| Variant | CC 57° C. | CC 50° C. | PCS 50° C. |
|---|---|---|---|
| CBH2.S291E/Q362I | 1.2 | 0.97 | 1.13 |
| CBH2.P98Q/S316P/Q362L/L439P | 1.52 | 0.97 | 0.1 |
| CBH2.P98Q/N182W/S291E/S316P/C400S | 1.26 | 0.97 | 0.75 |
| CBH2.P98Q/N182W/S291E/S316P/C400S | 1.24 | 0.97 | 1.02 |
| CBH2.P98L/N182W/S291E/Q362I/C400S | 1.26 | 0.97 | 1.05 |
| CBH2.P98L/N182W/S291E/Q362I/C400S | 1.28 | 0.97 | 1.14 |
| CBH2.T74S/P98L/N182W/S291E | 1.31 | 0.97 | 1.13 |
| CBH2.P98L/N182W/S291E/S316P/Q362I | 1.26 | 0.97 | 1.22 |
| CBH2.N182W/S291E/Q362L/C400S | 1.3 | 0.97 | 1.08 |
| CBH2.S291E/Q362L | 1.29 | 0.97 | 1.18 |

Example 9

CBH2 Singly and Doubly Substituted Variants and Activities Thereof

Synthetic genes encoding CBH2 variants were constructed by GeneOracle (Mountain View, Calif.) in pTTTpyrG. Table 9-1 lists the single and double variants that were constructed (numbered according to the CBH2 mature amino acid sequence).

TABLE 9-1

Singly and Doubly Substituted CBH2 Variants

| # | Substitution(s) |
|---|---|
| 1. | P98Q |
| 2. | T138C |
| 3. | S316P |
| 4. | S343Q |
| 5. | Q362I |
| 6. | S386C |
| 7. | C400S |
| 8. | S406P |
| 9. | P98Q/T138C |
| 10. | P98Q/S316P |
| 11. | P98Q/S343Q |
| 12. | P98Q/Q362I |
| 13. | P98Q/S386C |
| 14. | P98Q/C400S |
| 15. | P98Q/S406P |
| 16. | T138C/S316P |
| 17. | T138C/S343Q |
| 18. | T138C/Q362I |
| 19. | T138C/S386C |
| 20. | T138C/C400S |
| 21. | T138C/S406P |
| 22. | S316P/S343Q |
| 23. | S316P/Q362I |
| 24. | S316P/S386C |
| 25. | S316P/C400S |
| 26. | S316P/S406P |
| 27. | S343Q/Q362I |
| 28. | S343Q/S386C |
| 29. | S343Q/C400S |
| 30. | S343Q/S406P |
| 31. | Q362I/S386C |
| 32. | Q362I/C400S |
| 33. | Q362I/S406P |
| 34. | S386C/C400S |
| 35. | S386C/S406P |
| 36. | C400S/S406P |

The cbh2 variant genes were received from the abovementioned provider as purified PCR products in which primers GACCGGACGTGTTTTGCCCTTCAT (SEQ ID NO:20) and GTGTGACCGGCTTTGGCGAGTG (SEQ ID NO:21) were used to amplify the cbh2 gene flanked upstream by about 1000 bp of the cbh1 promoter and downstream by about 1000 bp of the amdS marker for forced integration in the pyr2 locus in the *H. jecorina* host strain. The nucleotide sequence of a PCR fragment (partial cbh1 promoter, cbh2 gene, and partial amdS gene) amplified from pTTTpyrG-CBH2 using the primers of SEQ ID NO:20 and SEQ ID NO:21, is provided above in Example 8 as SEQ ID NO:2q22.

Protoplasts of the MAD6 *H. jecorina* strain (Δegl1, Δegl2, Δegl3, Δcbh1, Δcbh2, Δbgl1) described in Example 6, were transformed with the linear DNA fragments as described (US 2006/0094080) and grown on selective agar containing acetamide at 28° C. for 7 days as described. After 24 hours the agar was overlain with selective agar supplemented with 1.2 g/L fluoro-orotic acid (FOA). Colonies were transferred to potato dextrose agar plates containing 1.2 g/L FOA and incubated at 28° C. for 4-5 days. Spores were transferred to potato dextrose agar plates, which were incubated at 28° C. for 3 days.

The variants were grown in microtiterplates as described in Example 8. For growth in shake flasks, 25 ml of YEG culture (5 g/L yeast extract, 20 g/L glucose) was inoculated with a sporulating *Trichoderma* strain on agar and incubated at 28° C. at 200 rpm for 2 days. Next, 5 ml of the YEG culture was used to inoculate 45 ml of glycine medium containing a 2% glucose sophorose mixture in a shake flask. Following inoculation, the cultures were incubated in a resonant acoustic incubator (Applikon) at 28° C. for 3 days. Cells were removed by filtration through a 0.2 μm filter. Supernatants were concentrated using Vivaspin spin cells with a 10 kD molecular weight cutoff.

Samples grown in microtiter plate were analyzed for CBH2 production levels by HPLC as described in Example 1. Both microtiter plate and shake flask grown samples were tested for properties of interest. Table 9-2 lists the performance of the CBH2 variants for multiple properties of interest.

TABLE 9-2

Performance of Singly and Doubly Substituted CBH2 Variants.

| Variant | HPLC | PASC | PCS | CC50 | CC57 | Tm[1] (° C.) | IR[2] |
|---|---|---|---|---|---|---|---|
| 1 | 0.53 | 1.04 | 1.03 | 0.98 | 1.04 | 57.4 | 1.11 |
| 2 | 0.76 | 1.00 | 1.06 | 1.03 | 1.10 | 50.1 | 1.06 |
| 3 | 1.01 | 0.98 | 1.04 | 0.99 | 1.00 | 55.2 | 1.40 |
| 4 | 0.98 | 0.91 | 0.99 | 0.94 | 0.94 | 56.9 | 1.05 |
| 5 | 0.97 | 0.93 | 1.02 | 1.03 | 1.08 | 56.3 | 1.20 |
| 6 | 0.48 | 1.01 | 1.01 | 1.02 | 1.05 | 54.2 | 0.89 |
| 7 | 1.07 | 0.94 | 0.96 | 0.95 | 0.97 | 64.9 | 2.29 |
| 8 | 1.02 | 0.95 | 1.05 | 0.99 | 1.07 | 58.6 | 1.22 |
| 9 | 0.53 | 1.01 | 1.03 | 1.00 | 1.03 | 59.3 | 1.19 |
| 10 | 0.63 | 0.94 | 0.97 | 0.96 | 1.06 | 59.5 | 1.50 |
| 11 | 0.56 | 0.98 | 0.94 | 1.05 | 0.95 | 57.6 | 1.12 |
| 12 | 0.50 | 0.99 | 1.01 | 1.15 | 1.07 | 58.7 | 1.39 |
| 13 | 0.19 | 1.19 | 0.87 | 1.02 | 1.12 | 50.3 | 1.21 |
| 14 | 0.96 | 0.97 | 1.01 | 0.97 | 1.11 | 59.3 | 2.39 |
| 15 | 0.66 | 0.97 | 0.97 | 1.00 | 1.10 | 57.0 | 1.40 |
| 16 | 0.84 | 0.99 | 1.03 | 1.03 | 1.15 | 59.4 | 1.60 |
| 17 | 0.78 | 1.00 | 1.00 | 1.04 | 1.04 | 52.0 | 1.45 |
| 18 | 0.72 | 1.02 | 1.00 | 0.98 | 1.03 | 57.6 | 1.28 |
| 19 | 0.40 | 1.02 | 1.05 | 1.01 | 1.08 | 56.6 | 1.08 |
| 20 | 0.94 | 0.96 | 1.02 | 0.92 | 1.10 | 59.0 | 2.30 |
| 21 | 0.83 | 0.94 | 0.99 | 0.96 | 1.04 | 54.4 | 1.37 |
| 22 | 1.04 | 0.88 | 0.96 | 0.92 | 0.99 | 47.3 | 1.26 |
| 23 | 1.00 | 0.91 | 0.96 | 1.00 | 0.97 | 60.4 | 1.48 |
| 24 | 0.55 | 1.02 | 1.04 | 1.07 | 1.04 | 58.7 | 1.30 |
| 25 | 1.15 | 0.96 | 0.94 | 0.87 | 0.93 | 64.6 | 3.19 |
| 26 | 0.89 | 0.94 | 0.98 | 0.98 | 0.99 | 59.2 | 1.67 |
| 27 | 0.95 | 0.89 | 0.93 | 0.95 | 0.96 | 55.8 | 1.33 |
| 28 | 0.47 | 0.98 | 0.98 | 1.00 | 1.12 | 56.9 | 1.27 |
| 29 | 1.12 | 0.93 | 1.02 | 0.93 | 1.01 | 62.3 | 2.57 |

TABLE 9-2-continued

Performance of Singly and Doubly Substituted CBH2 Variants.

| Variant | HPLC | PASC | PCS | CC50 | CC57 | Tm[1] (° C.) | IR[2] |
|---|---|---|---|---|---|---|---|
| 30 | 1.00 | 0.96 | 0.91 | 0.95 | 0.98 | 60.6 | 1.23 |
| 31 | 0.47 | 1.03 | 1.00 | 1.00 | 1.07 | 60.1 | 1.37 |
| 32 | 1.06 | 0.92 | 0.89 | 0.96 | 0.98 | 65.9 | 2.90 |
| 33 | 0.99 | 0.88 | 0.96 | 0.97 | 0.95 | 60.1 | 1.60 |
| 34 | 0.88 | 0.88 | 0.94 | 0.98 | 1.08 | 58.1 | 2.41 |
| 35 | 0.55 | 0.98 | 1.08 | 1.03 | 1.10 | 59.2 | 1.24 |
| 36 | 1.09 | 0.89 | 0.96 | 1.00 | 0.99 | 65.5 | 3.19 |
| Wt | 1.00 | 1.00 | 1.00 | 1.00 | 1.00 | 57.6 | 1.00 |

[1]Tm = pseudo melting point temperature (° C.) was determined by thermostability assay 2.
[2]IR = Performance index for stability as determined by thermostability assay 3.

CBH2 Thermostability Assay 3.

To analyze the thermostability of the CBH2 variants, 40 μl of supernatant was incubated in a PCR machine 58° C. in triplicate and samples were removed after 30, 60 and 120 min of incubation. The remaining activity was determined by incubating 10 μl supernatant with 50 μl of 1 mg/ml cellotriose in 50 mM sodium acetate buffer pH 5.0 with 0.0025% Tween20. After one hour, 40 μl of 100 mM glycine pH 10 was added. Fifty μl of 3× concentrated ABTS reagent (see above) was added and color development at OD420 was recorded for 3 min. The residual activity in time was fitted with a formula for exponential decay: $y = A_0 \cdot \exp(-k \cdot t)$, where $A_0$ is activity at t=0, t is time, and k is the decay constant. Performance indici (PI) were calculated by the following formula:

$$PI = -\log(k_{variant}) / -\log(k_{wt}).$$

We claim:

1. A recombinant cellulase variant, wherein the variant is a mature form having cellulase activity and comprising a substitution at position 362, wherein the position is numbered by correspondence with the amino acid sequence of a reference cellobiohydrolase II (CBH2) set forth as SEQ ID NO:3, wherein the variant is derived from a parent cellulase whose amino acid sequence is at least 90% identical to SEQ ID NO:3.

2. The recombinant cellulase variant of claim 1, wherein the variant comprises a further substitution at one or more further positions selected from 98 and 343, wherein the further positions are numbered by correspondence with the amino acid sequence of the reference cellobiohydrolase II (CBH2) set forth as SEQ ID NO:3.

3. A recombinant cellulase variant, wherein the variant is a mature form having cellulase activity and comprising a substitution at one or more positions selected from the group consisting of: 98 and 343, wherein the positions are numbered by correspondence with the amino acid sequence of a reference cellobiohydrolase II (CBH2) set forth as SEQ ID NO:3, and wherein when the cellulase variant consists of a single substitution, the single substitution is not P98L, wherein the variant is derived from a parent cellulase whose amino acid sequence is at least 90% identical to SEQ ID NO:3.

4. The recombinant cellulase variant of claim 3, wherein the variant comprises a further substitution at position 362, wherein the further positions are numbered by correspondence with the amino acid sequence of the reference cellobiohydrolase II (CBH2) set forth as SEQ ID NO:3.

5. A recombinant cellulase variant comprising a glutamine at position 98, and a substitution selected from the group consisting of S343Q and Q362I, wherein the positions are numbered by correspondence with the amino acid sequence of the reference cellobiohydrolase II (CBH2) set forth as SEQ ID NO:3, wherein the variant is derived from a parent cellulase whose amino acid sequence is at least 90% identical to SEQ ID NO:3.

6. A recombinant cellulase variant comprising a glutamine at position 343, and a substitution of Q362I, wherein the positions are numbered by correspondence with the amino acid sequence of the reference cellobiohydrolase II (CBH2) set forth as SEQ ID NO:3, wherein the variant is derived from a parent cellulase whose amino acid sequence is at least 90% identical to SEQ ID NO:3.

7. A recombinant cellulase variant, wherein the variant is a mature form having cellulase activity and comprising a substitution selected from the group consisting of 98, 362, and both 98 and 362, wherein the cellulase variant comprises:
Proline, leucine or glutamine at position 98;
glutamine, isoleucine or leucine at position 362;
wherein the positions are numbered by correspondence with the amino acid sequence of the reference cellobiohydrolase II (CBH2) set forth as SEQ ID NO:3, and wherein when the cellulase variant consists of a single substitution, the single substitution is not P98L substitution, wherein the variant is derived from a parent cellulase whose amino acid sequence is at least 90% identical to SEQ ID NO:3.

* * * * *

SEQUENCE LISTING

<160> NUMBER OF SEQ ID NOS: 23

<210> SEQ ID NO 1
<211> LENGTH: 1416
<212> TYPE: DNA
<213> ORGANISM: Hypocrea jecorina

<400> SEQUENCE: 1

```
atgattgtcg gcattctcac cacgctggct acgctggcca cactcgcagc tagtgtgcct      60
ctagaggagc ggcaagcttg ctcaagcgtc tggggccaat gtggtggcca gaattggtcg     120
ggtccgactt gctgtgcttc cggaagcaca tgcgtctact ccaacgacta ttactcccag     180
tgtcttcccg gcgctgcaag ctcaagctcg tccacgcgcg ccgcgtcgac gacttctcga     240
gtatccccca acatcccg gtcgagctcc gcgacgcctc cacctggttc tactactacc     300
agagtaccctc cagtcggatc gggaaccgct acgtattcag gcaacccttt tgttggggtc     360
actccttggg ccaatgcata ttacgcctct gaagttagca gcctcgctat tcctagcttg     420
actggagcca tggccactgc tgcagcagct gtcgcaaagg ttccctcttt tatgtggcta     480
gatactcttg acaagacccc tctcatggag caaaccttgg ccgacatccg caccgccaac     540
aagaatggcg gtaactatgc cggacagttt gtggtgtatg acttgccgga tcgcgattgc     600
gctgcccttg cctcgaatgg cgaatactct attgccgatg gtggcgtcgc caaatataag     660
aactatatcg acaccattcg tcaaattgtc gtggaatatt ccgatatccg gaccctcctg     720
gttattgagc ctgactctct tgccaacctg gtgaccaacc tcggtactcc aaagtgtgcc     780
aatgctcagt cagcctacct tgagtgcatc aactacgccg tcacacagct gaaccttcca     840
aatgttgcga tgtatttgga cgctggccat gcaggatggc ttggctggcc ggcaaaccaa     900
gacccggccg ctcagctatt tgcaaatgtt tacaagaatg catcgtctcc gagagctctt     960
cgcggattgg caaccaatgt cgccaactac aacgggtgga acattaccag cccccccatcg    1020
tacacgcaag gcaacgctgt ctacaacgag aagctgtaca tccacgctat tggaccttctt    1080
cttgccaatc acggctggtc caacgccttc ttcatcactg atcaaggtcg atcgggaaag    1140
cagcctaccg gacagcaaca gtggggagac tggtgcaatg tgatcggcac cggatttggt    1200
attcgcccat ccgcaaacac tggggactcg ttgctggatt cgtttgtctg ggtcaagcca    1260
ggcggcgagt gtgacggcac cagcgacagc agtgcgccac gatttgactc ccactgtgcg    1320
ctcccagatg ccttgcaacc ggcgcctcaa gctggtgctt ggttccaagc ctactttgtg    1380
cagcttctca caaacgcaaa cccatcgttc ctgtaa                              1416
```

```
<210> SEQ ID NO 2
<211> LENGTH: 471
<212> TYPE: PRT
<213> ORGANISM: Hypocrea jecorina

<400> SEQUENCE: 2

Met Ile Val Gly Ile Leu Thr Thr Leu Ala Thr Leu Ala
1               5                   10                  15

Ala Ser Val Pro Leu Glu Glu Arg Gln Ala Cys Ser Ser Val Trp Gly
                20                  25                  30

Gln Cys Gly Gly Gln Asn Trp Ser Gly Pro Thr Cys Cys Ala Ser Gly
            35                  40                  45

Ser Thr Cys Val Tyr Ser Asn Asp Tyr Tyr Ser Gln Cys Leu Pro Gly
    50                  55                  60

Ala Ala Ser Ser Ser Ser Ser Thr Arg Ala Ala Ser Thr Thr Ser Arg
65                  70                  75                  80

Val Ser Pro Thr Thr Ser Arg Ser Ser Ala Thr Pro Pro Gly
                85                  90                  95

Ser Thr Thr Thr Arg Val Pro Pro Val Gly Ser Gly Thr Ala Thr Tyr
                100                 105                 110

Ser Gly Asn Pro Phe Val Gly Val Thr Pro Trp Ala Asn Ala Tyr Tyr
            115                 120                 125

Ala Ser Glu Val Ser Ser Leu Ala Ile Pro Ser Leu Thr Gly Ala Met
            130                 135                 140

Ala Thr Ala Ala Ala Val Ala Lys Val Pro Ser Phe Met Trp Leu
145                 150                 155                 160

Asp Thr Leu Asp Lys Thr Pro Leu Met Glu Gln Thr Leu Ala Asp Ile
                165                 170                 175

Arg Thr Ala Asn Lys Asn Gly Gly Asn Tyr Ala Gly Gln Phe Val Val
            180                 185                 190

Tyr Asp Leu Pro Asp Arg Asp Cys Ala Ala Leu Ala Ser Asn Gly Glu
            195                 200                 205

Tyr Ser Ile Ala Asp Gly Gly Val Ala Lys Tyr Lys Asn Tyr Ile Asp
    210                 215                 220

Thr Ile Arg Gln Ile Val Val Glu Tyr Ser Asp Ile Arg Thr Leu Leu
225                 230                 235                 240

Val Ile Glu Pro Asp Ser Leu Ala Asn Leu Val Thr Asn Leu Gly Thr
                245                 250                 255

Pro Lys Cys Ala Asn Ala Gln Ser Ala Tyr Leu Glu Cys Ile Asn Tyr
            260                 265                 270

Ala Val Thr Gln Leu Asn Leu Pro Asn Val Ala Met Tyr Leu Asp Ala
            275                 280                 285

Gly His Ala Gly Trp Leu Gly Trp Pro Ala Asn Gln Asp Pro Ala Ala
            290                 295                 300

Gln Leu Phe Ala Asn Val Tyr Lys Asn Ala Ser Ser Pro Arg Ala Leu
305                 310                 315                 320

Arg Gly Leu Ala Thr Asn Val Ala Asn Tyr Asn Gly Trp Asn Ile Thr
                325                 330                 335

Ser Pro Pro Ser Tyr Thr Gln Gly Asn Ala Val Tyr Asn Glu Lys Leu
            340                 345                 350

Tyr Ile His Ala Ile Gly Pro Leu Leu Ala Asn His Gly Trp Ser Asn
            355                 360                 365

Ala Phe Phe Ile Thr Asp Gln Gly Arg Ser Gly Lys Gln Pro Thr Gly
            370                 375                 380
```

```
Gln Gln Gln Trp Gly Asp Trp Cys Asn Val Ile Gly Thr Gly Phe Gly
385                 390                 395                 400

Ile Arg Pro Ser Ala Asn Thr Gly Asp Ser Leu Leu Asp Ser Phe Val
                405                 410                 415

Trp Val Lys Pro Gly Gly Glu Cys Asp Gly Thr Ser Ser Ser Ser Ala
            420                 425                 430

Pro Arg Phe Asp Ser His Cys Ala Leu Pro Asp Ala Leu Gln Pro Ala
        435                 440                 445

Pro Gln Ala Gly Ala Trp Phe Gln Ala Tyr Phe Val Gln Leu Leu Thr
    450                 455                 460

Asn Ala Asn Pro Ser Phe Leu
465                 470

<210> SEQ ID NO 3
<211> LENGTH: 447
<212> TYPE: PRT
<213> ORGANISM: T. reesei

<400> SEQUENCE: 3

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285
```

```
Asn Ala Ser Ser Pro Arg Ala Leu Arg Gly Leu Ala Thr Asn Val Ala
        290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Ser His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 4
<211> LENGTH: 446
<212> TYPE: PRT
<213> ORGANISM: H. koningii

<400> SEQUENCE: 4

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ser Ser Thr Thr Ala Arg Ala Ser Ser Thr Thr Ser Arg Ser
    50                  55                  60

Ser Ala Thr Pro Pro Gly Ser Ser Thr Thr Arg Val Pro Pro Val
65                  70                  75                  80

Gly Ser Gly Thr Ala Thr Tyr Ser Gly Asn Pro Phe Val Gly Val Thr
                85                  90                  95

Pro Trp Ala Asn Ala Tyr Tyr Ala Ser Glu Val Ser Ser Leu Ala Ile
            100                 105                 110

Pro Ser Leu Thr Gly Ala Met Ala Thr Ala Ala Ala Val Ala Lys
        115                 120                 125

Val Pro Ser Ser Met Trp Leu Asp Thr Phe Asp Lys Thr Pro Leu Met
    130                 135                 140

Glu Gln Thr Leu Ala Asp Ile Arg Thr Ala Asn Lys Asn Gly Asn
145                 150                 155                 160

Tyr Ala Gly Gln Phe Val Val Tyr Asp Leu Pro Asp Arg Asp Cys Ala
                165                 170                 175

Ala Leu Ala Ser Asn Gly Glu Tyr Ser Ile Ala Asp Gly Gly Val Asp
            180                 185                 190

Lys Tyr Lys Asn Tyr Ile Asp Thr Ile Arg Gln Ile Val Val Glu Tyr
        195                 200                 205

Ser Asp Ile Arg Thr Leu Leu Val Ile Glu Pro Asp Ser Leu Ala Asn
    210                 215                 220
```

```
Leu Val Thr Asn Leu Gly Thr Pro Lys Cys Ala Asn Ala Gln Ser Ala
225                 230                 235                 240

Tyr Leu Glu Cys Ile Asn Tyr Ala Val Thr Gln Leu Asn Leu Pro Asn
            245                 250                 255

Val Ala Met Tyr Leu Asp Ala Gly His Ala Gly Trp Leu Gly Trp Pro
        260                 265                 270

Ala Asn Gln Asp Pro Ala Ala Gln Leu Phe Ala Asn Val Tyr Lys Asn
    275                 280                 285

Ala Ser Ser Pro Arg Ala Leu Arg Gly Leu Ala Thr Asn Val Ala Asn
290                 295                 300

Tyr Asn Gly Trp Asn Ile Thr Ser Pro Pro Ser Tyr Thr Gln Gly Asn
305                 310                 315                 320

Ala Val Tyr Asn Glu Gln Leu Tyr Ile His Ala Ile Gly Pro Leu Leu
                325                 330                 335

Ala Asn His Gly Trp Ser Asn Ala Phe Phe Ile Thr Asp Gln Gly Arg
            340                 345                 350

Ser Gly Lys Gln Pro Thr Gly Gln Gln Gln Trp Gly Asp Trp Cys Asn
        355                 360                 365

Val Ile Gly Thr Gly Phe Gly Ile Arg Pro Ser Ala Asn Thr Gly Asp
    370                 375                 380

Ser Leu Leu Asp Ser Phe Val Trp Ile Lys Pro Gly Gly Glu Cys Asp
385                 390                 395                 400

Gly Thr Ser Asp Ser Ser Ala Pro Arg Phe Asp Ser His Cys Ala Leu
                405                 410                 415

Pro Asp Ala Leu Gln Pro Ala Pro Gln Ala Gly Ala Trp Phe Gln Ala
            420                 425                 430

Tyr Phe Val Gln Leu Leu Thr Asn Ala Asn Pro Ser Phe Leu
        435                 440                 445

<210> SEQ ID NO 5
<211> LENGTH: 460
<212> TYPE: PRT
<213> ORGANISM: H. insolens

<400> SEQUENCE: 5

Ala Pro Val Val Glu Glu Arg Gln Asn Cys Ala Pro Thr Trp Gly Gln
1               5                   10                  15

Cys Gly Gly Ile Gly Phe Asn Gly Pro Thr Cys Cys Gln Ser Gly Ser
            20                  25                  30

Thr Cys Val Lys Gln Asn Asp Trp Tyr Ser Gln Cys Leu Pro Gly Ser
        35                  40                  45

Gln Val Thr Thr Thr Ser Thr Thr Ser Thr Ser Ser Ser Ser Thr Thr
    50                  55                  60

Ser Arg Ala Thr Ser Thr Thr Arg Thr Gly Gly Val Thr Ser Ile Thr
65                  70                  75                  80

Thr Ala Pro Thr Arg Thr Val Thr Ile Pro Gly Gly Ala Thr Thr Thr
                85                  90                  95

Ala Ser Tyr Asn Gly Asn Pro Phe Glu Gly Val Gln Leu Trp Ala Asn
            100                 105                 110

Asn Tyr Tyr Arg Ser Glu Val His Thr Leu Ala Ile Pro Gln Ile Thr
        115                 120                 125

Asp Pro Ala Leu Arg Ala Ala Ala Ser Ala Val Ala Glu Val Pro Ser
    130                 135                 140

Phe Gln Trp Leu Asp Arg Asn Val Thr Val Asp Thr Leu Leu Val Glu
145                 150                 155                 160
```

```
Thr Leu Ser Glu Ile Arg Ala Ala Asn Gln Ala Gly Ala Asn Pro Pro
                165                 170                 175

Tyr Ala Ala Gln Ile Val Val Tyr Asp Leu Pro Asp Arg Asp Cys Ala
            180                 185                 190

Ala Ala Ala Ser Asn Gly Glu Trp Ala Ile Ala Asn Asn Gly Ala Asn
        195                 200                 205

Asn Tyr Lys Gly Tyr Ile Asn Arg Ile Arg Glu Ile Leu Ile Ser Phe
    210                 215                 220

Ser Asp Val Arg Thr Ile Leu Val Ile Glu Pro Asp Ser Leu Ala Asn
225                 230                 235                 240

Met Val Thr Asn Met Asn Val Ala Lys Cys Ser Gly Ala Ala Ser Thr
                245                 250                 255

Tyr Arg Glu Leu Thr Ile Tyr Ala Leu Lys Gln Leu Asp Leu Pro His
            260                 265                 270

Val Ala Met Tyr Met Asp Ala Gly His Ala Gly Trp Leu Gly Trp Pro
        275                 280                 285

Ala Asn Ile Gln Pro Ala Ala Glu Leu Phe Ala Lys Ile Tyr Glu Asp
    290                 295                 300

Ala Gly Lys Pro Arg Ala Val Arg Gly Leu Ala Thr Asn Val Ala Asn
305                 310                 315                 320

Tyr Asn Ala Trp Ser Ile Ser Ser Pro Pro Tyr Thr Ser Pro Asn
                325                 330                 335

Pro Asn Tyr Asp Glu Lys His Tyr Ile Glu Ala Phe Arg Pro Leu Leu
            340                 345                 350

Glu Ala Arg Gly Phe Pro Ala Gln Phe Ile Val Asp Gln Gly Arg Ser
        355                 360                 365

Gly Lys Gln Pro Thr Gly Gln Lys Glu Trp Gly His Trp Cys Asn Ala
    370                 375                 380

Ile Gly Thr Gly Phe Gly Met Arg Pro Thr Ala Asn Thr Gly His Gln
385                 390                 395                 400

Tyr Val Asp Ala Phe Val Trp Val Lys Pro Gly Gly Glu Cys Asp Gly
                405                 410                 415

Thr Ser Asp Thr Thr Ala Ala Arg Tyr Asp Tyr His Cys Gly Leu Glu
            420                 425                 430

Asp Ala Leu Lys Pro Ala Pro Glu Ala Gly Gln Trp Phe Gln Ala Tyr
        435                 440                 445

Phe Glu Gln Leu Leu Arg Asn Ala Asn Pro Pro Phe
    450                 455                 460

<210> SEQ ID NO 6
<211> LENGTH: 457
<212> TYPE: PRT
<213> ORGANISM: A. cellulolyticus

<400> SEQUENCE: 6

Met Leu Arg Tyr Leu Ser Ile Val Ala Ala Thr Ala Ile Leu Thr Gly
1               5                   10                  15

Val Glu Ala Gln Gln Ser Val Trp Gly Gln Cys Gly Gly Gln Gly Trp
            20                  25                  30

Ser Gly Ala Thr Ser Cys Ala Ala Gly Ser Thr Cys Ser Thr Leu Asn
        35                  40                  45

Pro Tyr Tyr Ala Gln Cys Ile Pro Gly Thr Ala Thr Ser Thr Thr Leu
    50                  55                  60

Val Lys Thr Thr Ser Ser Thr Ser Val Gly Thr Thr Ser Pro Pro Thr
65                  70                  75                  80
```

Thr Thr Thr Thr Lys Ala Ser Thr Thr Ala Thr Thr Ala Ala Ala
            85                  90                  95

Ser Gly Asn Pro Phe Ser Gly Tyr Gln Leu Tyr Ala Asn Pro Tyr Tyr
            100                 105                 110

Ser Ser Glu Val His Thr Leu Ala Ile Pro Ser Leu Thr Gly Ser Leu
        115                 120                 125

Ala Ala Ala Ala Thr Lys Ala Ala Glu Ile Pro Ser Phe Val Trp Leu
    130                 135                 140

Asp Thr Ala Ala Lys Val Pro Thr Met Gly Thr Tyr Leu Ala Asn Ile
145                 150                 155                 160

Glu Ala Ala Asn Lys Ala Gly Ala Ser Pro Ile Ala Gly Ile Phe
                165                 170                 175

Val Val Tyr Asp Leu Pro Asp Arg Asp Cys Ala Ala Ala Ser Asn
                180                 185                 190

Gly Glu Tyr Thr Val Ala Asn Asn Gly Val Ala Asn Tyr Lys Ala Tyr
            195                 200                 205

Ile Asp Ser Ile Val Ala Gln Leu Lys Ala Tyr Pro Asp Val His Thr
        210                 215                 220

Ile Leu Ile Ile Glu Pro Asp Ser Leu Ala Asn Met Val Thr Asn Leu
225                 230                 235                 240

Ser Thr Ala Lys Cys Ala Glu Ala Gln Ser Ala Tyr Tyr Glu Cys Val
                245                 250                 255

Asn Tyr Ala Leu Ile Asn Leu Asn Leu Ala Asn Val Ala Met Tyr Ile
                260                 265                 270

Asp Ala Gly His Ala Gly Trp Leu Gly Trp Ser Ala Asn Leu Ser Pro
            275                 280                 285

Ala Ala Gln Leu Phe Ala Thr Val Tyr Lys Asn Ala Ser Ala Pro Ala
        290                 295                 300

Ser Leu Arg Gly Leu Ala Thr Asn Val Ala Asn Tyr Asn Ala Trp Ser
305                 310                 315                 320

Ile Ser Ser Pro Pro Ser Tyr Thr Ser Gly Asp Ser Asn Tyr Asp Glu
                325                 330                 335

Lys Leu Tyr Ile Asn Ala Leu Ser Pro Leu Leu Thr Ser Asn Gly Trp
            340                 345                 350

Pro Asn Ala His Phe Ile Met Asp Thr Ser Arg Asn Gly Val Gln Pro
        355                 360                 365

Thr Lys Gln Gln Ala Trp Gly Asp Trp Cys Asn Val Ile Gly Thr Gly
    370                 375                 380

Phe Gly Val Gln Pro Thr Thr Asn Thr Gly Pro Leu Glu Asp Ala
385                 390                 395                 400

Phe Val Trp Val Lys Pro Gly Gly Glu Ser Asp Gly Thr Ser Asn Ser
                405                 410                 415

Ser Ala Thr Arg Tyr Asp Phe His Cys Gly Tyr Ser Asp Ala Leu Gln
            420                 425                 430

Pro Ala Pro Glu Ala Gly Thr Trp Phe Gln Ala Tyr Phe Val Gln Leu
        435                 440                 445

Leu Thr Asn Ala Asn Pro Ala Leu Val
    450                 455

<210> SEQ ID NO 7
<211> LENGTH: 418
<212> TYPE: PRT
<213> ORGANISM: A. bisporus

<400> SEQUENCE: 7

```
Gln Ser Pro Val Trp Gly Gln Cys Gly Gly Asn Gly Trp Thr Gly Pro
1               5                   10                  15

Thr Thr Cys Ala Ser Gly Ser Thr Cys Val Lys Gln Asn Asp Phe Tyr
            20                  25                  30

Ser Gln Cys Leu Pro Asn Asn Gln Ala Pro Pro Ser Thr Thr Thr Gln
        35                  40                  45

Pro Gly Thr Thr Pro Pro Ala Thr Thr Thr Ser Gly Gly Thr Gly Pro
    50                  55                  60

Thr Ser Gly Ala Gly Asn Pro Tyr Thr Gly Lys Thr Val Trp Leu Ser
65                  70                  75                  80

Pro Phe Tyr Ala Asp Glu Val Ala Gln Ala Ala Asp Ile Ser Asn
                85                  90                  95

Pro Ser Leu Ala Thr Lys Ala Ala Ser Val Ala Lys Ile Pro Thr Phe
            100                 105                 110

Val Trp Phe Asp Thr Val Ala Lys Val Pro Asp Leu Gly Gly Tyr Leu
            115                 120                 125

Ala Asp Ala Arg Ser Lys Asn Gln Leu Val Gln Ile Val Val Tyr Asp
        130                 135                 140

Leu Pro Asp Arg Asp Cys Ala Ala Leu Ala Ser Asn Gly Glu Phe Ser
145                 150                 155                 160

Leu Ala Asn Asp Gly Leu Asn Lys Tyr Lys Asn Tyr Val Asp Gln Ile
                165                 170                 175

Ala Ala Gln Ile Lys Gln Phe Pro Asp Val Ser Val Val Ala Val Ile
            180                 185                 190

Glu Pro Asp Ser Leu Ala Asn Leu Val Thr Asn Leu Asn Val Gln Lys
        195                 200                 205

Cys Ala Asn Ala Gln Ser Ala Tyr Lys Glu Gly Val Ile Tyr Ala Val
210                 215                 220

Gln Lys Leu Asn Ala Val Gly Val Thr Met Tyr Ile Asp Ala Gly His
225                 230                 235                 240

Ala Gly Trp Leu Gly Trp Pro Ala Asn Leu Ser Pro Ala Ala Gln Leu
            245                 250                 255

Phe Ala Gln Ile Tyr Arg Asp Ala Gly Ser Pro Arg Asn Leu Arg Gly
            260                 265                 270

Ile Ala Thr Asn Val Ala Asn Phe Asn Ala Leu Arg Ala Ser Ser Pro
        275                 280                 285

Asp Pro Ile Thr Gln Gly Asn Ser Asn Tyr Asp Glu Ile His Tyr Ile
        290                 295                 300

Glu Ala Leu Ala Pro Met Leu Ser Asn Ala Gly Phe Pro Ala His Phe
305                 310                 315                 320

Ile Val Asp Gln Gly Arg Ser Gly Val Gln Asn Ile Arg Asp Gln Trp
            325                 330                 335

Gly Asp Trp Cys Asn Val Lys Gly Ala Gly Phe Gly Gln Arg Pro Thr
            340                 345                 350

Thr Asn Thr Gly Ser Ser Leu Ile Asp Ala Ile Val Trp Val Lys Pro
        355                 360                 365

Gly Gly Glu Cys Asp Gly Thr Ser Asp Asn Ser Ser Pro Arg Phe Asp
            370                 375                 380

Ser His Cys Ser Leu Ser Asp Ala His Gln Pro Ala Pro Glu Ala Gly
385                 390                 395                 400

Thr Trp Phe Gln Ala Tyr Phe Glu Thr Leu Val Ala Asn Ala Asn Pro
                405                 410                 415

Ala Leu
```

```
<210> SEQ ID NO 8
<211> LENGTH: 446
<212> TYPE: PRT
<213> ORGANISM: F. oxysporum

<400> SEQUENCE: 8
```

| | | | | | | | | | | | | | | | |
|---|---|---|---|---|---|---|---|---|---|---|---|---|---|---|---|
| Ala | Pro | Val | Glu | Glu | Arg | Gln | Ser | Cys | Ser | Asn | Gly | Val | Trp | Ala | Gln |
| 1 | | | | 5 | | | | | 10 | | | | | 15 | |
| Cys | Gly | Gly | Gln | Asn | Trp | Ser | Gly | Thr | Pro | Cys | Cys | Thr | Ser | Gly | Asn |
| | | | 20 | | | | | 25 | | | | | 30 | | |
| Lys | Cys | Val | Lys | Leu | Asn | Asp | Phe | Tyr | Ser | Gln | Cys | Gln | Pro | Gly | Ser |
| | | 35 | | | | | 40 | | | | | 45 | | | |
| Ala | Glu | Pro | Ser | Ser | Thr | Ala | Ala | Gly | Pro | Ser | Ser | Thr | Thr | Ala | Thr |
| | 50 | | | | | 55 | | | | | 60 | | | | |
| Lys | Thr | Thr | Ala | Thr | Gly | Gly | Ser | Ser | Thr | Thr | Ala | Gly | Gly | Ser | Val |
| 65 | | | | | 70 | | | | | 75 | | | | | 80 |
| Thr | Ser | Ala | Pro | Pro | Ala | Ala | Ser | Asp | Asn | Pro | Tyr | Ala | Gly | Val | Asp |
| | | | | 85 | | | | | 90 | | | | | 95 | |
| Leu | Trp | Ala | Asn | Asn | Tyr | Tyr | Arg | Ser | Glu | Val | Met | Asn | Leu | Ala | Val |
| | | | | 100 | | | | | 105 | | | | | 110 | |
| Pro | Lys | Leu | Ser | Gly | Ala | Lys | Ala | Thr | Ala | Ala | Ala | Lys | Val | Ala | Asp |
| | | | 115 | | | | | 120 | | | | | 125 | | |
| Val | Pro | Ser | Phe | Gln | Trp | Met | Asp | Thr | Tyr | Asp | His | Ile | Ser | Leu | Met |
| | 130 | | | | | 135 | | | | | 140 | | | | |
| Glu | Asp | Thr | Leu | Ala | Asp | Ile | Arg | Lys | Ala | Asn | Lys | Ala | Gly | Gly | Lys |
| 145 | | | | | 150 | | | | | 155 | | | | | 160 |
| Tyr | Ala | Gly | Gln | Phe | Val | Val | Tyr | Asp | Leu | Pro | Asn | Arg | Asp | Cys | Ala |
| | | | | 165 | | | | | 170 | | | | | 175 | |
| Ala | Ala | Ala | Ser | Asn | Gly | Glu | Tyr | Ser | Leu | Asp | Lys | Asp | Gly | Ala | Asn |
| | | | 180 | | | | | 185 | | | | | 190 | | |
| Lys | Tyr | Lys | Ala | Tyr | Ile | Ala | Lys | Ile | Lys | Gly | Ile | Leu | Gln | Asn | Tyr |
| | | 195 | | | | | 200 | | | | | 205 | | | |
| Ser | Asp | Thr | Lys | Val | Ile | Leu | Val | Ile | Glu | Pro | Asp | Ser | Leu | Ala | Asn |
| | 210 | | | | | 215 | | | | | 220 | | | | |
| Leu | Val | Thr | Asn | Leu | Asn | Val | Asp | Lys | Cys | Ala | Lys | Ala | Glu | Ser | Ala |
| 225 | | | | | 230 | | | | | 235 | | | | | 240 |
| Tyr | Lys | Glu | Leu | Thr | Val | Tyr | Ala | Ile | Lys | Glu | Leu | Asn | Leu | Pro | Asn |
| | | | | 245 | | | | | 250 | | | | | 255 | |
| Val | Ser | Met | Tyr | Leu | Asp | Ala | Gly | His | Gly | Gly | Trp | Leu | Gly | Trp | Pro |
| | | | 260 | | | | | 265 | | | | | 270 | | |
| Ala | Asn | Ile | Gly | Pro | Ala | Ala | Lys | Leu | Tyr | Ala | Gln | Ile | Tyr | Lys | Asp |
| | | 275 | | | | | 280 | | | | | 285 | | | |
| Ala | Gly | Lys | Pro | Ser | Arg | Val | Arg | Gly | Leu | Val | Thr | Asn | Val | Ser | Asn |
| | 290 | | | | | 295 | | | | | 300 | | | | |
| Tyr | Asn | Gly | Trp | Lys | Leu | Ser | Thr | Lys | Pro | Asp | Tyr | Thr | Glu | Ser | Asn |
| 305 | | | | | 310 | | | | | 315 | | | | | 320 |
| Pro | Asn | Tyr | Asp | Glu | Gln | Arg | Tyr | Ile | Asn | Ala | Phe | Ala | Pro | Leu | Leu |
| | | | | 325 | | | | | 330 | | | | | 335 | |
| Ala | Gln | Glu | Gly | Trp | Ser | Asn | Val | Lys | Phe | Ile | Val | Asp | Gln | Gly | Arg |
| | | | 340 | | | | | 345 | | | | | 350 | | |
| Ser | Gly | Lys | Gln | Pro | Thr | Gly | Gln | Lys | Ala | Gln | Gly | Asp | Trp | Cys | Asn |
| | | 355 | | | | | 360 | | | | | 365 | | | |
| Ala | Lys | Gly | Thr | Gly | Phe | Gly | Leu | Arg | Pro | Ser | Thr | Asn | Thr | Gly | Asp |
| | 370 | | | | | 375 | | | | | 380 | | | | |

Ala Leu Ala Asp Ala Phe Val Trp Val Lys Pro Gly Glu Ser Asp
385                 390                 395                 400

Gly Thr Ser Asp Thr Ser Ala Ala Arg Tyr Asp Tyr His Cys Gly Leu
            405                 410                 415

Asp Asp Ala Leu Lys Pro Ala Pro Glu Ala Gly Thr Trp Phe Gln Ala
            420                 425                 430

Tyr Phe Glu Gln Leu Leu Asp Asn Ala Asn Pro Ser Phe Leu
            435                 440                 445

<210> SEQ ID NO 9
<211> LENGTH: 460
<212> TYPE: PRT
<213> ORGANISM: P. chrysosporium

<400> SEQUENCE: 9

Met Lys Ser Thr Ala Phe Phe Ala Ala Leu Val Thr Leu Leu Pro Ala
1               5                   10                  15

Tyr Val Ala Gly Gln Ala Ser Glu Trp Gly Gln Cys Gly Gly Ile Gly
            20                  25                  30

Trp Thr Gly Pro Thr Thr Cys Val Ser Gly Thr Thr Cys Thr Val Leu
            35                  40                  45

Asn Pro Tyr Tyr Ser Gln Cys Leu Pro Gly Ser Ala Val Thr Thr Thr
50                  55                  60

Ser Val Ile Thr Ser His Ser Ser Ser Val Ser Val Ser Ser His
65                  70                  75                  80

Ser Gly Ser Ser Thr Ser Thr Ser Ser Pro Thr Gly Pro Thr Gly Thr
            85                  90                  95

Asn Pro Pro Pro Pro Ser Ala Asn Asn Pro Trp Thr Gly Phe Gln
            100                 105                 110

Ile Phe Leu Ser Pro Tyr Tyr Ala Asn Glu Val Ala Ala Ala Ala Lys
            115                 120                 125

Gln Ile Thr Asp Pro Thr Leu Ser Ser Lys Ala Ala Ser Val Ala Asn
            130                 135                 140

Ile Pro Thr Phe Thr Trp Leu Asp Ser Val Ala Lys Ile Pro Asp Leu
145                 150                 155                 160

Gly Thr Tyr Leu Ala Ser Ala Ser Ala Leu Gly Lys Ser Thr Gly Thr
            165                 170                 175

Lys Gln Leu Val Gln Ile Val Ile Tyr Asp Leu Pro Asp Arg Asp Cys
            180                 185                 190

Ala Ala Lys Ala Ser Asn Gly Glu Phe Ser Ile Ala Asn Asn Gly Gln
            195                 200                 205

Ala Asn Tyr Glu Asn Tyr Ile Asp Gln Ile Val Ala Gln Ile Gln Gln
            210                 215                 220

Phe Pro Asp Val Arg Val Val Ala Val Ile Glu Pro Asp Ser Leu Ala
225                 230                 235                 240

Asn Leu Val Thr Asn Leu Asn Val Gln Lys Cys Ala Asn Ala Lys Thr
            245                 250                 255

Thr Tyr Leu Ala Cys Val Asn Tyr Ala Leu Thr Asn Leu Ala Lys Val
            260                 265                 270

Gly Val Tyr Met Tyr Met Asp Ala Gly His Ala Gly Trp Leu Gly Trp
            275                 280                 285

Pro Ala Asn Leu Ser Pro Ala Ala Gln Leu Phe Thr Gln Val Trp Gln
            290                 295                 300

Asn Ala Gly Lys Ser Pro Phe Ile Lys Gly Leu Ala Thr Asn Val Ala
305                 310                 315                 320

```
Asn Tyr Asn Ala Leu Gln Ala Ser Pro Asp Pro Ile Thr Gln Gly
            325                 330                 335

Asn Pro Asn Tyr Asp Glu Ile His Tyr Ile Asn Ala Leu Ala Pro Leu
            340                 345                 350

Leu Gln Gln Ala Gly Trp Asp Ala Thr Phe Ile Val Asp Gln Gly Arg
            355                 360                 365

Ser Gly Val Gln Asn Ile Arg Gln Gln Trp Gly Asp Trp Cys Asn Ile
            370                 375                 380

Lys Gly Ala Gly Phe Gly Thr Arg Pro Thr Thr Asn Thr Gly Ser Gln
385                 390                 395                 400

Phe Ile Asp Ser Ile Val Trp Val Lys Pro Gly Gly Glu Cys Asp Gly
            405                 410                 415

Thr Ser Asn Ser Ser Ser Pro Arg Tyr Asp Ser Thr Cys Ser Leu Pro
            420                 425                 430

Asp Ala Ala Gln Pro Ala Pro Glu Ala Gly Thr Trp Phe Gln Ala Tyr
            435                 440                 445

Phe Gln Thr Leu Val Ser Ala Ala Asn Pro Pro Leu
            450                 455                 460

<210> SEQ ID NO 10
<211> LENGTH: 459
<212> TYPE: PRT
<213> ORGANISM: T. emersonii

<400> SEQUENCE: 10

Met Arg Asn Leu Leu Ala Leu Ala Pro Ala Ala Leu Leu Val Gly Ala
1               5                   10                  15

Ala Glu Ala Gln Gln Ser Leu Trp Gly Gln Cys Gly Gly Ser Ser Trp
            20                  25                  30

Thr Gly Ala Thr Ser Cys Ala Ala Gly Ala Thr Cys Ser Thr Ile Asn
            35                  40                  45

Pro Tyr Tyr Ala Gln Cys Val Pro Ala Thr Ala Thr Pro Thr Thr Leu
        50                  55                  60

Thr Thr Thr Thr Lys Pro Thr Ser Thr Gly Gly Ala Ala Pro Thr Thr
65                  70                  75                  80

Pro Pro Pro Thr Thr Thr Gly Thr Thr Thr Ser Pro Val Val Thr Arg
                85                  90                  95

Pro Ala Ser Ala Ser Gly Asn Pro Phe Glu Gly Tyr Gln Leu Tyr Ala
            100                 105                 110

Asn Pro Tyr Tyr Ala Ser Glu Val Ile Ser Leu Ala Ile Pro Ser Leu
        115                 120                 125

Ser Ser Glu Leu Val Pro Lys Ala Ser Glu Val Ala Lys Val Pro Ser
130                 135                 140

Phe Val Trp Leu Asp Gln Ala Ala Lys Val Pro Ser Met Gly Asp Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
            180                 185                 190

Ala Ala Ser Asn Gly Glu Phe Ser Ile Ala Asn Asn Gly Val Ala Leu
        195                 200                 205

Tyr Lys Gln Tyr Ile Asp Ser Ile Arg Glu Gln Leu Thr Thr Tyr Ser
    210                 215                 220

Asp Val His Thr Ile Leu Val Ile Glu Pro Asp Ser Leu Ala Asn Val
225                 230                 235                 240
```

```
Val Thr Asn Leu Asn Val Pro Lys Cys Ala Asn Ala Gln Asp Ala Tyr
            245                 250                 255

Leu Glu Cys Ile Asn Tyr Ala Ile Thr Gln Leu Asp Leu Pro Asn Val
        260                 265                 270

Ala Met Tyr Leu Asp Ala Gly His Ala Gly Trp Leu Gly Trp Gln Ala
    275                 280                 285

Asn Leu Ala Pro Ala Ala Gln Leu Phe Ala Ser Val Tyr Lys Asn Ala
    290                 295                 300

Ser Ser Pro Ala Ser Val Arg Gly Leu Ala Thr Asn Val Ala Asn Tyr
305                 310                 315                 320

Asn Ala Trp Ser Ile Ser Arg Cys Pro Ser Tyr Thr Gln Gly Asp Ala
            325                 330                 335

Asn Cys Asp Glu Glu Asp Tyr Val Asn Ala Leu Gly Pro Leu Phe Gln
            340                 345                 350

Glu Gln Gly Phe Pro Ala Tyr Phe Ile Ile Asp Thr Ser Arg Asn Gly
            355                 360                 365

Val Arg Pro Thr Lys Gln Ser Gln Trp Gly Asp Trp Cys Asn Val Ile
            370                 375                 380

Gly Thr Gly Phe Gly Val Arg Pro Thr Thr Asp Thr Gly Asn Pro Leu
385                 390                 395                 400

Glu Asp Ala Phe Val Trp Val Lys Pro Gly Gly Glu Ser Asp Gly Thr
                405                 410                 415

Ser Asn Thr Thr Ser Pro Arg Tyr Asp Tyr His Cys Gly Leu Ser Asp
                420                 425                 430

Ala Leu Gln Pro Ala Pro Glu Ala Gly Thr Trp Phe Gln Ala Tyr Phe
            435                 440                 445

Glu Gln Leu Leu Thr Asn Ala Asn Pro Leu Phe
    450                 455

<210> SEQ ID NO 11
<211> LENGTH: 558
<212> TYPE: PRT
<213> ORGANISM: T. fusc

<400> SEQUENCE: 11

Ala Gly Cys Ser Val Asp Tyr Thr Val Asn Ser Trp Gly Thr Gly Phe
1               5                   10                  15

Thr Ala Asn Val Thr Ile Thr Asn Leu Gly Ser Ala Ile Asn Gly Trp
                20                  25                  30

Thr Leu Glu Trp Asp Phe Pro Gly Asn Gln Gln Val Thr Asn Leu Trp
            35                  40                  45

Asn Gly Thr Tyr Thr Gln Ser Gly Gln His Val Ser Val Ser Asn Ala
        50                  55                  60

Pro Tyr Asn Ala Ser Ile Pro Ala Asn Gly Thr Val Glu Phe Gly Phe
65                  70                  75                  80

Asn Gly Ser Tyr Ser Gly Ser Asn Asp Ile Pro Ser Ser Phe Lys Leu
                85                  90                  95

Asn Gly Val Thr Cys Asp Gly Ser Asp Asp Pro Asp Pro Glu Pro Ser
            100                 105                 110

Pro Ser Pro Ser Pro Ser Pro Ser Thr Asp Pro Asp Glu Pro Gly Gly
        115                 120                 125

Gly Pro Thr Asn Pro Pro Thr Asn Pro Gly Glu Lys Val Asp Asn Pro
    130                 135                 140

Phe Glu Gly Ala Lys Leu Tyr Val Asn Pro Val Trp Ser Ala Lys Ala
145                 150                 155                 160
```

Ala Ala Glu Pro Gly Gly Ser Ala Val Ala Asn Glu Ser Thr Ala Val
            165                 170                 175

Trp Leu Asp Arg Ile Gly Ala Ile Glu Gly Asn Asp Ser Pro Thr Thr
            180                 185                 190

Gly Ser Met Gly Leu Arg Asp His Leu Glu Glu Ala Val Arg Gln Ser
            195                 200                 205

Gly Gly Asp Pro Leu Thr Ile Gln Val Val Ile Tyr Asn Leu Pro Gly
            210                 215                 220

Arg Asp Cys Ala Ala Leu Ala Ser Asn Gly Glu Leu Gly Pro Asp Glu
225                 230                 235                 240

Leu Asp Arg Tyr Lys Ser Glu Tyr Ile Asp Pro Ile Ala Asp Ile Met
            245                 250                 255

Trp Asp Phe Ala Asp Tyr Glu Asn Leu Arg Ile Val Ala Ile Ile Glu
            260                 265                 270

Ile Asp Ser Leu Pro Asn Leu Val Thr Asn Val Gly Gly Asn Gly Gly
            275                 280                 285

Thr Glu Leu Cys Ala Tyr Met Lys Gln Asn Gly Gly Tyr Val Asn Gly
            290                 295                 300

Val Gly Tyr Ala Leu Arg Lys Leu Gly Glu Ile Pro Asn Val Tyr Asn
305                 310                 315                 320

Tyr Ile Asp Ala Ala His His Gly Trp Ile Gly Trp Asp Ser Asn Phe
            325                 330                 335

Gly Pro Ser Val Asp Ile Phe Tyr Glu Ala Ala Asn Ala Ser Gly Ser
            340                 345                 350

Thr Val Asp Tyr Val His Gly Phe Ile Ser Asn Thr Ala Asn Tyr Ser
            355                 360                 365

Ala Thr Val Glu Pro Tyr Leu Asp Val Asn Gly Thr Val Asn Gly Gln
            370                 375                 380

Leu Ile Arg Gln Ser Lys Trp Val Asp Trp Asn Gln Tyr Val Asp Glu
385                 390                 395                 400

Leu Ser Phe Val Gln Asp Leu Arg Gln Ala Leu Ile Ala Lys Gly Phe
            405                 410                 415

Arg Ser Asp Ile Gly Met Leu Ile Asp Thr Ser Arg Asn Gly Trp Gly
            420                 425                 430

Gly Pro Asn Arg Pro Thr Gly Pro Ser Ser Ser Thr Asp Leu Asn Thr
            435                 440                 445

Tyr Val Asp Glu Ser Arg Ile Asp Arg Arg Ile His Pro Gly Asn Trp
            450                 455                 460

Cys Asn Gln Ala Gly Ala Gly Leu Gly Glu Arg Pro Thr Val Asn Pro
465                 470                 475                 480

Ala Pro Gly Val Asp Ala Tyr Val Trp Val Lys Pro Pro Gly Glu Ser
            485                 490                 495

Asp Gly Ala Ser Glu Glu Ile Pro Asn Asp Glu Gly Lys Gly Phe Asp
            500                 505                 510

Arg Met Cys Asp Pro Thr Tyr Gln Gly Asn Ala Arg Asn Gly Asn Asn
            515                 520                 525

Pro Ser Gly Ala Leu Pro Asn Ala Pro Ile Ser Gly His Trp Phe Ser
            530                 535                 540

Ala Gln Phe Arg Glu Leu Leu Ala Asn Ala Tyr Pro Pro Leu
545                 550                 555

<210> SEQ ID NO 12
<211> LENGTH: 410
<212> TYPE: PRT
<213> ORGANISM: T. fusc

```
<400> SEQUENCE: 12

Asn Asp Ser Pro Phe Tyr Val Asn Pro Asn Met Ser Ala Glu Trp
1               5                   10                  15

Val Arg Asn Asn Pro Asn Asp Pro Arg Thr Pro Val Ile Arg Asp Arg
            20                  25                  30

Ile Ala Ser Val Pro Gln Gly Thr Trp Phe Ala His His Asn Pro Gly
            35                  40                  45

Gln Ile Thr Gly Gln Val Asp Ala Leu Met Ser Ala Ala Gln Ala Ala
            50                  55                  60

Gly Lys Ile Pro Ile Leu Val Val Tyr Asn Ala Pro Gly Arg Asp Cys
65                  70                  75                  80

Gly Asn His Ser Ser Gly Gly Ala Pro Ser His Ser Ala Tyr Arg Ser
                85                  90                  95

Trp Ile Asp Glu Phe Ala Ala Gly Leu Lys Asn Arg Pro Ala Tyr Ile
            100                 105                 110

Ile Val Glu Pro Asp Leu Ile Ser Leu Met Ser Ser Cys Met Gln His
            115                 120                 125

Val Gln Gln Glu Val Leu Glu Thr Met Ala Tyr Ala Gly Lys Ala Leu
130                 135                 140

Lys Ala Gly Ser Ser Gln Ala Arg Ile Tyr Phe Asp Ala Gly His Ser
145                 150                 155                 160

Ala Trp His Ser Pro Ala Gln Met Ala Ser Trp Leu Gln Gln Ala Asp
                165                 170                 175

Ile Ser Asn Ser Ala His Gly Ile Ala Thr Asn Thr Ser Asn Tyr Arg
            180                 185                 190

Trp Thr Ala Asp Glu Val Ala Tyr Ala Lys Ala Val Leu Ser Ala Ile
            195                 200                 205

Gly Asn Pro Ser Leu Arg Ala Val Ile Asp Thr Ser Arg Asn Gly Asn
210                 215                 220

Gly Pro Ala Gly Asn Glu Trp Cys Asp Pro Ser Gly Arg Ala Ile Gly
225                 230                 235                 240

Thr Pro Ser Thr Thr Asn Thr Gly Asp Pro Met Ile Asp Ala Phe Leu
                245                 250                 255

Trp Ile Lys Leu Pro Gly Glu Ala Asp Gly Cys Ile Ala Gly Ala Gly
            260                 265                 270

Gln Phe Val Pro Gln Ala Ala Tyr Glu Met Ala Ile Ala Ala Gly Gly
            275                 280                 285

Thr Asn Pro Asn Pro Asn Pro Thr Pro Thr Pro Thr Pro Thr
290                 295                 300

Pro Thr Pro Pro Gly Ser Ser Gly Ala Cys Thr Ala Thr Tyr Thr
305                 310                 315                 320

Ile Ala Asn Glu Trp Asn Asp Gly Phe Gln Ala Thr Val Thr Val Thr
                325                 330                 335

Ala Asn Gln Asn Ile Thr Gly Trp Thr Val Thr Trp Thr Phe Thr Asp
            340                 345                 350

Gly Gln Thr Ile Thr Asn Ala Trp Asn Ala Asp Val Ser Thr Ser Gly
            355                 360                 365

Ser Ser Val Thr Ala Arg Asn Val Gly His Asn Gly Thr Leu Ser Gln
370                 375                 380

Gly Ala Ser Thr Glu Phe Gly Phe Val Gly Ser Lys Gly Asn Ser Asn
385                 390                 395                 400

Ser Val Pro Thr Leu Thr Cys Ala Ala Ser
                405                 410
```

<210> SEQ ID NO 13
<211> LENGTH: 418
<212> TYPE: PRT
<213> ORGANISM: C. fimi

<400> SEQUENCE: 13

```
Ala Pro Gly Cys Arg Val Asp Tyr Ala Val Thr Asn Gln Trp Pro Gly
 1               5                  10                  15

Gly Phe Gly Ala Asn Val Thr Ile Thr Asn Leu Gly Asp Pro Val Ser
             20                  25                  30

Ser Trp Lys Leu Asp Trp Thr Tyr Thr Ala Gly Gln Arg Ile Gln Gln
         35                  40                  45

Leu Trp Asn Gly Thr Ala Ser Thr Asn Gly Gln Val Ser Val Thr
 50                  55                  60

Ser Leu Pro Trp Asn Gly Ser Ile Pro Thr Gly Gly Thr Ala Ser Phe
 65                  70                  75                  80

Gly Phe Asn Gly Ser Trp Ala Gly Ser Asn Pro Thr Pro Ala Ser Phe
                 85                  90                  95

Ser Leu Asn Gly Thr Thr Cys Thr Gly Thr Val Pro Thr Thr Ser Pro
                100                 105                 110

Thr Pro Thr Pro Thr Pro Thr Thr Pro Thr Pro Thr Pro Thr Pro Thr
            115                 120                 125

Pro Thr Pro Thr Pro Thr Val Thr Pro Gln Pro Thr Ser Gly Phe Tyr
130                 135                 140

Val Asp Pro Thr Thr Gln Gly Tyr Arg Ala Trp Gln Ala Ala Ser Gly
145                 150                 155                 160

Thr Asp Lys Ala Leu Leu Glu Lys Ile Ala Leu Thr Pro Gln Ala Tyr
                165                 170                 175

Trp Val Gly Asn Trp Ala Asp Ala Ser His Ala Gln Ala Glu Val Ala
            180                 185                 190

Asp Tyr Thr Gly Arg Ala Val Ala Ala Gly Lys Thr Pro Met Leu Val
        195                 200                 205

Val Tyr Ala Ile Pro Gly Arg Asp Cys Gly Ser His Ser Gly Gly Gly
210                 215                 220

Val Ser Glu Ser Glu Tyr Ala Arg Trp Val Asp Thr Val Ala Gln Gly
225                 230                 235                 240

Ile Lys Gly Asn Pro Ile Val Ile Leu Glu Pro Asp Ala Leu Ala Gln
                245                 250                 255

Leu Gly Asp Cys Ser Gly Gln Gly Asp Arg Val Gly Phe Leu Lys Tyr
            260                 265                 270

Ala Ala Lys Ser Leu Thr Leu Lys Gly Ala Arg Val Tyr Ile Asp Ala
        275                 280                 285

Gly His Ala Lys Trp Leu Ser Val Asp Thr Pro Val Asn Arg Leu Asn
290                 295                 300

Gln Val Gly Phe Glu Tyr Ala Val Gly Phe Ala Leu Asn Thr Ser Asn
305                 310                 315                 320

Tyr Gln Thr Thr Ala Asp Ser Lys Ala Tyr Gly Gln Gln Ile Ser Gln
                325                 330                 335

Arg Leu Gly Gly Lys Lys Phe Val Ile Asp Thr Ser Arg Asn Gly Asn
            340                 345                 350

Gly Ser Asn Gly Glu Trp Cys Asn Pro Arg Gly Arg Ala Leu Gly Glu
        355                 360                 365

Arg Pro Val Ala Val Asn Asp Gly Ser Gly Leu Asp Ala Leu Leu Trp
370                 375                 380
```

Val Lys Leu Pro Gly Glu Ser Asp Gly Ala Cys Asn Gly Gly Pro Ala
385                 390                 395                 400

Ala Gly Gln Trp Trp Gln Glu Ile Ala Leu Glu Met Ala Arg Asn Ala
            405                 410                 415

Arg Trp

<210> SEQ ID NO 14
<211> LENGTH: 7685
<212> TYPE: DNA
<213> ORGANISM: Artificial Sequence
<220> FEATURE:
<223> OTHER INFORMATION: Chemically synthesized nucleotide sequence of
      the ku80 knockout cassette

<400> SEQUENCE: 14

```
ggccgcctca acacccacac tcgaggcaca cgagttcatc ggcggcttcc cccacaagct    60
ctcggccaac ctgctaccgg ctctctcgcg agacttccca aagcctacaa acgaggtcga   120
cgtcaaggag gccctcgagc gccagcccgg cagatggagc ctccagggcc agatcaaggc   180
caacaacatg agagcccaga gcgccgcact ccggctcgac gacaaggagg caaggcgag    240
agcctttgag gaggccaagc gcgagctact ggcgtatcac cacagcgccc tgcggaagcc   300
ttccggcgca agataatgag cttgatcgca atgacgagtt cacgtacgct ttgccatatt   360
gttgttgctt tttgtttggt cctacatgta cggcgcattg gttgggagga tatacccacg   420
gagagtgtcc gagtggcttc tgggatttag agcgtcatta gcaggataga gatggttggc   480
caggggaatg gaattgactt ttcactacaa ggaacttgtt cactctggtg ttgattccca   540
ttgcgtgact ggtagtaggg aggaatgctt ttactttgtg ccactagacc gcagagaagg   600
gttggttgca agcggggtcc gtgtataccg accaagagtg atgggcatac agcaacgttt   660
ctgaacgact tcattttgtc cgagtctact ggatgcgaga tgccagcgtg aagccgtacg   720
ccaccagggc gacgaactcg acaaggttga cgagggagga gatgccgtgc agcatgccaa   780
acttcttgtt gagggcacgc atctcatccg actgtgcatc cttgtcatac cactcctttc   840
cgtctcgctt ggctggtggg agggttcaac aaatccatcg tcagccatcc ggggtctcaa   900
atcaatggcg tgcatgcgga gtcgggcttg aggctaacct tgtccatggc ggtccttcat   960
ggtcttgaca gtggcgggaa gcagcacggc gaggttgacg aggccgctga cgaacatggt  1020
tgcgatgggc accaaggagc tccacttgtt gggagcgtcg acgaggccgc cgatgccgcc  1080
cttgatgccc aagagggcgt ttccggggaa cgtgagggcg agcagcgcgg ggatggccgt  1140
ctgcatgcca agtagatgg ggaacagctt gctctggatg gcggagaagg agggccggct  1200
gacggtgcgg aacatgacga tgccgttgac gaaggactgc agtagcgtag tgtgatggta  1260
agcagctggc cggcgcgcct gagacaatgg ccggcaatgg taaaaaggac caagatgtac  1320
taggtagttg caatgtggct tattacctac ctactacctg gtaggcacct actaggtact  1380
tgggtagacg gacaatgaaa tttgaagtcg gggttgcagg aaagcagggc gctggacaca  1440
ttgtgcttca gcggtaccc gtcgtcatcg tcagccaatg tcgaggcccg gcagcccgag  1500
gagcgagaca accttggccg gaggagcccg caggtacctg ccaaagcgcg gctggtacct  1560
ctcaaccctc tcaggcctgt tggatgccct atgacatgcc ctggggggatg cagctgttgc  1620
cccggccccg cactttcggg tgaccgcgag gctgctgatt ggctggttgc cacgggctgg  1680
gcggtccctg aagttgttgc catctgaact ctgtcggcgc tggcgtcggc tgcgcccaat  1740
gggaggcgag acaactcagg gtactagaat cactgacaga agaagagaat cgaaagtagg  1800
```

```
tagacagcca attcgttgca tggcaggcaa ccgcacagga gaaaaattga ctaccccaca    1860
atcaggcaca gtaagtaggg cacagtacgt atgtacagac aaggcgcaag cgatactgcg    1920
cgacccggta cctcgccggc ttgacacgtg cgacaggcta ctttactagt attcgcagcg    1980
gcgggtcgcg cattattaca tgtactgtgc cgccatttga tgactgggct gctgcagtat    2040
tagtagatct gcccggcatc gcccttccat gggcgcgacc cgggactgga ccctctgact    2100
ctacctacat gtacctaggc cggcccgggc ttggtgactt ttgtccgatc aggtcgttcg    2160
cctggctacc tattatttct ctttcttctt ctccatcctg cttctggcct tgcaattctt    2220
cttcgccact cctccctctt cccccgcgca taccccttgaa ttcgtcagag aggaaaagac    2280
gagaaaaaaa agggcagcag agacgtcggt ctggctcacg tgctgcatct ctgcgcactc    2340
tcattttttt tattgtccga cccctccctc aaccttctcc ttcgttgaca ggctaagcct    2400
tgcttcgacg ctctctcttt gaattttttct acttctacct tcttttcttg cgtgttaccc    2460
accatagctc gattcacgat gctccgaagt cgccaagtca cagccagggc cgtccgggct    2520
ctgggccagg cgcgcgcctt tacctcgacg accaagcctg tcatgatcca gagcagccag    2580
aggaaacagg ccaacgccag cgctgctccg taagtcgccc attgccattg catcttctgt    2640
ttgatatata cttcctgctg cttgcgtggc gtcgtctctc ggttatgcgt gtcaaggacc    2700
aggtgtgttc gcatcgtggt tttccagcgc cgattaccgg gggacgaatt tttggctgct    2760
caactcgcgc gcgcgcattc tgattcttcg ttttcaatct tgagcgacaa ctggctaaca    2820
taatggccat tggcaattgc ttcacacaga caagtccgcc ctgtaccgag ccctgctttc    2880
aacgctgaag acaaagaccg cagccatgtg cagcctctgg tcaacccgtc gaagcccgac    2940
atggatgaat cgtatgtcca cgtcccctcg tcccgcccta caaaatgaac acgattacac    3000
cagaattttt gcaacaatcg acacttctat aacagaccaa ttgagctttg ttctgaccaa    3060
tcatgttgct ctagattcat tggcaaaacc ggaggcgaaa tcttccacga gatgatgctg    3120
cgacagggtg tcaagcacat tgtaggttc cgatgccggc cgcccacacg ggctccatcc    3180
ttgctccatc tctccagcta ggcaaatctc gctaaccttg agtcaccatc cagtcggata    3240
ccctggcggc gctatcctgc ccgtcttcga cgccatctac aactcaaaac acttcgactt    3300
catcctgccc cgtcatgagc agggagctgg ccatatggcc gagggctatg cccgtgcctc    3360
gggcaaaccc ggtgtcgtcc tggtgacttc cggccccggt gctaccaatg tcatcacgcc    3420
catgcaggat gccctgtcgg acggaacgcc cttggtcgtc ttctgcggcc aggtccccac    3480
cacggccatc ggcagcgatg acttccaaga ggccgacgtc gtgggcatct cgcgggcctg    3540
caccaagtgg aacgtcatgg tcaagagcgt tgctgagctg ccgcggagaa tcaacgaggc    3600
ctttgagatt gccaccagcg gccgccctgg ccccgtcctc gtcgacctgc caaggatgt    3660 cacggctggt atcctgagga gagccatccc tacggagact gctctgccgt ctctgcccag    3720
tgccgcctcc cgcgccgcca tggagctgag ctccaagcag ctcaacgcct ccatcaagcg    3780
tgccgccgac ctcatcaaca tcgccaagaa gcccgtcatc tacgccggtc agggtgtcat    3840
ccagtccgag ggcggcgttg agctcctgaa gcagctggcg gacaaggcct ccatcccgt    3900 caccaccacc ctccatggcc tgggtgcctt tgatgagctg gacgagaagt cgctgcacat    3960
gctgggcatg cacggctcgg cgtatgccaa catggccatg cagcaggccg acctcatcat    4020
cgccctcggc agccgattcg acgaccgtgt tactctgaat gtctccaaat ttgcgcctgc    4080
agccaggcaa gctgctgccg agggccgcg cggcatcatt cactttgaga tcatgcccaa    4140
gaacatcaac aaggtcatcc aggcgaccga ggccgtcgag ggcgacgtcg ccaccaacct    4200
```

```
gaagcacctc attccccaga ttgccgaaaa gtccatggcg gaccgaggag agtggttcgg    4260
cctcatcaat gagtggaaga agaagtggcc cctgtcaaac taccagcgcg cggagcgggc    4320
tggcctcatc aagccgcaga cggtcatgga ggagattagc aacctgacgg ccaaccgaaa    4380
ggacaagacg tacattgcca cgggtgtcgg ccagcaccag atgtgggttg cccagcactt    4440
ccgctggagg caccctcgat ccatgattac ctctggtggt ctgggcacca tgggctacgg    4500
tctccccgcg gccattggcg ccaaggtggc ccagcccgac gctctcgtaa ttgacgttga    4560
tggcgatgcc tcgtttaaca tgacgctgac ggagctgtcg actgctgcac agttcaacat    4620
tggcgtcaag gtggttgtgc tcaacaacga ggagcagggc atggtgacgc agtggcagaa    4680
cctcttttac gaggaccgat atgcccacac gcaccagaag aaccccgact tcatgaagct    4740
ggccgacgcc atgggcgttc agcaccagcg cgtgacggag ccggagaagc tggtcgatgc    4800
cctgacgtgg ctgatcaaca ccgatggccc ggccctgttg gaggttgtca cggacaagaa    4860
ggtgcctgtc ctgcccatgg tgcccgccgg atcggccctg cacgagttcc tcgtctttga    4920
acctggtgag tctacttcag acatattgct tgcgcattgc agatactaac actctcacag    4980
aaaaggataa gcagcgccgt gagctgatga aggagagaac aaagggtgtg cactcctaaa    5040
gcgatgatgt ctgcgagggg ttcttcgttg aaccctagtt caggcaccat cttaccctct    5100
tattttttcc cgtgggcttt cattttgtgt catccgagca tgacgttgta gggttggagt    5160
ttcttccttt ttatcttgtc atttactggt acccataggc gcgagactag gcttccatgt    5220
tttgttttgc gactttcaaa aagtactttt agtggtttgg ggcacgacga gggggggcaa    5280
cctcttctgt cgaaaaaggt ggctggatgg atgagatgag atgagatgag ggtgaagata    5340
gatacctgca gtgttttttga cgcgacggga tggcgatcgc agcacccccg acagaactcg    5400
tcgagactgt gcagcctcat atcgatgcac tgattcacgc tgcagacgtg aagaaaggta    5460
ctgattccat tacatatgct tctctgcaca ctgatgtttg atttgtgcta acgccccct    5520 tagtgccgcc caaggccaag ggcaagcgcc aaagagaaac agttaaaccc atctcgggac    5580
tggatgtgga tgcccttctg ggagaagagc agaaaggttc cattagtccg gagaatgcca    5640
ttccggactt caaacgagcc ctcaactcgt ccgaagaagt cgagcagatt gccgacgcca    5700
caaaacaaat gggggccatt gtgcggtctc tcattacgga cagcttcggg gatagcaaat    5760
atgcccaggc aatggaaggc attggtgcga tgcgtgagga gctgatcaac ctggaagagc    5820
ctggcctgta caacgacttt gtgcgcgact gaagaaaag tttgctatct ggagccttgg    5880
gtggtgacag gcgagatttc tggttcaaga tgaggtgggc gaagctgggc ctgattgaca    5940
agaaacagtc ggaggtgtct tcggtcactc ttgaggaggc ggacgaggtg agtggtgcag    6000
catgctgtcg gattatacgg acgttgtttg ctaacttgtg ggatagtttt acaagtcgag    6060
gtgaggtatc tacgttgacc aagaatggga ccatgtatat gagcggtgta acaacagaat    6120
cctgtgcttt gagcattgta tgatatgatt attgatgaac cggacaaaag ggggtagggg    6180
attgatgcca tcacgaccga ttgaccagac ctggattctc gcacagcatg gctgctgatt    6240
ttgttgacct tgcgacgtaa catccctgaa gaacaaccta ctattaacct atcatttagc    6300
agaagctctg taaccttctt gattcttgta ttcagcttct gagtctgtca aatgtaatca    6360
tttcgaggtt gtgtaattcc ggccaagcag gcggccgtct gccagcgcct gcctaggctg    6420
caccgcaatc tgcccaatca gctgcccttc agtttcgttt gaccttgcag ctgcccttca    6480
tcctttatct gcacacaatt cttttcctc tgctctgcgc attcttctct ctctcgtctc    6540
ccttctcaag ctcaacttca cctcatccgc tccactacaa gccctcccgt cgtcgtctcg    6600
```

| | |
|---|---|
| catcctcatc tcgactgcgg ccagcaaaac aagcaaagcc gtgatcgatc ctcagcatgg | 6660 |
| ctaccttcaa cctcaccgtc cgcctggaga tgctcaaaga aattggaatc accgtccaat | 6720 |
| acggcgagca tgtagcgaaa gaagcagcca gcaacgaagc agcgatggca ttcgaagaag | 6780 |
| aagaagagtt ccccgccgtt gtgccgccca aggcagaaca gcacgcctct gaacacgacg | 6840 |
| ctggccacga tgcttgggac gcggctgccc acatctcgac ttcggcgcaa gaacagcaga | 6900 |
| agccccagga gatggacgac tcgtctatcg tgatgccgct ggactactcc aagtttgtcg | 6960 |
| ttggagagcc tgcggacgaa tccatcagct tttgctcgtg gaaggtcgtc gaggcttatc | 7020 |
| ctgaccagtt tatcggcaag gcaaacaggc ctcgtgtatg tagcgattgc tttctctgca | 7080 |
| ttatgggaat ctcaagagag tatggtagaa gataactgac aacttgcagg ccaagccgta | 7140 |
| ctttgacaag attttggaag acagagtctg ggatttgtga ggatcttgat tgatgtgcat | 7200 |
| atggcgacat gcctgctaat atcattgtag cttctatctc tacaaccccg agaagccttc | 7260 |
| agagaagcct cgcgtgctgg tgcccactgt tcagctcgaa ggctttctca aaagcatcaa | 7320 |
| cagagcgctc ggtacttctc tcaccattcc aggaggggca aaccaggacc gttttatct | 7380 |
| gaggttcggc cagggagaca ccccaaggcc tcgatatcta cagaggtcga gagaccagaa | 7440 |
| atccctaaag attgaaacgt tccccgattt tcaacaggcg gactacgaca gctttaggaa | 7500 |
| cgcgcatggc gccatccagg aggactggtt gaagaactgg cagatgctgg tacctcggcc | 7560 |
| gagtttcgac aagaagaaaa atgcagacaa aagagcagcc aagagaaggc tcgagcgaga | 7620 |
| gcgaatgctt cacaatacgc aggaatttct tcatttggca ggtaagggca aggggctga | 7680 |
| cgtgg | 7685 |

<210> SEQ ID NO 15
<211> LENGTH: 9259
<212> TYPE: DNA
<213> ORGANISM: Artificial sequence
<220> FEATURE:
<223> OTHER INFORMATION: Chemically synthesized nucleotide sequence of the pyr2 knockout cassette

<400> SEQUENCE: 15

| | |
|---|---|
| atcacgccct cgcataaaag accctcaaga gtccatgtgc cctatctgcc tgatcttcct | 60 |
| aacccttatt taacattggc cctatcacaa cctagttctt cttcagcctg ctttgtcaac | 120 |
| acttgtcacg gttcaactca acgtaatcag caggtagcag gacgaggata gggagagaaa | 180 |
| cgaagagaag aagaggagag aggaagaaaa aaaaagaaa agaaagaaaa agggaaaagg | 240 |
| aaagaaggag gaaagagaa gaaagtcaga tgaagaagca agaagacgcc atggtagcca | 300 |
| ccgcttgtca gggctcctta gcaacgaaca actctagctt ggggacttgt cgatgtgtcg | 360 |
| tttccttcct acccatcagc accaacgatg agttcgatat agacgaggac ctcatggaag | 420 |
| tagagaccat tgggttcgac aggatctctc agtttcactt ctatgaggtc tgtcgctcgg | 480 |
| atgactttt gaggagcttc cccttctgct tcaaccccaa actctctttc ctgaaaccgc | 540 |
| agcacgttgg cacggccgtg ttgctggagc agtttgcttt cgagcactct cagcgtggtt | 600 |
| tcagcagccc actggtgagt ggcctccttt gacgtccaca ccttgctcct gtcgcatgcg | 660 |
| tatctggtgg gaacgactgc tccaaggagg attgctaacg aggttgtagg ccgaatatcg | 720 |
| catcagattc tccggtaacc ttagctacgg cctcttcaac atctgtgaca tgacggagcg | 780 |
| caagtactgg tggttggcga ccaagatgcg cggctggaac atcgacggct gccccgaaga | 840 |
| cgtcaggaga ctcatgtttg ttcacatcat cgccaccctg ggatgcagcc ccgtcgtgac | 900 |
| ggatgaagac atggactacc ccaagaactg ggcggcaatt ctccacggta gagacagata | 960 |

```
tccgagtgaa cctgtgggcc accggcctca tgggcgcacc atctgcctcc actcggtggc    1020
cgtctgccct cgtctccagg gcttgggtct cggtactgcg actctgaagt cgtatgtgca    1080
gcgcatgaac agcctcggcg ccgcggaccg tgttgctctc gtttgccgca gcccgagac     1140 gagattttt gaaagatgcg gcttcaggaa cagcggccgg agtagtatca agactctggt     1200
cggcgaatac tacaacatgg tgtgtgcttc cacatcgact tggccagact ctatacgatt    1260
ttcaaacctc gctatacgtc atattgactt gtttctttag gtcttcgatt tgcccgggcc    1320
caaagacttt atcgactgga atagcattgc cgacgctgcc aagaagatgt gaaccatttg    1380
actgatacga tgtgtgctac gcatgtcgac cttctttgtt tgtttctttg gcggctcttt    1440
gtataccttg ggacacggca gacgcatgtc tatgtgaaga aaacgttcac ggcgctgttt    1500
gcatcaggaa tatgatcatt aaacatggag cgtaatggta ttaatgatca actagaaaaa    1560
tggtatggaa gggcgagagg gcgatcaaca aagcagcccg gggcatagtc tggaagcagc    1620
aggaattgga agggaaaagg aagctgcaca atgaagggat atcgtgagcg gagtggctca    1680
cgagagtatc aacagactgg cgaaagcaag caattgccaa cgccggctat taggccataa    1740
gatggcctgt tgtgagtccc agttgcacgt atccccatat gactgctctg tcgctgactt    1800 gaaaaaaat agggaggata aaggagaaag aaagtgagac aacccgtgag ggacttgggg     1860
tagtaggaga acacatgggc aaccgggcaa tacacgcgat gtgagacgag ttcaacggcg    1920
aatggaaaat cttgaaaaac aaaataaaat aactgccctc catacgggta tcaaattcaa    1980
gcagttgtac ggaggctagc tagagttgtg aagtcggtaa tcccgctgta tagtaatacg    2040
agtcgcatct aaatactccg aagctgctgc gaacccggag aatcgagatg tgctggaaag    2100
cttctagcga gcggctaaat tagcatgaaa ggctatgaga aattctggag acggcttgtt    2160
gaatcatggc gttccattct tcgacaagca aagcgttccg tcgcagtagc aggcactcat    2220
tcccgaaaaa actcggagat tcctaagtag cgatggaacc ggataatat aataggcaat     2280 acattgagtt gcctcgacgg ttgcaatgca ggggtactga gcttggacat aactgttccg    2340
taccccacct cttctcaacc tttggcgttt ccctgattca gcgtacccgt acaagtcgta    2400
atcactatta acccagactg accggacgtg ttttgcccct catttggaga aataatgtca    2460
ttgcgatgtg taatttgcct gcttgaccga ctggggctgt tcgaagcccg aatgtaggat    2520
tgttatccga actctgctcg tagaggcatg ttgtgaatct gtgtcgggca ggacacgcct    2580
cgaaggttca cggcaaggga accaccgat agcagtgtct agtagcaacc tgtaaagccg      2640
caatgcagca tcactggaaa atacaaacca atggctaaaa gtacataagt taatgcctaa    2700
agaagtcata taccagcggc taataattgt acaatcaagt ggctaaacgt accgtaattt    2760
gccaacggct tgtggggttg cagaagcaac ggcaaagccc cacttcccca cgtttgtttc    2820
ttcactcagt ccaatctcag ctggtgatcc cccaattggg tcgcttgttt gttccggtga    2880
agtgaaagaa gacagaggta agaatgtctg actcggagcg ttttgcatac aaccaagggc    2940
agtgatggaa gacagtgaaa tgttgacatt caaggagtat ttagccaggg atgcttgagt    3000
gtatcgtgta aggaggtttg tctgccgata cgacgaatac tgtatagtca cttctgatga    3060
agtggtccat attgaaatgt aaagtcggca ctgaacaggc aaaagattga gttgaaactg    3120
cctaagatct cgggccctcg ggccttcggc ctttgggtgt acatgtttgt gctccgggca    3180
aatgcaaagt gtggtaggat cgaacacact gctgccttta ccaagcagct gagggtatgt    3240
gataggcaaa tgttcagggg ccactgcatg gtttcgaata gaaagagaag cttagccaag    3300
aacaatagcc gataaagata gcctcattaa acggaatgag ctagtaggca aagtcagcga    3360
```

```
atgtgtatat ataaaggttc gaggtccgtg cctccctcat gctctcccca tctactcatc   3420
aactcagatc ctccaggaga cttgtacacc atcttttgag gcacagaaac ccaatagtca   3480
accgcggact gcgcatcatg tatcggaagt tggccgtcat ctcggccttc ttggccacac   3540
ctcgtgctag actaggcgcg ccaggaagcc cggaaggtaa gtggattctt cgccgtggct   3600
ggagcaaccg gtggattcca gcgtctccga cttggactga gcaattcagc gtcacggatt   3660
cacgatagac agctcagacc gctccacggc tggcggcatt attggttaac ccggaaactc   3720
agtctccttg gccccgtccc gaagggaccc gacttaccag gctgggaaag ccagggatag   3780
aatacactgt acgggcttcg tacgggaggt tcggcgtagg gttgttccca agttttacac   3840 acccccccaag acagctagcg cacgaaagac gcggagggtt tggtgaaaaa agggcgaaaa   3900
ttaagcggga gacgtattta ggtgctaggg ccggtttcct ccccattttt cttcggttcc   3960
ctttctctcc tggaagactt tctctctctc tcttcttctc ttcttccatc ctcagtccat   4020
cttcctttcc catcatccat ctcctcacct ccatctcaac tccatcacat cacaatcgat   4080
atgaaaaagc ctgaactcac cgcgacgtct gtcgagaagt ttctgatcga aaagttcgac   4140
agcgtctccg acctgatgca gctctcggag ggcgaagaat ctcgtgcttt cagcttcgat   4200
gtaggagggc gtggatatgt cctgcgggta aatagctgcg ccgatggttt ctacaaagat   4260
cgttatgttt atcggcactt tgcatcggcc gcgctcccga ttccggaagt gcttgacatt   4320
ggggaattca gcgagagcct gacctattgc atctcccgcc gtgcacaggg tgtcacgttg   4380
caagacctgc ctgaaaccga actgcccgct gttctgcagc cggtcgcgga ggccatggat   4440
gcgatcgctg cggccgatct tagccagacg agcgggttcg gcccattcgg accgcaagga   4500
atcggtcaat acactacatg gcgtgatttc atatgcgcga ttgctgatcc ccatgtgtat   4560
cactggcaaa ctgtgatgga cgacaccgtc agtgcgtccg tcgcgcaggc tctcgatgag   4620
ctgatgcttt gggccgagga ctgccccgaa gtccggcacc tcgtgcacgc ggatttcggc   4680
tccaacaatg tcctgacgga caatggccgc ataacagcgg tcattgactg gagcgaggcg   4740
atgttcgggg attcccaata cgaggtcgcc aacatcttct tctggaggcc gtggttggct   4800
tgtatggagc agcagacgcg ctacttcgag cggaggcatc cggagcttgc aggatcgccg   4860
cggctccggg cgtatatgct ccgcattggt cttgaccaac tctatcagag cttggttgac   4920
ggcaatttcg atgatgcagc ttgggcgcag ggtcgatgcg acgcaatcgt ccgatccgga   4980
gccgggactg tcgggcgtac acaaatcgcc cgcagaagcg cggccgtctg gaccgatggc   5040
tgtgtagaag tactcgccga tagtggaaac cgacgcccca gcactcgtcc gagggcaaag   5100
gaatagagta gatgccgacc gggatccact taacgttact gaaatcatca aacagcttga   5160
cgaatctgga tataagatcg ttggtgtcga tgtcagctcc ggagttgaga caaatggtgt   5220
tcaggatctc gataagatac gttcatttgt ccaagcagca aagagtgcct tctagtgatt   5280
taatagctcc atgtcaacaa gaataaaacg cgtttcgggt ttacctcttc cagatacagc   5340
tcatctgcaa tgcattaatg cattggacct cgcaaccta gtacgcccctt caggctccgg   5400 cgaagcagaa gaatagctta gcagagtcta ttttcatttt cgggagacta gcattctgta   5460
aacgggcagc aatcgcccag cagttagtag ggtcccctct acctctcagg gagatgtaac   5520
aacgccacct tatgggacta tcaagctgac gctggcttct gtgcagacaa actgcgccca   5580
cgagttcttc cctgacgccg ctctcgcgca ggcaagggaa ctcgatgaat actacgcaaa   5640
gcacaagaga cccgttggtc cactccatgg cctccccatc tctctcaaag accagcttcg   5700
agtcaaggta caccgttgcc cctaagtcgt tagatgtccc ttttttgtcag ctaacatatg   5760
```

| | |
|---|---|
| ccaccagggc tacgaaacat caatgggcta catctcatgg ctaaacaagt acgacgaagg | 5820 |
| ggactcggtt ctgacaacca tgctccgcaa agccggtgcc gtcttctacg tcaagacctc | 5880 |
| tgtcccgcag accctgatgg tctgcgagac agtcaacaac atcatcgggc gcaccgtcaa | 5940 |
| cccacgcaac aagaactggt cgtgcggcgg cagttctggt ggtgagggtg cgatcgttgg | 6000 |
| gattcgtggt ggcgtcatcg gtgtaggaac ggatatcggt ggctcgattc gagtgccggc | 6060 |
| cgcgttcaac ttcctgtacg gtctaaggcc gagtcatggg cggctgccgt atgcaaagat | 6120 |
| ggcgaacagc atggagggtc aggagacggt gcacagcgtt gtcgggccga ttacgcactc | 6180 |
| tgttgagggt gagtccttcg cctcttcctt cttttcctgc tctataccag gcctccactg | 6240 |
| tcctccttttc ttgcttttta tactatatac gagaccggca gtcactgatg aagtatgtta | 6300 |
| gacctccgcc tcttcaccaa atccgtcctc ggtcaggagc catggaaata cgactccaag | 6360 |
| gtcatcccca tgccctggcg ccagtccgag tcggacatta ttgcctccaa gatcaagaac | 6420 |
| ggcgggctca atatcggcta ctacaacttc gacggcaatg tccttccaca ccctcctatc | 6480 |
| ctgcgcggcg tggaaaccac cgtcgccgca ctcgccaaag ccggtcacac cgtgaccccg | 6540 |
| tggacgccat acaagcacga tttcggccac gatctcatct cccatatcta cgcggctgac | 6600 |
| ggcagcgccg acgtaatgcg cgatatcagt gcatccggcg agccggcgat tccaaatatc | 6660 |
| aaagacctac tgaacccgaa catcaaagct gttaacatga acgagctctg ggacacgcat | 6720 |
| ctccagaagt ggaattacca gatggagtac cttgagaaat ggcgggaggc tgaagaaaag | 6780 |
| gccgggaagg aactggacgc catcatcgcg ccgattacgc ctaccgctgc ggtacggcat | 6840 |
| gaccagttcc ggtactatgg gtatgcctct gtgatcaacc tgctggattt cacgagcgtg | 6900 |
| gttgttccgg ttacctttgc ggataagaac atcgataaga agaatgagag tttcaaggcg | 6960 |
| gttagtgagc ttgatgccct cgtgcaggaa gagtatgatc cggaggcgta ccatggggca | 7020 |
| ccggttgcag tgcaggttat cggacggaga ctcagtgaag agaggacgtt ggcgattgca | 7080 |
| gaggaagtgg ggaagttgct gggaaatgtg gtgactccat agctaataag tgtcagatag | 7140 |
| caatttgcac aagaaatcaa taccagcaac tgtaaataag cgctgaagtg accatgccat | 7200 |
| gctacgaaag agcagaaaaa aacctgccgt agaaccgaag agatatgaca cgcttccatc | 7260 |
| tctcaaagga agaatcccctt cagggttgcg tttccagtag tgattttacc gctgatgaaa | 7320 |
| tgactggact ccctcctcct gctcttatac gaaaaattgc ctgactctgc aaaggttgtt | 7380 |
| tgtcttggaa gatgatgtgc cccccatcg ctcttatctc ataccccgcc atctttctag | 7440 |
| attctcatct tcaacaagag gggcaatcca tgatctgcga tccagatgtg cttctggcct | 7500 |
| catactctgc cttcaggttg atgttcactt aattggtgac gaattcagct gatttgctgc | 7560 |
| agtatgcttt gtgttggttc tttccaggct tgtgccagcc atgagcgctt tgagagcatg | 7620 |
| ttgtcactta taaactcgag taacggccac atattgttca ctacttgaat cacataccta | 7680 |
| atttttgatag aattgacatg tttaaagagc tgaggtagct ttaatgcctc tgaagtattg | 7740 |
| tgacacagct tctcacagag tgagaatgaa aagttggact cccctaatg aagtaaaagt | 7800 |
| ttcgtctctg aacggtgaag agcatagatc cggcatcaac tacctggcta gactacgacg | 7860 |
| tcaattctgc ggccttttga cctttatata tgtccattaa tgcaatagat tcttttttt | 7920 |
| ttttttttt ttttttttt tttttttttt tttgcccaat ttcgcagatc aaagtggacg | 7980 |
| ttatagcatc ataactaagc tcagttgctg agggaagccg tctactacct tagcccatcc | 8040 |
| atccagctcc ataccttgat actttagacg tgaagcaatt cacactgtac gtctcgcagc | 8100 |
| tctccttccc gctcttgctt ccccactggg gtccatggtg cgtgtatcgt cccctccaca | 8160 |

```
attctatgcc atggtacctc cagcttatca atgccccgct aacaagtcgc ctctttgcct    8220
tgatagctta tcgataaaac ttttttttccg ccagaaaggc tccgcccaca gacaagaaaa    8280
aaaattcacc gcctagcctt tggccccggc atttggctaa acctcgagcc tctctcccgt    8340
cttggggtat caggaagaaa agaaaaaaat ccatcgccaa gggctgtttt ggcatcacca    8400
cccgaaaaca gcacttcctc gatcaaaagt tgcccgccat gaagaccacg tggaaggaca    8460
tccctccggt gcctacgcac caggagtttc tggacattgt gctgagcagg cccagcgca    8520 aactgcccac tcagatccgt gccggcttca agattagcag aattcgaggt acgtcgcatt    8580
gcccatcgca ggatgtctca ttatcggggt ccttggagaa cgatcatgat tgcatggcga    8640
tgctaacaca tagacagcct tctacactcg aaaggtcaag ttcacccagg agacgttttc    8700
cgaaaagttc gcctccatcc tcgacagctt ccctcgcctc caggacatcc acccttcca    8760 caaggacctt ctcaacaccc tctacgatgc cgaccacttc aagattgccc ttggccagat    8820
gtccactgcc aagcacctgg tcgagaccat ctcgcgcgca tacgtccgtc tcttgaaata    8880
cgcccagtcg ctctaccagt gcaagcagct caagcgggcc gctctcggtc gcatggccac    8940
gctggtcaag cgcctcaagg acccctgct gtacctggac caggtccgcc agcatctcgg    9000
ccgtcttccc tccatcgacc ccaacaccag gaccctgctc atctgcggtt accccaatgt    9060
tggcaagtcc agcttcctgc gaagtatcac ccgcgccgat gtggacgtcc agccctatgc    9120
tttcaccacc aagagtctgt tgtcggcca ctttgactac aagtacctgc gattccaggc    9180
cattgatacc cccggtattc tggaccaccc tcttgaggag atgaacacta tcgaaatgca    9240
gaggtatgtg gcgcggcta                                                 9259

<210> SEQ ID NO 16
<211> LENGTH: 9088
<212> TYPE: DNA
<213> ORGANISM: Artificial Sequence
<220> FEATURE:
<223> OTHER INFORMATION: Chemically synthesized nucleotide sequence of
      the hygR knockout cassette

<400> SEQUENCE: 16
atcacgccct cgcataaaag accctcaaga gtccatgtgc cctatctgcc tgatcttcct      60
aacccttatt taacattggc cctatcacaa cctagttctt cttcagcctg ctttgtcaac    120
acttgtcacg gttcaactca acgtaatcag caggtagcag gacgaggata gggagagaaa    180
cgaagagaag aagaggagag aggaagaaaa aaaaagaaa agaaagaaaa agggaaaagg    240
aaagaaggag gaaaagagaa gaaagtcaga tgaagaagca agaagacgcc atggtagcca    300
ccgcttgtca gggctcctta gcaacgaaca actctagctt ggggacttgt cgatgtgtcg    360
tttccttcct acccatcagc accaacgatg agttcgatat agacgaggac ctcatggaag    420
tagagaccat tgggttcgac aggatctctc agtttcactt ctatgaggtc tgtcgctcgg    480 atgactttt gaggagcttc ccttctgct tcaaccccaa actctctttc ctgaaaccgc    540
agcacgttgg cacggccgtg ttgctggagc agtttgcttt cgagcactct cagcgtggtt    600
tcagcagccc actggtgagt ggcctccttt gacgtccaca ccttgctcct gtcgcatgcg    660
tatctggtgg gaacgactgc tccaaggagg attgctaacg aggttgtagg ccgaatatcg    720
catcagattc tccggtaacc ttagctacgg cctcttcaac atctgtgaca tgacggagcg    780
caagtactgg tggttggcga ccaagatgcg cggctggaac atcgacggct gcccgaaga    840 cgtcaggaga ctcatgtttg ttcacatcat cgccaccctg gatgcagcc ccgtcgtgac    900
```

```
ggatgaagac atggactacc caagaactg gcggcaatt ctccacggta gagacagata    960
tccgagtgaa cctgtgggcc accggcctca tgggcgcacc atctgcctcc actcggtggc  1020
cgtctgccct cgtctccagg gcttgggtct cggtactgcg actctgaagt cgtatgtgca  1080
gcgcatgaac agcctcggcg ccgcggaccg tgttgctctc gtttgccgca gcccgagac   1140
gagattttt gaaagatgcg gcttcaggaa cagcggccgg agtagtatca agactctggt   1200
cggcgaatac tacaacatgg tgtgtgcttc cacatcgact tggccagact ctatacgatt  1260
ttcaaacctc gctatacgtc atattgactt gtttctttag gtcttcgatt tgcccgggcc  1320
caaagacttt atcgactgga atagcattgc cgacgctgcc aagaagatgt gaaccatttg  1380
actgatacga tgtgtgctac gcatgtcgac cttctttgtt tgtttctttg gcggctcttt  1440
gtataccttg ggacacggca gacgcatgtc tatgtgaaga aaacgttcac ggcgctgttt  1500
gcatcaggaa tatgatcatt aaacatggag cgtaatggta ttaatgatca actagaaaaa  1560
tggtatggaa gggcgagagg gcgatcaaca aagcagcccg gggcatagtc tggaagcagc  1620
aggaattgga agggaaaagg aagctgcaca atgaagggat atcgtgagcg gagtggctca  1680
cgagagtatc aacagactgg cgaaagcaag caattgccaa cgccggctat taggccataa  1740
gatggcctgt tgtgagtccc agttgcacgt atccccatat gactgctctg tcgctgactt  1800
gaaaaaaat agggaggata aaggagaaag aaagtgagac aacccgtgag ggacttgggg   1860
tagtaggaga acacatgggc aaccgggcaa tacacgcgat gtgagacgag ttcaacggcg  1920
aatgaaaat cttgaaaaac aaaataaaat aactgccctc catacgggta tcaaattcaa   1980
gcagttgtac ggaggctaga tagagttgtg aagtcggtaa tcccgctgta tagtaatacg  2040
agtcgcatct aaatactccg aagctgctgc gaacccggag aatcgagatg tgctggaaag  2100
cttctagcga gcggctaaat tagcatgaaa ggctatgaga aattctggag acggcttgtt  2160
gaatcatggc gttccattct tcgacaagca aagcgttccg tcgcagtagc aggcactcat  2220
tcccgaaaaa actcggagat tcctaagtag cgatggaacc ggaataatat aataggcaat  2280
acattgagtt gcctcgacgg ttgcaatgca ggggtactga gcttggacat aactgttccg  2340
tacccacct cttctcaacc tttggcgttt ccctgattca gcgtacccgt acaagtcgta   2400
atcactatta acccagactg accggacgtg ttttgcccctt catttggaga aataatgtca  2460
ttgcgatgtg taatttgcct gcttgaccga ctggggctgt tcgaagcccg aatgtaggat  2520
tgttatccga actctgctcg tagaggcatg ttgtgaatct gtgtcgggca ggacacgcct   2580
cgaaggttca cggcaaggga aaccaccgat agcagtgtct agtagcaacc tgtaaagccg   2640
caatgcagca tcactggaaa atacaaacca atggctaaaa gtacataagt taatgcctaa   2700
agaagtcata taccagcggc taataattgt acaatcaagt ggctaaacgt accgtaattt   2760
gccaacggct tgtggggttg cagaagcaac ggcaaagccc cacttcccca cgtttgtttc   2820
ttcactcagt ccaatctcag ctggtgatcc cccaattggg tcgcttgttt gttccggtga   2880
agtgaaagaa gacagaggta agaatgtctg actcggagcg ttttgcatac aaccaagggc   2940
agtgatggaa gacagtgaaa tgttgacatt caaggagtat ttagccaggg atgcttgagt   3000
gtatcgtgta aggaggtttg tctgccgata cgacgaatac tgtatagtca cttctgatga   3060
agtggtccat attgaaatgt aaagtcggca ctgaacaggc aaaagattga gttgaaactg   3120
cctaagatct cgggccctcg ggccttcggc cttgggtgt acatgtttgt gctccgggca    3180
aatgcaaagt gtggtaggat cgaacacact gctgccttta ccaagcagct gagggtatgt   3240
gataggcaaa tgttcagggg ccactgcatg gtttcgaata gaaagagaag cttagccaag   3300
```

```
aacaatagcc gataaagata gcctcattaa acggaatgag ctagtaggca aagtcagcga   3360
atgtgtatat ataaaggttc gaggtccgtg cctccctcat gctctcccca tctactcatc   3420
aactcagatc ctccaggaga cttgtacacc atcttttgag gcacagaaac ccaatagtca   3480
accgcggact gcgcatcatg tatcggaagt tggccgtcat ctcggccttc ttggccacac   3540
ctcgtgctag actaggcgcg tcaatatgtg gccgttactc gagtttataa gtgacaacat   3600
gctctcaaag cgctcatggc tggcacaagc tggaaagaa ccaacacaaa gcatactgca    3660
gcaaatcagc tgaattcgtc accaattaag tgaacatcaa cctgaaggca gagtatgagg   3720
ccagaagcac atctggatcg cagatcatgg attgcccctc ttgttgaaga tgagaatcta   3780
gaaagatggc ggggtatgag ataagagcga tgggggggca catcatcttc caagacaaac   3840
aacctttgca gagtcaggca atttttcgta taagagcagg aggagggagt ccagtcattt   3900
catcagcggt aaaatcactc tagacaatct tcaagatgag ttctgccttg ggtgacttat   3960
agccatcatc atacctagac agaagcttgt gggatactaa gaccaacgta caagctcgca   4020
ctgtacgctt tgacttccat gtgaaaactc gatacggcgc gcctctaaat tttatagctc   4080
aaccactcca atccaacctc tgcatccctc tcactcgtcc tgatctactg ttcaaatcag   4140
agaataagga cactatccaa atccaacaga atggctacca cctcccagct gcctgcctac   4200
aagcaggact tcctcaaatc cgccatcgac ggcggcgtcc tcaagtttgg cagcttcgag   4260
ctcaagtcca agcggatatc ccctacttc ttcaacgcgg gcgaattcca cacggcgcgc    4320
ctcgccggcg ccatcgcctc cgcctttgca aagaccatca tcgagcccca ggagaaggcc   4380
ggcctagagt tcgacatcgt cttcggcccg gcctacaagg gcatcccgct gtgctccgcc   4440
atcaccatca agctcggcga gctggcgccc cagaacctgg accgcgtctc ctactcgttt   4500
gaccgcaagg aggccaagga ccacggcgag ggcggcaaca tcgtcggcgc ttcgctcaag   4560
ggcaagaggg tcctgattgt cgacgacgtc atcaccgccg gcaccgccaa gagggacgcc   4620
attgagaaga tcaccaagga gggcggcatc gtcgccggca tcgtcgtggc cctggaccgc   4680
atggagaagc tccccgctgc ggatggcgac gactccaagc ctggaccgag tgccattggc   4740
gagctgagga aggagtacgg catccccatc tttgccatcc tcactctgga tgacattatc   4800
gatggcatga agggctttgc tacccctgag gatatcaaga acacggagga ttaccgtgcc   4860
aagtacaagg cgactgactg attgaggcgt tcaatgtcag aagggagaga aagactgaaa   4920
aggtggaaag aagaggcaaa ttgttgttat tattattatt ctatctcgaa tcttctagat   4980
cttgtcgtaa ataaacaagc gtaactagct agcctccgta caactgcttg aatttgatac   5040
ccgtatggag ggcagttatt ttatttgtt tttcaagatt ttccattcgc cgttgaactc     5100
gtctcacatc gcgtgtattg cccgttgcc catgtgtacg cgtttcgggt ttacctcttc    5160
cagatacagc tcatctgcaa tgcattaatg cattggacct cgcaacccta gtacgccctt   5220
caggctccgg cgaagcagaa gaatagctta gcagagtcta ttttcatttt cgggagacta   5280
gcattctgta aacgggcagc aatcgcccag cagttagtag ggtcccctct acctctcagg   5340
gagatgtaac aacgccacct tatgggacta tcaagctgac gctggcttct gtgcagacaa   5400
actgcgccca cgagttcttc cctgacgccg ctctcgcgca ggcaagggaa ctcgatgaat   5460
actacgcaaa gcacaagaga cccgttggtc cactccatgg cctccccatc tctctcaaag   5520
accagcttcg agtcaaggta caccgttgcc cctaagtcgt tagatgtccc tttttgtcag   5580
ctaacatatg ccaccagggc tacgaaacat caatgggcta catctcatgg ctaaacaagt   5640
acgacgaagg ggactcggtt ctgacaacca tgctccgcaa agccggtgcc gtcttctacg   5700
```

```
tcaagacctc tgtcccgcag accctgatgg tctgcgagac agtcaacaac atcatcgggc    5760
gcaccgtcaa cccacgcaac aagaactggt cgtgcggcgg cagttctggt ggtgagggtg    5820
cgatcgttgg gattcgtggt ggcgtcatcg gtgtaggaac ggatatcggt ggctcgattc    5880
gagtgccggc cgcgttcaac ttcctgtacg gtctaaggcc gagtcatggg cggctgccgt    5940
atgcaaagat ggcgaacagc atggagggtc aggagacggt gcacagcgtt gtcgggccga    6000
ttacgcactc tgttgagggt gagtccttcg cctcttcctt cttttcctgc tctataccag    6060
gcctccactg tcctcctttc ttgcttttta tactatatac gagaccggca gtcactgatg    6120
aagtatgtta gacctccgcc tcttcaccaa atccgtcctc ggtcaggagc catgaaata     6180 cgactccaag gtcatcccca tgccctggcg ccagtccgag tcggacatta ttgcctccaa    6240
gatcaagaac ggcgggctca atatcggcta ctacaacttc gacggcaatg tccttccaca    6300
ccctcctatc ctgcgcggcg tggaaaccac cgtcgccgca ctcgccaaag ccggtcacac    6360
cgtgaccccg tggacgccat acaagcacga tttcggccac gatctcatct cccatatcta    6420
cgcggctgac ggcagcgccg acgtaatgcg cgatatcagt gcatccggcg agccggcgat    6480
tccaaatatc aaagacctac tgaacccgaa catcaaagct gttaacatga acgagctctg    6540
ggacacgcat ctccagaagt ggaattacca gatggagtac cttgagaaat ggcgggaggc    6600
tgaagaaaag gccgggaagg aactggacgc catcatcgcg ccgattacgc ctaccgctgc    6660
ggtacggcat gaccagttcc ggtactatgg gtatgcctct gtgatcaacc tgctggattt    6720
cacgagcgtg gttgttccgg ttacctttgc ggataagaac atcgataaga gaatgagag     6780 tttcaaggcg gttagtgagc ttgatgccct cgtgcaggaa gagtatgatc cggaggcgta    6840
ccatggggca ccggttgcag tgcaggttat cggacggaga ctcagtgaag agaggacgtt    6900
ggcgattgca gaggaagtgg ggaagttgct gggaaatgtg gtgactccat agctaataag    6960
tgtcagatag caatttgcac aagaaatcaa taccagcaac tgtaaataag cgctgaagtg    7020
accatgccat gctacgaaag agcagaaaaa aacctgccgt agaaccgaag agatatgaca    7080
cgcttccatc tctcaaagga gaatcccctt cagggttgcg tttccagtag tgattttacc    7140
gctgatgaaa tgactggact ccctcctcct gctcttatac gaaaaattgc ctgactctgc    7200
aaaggttgtt tgtcttggaa gatgatgtgc cccccatcg ctcttatctc ataccccgcc     7260
atctttctag attctcatct tcaacaagag gggcaatcca tgatctgcga tccagatgtg    7320
cttctggcct catactctgc cttcaggttg atgttcactt aattggtgac gaattcagct    7380
gatttgctgc agtatgcttt tgtgttggttc tttccaggct tgtgccagcc atgagcgctt    7440
tgagagcatg ttgtcactta taaactcgag taacggccac atattgttca ctacttgaat    7500 cacatacca  attttgatag aattgacatg tttaaagagc tgaggtagct ttaatgcctc     7560
tgaagtattg tgacacagct tctcacagag tgagaatgaa aagttggact cccctaatg     7620 aagtaaaagt ttcgtctctg aacggtgaag agcatagatc cggcatcaac tacctggcta    7680
gactacgacg tcaattctgc ggccttttga cctttatata tgtccattaa tgcaatagat    7740
tctttttttt tttttttttt tttttttttt tttttttttt tttgcccaat ttcgcagatc    7800
aaagtggacg ttatagcatc ataactaagc tcagttgctg agggaagccg tctactacct    7860
tagcccatcc atccagctcc ataccttgat actttagacg tgaagcaatt cacactgtac    7920
gtctcgcagc tctccttccc gctcttgctt ccccactggg gtccatggtg cgtgtatcgt    7980
cccctccaca attctatgcc atggtacctc cagcttatca atgccccgct aacaagtcgc    8040
ctctttgcct tgatagctta tcgataaaac ttttttttccg ccagaaaggc tccgcccaca    8100
```

-continued

```
gacaagaaaa aaaattcacc gcctagcctt tggccccggc atttggctaa acctcgagcc    8160
tctctcccgt cttggggtat caggaagaaa agaaaaaaat ccatcgccaa gggctgtttt    8220
ggcatcacca cccgaaaaca gcacttcctc gatcaaaagt tgcccgccat gaagaccacg    8280
tggaaggaca tccctccggt gcctacgcac caggagtttc tggacattgt gctgagcagg    8340
acccagcgca aactgcccac tcagatccgt gccggcttca agattagcag aattcgaggt    8400
acgtcgcatt gcccatcgca ggatgtctca ttatcgggt ccttggagaa cgatcatgat     8460
tgcatggcga tgctaacaca tagacagcct tctacactcg aaaggtcaag ttcacccagg    8520
agacgttttc cgaaaagttc gcctccatcc tcgacagctt ccctcgcctc caggacatcc    8580
accccttcca caggaccctt ctcaacaccc tctacgatgc cgaccacttc aagattgccc    8640
ttggccagat gtccactgcc aagcacctgg tcgagaccat ctcgcgcgac tacgtccgtc    8700
tcttgaaata cgcccagtcg ctctaccagt gcaagcagct caagcgggcc gctctcggtc    8760
gcatggccac gctggtcaag cgcctcaagg acccctgct gtacctggac caggtccgcc     8820
agcatctcgg ccgtcttccc tccatcgacc ccaacaccag gaccctgctc atctgcggtt    8880
accccaatgt tggcaagtcc agcttcctgc gaagtatcac ccgcgccgat gtggacgtcc    8940
agccctatgc tttcaccacc aagagtctgt tgtcggcca ctttgactac aagtacctgc      9000
gattccaggc cattgatacc cccggtattc tggaccaccc tcttgaggag atgaacacta    9060
tcgaaatgca gaggtatgtg gcgcggct                                        9088
```

<210> SEQ ID NO 17
<211> LENGTH: 5610
<212> TYPE: DNA
<213> ORGANISM: Artificial Sequence
<220> FEATURE:
<223> OTHER INFORMATION: Chemically synthesized nucleotide sequence of
      the bgl1 knockout cassette

<400> SEQUENCE: 17

```
aatggtagga atgctgggat ataggctctg tgctggcaag ttgatggatc ctcgaatgag     60
gccgccctgc aaggggaaca tcagagatct accattgcct ccttggccca atccactatc    120
atacctacct catgatcatt cctgcgaagg tctaccagta aatatttcct cgtcccgtgt    180
ttcatcatgt ccagaacctc atctcgccaa attgactttg ccacagtgtc tggagctggg   240
taagcagcgt gccaaggaat tgttgtcgag tctgtgccag gcattgtgcc cgacattgtg    300
aacttcagcc aggagaactt ttcgatcgca cctatgctga gcaccgtggg catgcgatgg    360
cttcaataat gcagttcgag agggagtgtg tcatgcccta aagctcattg ccacctcca     420 caggctagct ctacctgcat ctgtagatgg actttccttg tcctcctcct tcagaaaacc    480
tcttggtcgc tcgcaggtaa ctgttgttgc cgtcattgtt tgacagtgga tagccaaggc    540
aaaaccgtct gctttcaacg gaagcattcg gcggttgttt gtcatcgtgt tatcgatcga    600
ccaggagaac ccagacgagt gttgttcgag agaatcatcg acgatgtgaa gaggcgacga    660
ctagtatcta gaagattata atcgaacaaa tcagcgtttg tctgtcgggc gtttgagggc    720
gcagttgccc gccaaagcag cgtcgcaata tataggcagc gagagactgt caacagccag    780
ccgccatgtg atcgatcgta gccgtcttcc cgatcttccc taaacccctt tctttggggg    840 gcggggcag cggcgttcta atatttgctg gctgtctgga taacgtgaat ggtagacatg      900
gtaatgttcg gtctgcgaaa catttgtaca attggagttt acgatcgaga tggaaggaaa    960
cgctccacaa actcggtgac tgggttgcca tcaggtgctc agggcatagc gttctctgca    1020
aatagaggaa agagaatagc actagtgaaa gtgtgaatca caatgaagag gaggttgttg    1080
```

```
ccggaatgct tgagcagcg tcaaagttga acttgaagct atcacaaatt gcagggtaaa    1140
gtacatgttg gtgccagttt gacagcacag tgcgcggagc ggaggatgtc gcggaagagg   1200
cgcgacgcta acccgggcct tcttctcagt gagcagaact cctgctgcaa gagttccttc    1260
tctctgcgag atgacgtgag gcccaatttg cagcttccct cgaacaaggt gattgaacat    1320
ctctcttccc tcacatttca tcatcactac ctcctcaatt cacttctgct tcggccgtct    1380
tcatcattca tgttactgct ctgatgccta tcctgaagat tgtattcctg cagtattcac    1440
gccatcccac cttcggtcct cactcacagt cacaggtcaa ccgccttcac cctcctcgcg    1500
atgatgtcgg caatctggtg gatcaatgtg cggttgaggg ccgccgtagt gaggatgggc    1560
atggggaacg aggtcgccca ttcgcccaca gataacttcg tatagcatac attatacgaa    1620
gttatcctgg gcttgtgact ggtcgcgagc tgccactaag tggggcagta ccattttatc    1680
ggacccatcc agctatggga cccactcgca aattttaca tcattttctt tttgctcagt     1740
aacggccacc ttttgtaaag cgtaaccagc aaacaaattg caattggccc gtagcaaggt    1800
agtcagggct tatcgtgatg gaggagaagg ctatatcagc ctcaaaaata tgttgccagc    1860
tggcggaagc ccggaaggta agtggattct tcgccgtggc tggagcaacc ggtggattcc    1920
agcgtctccg acttggactg agcaattcag cgtcacggat tcacgataga cagctcagac    1980
cgctccacgc ctggcggcat tattggttaa cccggaaact cagtctcctt ggccccgtcc    2040
cgaagggacc cgacttacca ggctgggaaa gccagggata gaatacactg tacgggcttc    2100
gtacgggagg ttcggcgtag ggttgttccc aagtttaca caccccccaa gacagctagc     2160
gcacgaaaga cgcggagggt ttggtgaaaa aagggcgaaa attaagcggg agacgtattt    2220
aggtgctagg gccggtttcc tccccatttt tcttcggttc cctttctctc ctggaagact    2280
ttctctctct ctcttcttct cttcttccat cctcagtcca tcttcctttc ccatcatcca    2340
tctcctcacc tccatctcaa ctccatcaca tcacaatcga tatgaaaaag cctgaactca    2400
ccgcgacgtc tgtcgagaag tttctgatcg aaaagttcga cagcgtctcc gacctgatgc    2460
agctctcgga gggcgaagaa tctcgtgctt tcagcttcga tgtaggaggg cgtggatatg    2520
tcctgcgggt aaatagctgc gccgatggtt tctacaaaga tcgttatgtt tatcggcact    2580
ttgcatcggc cgcgctcccg attccggaag tgcttgacat tggggaattc agcgagagcc    2640
tgacctattg catctcccgc cgtgcacagg gtgtcacgtt gcaagacctg cctgaaaccg    2700
aactgcccgc tgttctgcag ccggtcgcgg aggccatgga tgcgatcgct gcggccgatc    2760
ttagccagac gagcgggttc ggcccattcg gaccgcaagg aatcggtcaa tacactacat    2820
ggcgtgattt catatgcgcg attgctgatc cccatgtgta tcactggcaa actgtgatgg    2880
acgacaccgt cagtgcgtcc gtcgcgcagg ctctcgatga gctgatgctt tgggccgagg    2940
actgccccga gtccggcac ctcgtgcacg cggatttcgg ctccaacaat gtcctgacgg     3000
acaatggccg cataacagcg gtcattgact ggagcgaggc gatgttcggg gattcccaat    3060
acgaggtcgc caacatcttc ttctggaggc cgtggttggc ttgtatggag cagcagacgc    3120
gctacttcga gcggaggcat ccggagcttg caggatcgcc gcggctccgg gcgtatatgc    3180
tccgcattgg tcttgaccaa ctctatcaga gcttggttga cggcaatttc gatgatgcag    3240
cttgggcgca gggtcgatgc gacgcaatcg tccgatccgg agccgggact gtcgggcgta    3300
cacaaatcgc ccgcagaagc gcggccgtct ggaccgatgg ctgtgtagaa gtactcgccg    3360
atagtggaaa ccgacgcccc agcactcgtc cgagggcaaa ggaatagagt agatgccgac    3420
cgggatccac ttaacgttac tgaaatcatc aaacagcttg acgaatctgg atataagatc    3480
```

```
gttggtgtcg atgtcagctc cggagttgag acaaatggtg ttcaggatct cgataagata    3540
cgttcatttg tccaagcagc aaagagtgcc ttctagtgat ttaatagctc catgtcaaca    3600
agaataaaac gcgtttcggg tttacctctt ccagatacag ctcatctgca atgcattaat    3660
gcattggacc tcgcaaccct agtacgccct tcaggctccg gcgaagcaga agaatagctt    3720
agcagagtct attttcattt tcgggagacg agatcaagca gatcaacggt cgtcaagaga    3780
cctacgagac tgaggaatcc gctcttggct ccacgcgact atatatttgt ctctaattgt    3840
actttgacat gctcctcttc tttactctga tagcttgact atgaaaattc cgtcaccagc    3900
ccctgggttc gcaaagataa ttgcactgtt tcttccttga actctcaagc ctacaggaca    3960
cacattcatc gtaggtataa acctcgaaaa tcattcctac taagatgggt atacaatagt    4020
aaccatggtt gcctagtgaa tgctccgtaa cacccaatac gccggccgat aacttcgtat    4080
agcatacatt atacgaagtt atacttggcg cgcctagtgg aacacgagca cataagcttt    4140
tacctatggt tatcgcttgc atctacgcgc cgttgatggt ggaggatggt ggacgttccc    4200 gagacccta cgagctgtgg catcgtcaaa ctgtgcccac agacctttgt cttgctttca    4260
taacctcgag gagtgtttcc agactcatca tccatacaca agcagtatta atcaaagaaa    4320
ctcggtcgca atggcaaaaa tggttttgcaa acagaaaact atggcctctt cctattccat    4380
cattaactac tctacccgtt tgtcataaca acatcattaa aacccttatg cgtcaggtgt    4440
agcatccttg atctgttgct cctccaacgg ccagttctca atcgttacct cttctcccac    4500
caactcaaac tcaagcttca cagactcgtc ggtgttcaag gctagctcat acttgccggg    4560
gtatacaatc cggtttccgt gagaatcaac acgggcgaga gcactgacag ggatggggat    4620
gctgagcttg gaagagtgac caggcttgat gtcggcaagt cggtcgaatc cgacgagcca    4680
cttgttcggg tacggggctg ggccagcgtt gcttgtgcga acaaacagca tggccgtata    4740
tggggactcc gtcttgcccg agttcttgat gttggcctcg aaggtgaaga cgggaatctg    4800
ctcgctgtaa gtgtatccgg ggtgaggagc agagaggatc gatgaggtgt tgaacttgag    4860
gctcttgggg tggctggcga gagtctcctt gaaggtggtg tagaagagac cactgccaaa    4920
ctcgtagacg ggtttgccgg tgtaccagat gtaagtctgt ccagggtttg actttccatc    4980
gggtcggagg ttcatgtcat tctgggggaa ttggtgaaca tactcagccg ggtactgagt    5040
ggtgaccagt cggccggcag gagcacgctt gccagagaga atgtcgaaga gggcaacgcc    5100
tcccgactgg ccgggatatc cgccccagac gaggagttg accttcttgt tgctcttgag    5160
cgaggatgag tctacctgac caccgcccat ttgcaggacg acaaggggtt tgccgacctc    5220
gctgagctgc ttgatgagat ccagctgatt accgggccaa gcaatgtccg tgcggtcagc    5280
gccctcctgt tcaatggtgt tgtcaattcc accgaggtag atgatggcat ccgacttctt    5340
ggcggcagca atggccttgg caaagccagt ggtgctgttg ccggcgatct ctgtgccgag    5400
ttcaaagttg acgtgatagc cggccttctt agcagcttcc agagggctga tgaggtatgg    5460
ggcagggcca tagtagttgc cttgcatttg ggttgtggca ttggcccatg gtccgatcag    5520
agcaatgctg cgcaccttct tggacagagg gagagtgcca tcgttcttga gcaggacgat    5580
gccctcaaca gcagcctcgt acgagatgtt                                    5610
```

<210> SEQ ID NO 18
<211> LENGTH: 13862
<212> TYPE: DNA
<213> ORGANISM: Artificial Sequence
<220> FEATURE:
<223> OTHER INFORMATION: Chemically synthesized nucleotide sequence of the telomeric vector, pTTT-cre

<400> SEQUENCE: 18

```
ttgtacaaag tggtgatcgc gccgcgcgcc agctccgtgc gaaagcctga cgcaccggta        60
gattcttggt gagcccgtat catgacggcg gcgggagcta catggcccg ggtgatttat        120
ttttttttgta tctacttctg acccttttca aatatacggt caactcatct ttcactggag      180
atgcggcctg cttggtattg cgatgttgtc agcttggcaa attgtggctt tcgaaaacac      240
aaaacgattc cttagtagcc atgcatttta agataacgga atagaagaaa gaggaaatta      300
aaaaaaaaaa aaaacaaac atcccgttca taacccgtag aatcgccgct cttcgtgtat       360
cccagtacca gtttattttg aatagctcgc ccgctggaga gcatcctgaa tgcaagtaac      420
aaccgtagag gctgacacgg caggtgttgc tagggagcgt cgtgttctac aaggccagac      480
gtcttcgcgg ttgatatata tgtatgtttg actgcaggct gctcagcgac gacagtcaag      540
ttcgccctcg ctgcttgtgc aataatcgca gtggggaagc cacaccgtga ctcccatctt      600
tcagtaaagc tctgttggtg tttatcagca atacacgtaa tttaaactcg ttagcatggg      660
gctgatagct taattaccgt ttaccagtgc catggttctg cagcttttcct tggcccgtaa     720
aattcggcga agccagccaa tcaccagcta ggcaccagct aaaccctata attagtctct      780
tatcaacacc atccgctccc ccgggatcaa tgaggagaat gaggggatg cggggctaaa       840
gaagcctaca taaccctcat gccaactccc agtttacact cgtcgagcca acatcctgac      900
tataagctaa cacagaatgc ctcaatcctg ggaagaactg gccgctgata agcgcgcccg      960
cctcgcaaaa accatccctg atgaatggaa agtccagacg ctgcctgcgg aagacagcgt     1020
tattgatttc ccaaagaaat cggggatcct ttcagaggcc gaactgaaga tcacagaggc     1080
ctccgctgca gatcttgtgt ccaagctggc ggccggagag ttgacctcgg tggaagttac     1140
gctagcattc tgtaaacggg cagcaatcgc ccagcagtta gtagggtccc ctctacctct     1200
cagggagatg taacaacgcc accttatggg actatcaagc tgacgctggc ttctgtgcag     1260
acaaactgcg cccacgagtt cttccctgac gccgctctcg cgcaggcaag ggaactcgat     1320
gaatactacg caaagcacaa gagacccgtt ggtccactcc atggcctccc catctctctc     1380
aaagaccagc ttcgagtcaa ggtacaccgt tgcccctaag tcgttagatg tcccttttg      1440
tcagctaaca tatgccacca gggctacgaa acatcaatgg gctacatctc atggctaaac     1500
aagtacgacg aaggggactc ggttctgaca accatgctcc gcaaagccgg tgccgtcttc     1560
tacgtcaaga cctctgtccc gcagaccctg atggtctgcg agacagtcaa caacatcatc     1620
gggcgcaccg tcaacccacg caacaagaac tggtcgtgcg gcggcagttc tggtggtgag     1680
ggtgcgatcg ttgggattcg tgtggcgtc atcggtgtag aacggatat cggtggctcg       1740
attcgagtgc cggccgcgtt caacttcctg tacggtctaa ggccgagtca tgggcggctg     1800
ccgtatgcaa agatggcgaa cagcatggag ggtcaggaga cggtgcacag cgttgtcggg     1860
ccgattacgc actctgttga gggtgagtcc ttcgcctctt ccttcttttc ctgctctata     1920
ccaggcctcc actgtcctcc tttcttgctt tttatactat atacgagacc ggcagtcact     1980
gatgaagtat gttagacctc cgcctcttca ccaaatccgt cctcggtcag gagccatgga     2040
aatacgactc caaggtcatc cccatgccct ggcgccagtc cgagtcggac attattgcct     2100
ccaagatcaa gaacggcggg ctcaatatcg gctactacaa cttcgacggc aatgtccttc     2160
cacaccctcc tatcctgcgc ggcgtggaaa ccacgtcgc cgcactcgcc aaagccggtc      2220
acaccgtgac cccgtggacg ccatacaagc acgatttcgg ccacgatctc atctcccata     2280
```

```
tctacgcggc tgacggcagc gccgacgtaa tgcgcgatat cagtgcatcc ggcgagccgg      2340
cgattccaaa tatcaaagac ctactgaacc cgaacatcaa agctgttaac atgaacgagc      2400
tctgggacac gcatctccag aagtggaatt accagatgga gtaccttgag aaatggcggg      2460
aggctgaaga aaaggccggg aaggaactgg acgccatcat cgcgccgatt acgcctaccg      2520
ctgcggtacg gcatgaccag ttccggtact atgggtatgc ctctgtgatc aacctgctgg      2580
atttcacgag cgtggttgtt ccggttacct ttgcggataa aacatcgat  aagaagaatg      2640 agagtttcaa ggcggttagt gagcttgatg ccctcgtgca ggaagagtat gatccggagg      2700
cgtaccatgg ggcaccggtt gcagtgcagg ttatcggacg gagactcagt gaagagagga      2760
cgttggcgat tgcagaggaa gtggggaagt tgctgggaaa tgtggtgact ccatagctaa      2820
taagtgtcag atagcaattt gcacaagaaa tcaataccag caactgtaaa taagcgctga      2880
agtgaccatg ccatgctacg aaagagcaga aaaaaacctg ccgtagaacc gaagagatat      2940
gacacgcttc catctctcaa aggaagaatc ccttcagggt tgcgtttcca gtctagacac      3000
gtataacggc acaagtgtct ctcaccaaat gggttatatc tcaaatgtga tctaaggatg      3060
gaaagcccag aatatcgatc gcgcgcagat ccatatatag ggcccgggtt ataattacct      3120
caggaaatag cttttaagtag cttattaagt attaaaatta tatatatttt taatataact      3180
atatttcttt aataaatagg tattttaagc tttatatata aatataataa taaaataata      3240
tattatatag ctttttatta ataaataaaa tagctaaaaa tataaaaaaa atagctttaa      3300
aatacttatt tttaattaga attttatata tttttaatat ataagatctt ttacttttt       3360 ataagcttcc taccttaaat taaatttta  ctttttttta ctattttact atatcttaaa      3420
taaaggcttt aaaaatataa aaaaaatctt cttatatatt ataagctata aggattatat      3480 atatatttt ttttaattttt taaagtaagt attaaagcta gaattaaagt tttaattttt      3540 taaggctta  tttaaaaaaa ggcagtaata gcttataaaa gaaatttctt tttctttat      3600 actaaaagta cttttttttt aataaggtta gggttagggt tagggttagg gttagggtta      3660
gggttagggt tagggttagg gttagggtta gggttagggt tagggttagg gttagggtaa      3720
gggtttaaac aaagccacgt tgtgtctcaa aatctctgat gttacattgc acaagataaa      3780
aatatatcat catgaacaat aaaactgtct gcttacataa acagtaatac aagggtgtt       3840 atgagccata ttcaacggga aacgtcttgc tcgaggccgc gattaaattc caacatggat      3900
gctgatttat atgggtataa atgggctcgc gataatgtcg ggcaatcagg tgcgacaatc      3960
tatcgattgt atgggaagcc cgatgcgcca gagttgtttc tgaaacatgg caaaggtagc      4020
gttgccaatg atgttacaga tgagatggtc agactaaact ggctgacgga atttatgcct      4080
cttccgacca tcaagcattt tatccgtact cctgatgatg catggttact caccactgcg      4140
atccccggga aaacagcatt ccaggtatta gaagaatatc ctgattcagg tgaaaatatt      4200
gttgatgcgc tggcagtgtt cctgcgccgg ttgcattcga ttcctgtttg taattgtcct      4260
tttaacagcg atcgcgtatt tcgtctcgct caggcgcaat cacgaatgaa taacggtttg      4320
gttgatgcga gtgattttga tgacgagcgt aatggctggc ctgttgaaca agtctggaaa      4380
gaaatgcata agcttttgcc attctcaccg gattcagtcg tcactcatgg tgatttctca      4440
cttgataacc ttatttttga cgaggggaaa ttaataggtt gtattgatgt tggacgagtc      4500
ggaatcgcag accgatacca ggatcttgcc atcctatgga actgcctcgg tgagttttct      4560
ccttcattac agaaacggct ttttcaaaaa tatggtattg ataatcctga tatgaataaa      4620
ttgcagtttc atttgatgct cgatgagttt ttctaatcag aattggttaa ttggttgtaa      4680
```

```
cactggcaga gcattacgct gacttgacgg gacggcggct tgttgaata aatcgaactt    4740 ttgctgagtt gaaggatcag atcacgcatc ttcccgacaa cgcagaccgt tccgtggcaa    4800
agcaaaagtt caaaatcacc aactggtcca cctacaacaa agctctcatc aaccgtggct    4860
ccctcacttt ctggctggat gatggggcga ttcaggcctg gtatgagtca gcaacacctt    4920
cttcacgagg cagacctcag cggtttaaac ctaaccctaa ccctaacccct aaccctaacc    4980 ctaaccctaa ccctaacccct aaccctaacc ctaaccctaa ccctaacccct aaccctaacc    5040 taaccctaat ggggtcgatc tgaaccgagg atgagggttc tatagactaa tctacaggcc    5100
gtacatggtg tgattgcaga tgcgacgggc aaggtgtaca gtgtccagaa ggaggagagc    5160
ggcataggta ttgtaataga ccagctttac ataataatcg cctgttgcta ctgactgatg    5220
accttcttcc ctaaccagtt tcctaattac cactgcagtg aggataaccc taactcgctc    5280
tggggttatt attatactga ttagcaggtg gcttatatag tgctgaagta ctataagagt    5340
ttctgcggga ggaggtggaa ggactataaa ctggacacag ttagggatag agtgatgaca    5400
agacctgaat gttatcctcc ggtgtggtat agcgaattgg ctgaccttgc agatggtaat    5460
ggtttaggca gggttttttgc agaggggggac gagaacgcgt tctgcgattt aacggctgct    5520
gccgccaagc tttacggttc tctaatgggc ggccgcctca ggtcgacgtc ccatggccat    5580
tcgaattcgt aatcatggtc atagctgttt cctgtgtgaa attgttatcc gctcacaatt    5640
ccacacaaca tacgagccgg aagcataaag tgtaaagcct ggggtgccta atgagtgagc    5700
taactcacat taattgcgtt gcgctcactg cccgctttcc agtcgggaaa cctgtcgtgc    5760
cagctgcatt aatgaatcgg ccaacgcgcg gggagaggcg gtttgcgtat tgggcgctct    5820
tccgcttcct cgctcactga ctcgctgcgc tcggtcgttc ggctgcggcg agcggtatca    5880
gctcactcaa aggcggtaat acggttatcc acagaatcag gggataacgc aggaaagaac    5940
atgtgagcaa aaggccagca aaaggccagg aaccgtaaaa aggccgcgtt gctggcgttt    6000
ttccataggc tccgcccccc tgacgagcat cacaaaaatc gacgctcaag tcagaggtgg    6060
cgaaacccga caggactata aagataccag gcgtttcccc ctggaagctc cctcgtgcgc    6120
tctcctgttc cgaccctgcc gcttaccgga tacctgtccg cctttctccc ttcgggaagc    6180
gtggcgcttt ctcatagctc acgctgtagg tatctcagtt cggtgtaggt cgttcgctcc    6240
aagctgggct gtgtgcacga accccccgtt cagcccgacc gctgcgcctt atccggtaac    6300
tatcgtcttg agtccaaccc ggtaagacac gacttatcgc cactggcagc agccactggt    6360
aacaggatta gcagagcgag gtatgtaggc ggtgctacag agttcttgaa gtggtggcct    6420
aactacggct acactagaag aacagtattt ggtatctgcg ctctgctgaa gccagttacc    6480
ttcggaaaaa gagttggtag ctcttgatcc ggcaaacaaa ccaccgctgg tagcggtggt    6540
ttttttgttt gcaagcagca gattacgcgc agaaaaaaag gatctcaaga agatcctttg    6600
atcttttcta cggggtctga cgctcagtgg aacgaaaact cacgttaagg gattttggtc    6660
atgagattat caaaaaggat cttcacctag atccttttaa attaaaaatg aagttttaaa    6720
tcaatctaaa gtatatatga gtaaacttgg tctgacagtt accaatgctt aatcagtgag    6780
gcacctatct cagcgatctg tctatttcgt tcatccatag ttgcctgact ccccgtcgtg    6840
tagataacta cgatacggga gggcttacca tctggcccca gtgctgcaat gataccgcga    6900
gacccacgct caccggctcc agatttatca gcaataaacc agccagccgg aagggccgag    6960
cgcagaagtg gtcctgcaac tttatccgcc tccatccagt ctattaattg ttgccgggaa    7020
gctagagtaa gtagttcgcc agttaatagt ttgcgcaacg ttgttgccat tgctacaggc    7080
```

```
atcgtggtgt cacgctcgtc gtttggtatg gcttcattca gctccggttc ccaacgatca   7140
aggcgagtta catgatcccc catgttgtgc aaaaaagcgg ttagctcctt cggtcctccg   7200
atcgttgtca gaagtaagtt ggccgcagtg ttatcactca tggttatggc agcactgcat   7260
aattctctta ctgtcatgcc atccgtaaga tgcttttctg tgactggtga gtactcaacc   7320
aagtcattct gagaatagtg tatgcggcga ccgagttgct cttgcccggc gtcaatacgg   7380
gataataccg cgccacatag cagaacttta aaagtgctca tcattggaaa acgttcttcg   7440
gggcgaaaac tctcaaggat cttaccgctg ttgagatcca gttcgatgta acccactcgt   7500
gcacccaact gatcttcagc atcttttact ttcaccagcg tttctgggtg agcaaaaaca   7560
ggaaggcaaa atgccgcaaa aaagggaata agggcgacac ggaaatgttg aatactcata   7620
ctcttccttt ttcaatatta ttgaagcatt tatcagggtt attgtctcat gagcggatac   7680
atatttgaat gtatttagaa aaataaacaa ataggggttc cgcgcacatt tccccgaaaa   7740
gtgccacctg acgtctaaga aaccattatt atcatgacat taacctataa aaataggcgt   7800
atcacgaggc cctttcgtct cgcgcgtttc ggtgatgacg gtgaaaacct ctgacacatg   7860
cagctcccgg agacggtcac agcttgtctg taagcggatg ccgggagcag acaagcccgt   7920
cagggcgcgt cagcgggtgt tggcgggtgt cggggctggc ttaactatgc ggcatcagag   7980
cagattgtac tgagagtgca ccataaaatt gtaaacgtta atattttgtt aaaattcgcg   8040
ttaaattttt gttaaatcag ctcatttttt aaccaatagg ccgaaatcgg caaaatccct   8100
tataaatcaa aagaatagcc cgagataggg ttgagtgttg ttccagtttg gaacaagagt   8160
ccactattaa agaacgtgga ctccaacgtc aaagggcgaa aaaccgtcta tcagggcgat   8220
ggcccactac gtgaaccatc acccaaatca gttttttgg ggtcgaggtg ccgtaaagca   8280
ctaaatcgga accctaaagg gagcccccga tttagagctt gacggggaaa gccggcgaac   8340
gtggcgagaa aggaagggaa gaaagcgaaa ggagcgggcg ctagggcgct ggcaagtgta   8400
gcggtcacgc tgcgcgtaac caccacaccc gccgcgctta atgcgccgct acagggcgcg   8460
tactatggtt gctttgacgt atgcggtgtg aaataccgca cagatgcgta aggagaaaat   8520
accgcatcag cgccattcg ccattcaggc tgcgcaactg ttgggaaggg cgatcggtgc   8580
gggcctcttc gctattacgc cagctggcga aggggggatg tgctgcaagg cgattaagtt   8640
gggtaacgcc agggttttcc cagtcacgac gttgtaaaac gacggccagt gccaagctt    8700
actagatgca tgctcgagcg gccgccagtg tgatggatat ctgcagaatt cgcccttgac   8760
tagtgctctc tatcctggtg gcaggcgtca agtaccagga ggcagcagcg ggcttaggag   8820
cggcctgggt tgttctccgc accctctaca tgctgggcta tatttatagc gacaagccga   8880
acggcaccgg caggtacaat ggttcgctgt acttgcttgc gcaagcgggt ctttggggat   8940
tgagcgcatt tggtgttgca aaggatttga tgtaaatgta gtcgacatct tagcacagag   9000
gggagagtta ataaaatgtg gtctgtttga atgatagtcg ggttcgtgac ctatattcgt   9060
gatagtggag ataggtctgc gcctatctta tcgggccgga gcaaaaattc caccgcagcg   9120
gggtgagttt tcgttataca gccatcccac ttccagcttc aaattgtcag tttaatccag   9180
cccaattcaa tcattggaga accgccatca tgtcttcgaa gtcccacctc ccctacgcaa   9240
ttcgcgcaac caaccatccc aaccctttaa catctaaact cttctccatc gccgaggaga   9300
agaaaaccaa cgtcaccgtc tccgcagacg ttactacttc cgccgagctc ctcgatcttg   9360
ctgaccgtac atcctgcacc aatgcccctc caggataaca aatagctgat gcgtagtgag   9420
tacaggccta ggcccctata tcgcagttct gaaaacccac atcgacatcc tcaccgatct   9480
```

```
caccccgtcg acccttcct cgctccaatc cctcgcgaca agcacaact tcctcatctt    9540
tgaggaccgc aagttcatcg acatcggcaa caccgtgcaa aagcagtacc acggtggcgc  9600
tctccgcatc tccgaatggg cacacatcat caactgcgcc atcctgccgg gcgaagggat  9660
cgtcgaggcc ctcgcacaga caaccaagtc tcctgacttt aaagacgcga atcaacgagg  9720
tctcctgatt cttgccgaga tgacgagtaa gggatctctt gcgacagggg agtcacaggc  9780
acgctcggtt gagtacgcgc ggaagtataa ggggtttgtg atgggattcg tgagtacaag  9840
ggcgttgagt gaggtgctgc ccgaacagaa agaggagagc gaggattttg tcgtctttac  9900
gactggggta atctgtcgg ataaggggga taagctgggg cagcagtatc agacacctgg   9960
gtcggcggtt gggcgaggtg cggactttat cattgcgggt aggggcatct ataaggcgga  10020
cgatccagtc gaggcggttc agaggtaccg ggaggaaggc tggaaagctt acgagaaaag  10080
agttggactt tgagtgtgag tggaaatgtg taacggtatt gactaaaagg gatccatatg  10140
tttattgcag ccagcatagt attaccagaa agagcctcac tgacggctct agtagtattc  10200
gaacagatat tattgtgacc agctctgaac gatatgctcc ctaatctggt agacaagcac  10260
tgatctaccc cttggaacgc agcatctagg ctctggctgt gctctaaccc taactagacg  10320
attgatcgca gaccatccaa tactgaaaag tctctatcag aggaaatccc caacattgta  10380
gtagtcaggt tcctttgtgg ctgggagaga attggttcgc tccactgatt ccagttgaga  10440
aagtgggcta gaaaaaagtc ttgaagattg gagttgggct gtggttatct agtacttctc  10500
gagctctgta catgtccggt cgcgacgtac gcgtatcgat ggcgccagct gcaggcggcc  10560
gcctgcagcc acttgcagtc ccgtggaatt ctcacggtga atgtaggcct tttgtagggt  10620
aggaattgtc actcaagcac ccccaacctc cattacgcct cccccataga gttcccaatc  10680
agtgagtcat ggcactgttc tcaaatagat tggggagaag ttgacttccg cccagagctg  10740
aaggtcgcac aaccgcatga tatagggtcg gcaacggcaa aaaagcacgt ggctcaccga  10800
aaagcaagat gtttgcgatc taacatccag gaacctggat acatccatca tcacgcacga  10860
ccactttgat ctgctggtaa actcgtattc gccctaaacc gaagtgcgtg gtaaatctac  10920
acgtgggccc ctttcggtat actgcgtgtg tcttctctag gtgccattct tttcccttcc  10980
tctagtgttg aattgtttgt gttggagtcc gagctgtaac tacctctgaa tctctggaga  11040
atggtggact aacgactacc gtgcacctgc atcatgtata taatagtgat cctgagaagg  11100
ggggtttgga gcaatgtggg actttgatgg tcatcaaaca aagaacgaag acgcctcttt  11160
tgcaaagttt tgtttcggct acggtgaaga actggatact tgttgtgtct tctgtgtatt  11220
tttgtggcaa caagaggcca gagacaatct attcaaacac caagcttgct cttttgagct  11280
acaagaacct gtggggtata tatctagagt tgtgaagtcg gtaatcccgc tgtatagtaa  11340
tacgagtcgc atctaaatac tccgaagctg ctgcgaaccc ggagaatcga gatgtgctgg  11400
aaagcttcta gcgagcggct aaattagcat gaaaggctat gagaaattct ggagacggct  11460
tgttgaatca tggcgttcca ttcttcgaca agcaaagcgt tccgtcgcag tagcaggcac  11520
tcattcccga aaaaactcgg agattcctaa gtagcgatgg aaccggaata atataatagg  11580
caatacattg agttgcctcg acggttgcaa tgcagggtta ctgagcttgg acataactgt  11640
tccgtacccc acctcttctc aacctttggc gtttccctga ttcagcgtac ccgtacaagt  11700
cgtaatcact attaacccag actgaccgga cgtgttttgc ccttcatttg gagaaataat  11760
gtcattgcga tgtgtaattt gcctgcttga ccgactgggg ctgttcgaag cccgaatgta  11820
ggattgttat ccgaactctg ctcgtagagg catgttgtga atctgtgtcg ggcaggacac  11880
```

```
gcctcgaagg ttcacggcaa gggaaaccac cgatagcagt gtctagtagc aacctgtaaa    11940
gccgcaatgc agcatcactg gaaaatacaa accaatggct aaaagtacat aagttaatgc    12000
ctaaagaagt catataccag cggctaataa ttgtacaatc aagtggctaa acgtaccgta    12060
atttgccaac ggcttgtggg gttgcagaag caacggcaaa gccccacttc ccacgtttg     12120 tttcttcact cagtccaatc tcagctggtg atcccccaat tgggtcgctt gtttgttccg    12180
gtgaagtgaa agaagacaga ggtaagaatg tctgactcgg agcgttttgc atacaaccaa    12240
gggcagtgat ggaagacagt gaaatgttga cattcaagga gtatttagcc agggatgctt    12300
gagtgtatcg tgtaaggagg tttgtctgcc gatacgacga atactgtata gtcacttctg    12360
atgaagtggt ccatattgaa atgtaaagtc ggcactgaac aggcaaaaga ttgagttgaa    12420
actgcctaag atctcgggcc ctcgggcctt cggcctttgg gtgtacatgt ttgtgctccg    12480
ggcaaatgca aagtgtggta ggatcgaaca cactgctgcc tttaccaagc agctgagggt    12540
atgtgatagg caaatgttca ggggccactg catggtttcg aatagaaaga gaagcttagc    12600
caagaacaat agccgataaa gatagcctca ttaaacggaa tgagctagta ggcaaagtca    12660
gcgaatgtgt atatataaag gttcgaggtc cgtgcctccc tcatgctctc ccatctact    12720 catcaactca gatcctccag gagacttgta caccatcttt tgaggcacag aaacccaata    12780
gtcaaccatc acaagtttgt acaaaaaagc aggctcacca tgagcaacct gctcaccgtc    12840
caccagaacc tccctgccct ccctgtcgac gccacctctg acgaggtccg caagaacctc    12900
atggacatgt tccgcgaccg ccaggccttt agcgagcaca cctggaagat gctcctcagc    12960
gtctgccgat cttgggccgc ctggtgcaag ctcaacaacc gcaagtggtt ccccgccgag    13020
ccggaggacg tccgcgacta cctcctctac ctgcaggccc gaggcctggc cgtcaagacc    13080
atccagcagc acctcggcca gctcaacatg ctccaccgac gctctggcct gcctcgccct    13140
agcgactcta acgccgtcag cctggtcatg cgccgcatcc gcaaggagaa cgtcgacgct    13200
ggcgagcgag ccaagcaggc cctcgccttc gagcgcaccg acttcgacca ggtccgcagc    13260
ctcatggaga acagcgaccg ctgccaggat atccgcaacc tcgcctttct cggcattgcc    13320
tacaacaccc tgctccgcat tgccgagatc gcccgcatcc gcgtcaagga catctctcgc    13380
accgacggcg ccgcatgct cattcacatc ggccgcacca agaccctcgt gtctaccgcc    13440
ggcgtcgaga aggccctcag cctcggcgtc accaagctcg tcgagcgctg gatttctgtc    13500
tccggcgtcg ctgacgaccc caacaactac ctcttctgcc gcgtccgaaa gaacggcgtc    13560
gccgcccctt ctgccacctc tcagctcagc acccgagccc tggagggcat ctttgaggcc    13620
acccaccgcc tcatctacgg cgccaaggac gactctggcc agcgctacct cgcctggtct    13680
ggccactctg cccgagtcgg cgctgcccga gacatggccc gagccggcgt cagcatcccc    13740
gagattatgc aggccggcgg ctggaccaac gtcaacatcg tcatgaacta catccgcacc    13800
ctcgactctg agaccggcgc catggtccga ctcctcgagg acggcgacta aacccagctt    13860
tc                                                                    13862

<210> SEQ ID NO 19
<211> LENGTH: 6511
<212> TYPE: DNA
<213> ORGANISM: Artificial Sequence
<220> FEATURE:
<223> OTHER INFORMATION: Chemically synthesized nucleotide sequence of
      the egl3 deletion cassette

<400> SEQUENCE: 19
gggaggtagg cgcagatacg gtgcatggga cccgaacccg taaccggaac acgaccttat       60
```

| | |
|---|---|
| cagccctcca actcacaccc tctcgcctat cactatccta gatagttcat cggccaactc | 120 |
| atgtaaccta gctacctacc tacctggtaa gaatgcgggc tatcatgtct cacggcgcgg | 180 |
| tacatgtcgg tatctcgctg cttccccgca ggttgacgtc ggaatccatg caagtactcc | 240 |
| ctgaaatcga gacgacagag agaacaacca acgcgcttaa acgcttcatg ttcatctaag | 300 |
| aggcacattc gaagaactag cttaacacac tagacctggc ttttcgaccc cctccgcaga | 360 |
| aagccgtttt ctcctcaatc ctcccgggct tggcttttgt cagtccgtac ttgctgcgct | 420 |
| aacagagtct tggacgcagc gtttgcgcat cagtcttgca ggcggttcac gggactagga | 480 |
| caacagggga tgtgacaggc cggatagtaa ttatgggtta tccggggtaa gcagggaatt | 540 |
| tacgaggccg cttacgtgg gggaacagcc acttgcgggg ggaagaggag tagtaggcga | 600 |
| ctcggtcgat gagctcgagg tgtctggttg acttggactg cagagcgtag gtaattgaga | 660 |
| tcgggcaaca ttatcggtgt tcggctcggt atggccgagt tgcgactgct tggtcattcg | 720 |
| gcgaagctga tgtcgtggta tcctgaagca tcgatatcgg aaaccatgat ggtcagtcta | 780 |
| tctgacgtgt gcggtgacaa gcgagtccgg attttgtgac atgacgttca acttcagtca | 840 |
| atgccttagg gctcgataag attaagattg ggttctggca gcggtctaga acaccgccac | 900 |
| aaattctgtc cattgaggag cgtgatgtct aggcgcatca ctaacacgga gctgtatgac | 960 |
| cggcagctca acggacttct cttcgttcaa cggcagtcta tttgcggtac acgaatggat | 1020 |
| cttcttcct ggtcttgaag tgccgcagtg gcgtgcgaat gtatagatgt ctcgctacct | 1080 |
| agaaaagctg gcttttctga cagggtccct tccacctctc ctaccaacga caaactgaac | 1140 |
| aagtatctgg cggttcccca acgccgaata ggccagtcgc caatactccc tccagccctg | 1200 |
| attgggcccc tcgaagtatc gccatgtctg tgtgttgaga ttattcgatg gacgtcactc | 1260 |
| ccccaaccta caggaagagc aaaatgggag cagtgttctg caatgagcta tataatagat | 1320 |
| cgctcgatct catacaaatt gtatgctcag tcaatacaac gagcggttcc aagatccctt | 1380 |
| ctccaacgac cctcgaaaca ttgcaacccg gtgcagcctg aacttgttcg tatagcctag | 1440 |
| aaagcgacgc catcttcatc ttttacgcga ttagcctcat ggctatttgt gccgaagtgg | 1500 |
| gagttgtatg gtagcagtga ggagattgtg gctacgacac aggcgggttc tcttgagcgg | 1560 |
| cttacatctc cgcattaggc ctgcgtacga tccagatcat gggaaacttt acaatggctt | 1620 |
| actcgtttta tctcaacact gagcttccaa ttcactctat gcattgatta acacgtttgg | 1680 |
| tcatgtggtt cttcagctgt aaatcttcag cttcccaaga attgcaacct cgctgattgc | 1740 |
| taatagtgtt gcatgcgttg catcctggtg cggcagtgca aaggagagtc aaagtagccg | 1800 |
| gcagattaat ttaagcttat atcactcagg ggtaaacagc cgtaaaggac cttttgatct | 1860 |
| aacatgccga tgtgtatgta gatcacgcaa tgcccaccat atcttggcag tcagatttgt | 1920 |
| ccgtggcgcg ccaagtataa cttcgtataa tgtatgctat acgaagttat cggccggcgt | 1980 |
| attgggtgtt acggagcatt cactaggcaa ccatggttac tattgtatac ccatcttagt | 2040 |
| aggaatgatt ttcgaggttt atacctacga tgaatgtgtg tcctgtaggc ttgagagttc | 2100 |
| aaggaagaaa cagtgcaatt atcttttgcga acccagggc tggtgacgga attttcatag | 2160 |
| tcaagctatc agagtaaaga agaggagcat gtcaaagtac aattagagac aaatatatag | 2220 |
| tcgcgtggag ccaagagcgg attcctcagt ctcgtaggtc tcttgacgac cgttgatctg | 2280 |
| cttgatctcg tctcccgaaa atgaaaatag actctgctaa gctattcttc tgcttcgccg | 2340 |
| gagcctgaag ggcgtactag ggttgcgagg tccaatgcat taatgcattg cagatgagct | 2400 |
| gtatctggaa gaggtaaacc cgaaacgcgt tttattcttg ttgacatgga gctattaaat | 2460 |

```
cactagaagg cactctttgc tgcttggaca aatgaacgta tcttatcgag atcctgaaca   2520
ccatttgtct caactccgga gctgacatcg acaccaacga tcttatatcc agattcgtca   2580
agctgtttga tgatttcagt aacgttaagt ggatcccggt cggcatctac tctattcctt   2640
tgccctcgga cgagtgctgg ggcgtcggtt ccactatcg gcgagtactt ctacacagcc    2700
atcggtccag acggccgcgc ttctgcgggc gatttgtgta cgcccgacag tcccggctcc   2760
ggatcggacg attgcgtcgc atcgaccctg cgcccaagct gcatcatcga aattgccgtc   2820
aaccaagctc tgatagagtt ggtcaagacc aatgcggagc atatacgccc ggagccgcgg   2880
cgatcctgca agctccggat gcctccgctc gaagtagcgc gtctgctgct ccatacaagc   2940
caaccacggc ctccagaaga agatgttggc gacctcgtat tgggaatccc cgaacatcgc   3000
ctcgctccag tcaatgaccg ctgttatgcg gccattgtcc gtcaggacat tgttggagcc   3060
gaaatccgcg tgcacgaggt gccggacttc ggggcagtcc tcggcccaaa gcatcagctc   3120
atcgagagcc tgcgcgacgg acgcactgac ggtgtcgtcc atcacagttt gccagtgata   3180
cacatgggga tcagcaatcg cgcatatgaa atcacgccat gtagtgtatt gaccgattcc   3240
ttgcggtccg aatgggccga acccgctcgt ctggctaaga tcggccgcag cgatcgcatc   3300
catggcctcc gcgaccggct gcagaacagc gggcagttcg gtttcaggca ggtcttgcaa   3360
cgtgacaccc tgtgcacggc gggagatgca ataggtcagg ctctcgctga attccccaat   3420
gtcaagcact tccggaatcg ggagcgcggc cgatgcaaag tgccgataaa cataacgatc   3480
tttgtagaaa ccatcggcgc agctatttac ccgcaggaca tatccacgcc ctcctacatc   3540
gaagctgaaa gcacgagatt cttcgccctc cgagagctgc atcaggtcgg agacgctgtc   3600
gaacttttcg atcagaaact tctcgacaga cgtcgcggtg agttcaggct ttttcatatc   3660
gattgtgatg tgatggagtt gagatggagg tgaggagatg gatgatggga aaggaagatg   3720
gactgaggat ggaagaagag aagaagagag agagagaaag tcttccagga gagaaaggga   3780
accgaagaaa aatggggagg aaaccggccc tagcacctaa atacgtctcc cgcttaatttt  3840 tcgccctttt ttcaccaaac cctccgcgtc tttcgtgcgc tagctgtctt gggggtgtg    3900 taaaacttgg gaacaaccct acgccgaacc tcccgtacga agcccgtaca gtgtattcta   3960
tccctggctt tccagcctg gtaagtcggg tcccttcggg acggggccaa ggagactgag    4020
tttccgggtt aaccaataat gccgccagcc gtggagcggt ctgagctgtc tatcgtgaat   4080
ccgtgacgct gaattgctca gtccaagtcg gagacgctgg aatccaccgg ttgctccagc   4140
cacggcgaag aatccactta ccttccgggc ttccgccagc tggcaacata ttttgaggc    4200 tgatatagcc ttctcctcca tcacgataag ccctgactac cttgctacgg gccaattgca   4260
atttgtttgc tggttacgct ttacaaaagg tggccgttac tgagcaaaaa gaaaatgatg   4320
taaaaatttg cgagtgggtc ccatagctgg atgggtccga taaaatggta ctgcccact    4380 tagtggcagc tcgcgaccag tcacaagccc aggataactt cgtataatgt atgctatacg   4440
aagttatctg tgggcgttat gaataataga ctggaaccgg gccctttgat tgacgactcc   4500 atatttgta gatgtagcaa ctcggcaaga gcattatgtg caatacattt gttaccatac    4560
aaaggcagct gccagacgac ttgtattgcg tacaattctc acggcaagct ttccaggtgt   4620
tatgcattat gcgcaaatgc ttgatgctta ccgcaggatt aatctcggaa gaagcgctgc   4680
aagctatatg ggtgtagtag atatgtagat gtaccaacca atgaagaaca tttatggtct   4740
agaacgtagt gatgaaggtt ttgagtaatt tgtatcaagt aagacgatat tattgatata   4800
ataccaagca tatattcatg ataaaattact tggaaccacc cttgcgtccg gcctcacgag   4860
```

-continued

```
ccttctcact gccgggctcg aaggagccac tggaggcctg tccacccttg gatgcgattt      4920
cctgcacctt ttccttgggc ctgcacgtcg attagacatg attcaaatcg agatcttgga      4980
atatcttaca tgctggcgaa gccaccggtg tggctggact gtccgccctt ctgcgcaatg      5040
cttTgaacct cctccttggg gctgtgtaga aaggtttgtt agcaacatta ctacaactct      5100
caggactcgg tggtcgtacc ggttggcgaa gtttccgggg ttatcgttgc cagacattgt      5160
gtgattattt ggtgtgcaaa tgtgtgctat gtgtgttgtt gctgttggtg atgatgctga      5220
agctgttgaa agcaggctgg ttctgtggga gagacttggg atatttatat ccaaagttcg      5280
gtcgtgttcc ttctggaagc tcttctctac tccatacaat catccaaagt tgtcgtcatt      5340
gagcgttgat cagtagtagc ctctgaggtc atcaccatga tccttccggc aacagtcgg      5400 cactcatcaa cagcaacaat cagccgccac aaacataggt acagtaagga gttagatatc      5460
atgtagtcgt cgagtactcg acatcatgac gtacaagctt tgccagtgtc ggtaggtgca      5520
agtatgatga tcgtatccgc cgttgttcga tcgaacagag tgcggtcaga ttcacggttt      5580
ctctcacctt gaacattgga tgcaattgga ttgatccaca atcctggaga atggcttcaa      5640
gctcactgct ccagtcgcaa gcttcagagc ctattactaa gggtagagct acctatgtca      5700
agagttttca aggtacctaa gctacatgtg atagtcggca agccatttTg aacgcagacc      5760
gtgaacggtg atgtaaatcc gggatagacg cccaagcgtg ccgtgtcaat gacgctagat      5820
acacctcgat ttacgtagag tgaatgccag ccaatggagt catgcacata acccgcttag      5880
actctgctcg gggcgatacc cgatcgcaga ggcagagccg cttaaacgcg atcgcggtaa      5940
cctgtaatca gagccagcgc tcgatgaatt gcatcatgga agccattgat gtggaatgtt      6000
gagcgtataa caacacgaat tgaagacgac attgacttgc ttcaagtgag tggagaattg      6060
ccgggcagac aagataggta ggctcttggt gcgctgtcac atcaatccat tcctttTcct      6120
ctgttcaatc tctatgttga cattctgata gggatcattg gatgccaatg caaagaacat      6180
gagagtgtgg tctgcattca agtatcctgg tcgtaagctg tggccatggg cgctgcggtc      6240
aaggtcaatc gcgatgacta atcagtctcg gtgactctgg ggcggtagag gcagtgtcgt      6300
gaaccaaagc ttgagccgag ggcaaaaaca acggcgcatc aaacaatcaa cgaaagcatc      6360
gtcaacagtg tctcttccca gtcaattact tcgcaaaacc ttctcgatag aacccttcag      6420
acgatgaaca ggccacgcaa ccgtcagccg cgccccccag gacagactca gcgcccggga      6480
ggcagatcgt cacaccttgg tcgacgagct c                                    6511
```

<210> SEQ ID NO 20
<211> LENGTH: 24
<212> TYPE: DNA
<213> ORGANISM: Artificial Sequence
<220> FEATURE:
<223> OTHER INFORMATION: Synthetic primer

<400> SEQUENCE: 20

```
gaccggacgt gttttgccct tcat                                               24
```

<210> SEQ ID NO 21
<211> LENGTH: 22
<212> TYPE: DNA
<213> ORGANISM: Artificial Sequence
<220> FEATURE:
<223> OTHER INFORMATION: Synthetic primer

<400> SEQUENCE: 21

```
gtgtgaccgg ctttggcgag tg                                                 22
```

-continued

<210> SEQ ID NO 22
<211> LENGTH: 4979
<212> TYPE: DNA
<213> ORGANISM: Artificial Sequence
<220> FEATURE:
<223> OTHER INFORMATION: Chemically synthesized nucleotide sequence of a
      PCR fragment amplified from pTTTpyrG-CBH2

<400> SEQUENCE: 22

```
gaccggacgt gttttgccct tcatttggag aaataatgtc attgcgatgt gtaatttgcc      60
tgcttgaccg actggggctg ttcgaagccc gaatgtagga ttgttatccg aactctgctc     120
gtagaggcat gttgtgaatc tgtgtcgggc aggacacgcc tcgaaggttc acggcaaggg     180
aaaccaccga tagcagtgtc tagtagcaac ctgtaaagcc gcaatgcagc atcactggaa     240
aatacaaacc aatggctaaa agtacataag ttaatgccta agaagtcat ataccagcgg      300
ctaataattg tacaatcaag tggctaaacg taccgtaatt tgccaacggc ttgtggggtt     360
gcagaagcaa cggcaaagcc ccacttcccc acgtttgttt cttcactcag tccaatctca     420
gctggtgatc ccccaattgg gtcgcttgtt tgttccggtg aagtgaaaga agacagaggt     480
aagaatgtct gactcggagc gttttgcata caaccaaggg cagtgatgga agacagtgaa     540
atgttgacat tcaaggagta tttagccagg gatgcttgag tgtatcgtgt aaggaggttt     600
gtctgccgat acgacgaata ctgtatagtc acttctgatg aagtggtcca tattgaaatg     660
taaagtcggc actgaacagg caaaagattg agttgaaact gcctaagatc tcgggccctc     720
gggccttcgg cctttgggtg tacatgtttg tgctccgggc aaatgcaaag tgtggtagga     780
tcgaacacac tgctgccttt accaagcagc tgagggtatg tgataggcaa atgttcaggg     840
gccactgcat ggtttcgaat agaaagagaa gcttagccaa gaacaatagc cgataaagat     900
agcctcatta aacggaatga gctagtaggc aaagtcagcg aatgtgtata tataaaggtt     960
cgaggtccgt gcctccctca tgctctcccc atctactcat caactcagat cctccaggag    1020
acttgtacac catcttttga ggcacagaaa cccaatagtc aaccatcaca agtttgtaca    1080
aaaaagcagg ctccgcggcc gccccttca ccaccatga ttgtcggcat tctcaccacg      1140
ctggctacgc tggccacact cgcagctagt gtgcctctag aggagcggca agcttgctca    1200
agcgtctggt aattatgtga accctctcaa gagacccaaa tactgagata tgtcaagggg    1260
ccaatgtggt ggccagaatt ggtcgggtcc gacttgctgt gcttccggaa gcacatgcgt    1320
ctactccaac gactattact cccagtgtct tcccggcgct gcaagctcaa gctcgtccac    1380
gcgcgccgcg tcgacgactt ctcgagtatc ccccacaaca tcccggtcga gctccgcgac    1440
gcctccacct ggttctacta ctaccagagt acctccagtc ggatcgggaa ccgctacgta    1500
ttcaggcaac ccttttgttg gggtcactcc ttgggccaat gcatattacg cctctgaagt    1560
tagcagcctc gctattccta gcttgactgg agccatggcc actgctgcag cagctgtcgc    1620
aaaggttccc tcttttatgt ggctgtaggt cctcccggaa ccaaggcaat ctgttactga    1680
aggctcatca ttcactgcag agatactctt gacaagaccc ctctcatgga gcaaccttg     1740
gccgacatcc gcaccgccaa caagaatggc ggtaactatg ccggacagtt tgtggtgtat    1800
gacttgccgg atcgcgattg cgctgccctt gcctcgaatg gcgaatactc tattgccgat    1860
ggtggcgtcg ccaaatataa gaactatatc gacaccattc gtcaaattgt cgtggaatat    1920
tccgatatcc ggaccctcct ggttattggt atgagtttaa acacctgcct cccccccccc    1980
ttcccttcct ttcccgccgg catcttgtcg ttgtgctaac tattgttccc tcttccagag    2040
```

```
cctgactctc ttgccaacct ggtgaccaac ctcggtactc caaagtgtgc caatgctcag    2100
tcagcctacc ttgagtgcat caactacgcc gtcacacagc tgaaccttcc aaatgttgcg    2160
atgtatttgg acgctggcca tgcaggatgg cttggctggc cggcaaacca agacccggcc    2220
gctcagctat ttgcaaatgt ttacaagaat gcatcgtctc cgagagctct tcgcggattg    2280
gcaaccaatg tcgccaacta caacgggtgg aacattacca gcccccatc gtacacgcaa     2340 ggcaacgctg tctacaacga gaagctgtac atccacgcta ttggacctct tcttgccaat    2400
cacggctggt ccaacgcctt cttcatcact gatcaaggtc gatcgggaaa gcagcctacc    2460
ggacagcaac agtggggaga ctggtgcaat gtgatcggca ccggatttgg tattcgccca    2520
tccgcaaaca ctggggactc gttgctggat tcgtttgtct gggtcaagcc aggcggcgag    2580
tgtgacggca ccagcgacag cagtgcgcca cgatttgact cccactgtgc gctcccagat    2640
gccttgcaac cggcgcctca agctggtgct tggttccaag cctactttgt gcagcttctc    2700
acaaacgcaa acccatcgtt cctgtaaaag ggtgggcgcg ccgacccagc tttcttgtac    2760
aaagtggtga tcgcgccgcg cgccagctcc gtgcgaaagc ctgacgcacc ggtagattct    2820
tggtgagccc gtatcatgac ggcggcggga gctacatggc cccgggtgat ttatttttt    2880 tgtatctact tctgacccctt ttcaaatata cggtcaactc atctttcact ggagatgcgg   2940
cctgcttggt attgcgatgt tgtcagcttg gcaaattgtg gctttcgaaa acacaaaacg    3000
attccttagt agccatgcat tttaagataa cggaatagaa gaaagaggaa attaaaaaaa    3060
aaaaaaaaac aaacatcccg ttcataaccc gtagaatcgc cgctcttcgt gtatcccagt    3120
accagtttat tttgaatagc tcgcccgctg gagagcatcc tgaatgcaag taacaaccgt    3180
agaggctgac acggcaggtg ttgctaggga gcgtcgtgtt ctacaaggcc agacgtcttc    3240
gcggttgata tatatgtatg tttgactgca ggctgctcag cgacgacagt caagttcgcc    3300
ctcgctgctt gtgcaataat cgcagtgggg aagccacacc gtgactccca tctttcagta    3360
aagctctgtt ggtgtttatc agcaatacac gtaatttaaa ctcgttagca tggggctgat    3420
agcttaatta ccgtttacca gtgccatggt tctgcagctt ccttggccc gtaaaattcg     3480 gcgaagccag ccaatcacca gctaggcacc agctaaaccc tataattagt ctcttatcaa    3540
caccatccgc tcccccggga tcaatgagga gaatgagggg gatgcggggc taaagaagcc    3600
tacataaccc tcatgccaac tcccagttta cactcgtcga gccaacatcc tgactataag    3660
ctaacacaga atgcctcaat cctgggaaga actggccgct gataagcgcg cccgcctcgc    3720
aaaaaccatc cctgatgaat ggaaagtcca gacgctgcct gcggaagaca gcgttattga    3780
tttcccaaag aaatcgggga tccttcaga ggccgaactg aagatcacag aggcctccgc    3840
tgcagatctt gtgtccaagc tggcggccgg agagttgacc tcggtggaag ttacgctagc    3900
attctgtaaa cgggcagcaa tcgcccagca gttagtaggg tcccctctac ctctcaggga    3960
gatgtaacaa cgccaccta tgggactatc aagctgacgc tggcttctgt gcagacaaac    4020
tgcgcccacg agttcttccc tgacgccgct ctcgcgcagg caagggaact cgatgaatac    4080
tacgcaaagc acaagagacc cgttggtcca ctccatggcc tccccatctc tctcaaagac    4140
cagcttcgag tcaaggtaca ccgttgcccc taagtcgtta gatgtcccctt tttgtcagct   4200 aacatatgcc accagggcta cgaaacatca atgggctaca tctcatggct aaacaagtac    4260
gacgaagggg actcggttct gacaaccatg ctccgcaaag ccggtgccgt cttctacgtc    4320
aagacctctg tcccgcagac cctgatggtc tgcgagacag tcaacaacat catcgggcgc    4380
accgtcaacc cacgcaacaa gaactggtcg tgcggcggca gttctggtgg tgagggtgcg    4440
```

-continued

| | |
|---|---|
| atcgttggga ttcgtggtgg cgtcatcggt gtaggaacgg atatcggtgg ctcgattcga | 4500 |
| gtgccggccg cgttcaactt cctgtacggt ctaaggccga gtcatgggcg gctgccgtat | 4560 |
| gcaaagatgg cgaacagcat ggagggtcag gagacggtgc acagcgttgt cgggccgatt | 4620 |
| acgcactctg ttgagggtga gtccttcgcc tcttccttct tttcctgctc tataccaggc | 4680 |
| ctccactgtc ctcctttctt gcttttata ctatatacga gaccggcagt cactgatgaa | 4740 |
| gtatgttaga cctccgcctc ttcaccaaat ccgtcctcgg tcaggagcca tggaaatacg | 4800 |
| actccaaggt catccccatg ccctggcgcc agtccgagtc ggacattatt gcctccaaga | 4860 |
| tcaagaacgg cgggctcaat atcggctact acaacttcga cggcaatgtc cttccacacc | 4920 |
| ctcctatcct gcgcggcgtg gaaaccaccg tcgccgcact cgccaaagcc ggtcacacc | 4979 |

<210> SEQ ID NO 23
<211> LENGTH: 2593
<212> TYPE: DNA
<213> ORGANISM: T. ressei

<400> SEQUENCE: 23

| | |
|---|---|
| atggcggaca aggaagcaac cgtcttcatc atcgacctcg gcgcgtccat ggcagctgtc | 60 |
| aatgggggtc gagaagaatc cgaccttgat tggagcatga gctacgtctg ggacaagatc | 120 |
| agcaacgtcg tggcctcgaa tcgcaagacg ctgtgcgttg gcgtcgtggg gttcagaacc | 180 |
| gacgagacaa accacacgct gagcgaggat gggtacgaga acatctccat attgcagccc | 240 |
| ctggggccga tgagcatgtc cagcctcaag gctcttcagc ccaaggtgaa gccgagcagg | 300 |
| acggtggaag gcgatgccat ctcggcgatt gtcattgccg tcgacatgat tgacaagtac | 360 |
| acgaagaaga acaaatggaa gcggcagatt gttctcatta ccgacggcca aggcgagatt | 420 |
| gatccagatg atattggcga cattgctaga agatgcgcg actcgaatat tgaattgaca | 480 |
| gtcttgtgag ttggcgagac cgtttggcgg acggtaatgg tgctgacggt gatgcaaggg | 540 |
| gcgtcgactt tgatgctccc gattacggct tcaaagagga ggacaaacct tcagtcaagg | 600 |
| tactccatat gttcacttct tttctttttc ttctttattt tctttctctt tgaagctttc | 660 |
| attaacctct tcgttagaag caaaacgaag agacctaaa aaagctcgtg gatggctgtg | 720 |
| gcgacgactc aaggttcgcc tccatggtcg aggccattga cgacttgaat gagccacgag | 780 |
| caaagtcggt caagccttac aaaacgtacg aaggtctctt gaccttggga gatccgaaaa | 840 |
| acgctcccgc agtggtggaa atccgcgtcg agagatactt caagacccat ctagccaggc | 900 |
| cacctgccgc cagcaccgtg gtggtcaagg aggagcaagc tgggccgtct caggcagacg | 960 |
| aggacgaaca gatggacgga gcggaactta cagctgtgag gcaggccagg acatacaagg | 1020 |
| tcaatgatcc agatgcccct ggcggtaagc gtgacgttga gtttgagtct ctggccaaag | 1080 |
| ggtacgagta cggcaggacg gcagtccaca tcagcgagtc tgatcaaaac gtcaccaagc | 1140 |
| tcgcgacaga aaagagcttc aagatcatcg gcttcgtcca gaaagaaaag gtattggctt | 1200 |
| ggctctcagc atttgacccg ttgctcttgg ctaacccttg tttagtatga aatgctcctt | 1260 |
| aatcttggcg aaacctgcgt taccgttgca tccaagtacg atgaaaagtc tgagctggct | 1320 |
| tttagctctc tggtgtgggc gctctcggag ctcgacgcct acgccgtggc ccgcctagta | 1380 |
| actaaggacc aaaaggaccc catgctggtg ttactgatgc cgtatatgga gcctgattat | 1440 |
| gtttgtctct atgatgtgcc tctgcctttc gcagaggaca tcaggacgta ccagtttcct | 1500 |
| cccttggaca gagtcgttac cgtcagtggc caaacgctca ccaaccatcg cctattgcca | 1560 |
| tccgacgagc tcaaccaagc gatgagcgac tacgtagatg ccatggacat ttcaagttat | 1620 |

```
ggtatcgatg aagatgggtg agtatagaag atgattgttc aaatctttca cttctaagca   1680
ttgcttctga tctaggcaac cggctgaata tgccaccatc gatgagttat acaaccctgc   1740
gatacatcgc ataggccatg cgatcaaaca acgagcgatc cacccagaga aacccgtgcc   1800
cgagatcccc ccagtcttgc ttagattcgc agcaccccg acagaactcg tcgagactgt    1860
gcagcctcat atcgatgcac tgattcacgc tgcagacgtg aagaaaggta ctgattccat   1920
tacatatgct tctctgcaca ctgatgtttg atttgtgcta acgcccccct tagtgccgcc   1980
caaggccaag ggcaagcgcc aaagagaaac agttaaaccc atctcgggac tggatgtgga   2040
tgcccttctg ggagaagagc agaaaggttc cattagtccg gagaatgcca ttccggactt   2100
caaacgagcc ctcaactcgt ccgaagaagt cgagcagatt gccgacgcca caaaacaaat   2160
gggggccatt gtgcggtctc tcattacgga cagcttcggg gatagcaaat atgcccaggc   2220
aatggaaggc attggtgcga tgcgtgagga gctgatcaac ctggaagagc ctggcctgta   2280
caacgacttt gtgcgcgact tgaagaaaag tttgctatct ggagccttgg gtggtgacag   2340
gcgagatttc tggttcaaga tgaggtgggc gaagctgggc ctgattgaca agaaacagtc   2400
ggaggtgtct tcggtcactc ttgaggaggc ggacgaggtg agtggtgcag catgctgtcg   2460
gattatacgg acgttgtttg ctaacttgtg ggatagtttt acaagtcgag gtgaggtatc   2520
tacgttgacc aagaatggga ccatgtatat gagcggtgta acaacagaat cctgtgcttt   2580
gagcattgta tga                                                     2593
```